(12) United States Patent  
Steurer et al.

(10) Patent No.: US 8,778,929 B2  
(45) Date of Patent: *Jul. 15, 2014

(54) SUBSTITUTED HETEROARYL INHIBITORS OF B-RAF

(75) Inventors: Steffen Steurer, Vienna (AT); Peter Ettmayer, Vienna (AT); Andreas Mantoulidis, Vienna (AT)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 253 days.

This patent is subject to a terminal disclaimer.

(21) Appl. No.: 13/121,241

(22) PCT Filed: Sep. 28, 2009

(86) PCT No.: PCT/EP2009/062551
§ 371 (c)(1),
(2), (4) Date: May 27, 2011

(87) PCT Pub. No.: WO2010/034838
PCT Pub. Date: Apr. 1, 2010

(65) Prior Publication Data
US 2011/0312939 A1    Dec. 22, 2011

(30) Foreign Application Priority Data
Sep. 29, 2008  (EP) .................... 08165437

(51) Int. Cl.
| A61P 35/00 | (2006.01) |
| A61K 31/4439 | (2006.01) |
| C07D 401/14 | (2006.01) |
| C07D 413/14 | (2006.01) |
| C07D 417/14 | (2006.01) |
| C07D 487/04 | (2006.01) |

(52) U.S. Cl.
USPC .............. 514/211.15; 514/218; 514/236.2; 514/249; 514/252.18; 514/253.09; 514/253.1; 514/256; 514/278; 514/316; 514/318; 514/333; 514/341; 514/342; 540/544; 540/575; 544/121; 544/130; 544/131; 544/295; 544/333; 544/350; 544/364; 546/16; 546/187; 546/194; 546/256; 546/270.7; 546/272.1; 546/275.4

(58) Field of Classification Search
USPC ........... 514/211.15, 218, 236.2, 249, 252.18, 514/253.09, 253.1, 256, 278, 316, 318, 333, 514/341, 342; 540/544, 575; 544/121, 130, 544/131, 295, 333, 350, 364; 546/16, 187, 546/194, 256, 270.7, 272.1, 275.4
See application file for complete search history.

(56) References Cited

U.S. PATENT DOCUMENTS

| 4,218,457 A | 8/1980 | Atsumi et al. |
| 5,990,133 A | 11/1999 | Gaster et al. |
| 6,492,403 B1 | 12/2002 | Illig et al. |
| 7,166,628 B2 | 1/2007 | Cogan et al. |
| 7,214,802 B2 | 5/2007 | Cogan et al. |
| 7,485,657 B2 | 2/2009 | Cogan et al. |
| 7,511,042 B2 | 3/2009 | Cogan et al. |
| 7,514,458 B2 | 4/2009 | Cogan et al. |
| 7,531,560 B2 | 5/2009 | Cogan et al. |
| 7,569,568 B2 | 8/2009 | Cogan et al. |
| 7,858,804 B2 | 12/2010 | Frutos et al. |
| 8,198,308 B2 | 6/2012 | Steurer et al. |
| 2004/0102492 A1 | 5/2004 | Cogan et al. |
| 2005/0153972 A1 | 7/2005 | Cogan et al. |
| 2005/0256113 A1 | 11/2005 | Cogan et al. |
| 2006/0079519 A1 | 4/2006 | Cogan et al. |
| 2006/0100204 A1 | 5/2006 | Cogan et al. |
| 2007/0032492 A1 | 2/2007 | Cogan et al. |
| 2007/0142371 A1 | 6/2007 | Cogan et al. |
| 2008/0009497 A1 | 1/2008 | Wittman et al. |
| 2008/0027070 A1 | 1/2008 | Noronha et al. |
| 2008/0045489 A1 | 2/2008 | Chao et al. |
| 2008/0132459 A1 | 6/2008 | Moradei et al. |
| 2008/0182837 A1 | 7/2008 | Steurer et al. |
| 2009/0127815 A1 | 5/2009 | Tani et al. |
| 2009/0239838 A1 | 9/2009 | Wittman et al. |
| 2010/0240657 A1 | 9/2010 | Sapountzis et al. |
| 2011/0059938 A1 | 3/2011 | Steurer et al. |

(Continued)

FOREIGN PATENT DOCUMENTS

| EP | 1 364 949 A1 | 11/2003 |
| FR | 2401916 A1 | 3/1979 |

(Continued)

OTHER PUBLICATIONS

International Search Report for PCT/EP2009/062551 mailed Jan. 10, 2010.
Caplus: Chan, et al., 2002, CAS: 138:198127.
International Search Report for PCT/EP08/058432 mailed Dec. 17, 2008.
International Search Report for PCT/EP098/058433 mailed Jun. 4, 2009.
International Search Report for PCT/EP2007/056860 mailed Nov. 15, 2007.

(Continued)

*Primary Examiner* — Brenda Coleman
(74) *Attorney, Agent, or Firm* — Michael P. Morris; Edward S. Lazer

(57) ABSTRACT

The present invention relates to new compounds of general formula (I), wherein the groups $R^1$ to $R^3$, $X^1$, $X^2$, $X^3$ and $L^1$ are defined as in claim 1, which are suitable for the treatment of diseases characterised by excessive or abnormal cell proliferation, and the use thereof in such a treatment.

(1)

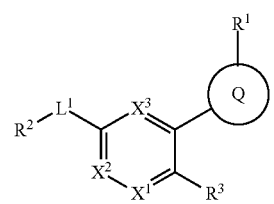

14 Claims, No Drawings

(56) References Cited

U.S. PATENT DOCUMENTS

| | | |
|---|---|---|
| 2011/0124623 A1 | 5/2011 | Wittman et al. |
| 2011/0183952 A1 | 7/2011 | Sapountzis et al. |
| 2011/0312939 A1 | 12/2011 | Steurer et al. |
| 2012/0046270 A1 | 2/2012 | Ettmayer et al. |
| 2012/0094975 A1 | 4/2012 | Mantoulidis et al. |
| 2013/0190286 A1 | 7/2013 | Steurer et al. |

FOREIGN PATENT DOCUMENTS

| | | |
|---|---|---|
| JP | 03174153 A | 7/1991 |
| WO | 9703967 A1 | 2/1997 |
| WO | 0075120 A1 | 12/2000 |
| WO | 0162737 A2 | 8/2001 |
| WO | 03037274 A2 | 5/2003 |
| WO | 03051358 A1 | 6/2003 |
| WO | 03059886 A1 | 7/2003 |
| WO | 2004050642 A1 | 6/2004 |
| WO | 2005023761 A2 | 3/2005 |
| WO | 2005030705 A1 | 4/2005 |
| WO | 2005040152 A1 | 5/2005 |
| WO | 2005056535 A1 | 6/2005 |
| WO | 2005090333 A1 | 9/2005 |
| WO | 2005115991 A1 | 12/2005 |
| WO | 2006053227 A2 | 5/2006 |
| WO | 2007056016 A2 | 5/2007 |
| WO | 2007075896 A2 | 7/2007 |
| WO | 2007121390 A1 | 10/2007 |
| WO | 2007132010 A1 | 11/2007 |
| WO | 2008/003770 A1 | 1/2008 |
| WO | 2008/021388 A1 | 2/2008 |
| WO | 2008079909 A1 | 7/2008 |
| WO | 2008089034 A2 | 7/2008 |
| WO | 2008/106692 A1 | 9/2008 |
| WO | 2009003998 A2 | 1/2009 |
| WO | 2009003999 A2 | 1/2009 |
| WO | 2009012283 A1 | 1/2009 |
| WO | 2010010154 A1 | 1/2010 |
| WO | 2010026262 A1 | 3/2010 |
| WO | 2010034838 A2 | 4/2010 |
| WO | 2010094695 A1 | 8/2010 |
| WO | 2011117381 A1 | 9/2011 |
| WO | 2011117382 A1 | 9/2011 |
| WO | 2012085127 A1 | 6/2012 |
| WO | 2012101238 A1 | 8/2012 |
| WO | 2012104388 A1 | 8/2012 |

OTHER PUBLICATIONS

International Search Report for PCT/EP2011/054611 mailed Apr. 21, 2011.
International Search Report for PCT/EP2011/054612 mailed Jul. 28, 2011.
International Search Report for PCT/EP2011/073654 mailed Feb. 2, 2012.
Subasinghe, N. L. et al., "Structure-based Design, Synthesis and SAR of a Novel Series of Thiopheneamidine Urokinase Plasminogen Activator Inhibitors", Bioorganice and Medicinal Chemistry Letters, 11, 2001, pp. 1379-1382.
Williams, D.A. et al., Foye's Principles of Medicinal Chemistry, Fifth Edition, 2002, pp. 59-63.
Patani, G.A. et al., "Bioisosterism: A Rational Approach in Drug Design", Chem Rev, 96, 1996, pp. 3147-3176.
Sparreboom, A. et al., "The Use of Oral Cytotoxic and Cytostatic Drugs in Cancer Treatment." European Journal of Cancer 38, 2002, pp. 18-22.

SUBSTITUTED HETEROARYL INHIBITORS OF B-RAF

The present invention relates to new compounds of general formula (1)

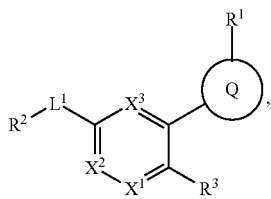

(1)

wherein the groups $R^1$ to $R^3$, $X^1$, $X^2$, $X^3$, Q and $L^1$ have the meanings given in the claims and specification and the tautomers, racemates, enantiomers, diastereomers and mixtures thereof and the salts of all these forms and their use as medicaments.

BACKGROUND TO THE INVENTION

Phenyl substituted, nitrogen-containing five-membered ring heteroaryls are described in WO 2005/090333 and US 2006/0100204 for the inhibition of cytokine production and hence for the treatment of inflammatory diseases and in WO 2008/003770 for the inhibition of signal enzymes and hence for the treatment of diseases characterised by excessive or abnormal cell proliferation. Other phenyl- and pyridyl-substituted five-membered ring heteroaryls for inhibiting cytokines are described in WO 2007/075896, while pyridyl-substituted triazoles with the same activity are described in WO 2008/021388.

The aim of the present invention is to discover new active substances which can be used for the prevention and/or treatment of diseases characterised by excessive or abnormal cell proliferation.

DETAILED DESCRIPTION OF THE INVENTION

It has now been found that, surprisingly, compounds of general formula (1), wherein the groups $R^1$ to $R^3$, $X^1$, $X^2$, $X^3$, Q and $L^1$ have the meanings given hereinafter act as inhibitors of specific signal enzymes which are involved in controlling cell proliferation. Thus, the compounds according to the invention may be used for example for the treatment of diseases connected with the activity of these signal enzymes and characterised by excessive or abnormal cell proliferation.

The present invention therefore relates to compounds of general formula (1)

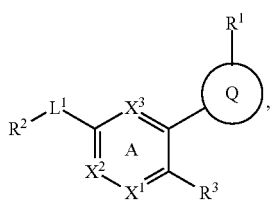

(1)

wherein
$R^1$ denotes a 5- or 6-membered monocyclic or 9 or 10-membered bicyclic heteroaryl optionally substituted by one or more identical or different $R^b$ and/or $R^c$, with the partial structure (i)

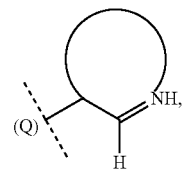

(i)

wherein the ring that binds directly to Q is heteroaromatic;
$R^2$ is a group optionally substituted by one or more identical or different $R^b$ and/or $R^c$, selected from among $C_{6-10}$aryl and 5-12 membered heteroaryl;
$R^3$ is selected from among hydrogen, —CN, —NO$_2$, —NH$_2$, —NH(C$_{1-4}$alkyl), —N(C$_{1-4}$alkyl)$_2$, C$_{1-4}$alkyl, C$_{1-4}$haloalkyl, C$_{1-4}$alkoxy, C$_{1-4}$haloalkoxy, C$_{3-5}$cycloalkyl and halogen;
$X^1$, $X^2$ and $X^3$ are each selected independently of one another from among nitrogen and CR$^4$,
while at least one and not more than two of the atoms $X^1$, $X^2$ and $X^3$ in ring A are nitrogen atoms and each $R^4$ is selected independently of one another from among hydrogen, —CN, —NO$_2$, —NH$_2$, —NH(C$_{1-4}$ alkyl), —N(C$_{1-4}$ alkyl)$_2$, C$_{1-4}$ alkyl, C$_{1-4}$haloalkyl, C$_{1-4}$alkoxy, C$_{1-4}$haloalkoxy, C$_{3-5}$cycloalkyl and halogen;
Q is selected from among

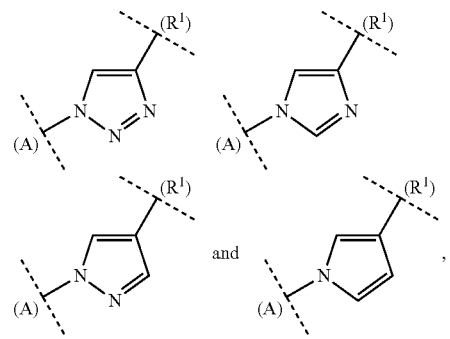

and while in the five-membered ring heteroaryls described above one to three cyclic hydrogen atoms may each be substituted independently of one another by C$_{1-6}$alkyl;
$L^1$ is selected from among (R$^2$)—C(O)NH— and (R$^2$)—NHC(O)—;
each $R^b$ is a suitable substituent and is selected independently of one another from among —OR$^c$, —SR$^c$, —NR$^c$R$^c$, —ONR$^c$R$^c$, —N(OR$^c$)R$^c$, —NR$^g$NR$^c$R$^c$, halogen, —CN, —NO$_2$, —N$_3$, —C(O)R$^c$, —C(O)OR$^c$, —C(O)NR$^c$R$^c$, —C(O)NR$^g$NR$^c$R$^c$, —C(O)NR$^g$OR$^c$, —C(NR$^g$)R$^c$, —N═CR$^c$R$^c$, —C(NR$^g$)OR$^c$, —C(NR$^g$)NR$^c$R$^c$, —C(NR$^g$)NR$^g$NR$^c$R$^c$, —C(NOR$^g$)R$^c$, —C(NOR$^g$)NR$^c$R$^c$, —C(NNR$^g$R$^g$)R$^c$, —OS(O)R$^c$, —OS(O)OR$^c$, —OS(O)NR$^c$R$^c$, —OS(O)$_2$R$^c$, —OS(O)$_2$OR$^c$, —OS(O)$_2$NR$^c$R$^c$, —OC(O)R$^c$, —OC(O)OR$^c$, —OC(O)NR$^c$R$^c$, —OC(NR$^g$)R$^c$, —OC(NR$^g$)NR$^c$R$^c$, —ONR$^g$C(O)R$^c$, —S(O)R$^c$, —S(O)OR$^c$, —S(O)NR$^c$R$^c$, —S(O)$_2$R$^c$, —S(O)$_2$OR$^c$, —S(O)$_2$NR$^c$R$^c$, —NR$^g$C(O)R$^c$, —NR$^g$C(O)OR$^c$, —NR$^g$C(O)NR$^c$R$^c$, —NR$^g$C(O)NR$^g$NR$^c$R$^c$, —NR$^g$C(NR$^g$)R$^c$, —N═CR$^c$NR$^c$R$^c$, —NR$^g$C(NR$^g$)OR$^c$, —NR$^g$C(NR$^g$)NR$^c$R$^c$, —NR$^g$S(O)R$^c$, —NR$^g$S(O)OR$^c$, —NR$^g$S(O)$_2$R$^c$, —NR$^g$S(O)$_2$OR$^c$, —NR$^g$S(O)$_2$NR$^c$R$^c$, —NR$^g$NR$^g$C(O)R$^c$, —NR$^g$NR$^g$C(O)NR$^c$R$^c$, —NR$^g$NR$^g$C(NR$^g$)R$^c$ and —N(OR$^g$)C(O)R$^c$ and the bivalent substituents =O, =S, =NR$^g$, =NOR$^g$, =NNR$^g$R$^g$ and =NNR$^g$C(O)NR$^g$R$^g$, while these bivalent substituents may only be substituents in non-aromatic ring systems;

each R$^c$ independently of one another denotes hydrogen or a group optionally substituted by one or more identical or different R$^d$ and/or R$^e$, selected from among C$_{1-6}$alkyl, 2-6 membered heteroalkyl, C$_{1-6}$haloalkyl, C$_{3-10}$cycloalkyl, C$_{6-10}$aryl, 5-12 membered heteroaryl and 3-14 membered heterocycloalkyl;

each R$^d$ is a suitable substituent and is selected independently of one another from among —OR$^e$, —SR$^e$, —NR$^e$R$^e$, —ONR$^e$R$^e$, —N(OR$^e$)R$^e$, —N(R$^g$)NR$^e$R$^e$, halogen, —CN, —NO$_2$, —N$_3$, —C(O)R$^e$, —C(O)OR$^e$, —C(O)NR$^e$R$^e$, —C(O)NR$^g$NR$^e$R$^e$, —C(O)NR$^g$OR$^e$, —C(NR$^g$)R$^e$, —N=CR$^e$R$^e$, —C(NR$^g$)OR$^e$, —C(NR$^g$)NR$^e$R$^e$, —C(NR$^g$)NR$^g$NR$^e$R$^e$, —C(NOR$^g$)R$^e$, —C(NOR$^g$)NR$^e$R$^e$, —C(NNR$^g$R$^g$)R$^e$, —OS(O)R$^e$, —OS(O)OR$^e$, —OS(O)NR$^e$R$^e$, —OS(O)$_2$R$^e$, —OS(O)$_2$OR$^e$, —OS(O)$_2$NR$^e$R$^e$, —OC(O)R$^e$, —OC(O)OR$^e$, —OC(O)NR$^e$R$^e$, —OC(NR$^g$)R$^e$, —OC(NR$^g$)NR$^e$R$^e$, —ONR$^g$C(O)R$^e$, —S(O)R$^e$, —S(O)OR$^e$, —S(O)NR$^e$R$^e$, —S(O)$_2$R$^e$, —S(O)$_2$OR$^e$, —S(O)$_2$NR$^e$R$^e$, —NR$^g$C(O)R$^e$, —NR$^g$C(O)OR$^e$, —NR$^g$C(O)NR$^e$R$^e$, —NR$^g$C(O)NR$^g$NR$^e$R$^e$, —NR$^g$C(NR$^g$)R$^e$, —N=CR$^e$NR$^e$R$^e$, —NR$^g$C(NR$^g$)OR$^e$, —NR$^g$C(NR$^g$)NR$^e$R$^e$, —NR$^g$C(NR$^g$)SR$^e$, —NR$^g$C(NOR$^g$)R$^e$, —NR$^g$S(O)R$^e$, —NR$^g$S(O)OR$^e$, —NR$^g$S(O)$_2$R$^e$, —NR$^g$S(O)$_2$OR$^e$, —NR$^g$S(O)$_2$NR$^e$R$^e$, —NR$^g$NR$^g$C(O)R$^e$, —NR$^g$NR$^g$C(O)NR$^e$R$^e$, —NR$^g$NR$^g$C(NR$^g$)R$^e$ and —N(OR$^g$)C(O)R$^e$ and the bivalent substituents =O, =S, =NR$^g$, =NOR$^g$, =NNR$^g$R$^g$ and =NNR$^g$C(O)NR$^g$R$^g$, while these bivalent substituents may only be substituents in non-aromatic ring systems;

each R$^e$ independently of one another denotes hydrogen or a group optionally substituted by one or more identical or different R$^f$ and/or R$^g$, selected from among C$_{1-6}$alkyl, 2-6 membered heteroalkyl, C$_{1-6}$haloalkyl, C$_{3-10}$cycloalkyl, C$_{6-10}$aryl, 5-12 membered heteroaryl and 3-14 membered heterocycloalkyl;

each R$^f$ is a suitable substituent and is selected independently of one another from among —OR$^g$, —SR$^g$, —NR$^g$R$^g$, —ONR$^g$R$^g$, —N(OR$^g$)R$^g$, —N(R$^h$)NR$^g$R$^g$, halogen, —CN, —NO$_2$, —N$_3$, —C(O)R$^g$, —C(O)OR$^g$, —C(O)NR$^g$R$^g$, —C(O)NR$^h$NR$^g$R$^g$, —C(O)NR$^h$OR$^g$, —C(NR$^h$)R$^g$, —N=CR$^g$R$^g$, —C(NR$^h$)OR$^g$, —C(NR$^h$)NR$^g$R$^g$, —C(NR$^h$)NR$^h$NR$^g$R$^g$, —C(NOR$^h$)R$^g$, —C(NOR$^h$)NR$^g$R$^g$, —C(NNR$^h$R$^h$)R$^g$, —OS(O)R$^g$, —OS(O)OR$^g$, —OS(O)NR$^g$R$^g$, —OS(O)$_2$R$^g$, —OS(O)$_2$OR$^g$, —OS(O)$_2$NR$^g$R$^g$, —OC(O)R$^g$, —OC(O)OR$^g$, —OC(O)NR$^g$R$^g$, —OC(NR$^h$)R$^g$, —OC(NR$^h$)NR$^g$R$^g$, —ONR$^h$C(O)R$^g$, —S(O)R$^g$, —S(O)OR$^g$, —S(O)NR$^g$R$^g$, —S(O)$_2$R$^g$, —S(O)$_2$OR$^g$, —S(O)$_2$NR$^g$R$^g$, —NR$^h$C(O)R$^g$, —NR$^h$C(O)OR$^g$, —NR$^h$C(O)NR$^g$R$^g$, —NR$^h$C(O)NR$^h$NR$^g$R$^g$, —NR$^h$C(NR$^h$)R$^g$, —N=CR$^g$NR$^g$R$^g$, —NR$^h$C(NR$^h$)OR$^g$, —NR$^h$C(NR$^h$)NR$^g$R$^g$, —NR$^h$C(NOR$^h$)R$^g$, —NR$^h$S(O)R$^g$, —NR$^h$S(O)OR$^g$, —NR$^h$S(O)$_2$R$^g$, —NR$^h$S(O)$_2$OR$^g$, —NR$^h$S(O)$_2$NR$^g$R$^g$, —NR$^h$NR$^h$C(O)R$^g$, —NR$^h$NR$^h$C(O)NR$^g$R$^g$, —NR$^h$NR$^h$C(NR$^h$)R$^g$ and —N(OR$^h$)C(O)R$^g$ and the bivalent substituents =O, =S, =NR$^h$, =NOR$^h$, =NNR$^h$R$^h$ and =NNR$^h$C(O)NR$^h$R$^h$, while these bivalent substituents may only be substituents in non-aromatic ring systems;

each R$^g$ independently of one another denotes hydrogen or a group optionally substituted by one or more identical or different R$^h$, selected from among C$_{1-6}$alkyl, 2-6 membered hetero alkyl, C$_{1-6}$haloalkyl, C$_{3-10}$cycloalkyl, C$_{6-10}$aryl, 5-12 membered hetero aryl and 3-14 membered heterocycloalkyl;

each R$^h$ is selected independently of one another from among hydrogen, C$_{1-6}$alkyl, 2-6 membered heteroalkyl, C$_{1-6}$haloalkyl, C$_{3-10}$cycloalkyl, C$_{6-10}$aryl, 5-12 membered heteroaryl and 3-14 membered heterocycloalkyl;

while the compounds (1) may optionally also be present in the form of their tautomers, racemates, enantiomers, diastereomers and mixtures thereof, or also as pharmacologically acceptable salts of all the above-mentioned forms.

In one aspect (A1) the invention relates to compounds (1), wherein
Q is selected from among

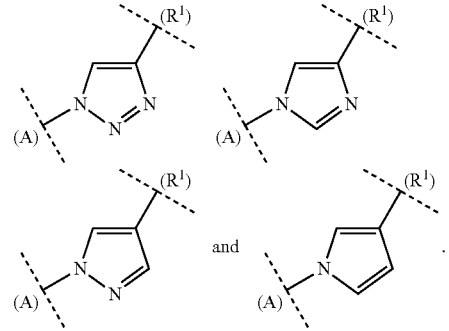

In another aspect (A2) the invention relates to compounds (1), wherein
Q denotes

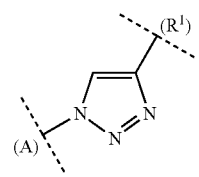

The present invention further relates to compounds of general formula (1)

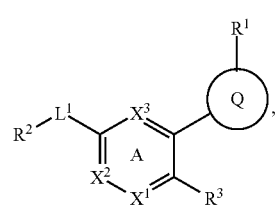

(1)

wherein
R$^1$ is a 5-10 membered heteroaryl optionally substituted by one or more identical or different R$^b$ and/or R$^c$;
R$^2$ is a group optionally substituted by one or more identical or different R$^b$ and/or R$^c$, selected from among C$_{6-10}$aryl and 5-12 membered heteroaryl;
R$^3$ is selected from among hydrogen, —CN, —NO$_2$, —NH$_2$, —NH(C$_{1-4}$alkyl), —N(C$_{1-4}$alkyl)$_2$, C$_{1-4}$alkyl, C$_{1-4}$haloalkyl, C$_{1-4}$alkoxy, C$_{1-4}$haloalkoxy, C$_{3-5}$cycloalkyl and halogen;

$X^1$, $X^2$ and $X^3$ are each selected independently of one another from among nitrogen and $CR^4$,
while at least one and not more than two of the atoms $X^1$, $X^2$ and $X^3$ are nitrogen atoms and each $R^4$ is selected independently of one another from among hydrogen, —CN, —NO$_2$, —NH$_2$, —NH(C$_{1-4}$alkyl), —N(C$_{1-4}$alkyl)$_2$, C$_{1-4}$ alkyl, C$_{1-4}$haloalkyl, C$_{1-4}$alkoxy, C$_{1-4}$haloalkoxy, C$_{3-5}$cycloalkyl and halogen;

Q is a five-membered heteroaromatic group with one to three heteroatoms selected independently of one another from among nitrogen, oxygen and sulphur, optionally substituted by a C$_{1-6}$alkyl,
while the ring A and $R^1$ are arranged in a 1, 3 position with one another in terms of their link to Q and the rings A and Q are linked by a carbon-carbon bond;

$L^1$ is selected from among $(R^2)$—C(O)NH— and $(R^2)$—NHC(O)—;

each $R^b$ is a suitable substituent and is selected independently of one another from among —OR$^c$, —SR$^c$, —NR$^c$R$^c$, —ONR$^c$R$^c$, —N(OR$^c$)R$^c$, —NR$^g$NR$^c$R$^c$, halogen, —CN, —NO$_2$, —N$_3$, —C(O)R$^c$, —C(O)OR$^c$, —C(O)NR$^c$R$^c$, —C(O)NR$^g$NR$^c$R$^c$, —C(O)NR$^g$OR$^c$, —C(NR$^g$)R$^c$, —N=CR$^c$R$^c$, —C(NR$^g$)OR$^c$, —C(NR$^g$)NR$^c$R$^c$, —C(NR$^g$)NR$^g$NR$^c$R$^c$, —C(NOR$^g$)R$^c$, —C(NOR$^g$)NR$^c$R$^c$, —C(NNR$^g$R$^g$)R$^c$, —OS(O)R$^c$, —OS(O)OR$^c$, —OS(O)NR$^c$R$^c$, —OS(O)$_2$R$^c$, —OS(O)$_2$OR$^c$, —OS(O)$_2$NR$^c$R$^c$, —OC(O)R$^c$, —OC(O)OR$^c$, —OC(O)NR$^c$R$^c$, —OC(NR$^g$)R$^c$, —OC(NR$^g$)NR$^c$R$^c$, —ONR$^g$C(O)R$^c$, —S(O)R$^c$, —S(O)OR$^c$, —S(O)NR$^c$R$^c$, —S(O)$_2$R$^c$, —S(O)$_2$OR$^c$, —S(O)$_2$NR$^c$R$^c$, —NR$^g$C(O)R$^c$, —NR$^g$C(O)OR$^c$, —NR$^g$C(O)NR$^c$R$^c$, —NR$^g$C(O)NR$^g$NR$^c$R$^c$, —NR$^g$C(NR$^g$)R$^c$, —N=CR$^c$NR$^c$R$^c$, —NR$^g$C(NR$^g$)OR$^c$, —NR$^g$C(NR$^g$)NR$^c$R$^c$, —NR$^g$C(NOR$^g$)R$^c$, —NR$^g$S(O)R$^c$, —NR$^g$S(O)OR$^c$, —NR$^g$S(O)$_2$R$^c$, —NR$^g$S(O)$_2$OR$^c$, —NR$^g$S(O)$_2$NR$^c$R$^c$, —NR$^g$NR$^g$C(O)R$^c$, —NR$^g$NR$^g$C(O)NR$^c$R$^c$, —NR$^g$NR$^g$C(NR$^g$)R$^c$ and —N(OR$^g$)C(O)R$^c$ and the bivalent substituents =O, =S, =NR$^g$, =NOR$^g$, =NNR$^g$R$^g$ and =NNR$^g$C(O)NR$^g$R$^g$, while these bivalent substituents may only be substituents in non-aromatic ring systems;

each $R^c$ independently of one another denotes hydrogen or a group optionally substituted by one or more identical or different $R^d$ and/or $R^e$, selected from among C$_{1-6}$alkyl, 2-6 membered heteroalkyl, C$_{1-6}$haloalkyl, C$_{3-10}$cycloalkyl, C$_{6-10}$aryl, 5-12 membered heteroaryl and 3-14 membered heterocycloalkyl;

each $R^d$ is a suitable substituent and is selected independently of one another from among —OR$^e$, —SR$^e$, —NR$^e$R$^e$, —ONR$^e$R$^e$, —N(OR$^e$)R$^e$, —N(R$^g$)NR$^e$R$^e$, halogen, —CN, —NO$_2$, —N$_3$, —C(O)R$^e$, —C(O)OR$^e$, —C(O)NR$^e$R$^e$, —C(O)NR$^g$NR$^e$R$^e$, —C(O)NR$^g$OR$^e$, —C(NR$^g$)R$^e$, —N=CR$^e$R$^e$, —C(NR$^g$)OR$^e$, —C(NR$^g$)NR$^e$R$^e$, —C(NR$^g$)NR$^g$NR$^e$R$^e$, —C(NOR$^g$)R$^e$, —C(NOR$^g$)NR$^e$R$^e$, —C(NNR$^g$R$^g$)R$^e$, —OS(O)R$^e$, —OS(O)OR$^e$, —OS(O)NR$^e$R$^e$, —OS(O)$_2$R$^e$, —OS(O)$_2$OR$^e$, —OS(O)$_2$NR$^e$R$^e$, —OC(O)R$^e$, —OC(O)OR$^e$, —OC(O)NR$^e$R$^e$, —OC(NR$^g$)R$^e$, —OC(NR$^g$)NR$^e$R$^e$, —ONR$^g$C(O)R$^e$, —S(O)R$^e$, —S(O)OR$^e$, —S(O)NR$^e$R$^e$, —S(O)$_2$R$^e$, —S(O)$_2$OR$^e$, —S(O)$_2$NR$^e$R$^e$, —NR$^g$C(O)R$^e$, —NR$^g$C(O)OR$^e$, —NR$^g$C(O)NR$^e$R$^e$, —NR$^g$C(O)NR$^g$NR$^e$R$^e$, —NR$^g$C(NR$^g$)R$^e$, —N=CR$^e$NR$^e$R$^e$, —NR$^g$C(NR$^g$)OR$^e$, —NR$^g$C(NR$^g$)NR$^e$R$^e$, —NR$^g$C(NR$^g$)SR$^e$, —NR$^g$C(NOR$^g$)R$^e$, —NR$^g$S(O)R$^e$, —NR$^g$S(O)OR$^e$, —NR$^g$S(O)$_2$R$^e$, —NR$^g$S(O)$_2$OR$^e$, —NR$^g$S(O)$_2$NR$^e$R$^e$, —NR$^g$NR$^g$C(O)R$^e$, —NR$^g$NR$^g$C(O)NR$^e$R$^e$, —NR$^g$NR$^g$C(NR$^g$)R$^e$ and —N(OR$^g$)C(O)R$^e$ and the bivalent substituents =O, =S, =NR$^g$, =NOR$^g$, =NNR$^g$R$^g$ and =NNR$^g$C(O)NR$^g$R$^g$, while these bivalent substituents may only be substituents in non-aromatic ring systems;

each $R^e$ independently of one another denotes hydrogen or a group optionally substituted by one or more identical or different $R^f$ and/or $R^g$, selected from among C$_{1-6}$alkyl, 2-6 membered heteroalkyl, C$_{1-6}$haloalkyl, C$_{3-10}$cycloalkyl, C$_{6-10}$aryl, 5-12 membered heteroaryl and 3-14 membered heterocycloalkyl;

each $R^f$ is a suitable substituent and is selected independently of one another from among —OR$^g$, —SR$^g$, —NR$^g$R$^g$, —ONR$^g$R$^g$, —N(OR$^g$)R$^g$, —N(R$^h$)NR$^g$R$^g$, halogen, —CN, —NO$_2$, —N$_3$, —C(O)R$^g$, —C(O)OR$^g$, —C(O)NR$^g$R$^g$, —C(O)NR$^h$NR$^g$R$^g$, —C(O)NR$^h$OR$^g$, —C(NR$^h$)R$^g$, —N=CR$^g$R$^g$, —C(NR$^h$)OR$^g$, —C(NR$^h$)NR$^g$R$^g$, —C(NR$^h$)NR$^h$NR$^g$R$^g$, —C(NOR$^h$)R$^g$, —C(NOR$^h$)NR$^g$R$^g$, —C(NNR$^h$R$^h$)R$^g$, —OS(O)R$^g$, —OS(O)OR$^g$, —OS(O)NR$^g$R$^g$, —OS(O)$_2$R$^g$, —OS(O)$_2$OR$^g$, —OS(O)$_2$NR$^g$R$^g$, —OC(O)R$^g$, —OC(O)OR$^g$, —OC(O)NR$^g$R$^g$, —OC(NR$^h$)R$^g$, —OC(NR$^h$)NR$^g$R$^g$, —ONR$^h$C(O)R$^g$, —S(O)R$^g$, —S(O)OR$^g$, —S(O)NR$^g$R$^g$, —S(O)$_2$R$^g$, —S(O)$_2$OR$^g$, —S(O)$_2$NR$^g$R$^g$, —NR$^h$C(O)R$^g$, —NR$^h$C(O)OR$^g$, —NR$^h$C(O)NR$^g$R$^g$, —NR$^h$C(O)NR$^h$NR$^g$R$^g$, —NR$^h$C(NR$^h$)R$^g$, —N=CR$^g$NR$^g$R$^g$, —NR$^h$C(NR$^h$)OR$^g$, —NR$^h$C(NR$^h$)NR$^g$R$^g$, —NR$^h$C(NOR$^h$)R$^g$, —NR$^h$S(O)R$^g$, —NR$^h$S(O)OR$^g$, —NR$^h$S(O)$_2$R$^g$, —NR$^h$S(O)$_2$OR$^g$, —NR$^h$S(O)$_2$NR$^g$R$^g$, —NR$^h$NR$^h$C(O)R$^g$, —NR$^h$NR$^h$C(O)NR$^g$R$^g$, —NR$^h$NR$^h$C(NR$^h$)R$^g$ and —N(OR$^h$)C(O)R$^g$ and the bivalent substituents =O, =S, =NR$^h$, =NOR$^h$, =NNR$^h$R$^h$ and =NNR$^h$C(O)NR$^h$R$^h$, while these bivalent substituents may only be substituents in non-aromatic ring systems;

each $R^g$ independently of one another denotes hydrogen or a group optionally substituted by one or more identical or different $R^h$, selected from among C$_{1-6}$alkyl, 2-6 membered heteroalkyl, C$_{1-6}$haloalkyl, C$_{3-10}$cycloalkyl, C$_{6-10}$aryl, 5-12 membered heteroaryl and 3-14 membered heterocycloalkyl;

each $R^h$ is selected independently of one another from among hydrogen, C$_{1-6}$alkyl, 2-6 membered heteroalkyl, C$_{1-6}$haloalkyl, C$_{3-10}$cycloalkyl, C$_{6-10}$aryl, 5-12 membered heteroaryl and 3-14 membered heterocycloalkyl;

while the compounds (1) may optionally also be present in the form of their tautomers, racemates, enantiomers, diastereomers and mixtures thereof, or also as pharmacologically acceptable salts of all the above-mentioned forms.

In another aspect (A3) the invention relates to compounds (1), wherein
Q is a nitrogen-containing heteroaromatic group optionally substituted by a C$_{1-6}$alkyl.

In another aspect (A4) the invention relates to compounds (1), wherein
Q is a triazole, pyrrole, pyrazole, imidazole, thiazole, oxazole, isoxazole or oxadiazole optionally substituted by a C$_{1-6}$alkyl.

In another aspect (A5) the invention relates to compounds (1), wherein
Q is selected from among

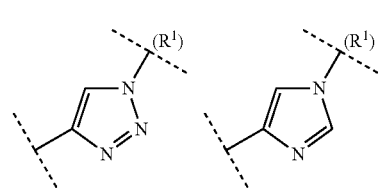

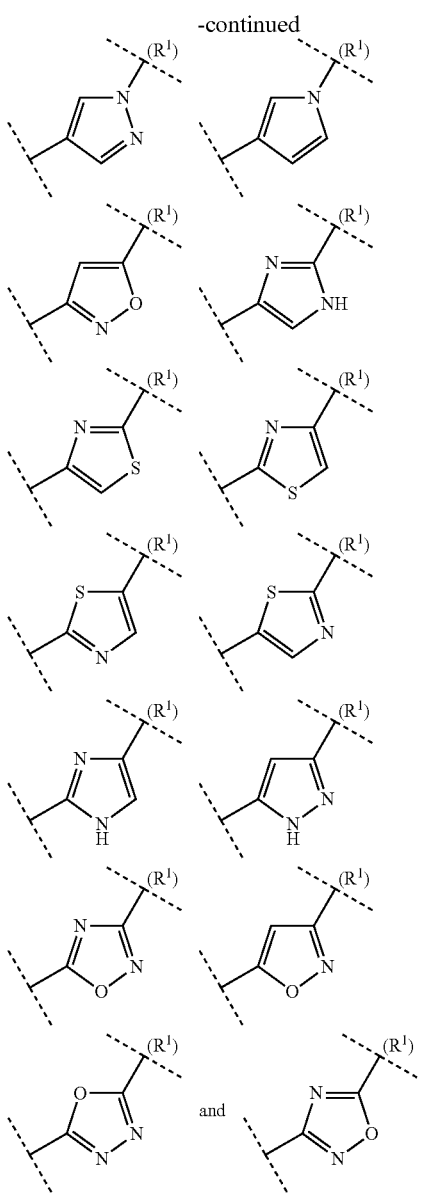

In another aspect (A6) the invention relates to compounds (1), wherein
Q denotes

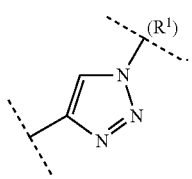

In another aspect (B1) the invention relates to compounds (1), wherein
$R^1$ is a 5- or 6-membered monocyclic or 9 or 10-membered bicyclic heteroaryl optionally substituted by one or more identical or different $R^b$ and/or $R^c$ and
$R^b$ and $R^c$ are as hereinbefore defined.

In another aspect (B2) the invention relates to compounds (1), wherein $R^1$ is a heteroaryl, selected from among pyridyl, pyrazolyl, thiazolyl, pyrimidyl and imidazolyl, optionally substituted by one or more identical or different $R^b$ and/or $R^c$ and
$R^b$ and $R^c$ are as hereinbefore defined.

In another aspect (B3) the invention relates to compounds (1), wherein
$R^1$ is a heteroaryl, optionally substituted by one or more identical or different $R^b$ and/or $R^c$, with the partial structure (i)

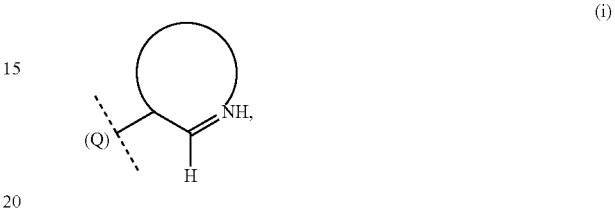

(i)

wherein the ring that binds directly to Q is heteroaromatic, and
$R^b$ and $R^c$ are as hereinbefore defined.

In another aspect (B4) the invention relates to compounds (1), wherein
$R^1$ is a heteroaryl which is substituted by one or more identical or different $R^{b2}$ and/or $R^{c2}$;
each $R^{b2}$ is a suitable substituent and is selected independently of one another from among halogen, $-OR^{c2}$, $-NR^{c2}R^{c2}$, $-SR^{c2}$, $-C(O)R^{c2}$, $-S(O)_2R^{c2}$, $-S(O)R^{c2}$, $-C(O)OR^{c2}$, $-NHC(O)R^{c2}$, $-C(O)NR^{c2}R^{c2}$, $-NHC(O)OR^{c2}$, $-CN$, $-NO_2$ and halogen and the bivalent substituent $=O$, while this bivalent substituent may only be a substituent in non-aromatic ring systems;
each $R^{c2}$ independently of one another denotes hydrogen or a group optionally substituted by one or more identical or different $R^{d2}$ and/or $R^{e2}$, selected from among $C_{1-6}$alkyl, $C_{1-6}$haloalkyl, $C_{3-10}$cycloalkyl, $C_{6-10}$aryl, 5-12 membered heteroaryl and 3-14 membered heterocycloalkyl;
each $R^{d2}$ is a suitable substituent and is selected independently of one another from among $-OR^{e2}$, $-NR^{e2}R^{e2}$, halogen and $-C(O)OR^{e2}$;
each $R^{e2}$ independently of one another denotes hydrogen or a group optionally substituted by one or more identical or different $R^{f2}$ and/or $R^{g2}$, selected from among $C_{1-6}$alkyl, $C_{1-6}$haloalkyl, $C_{3-10}$cycloalkyl, $C_{6-10}$aryl and 3-14 membered heterocycloalkyl;
each $R^{f2}$ is a suitable substituent and is selected independently of one another from among $-OR^{g2}$, $-CN$, $-C(O)NR^{g2}R^{g2}$ and halogen;
each $R^{g2}$ is selected independently of one another from among hydrogen, $C_{1-6}$alkyl, $C_{3-10}$cycloalkyl and $C_{6-10}$aryl.

In another aspect (B5) the invention relates to compounds (1), wherein
$R^1$ is a heteroaryl which carries at least one substituent different from hydrogen.

In another aspect (B6) the invention relates to compounds (1), wherein
$R^1$ is a heteroaryl which carries at least one nitrogen-containing substituent.

In another aspect (B7) the invention relates to compounds (1), wherein

R¹ is

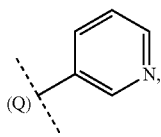

optionally substituted by one or more identical or different $R^b$ and/or $R^c$, wherein $R^b$ and $R^c$ are as hereinbefore defined.

In another aspect (B8) the invention relates to compounds (1), wherein
R¹ is

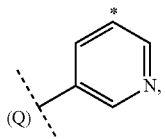

substituted by one $R^b$ or $R^c$ in position 5 (*), wherein $R^b$ and $R^c$ are as hereinbefore defined.

In another aspect (B9) the invention relates to compounds (1), wherein
R¹ denotes

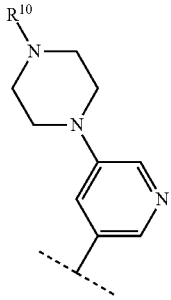 or 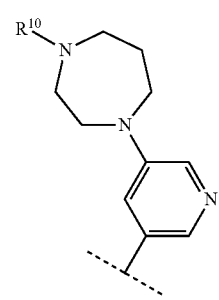

and
$R^{10}$ is selected from among hydrogen, $C_{1-6}$alkyl, $C_{1-6}$haloalkyl and $C_{3-6}$cycloalkyl,
while the above-mentioned groups, wherever possible, may optionally be substituted by one or more identical or different substituents, selected from among —OH, —$OC_{1-6}$alkyl, —$C_{1-6}$haloalkyl, —$OC_{3-6}$cycloalkyl, $C_{3-6}$cycloalkyl, —CN, —$C(O)NH_2$, —$C(O)NH(C_{1-6}$alkyl) and —$C(O)N(C_{1-6}$alkyl$)_2$.

In another aspect (B10) the invention relates to compounds (1), wherein
R¹ denotes

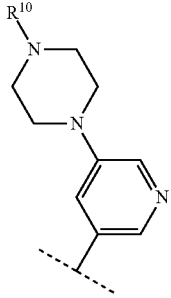 or 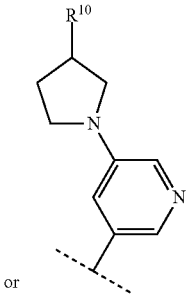

and
$R^{10}$ is selected from among hydrogen, $C_{1-6}$alkyl, $C_{1-6}$haloalkyl, 3-6 membered heterocycloalkyl, —$NH_2$, —NH($C_{1-6}$Alkyl), —$N(C_{1-6}$Alkyl$)_2$ and $C_{3-6}$cycloalkyl,
while the above-mentioned groups, wherever possible, may optionally be substituted by one or more identical or different substituents, selected from among —OH, —$OC_{1-6}$alkyl, —$C_{1-6}$haloalkyl, —$OC_{3-6}$cycloalkyl, $C_{3-6}$cycloalkyl, —CN, —$C(O)NH_2$, —$C(O)NH(C_{1-6}$alkyl) and —$C(O)N(C_{1-6}$alkyl$)_2$.

In another aspect (B11) the invention relates to compounds (1), wherein
R¹ denotes

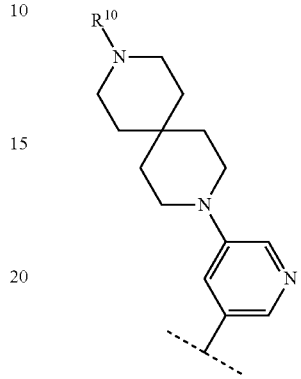

and
$R^{10}$ is selected from among hydrogen, $C_{1-6}$alkyl, $C_{1-6}$haloalkyl and $C_{3-6}$cycloalkyl,
while the above-mentioned groups, wherever possible, may optionally be substituted by one or more identical or different substituents, selected from among —OH, —$OC_{1-6}$alkyl, —$C_{1-6}$haloalkyl, —$OC_{3-6}$cycloalkyl, $C_{3-6}$cycloalkyl, —CN, —$C(O)NH_2$, —$C(O)NH(C_{1-6}$alkyl) and —$C(O)N(C_{1-6}$alkyl$)_2$.

In another aspect (B12) the invention relates to compounds (1), wherein
R¹ denotes

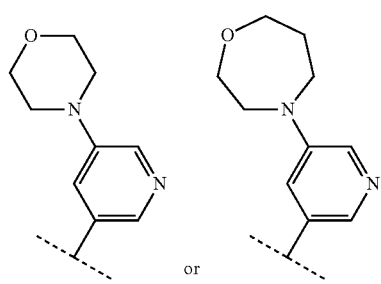

In another aspect (B13) the invention relates to compounds (1), wherein

R¹ denotes

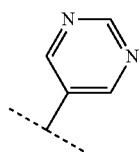

In another aspect (B14) the invention relates to compounds (1), wherein
R¹ denotes
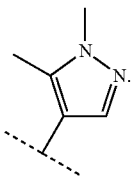
In another aspect (B15) the invention relates to compounds (1), wherein
R¹ is selected from among
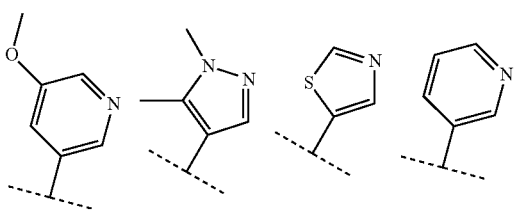
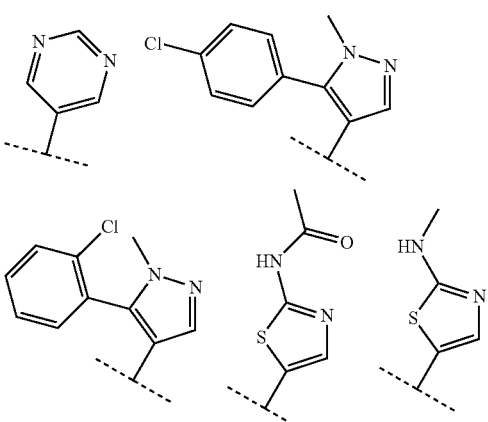
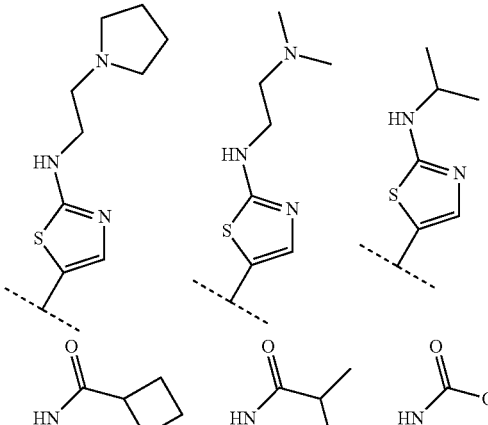
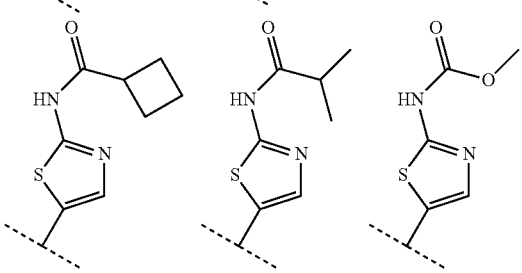
-continued
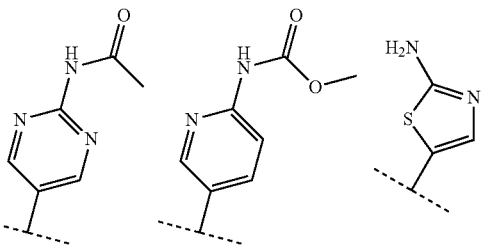
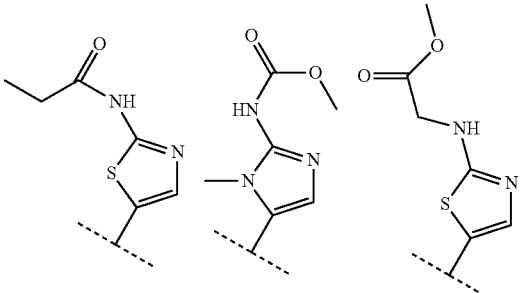
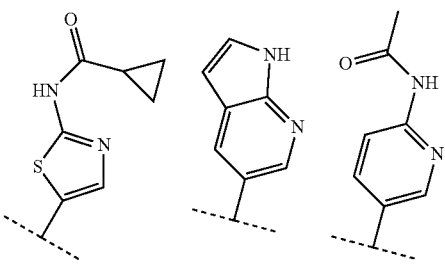
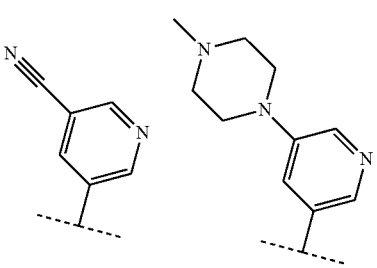
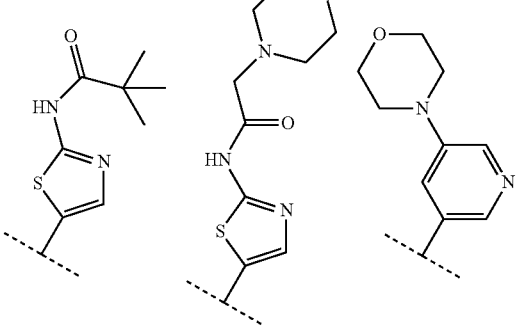

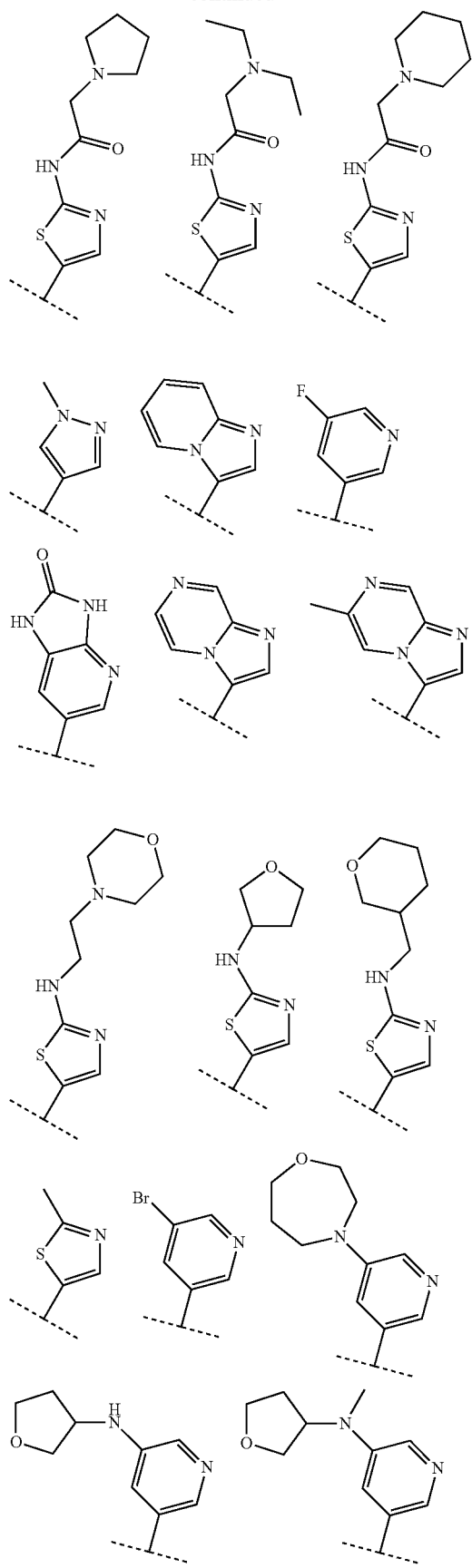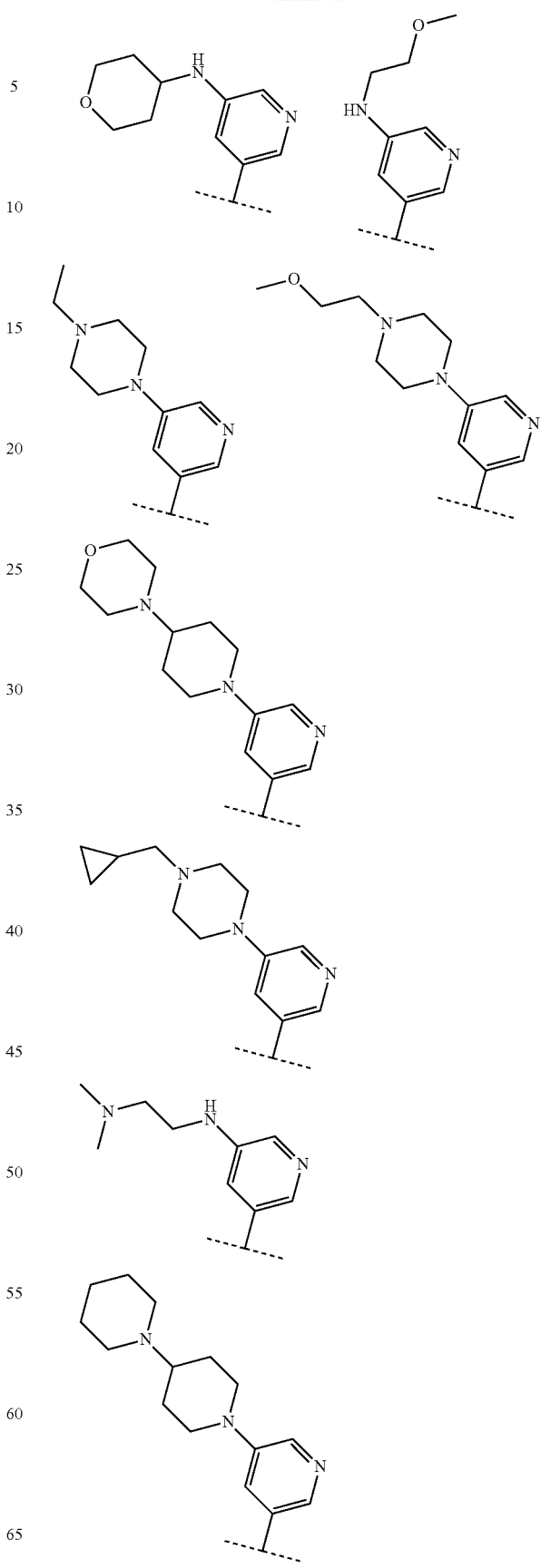

-continued
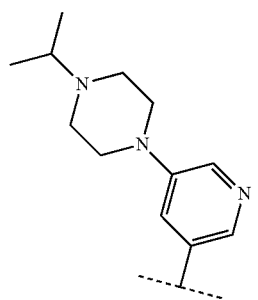
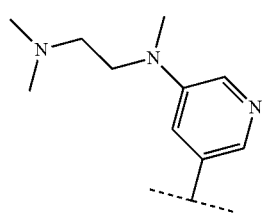
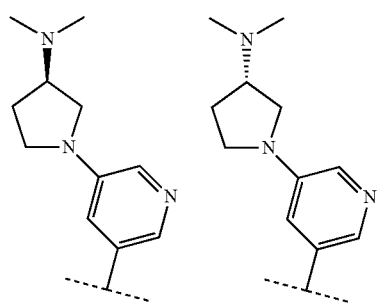
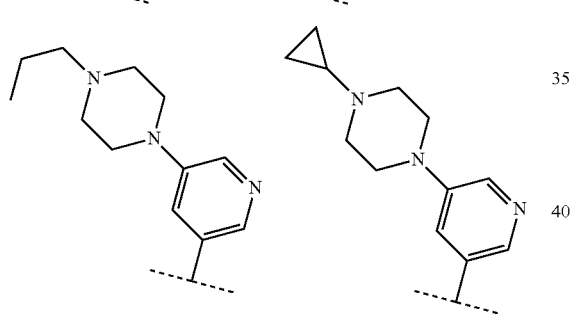
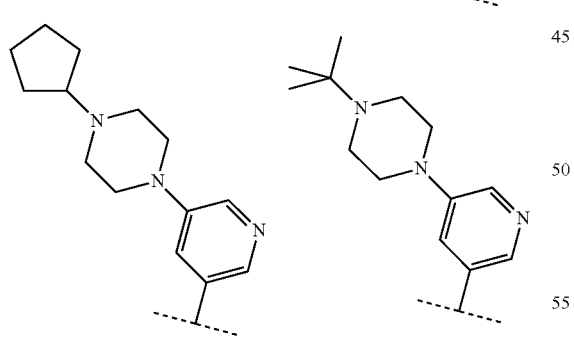
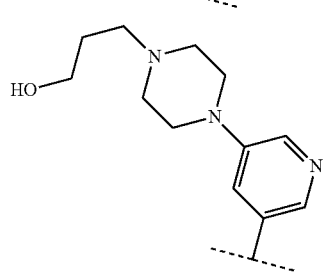
-continued
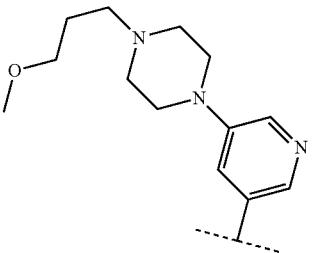
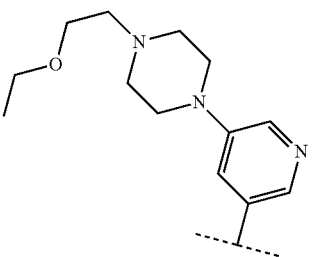
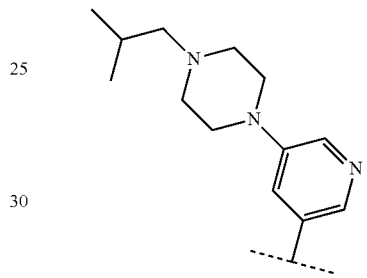
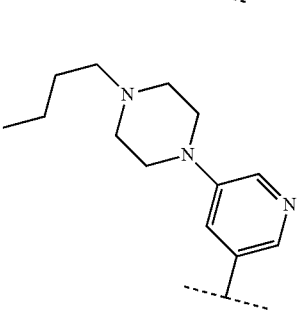
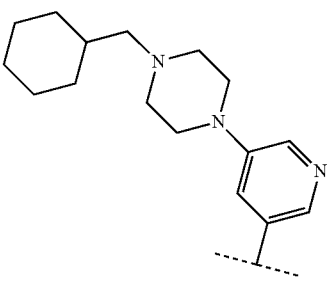
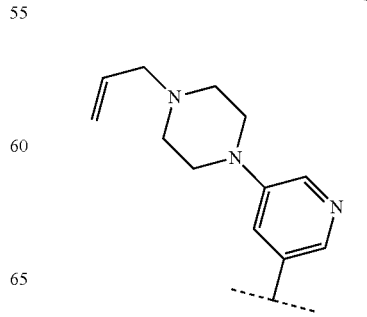

-continued
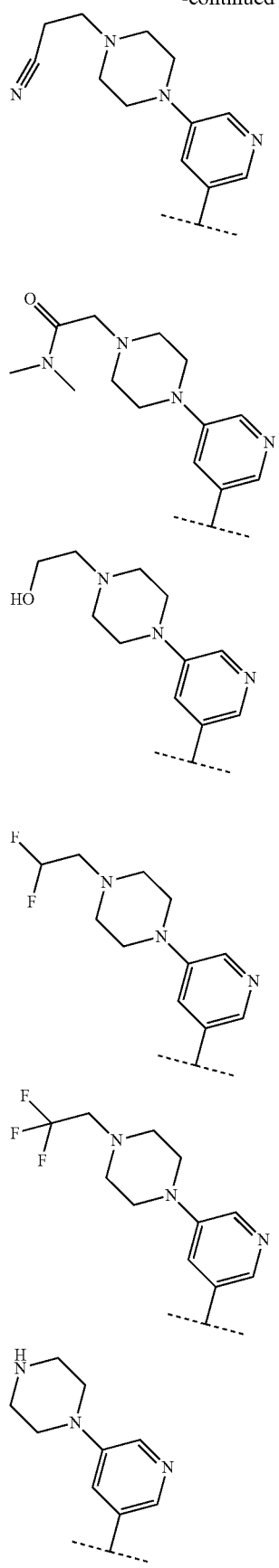
-continued
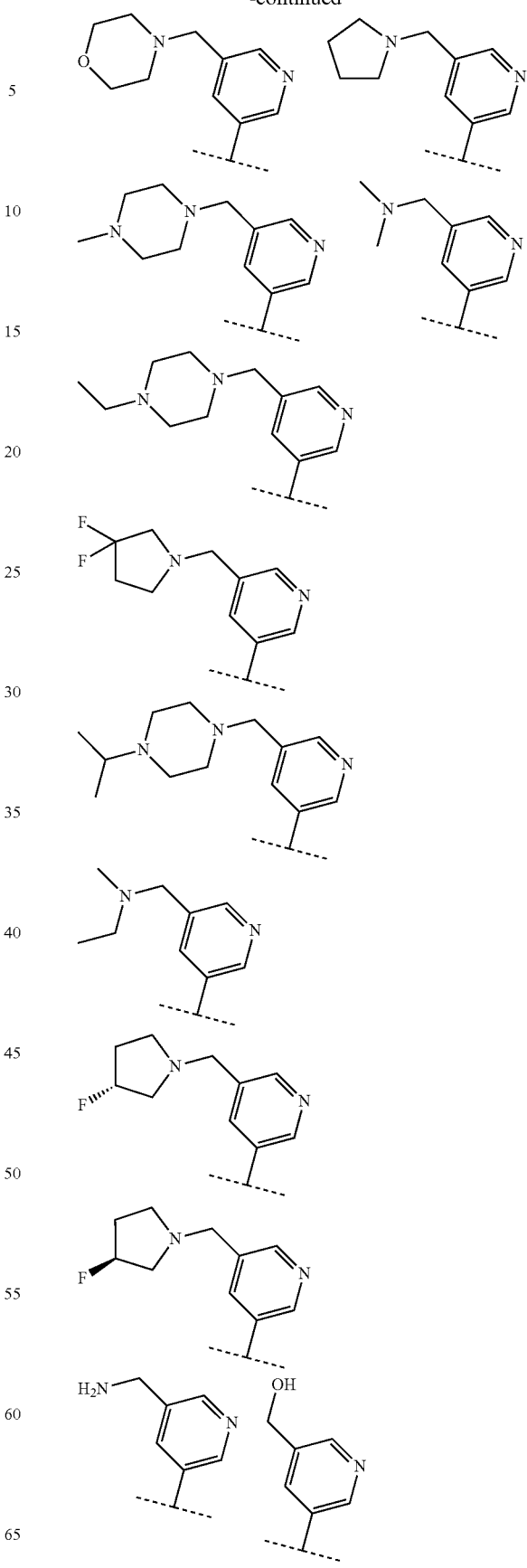

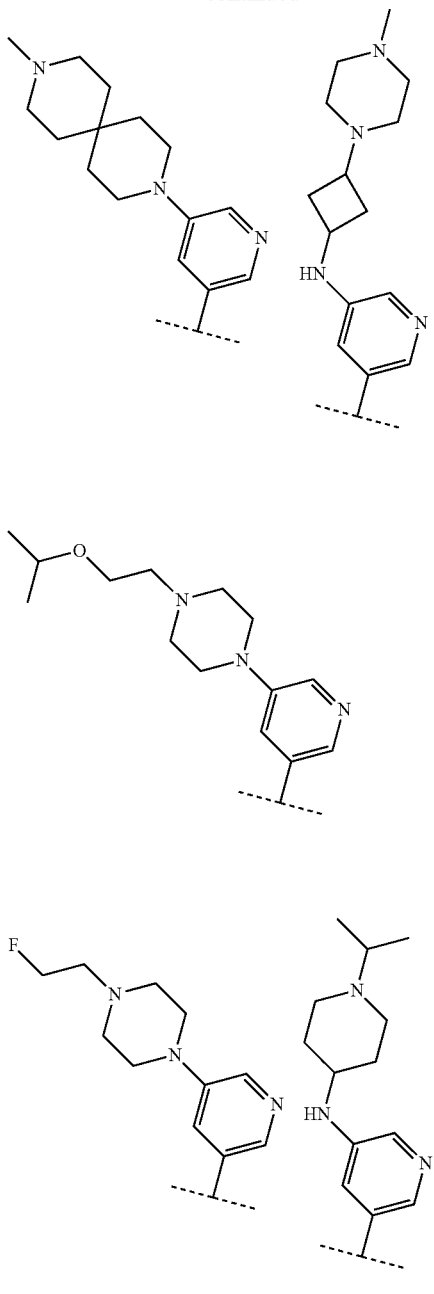
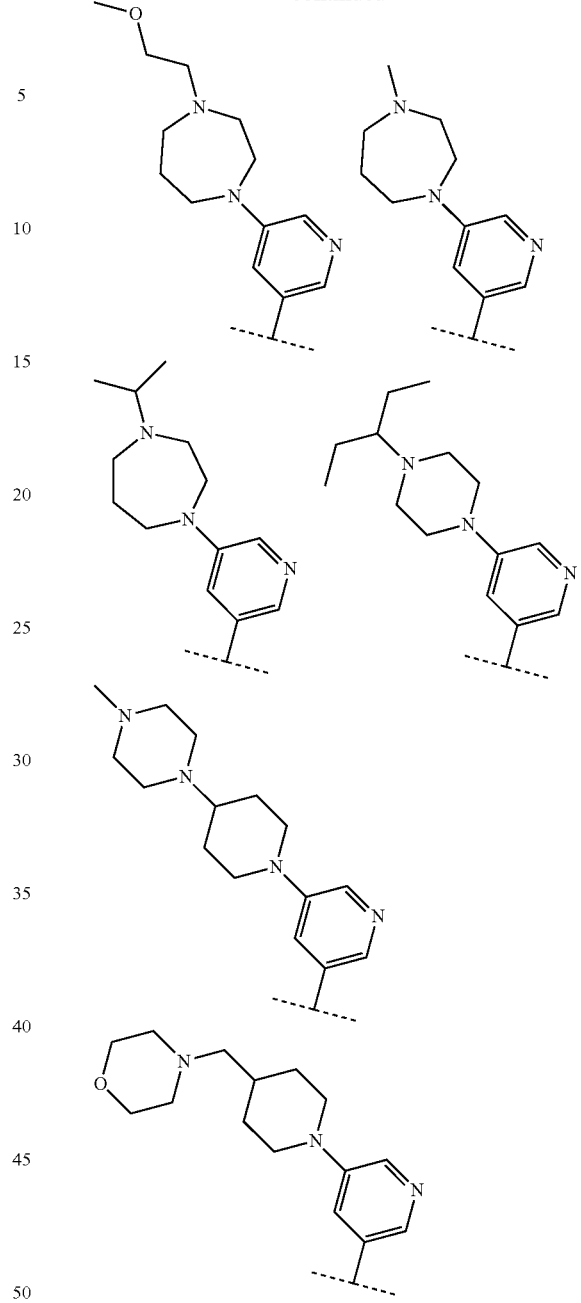
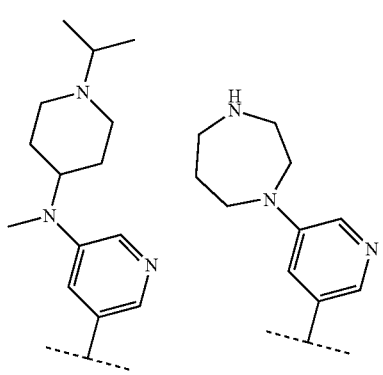

In another aspect (C1) the invention relates to compounds (1), wherein $R^3$ denotes fluorine, chlorine, bromine or methyl.

In another aspect (D1) the invention relates to compounds (1), wherein $X^1$ denotes nitrogen, $X^2$ denotes $CR^{4-1}$ and $X^3$ denotes $CR^{4-2}$ and $R^{4-1}$ and $R^{4-2}$ are each independently selected from among hydrogen, fluorine, chlorine and methyl and at least one of the groups $R^{4-1}$ and $R^{4-2}$ denotes hydrogen.

In another aspect (D2) the invention relates to compounds (1), wherein $X^1$ denotes nitrogen, $X^2$ denotes CH and $X^3$ denotes CH.

In another aspect (E1) the invention relates to compounds (1), wherein
$R^2$ is a group optionally substituted by one or more identical or different $R^b$ and/or $R^c$, selected from among phenyl and 5-6 membered heteroaryl,
and $R^b$ and $R^c$ are as hereinbefore defined.

In another aspect (E2) the invention relates to compounds (1), wherein
$R^2$ is a 5-6 membered heteroaryl optionally substituted by one or more identical or different $R^b$ and/or $R^c$
and $R^b$ and $R^c$ are as hereinbefore defined.

In another aspect (E3) the invention relates to compounds (1), wherein
$R^2$ is isoxazolyl optionally substituted by one or more identical or different $R^b$ and/or $R^c$
and $R^b$ and $R^c$ are as hereinbefore defined.

In another aspect (E4) the invention relates to compounds (1), wherein
$R^2$ is pyridyl optionally substituted by one or more identical or different $R^b$ and/or $R^c$
and $R^b$ and $R^c$ are as hereinbefore defined.

In another aspect (E5) the invention relates to compounds (1), wherein
$R^2$ is

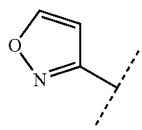

optionally substituted by one or more identical or different $R^b$ and/or $R^c$
and $R^b$ and $R^c$ are as hereinbefore defined.

In another aspect (E6) the invention relates to compounds (1), wherein
$R^2$ is

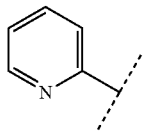

optionally substituted by one or more identical or different $R^b$ and/or $R^c$ and $R^b$ and $R^c$ are as hereinbefore defined.

In another aspect (E7) the invention relates to compounds (1), wherein
$R^2$ is

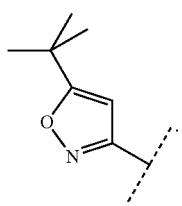

In another aspect (E8) the invention relates to compounds (1), wherein
$R^2$ is

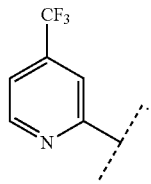

In another aspect (E9) the invention relates to compounds (1), wherein
$R^2$ is a heteroaryl which is selected from among furyl, thienyl, pyrrolyl, oxazolyl, thiazolyl, triazolyl, isoxazolyl, isothiazolyl, pyrazolyl, imidazolyl, oxadiazolyl, thiadiazolyl, pyridyl and pyrimidyl, and is optionally substituted by one or two substituents, each independently selected from among $C_{3-7}$cycloalkyl, phenyl, 4-7 membered heterocycloalkyl, methyl, ethyl, n-propyl, isopropyl, n-butyl, 1-methylpropyl, isobutyl, sec.-butyl, tert.-butyl, n-pentyl, 1-methylbutyl, 1-ethylpropyl, isopentyl, neopentyl, trifluoromethyl, difluoromethyl, fluoromethyl, tert.-butoxy, trifluoromethoxy,

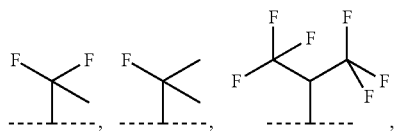

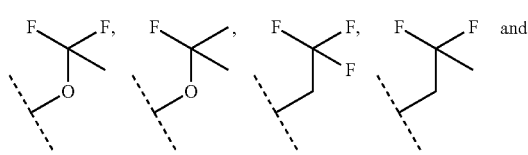

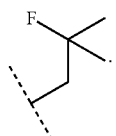

In another aspect (E10) the invention relates to compounds (1), wherein
$R^2$ is a phenyl optionally substituted by one or more identical or different $R^b$ and/or $R^c$ and $R^b$ and $R^c$ are as hereinbefore defined.

In another aspect (E11) the invention relates to compounds (1), wherein
$R^2$ denotes a phenyl

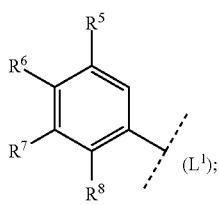

R⁵ is selected from among hydrogen, $C_{1-6}$alkyl, —$OC_{1-6}$alkyl, $C_{1-6}$haloalkyl, —$OC_{1-6}$haloalkyl, $C_{3-7}$cycloalkyl and 3-7 membered heterocycloalkyl, all the above-mentioned groups optionally being substituted by $C_{1-6}$alkyl, —CN or —OH;

R⁶ is selected from among hydrogen, $C_{1-6}$alkyl, —$OC_{1-6}$alkyl, $C_{1-6}$haloalkyl, —$OC_{1-6}$haloalkyl, —CN, —OH, halogen, —$NHC_{1-6}$alkyl and —$N(C_{1-6}$alkyl$)_2$, the latter two optionally being substituted in the alkyl part by a substituent —$N(C_{1-6}$alkyl$)_2$;

R⁷ is selected from among hydrogen, —$OC_{1-6}$alkyl, halogen, —$NHS(O)_2C_{1-6}$alkyl, —$S(O)_2NH_2$, —$S(O)_2NHC_{1-6}$alkyl, —$S(O)_2N(C_{1-6}$alkyl$)_2$,

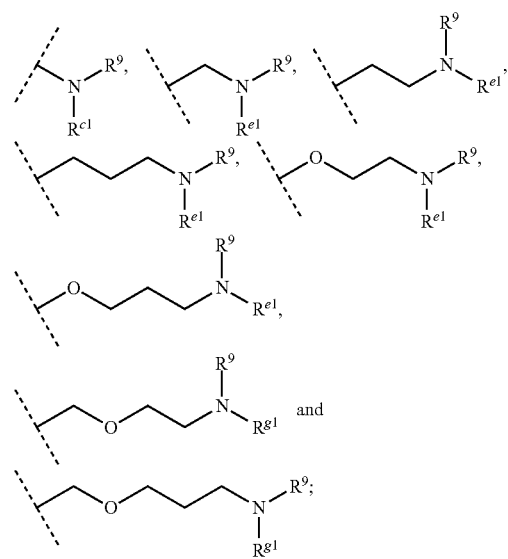

R⁹ is selected from among hydrogen and $C_{1-6}$alkyl;

$R^{c1}$ is hydrogen or a group optionally substituted by one or more identical or different $R^{d1}$ and/or $R^{e1}$, selected from among $C_{1-6}$alkyl and 3-14 membered heterocycloalkyl;

each $R^{d1}$ is a suitable substituent and is selected independently of one another from among —$OR^{e1}$, —$NR^{e1}R^{e1}$ and halogen;

each $R^{e1}$ independently of one another denotes hydrogen or a group optionally substituted by one or more identical or different $R^{f1}$ and/or $R^{g1}$, selected from among $C_{1-6}$alkyl, $C_{1-6}$haloalkyl, $C_{3-10}$cycloalkyl, $C_{6-10}$aryl, 5-12 membered heteroaryl and 3-14 membered heterocycloalkyl;

each $R^{f1}$ is a suitable substituent and is selected independently of one another from among —$OR^{g1}$, —$NR^{g1}R^{g1}$ and halogen and the bivalent substituent =O, which may only be a substituent in non-aromatic ring systems;

each $R^{g1}$ independently of one another denotes hydrogen or a group optionally substituted by one or more identical or different $R^{h1}$, selected from among $C_{1-6}$alkyl, $C_{3-10}$cycloalkyl, 5-12 membered heteroaryl and 3-14 membered heterocycloalkyl;

each $R^{h1}$ is selected independently of one another from among $C_{1-6}$alkyl and the bivalent substituent =O, which may only be a substituent in non-aromatic ring systems;

or the group —$NR^9R^{c1}$ denotes a nitrogen-containing, 3-14 membered heterocycloalkyl or 5-12 membered heteroaryl, optionally substituted by one or more identical or different group(s) selected from among $R^{d1}$ and $R^{e1}$;

the group —$NR^9R^{e1}$ denotes a nitrogen-containing, 3-14 membered heterocycloalkyl or 5-12 membered heteroaryl, optionally substituted by one or more, identical or different group(s) selected from among $R^{f1}$ and $R^{g1}$;

the group —$NR^9R^{g1}$ denotes a nitrogen-containing, 3-14 membered heterocycloalkyl or 5-12 membered heteroaryl, optionally substituted by one or more identical or different group(s) $R^{h1}$;

R⁸ is selected from among hydrogen, $C_{1-6}$alkyl, —$OC_{1-6}$alkyl, —CN, halogen, 5-12 membered heteroaryl and 3-14 membered heterocycloalkyl.

In another aspect (E12) the invention relates to compounds (1) with the structural aspect E11, wherein at least one of the groups R⁵ to R⁸ is not hydrogen.

In another aspect (E13) the invention relates to compounds (1) with the structural aspect E11, wherein R⁵ is selected from among

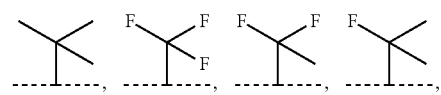

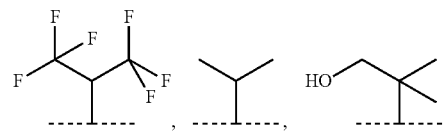

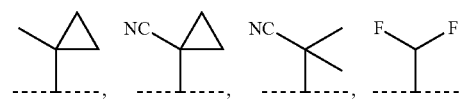

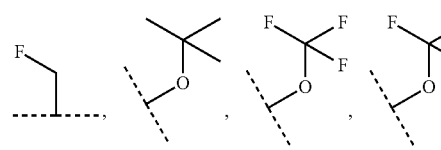

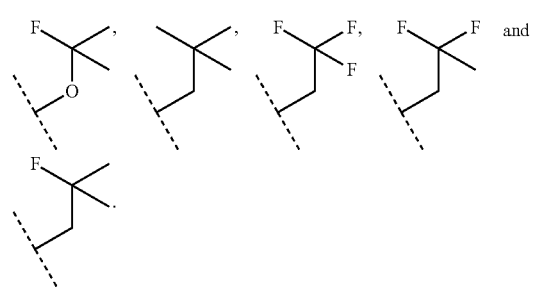

In another aspect (E14) the invention relates to compounds (1), wherein
R² is selected from among
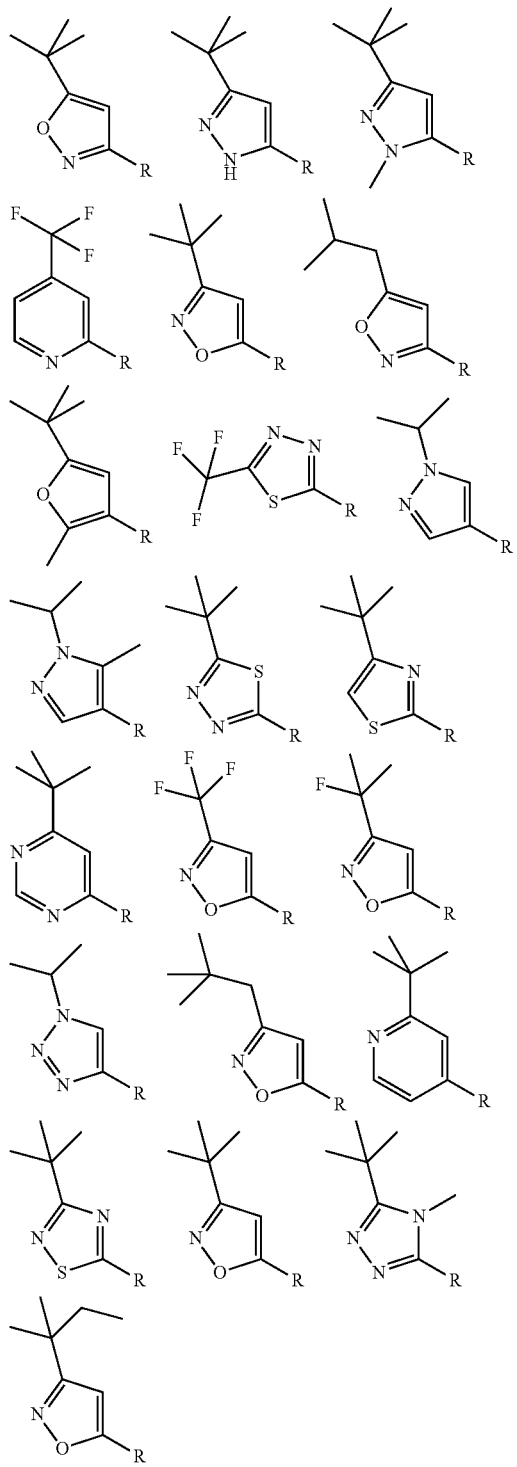
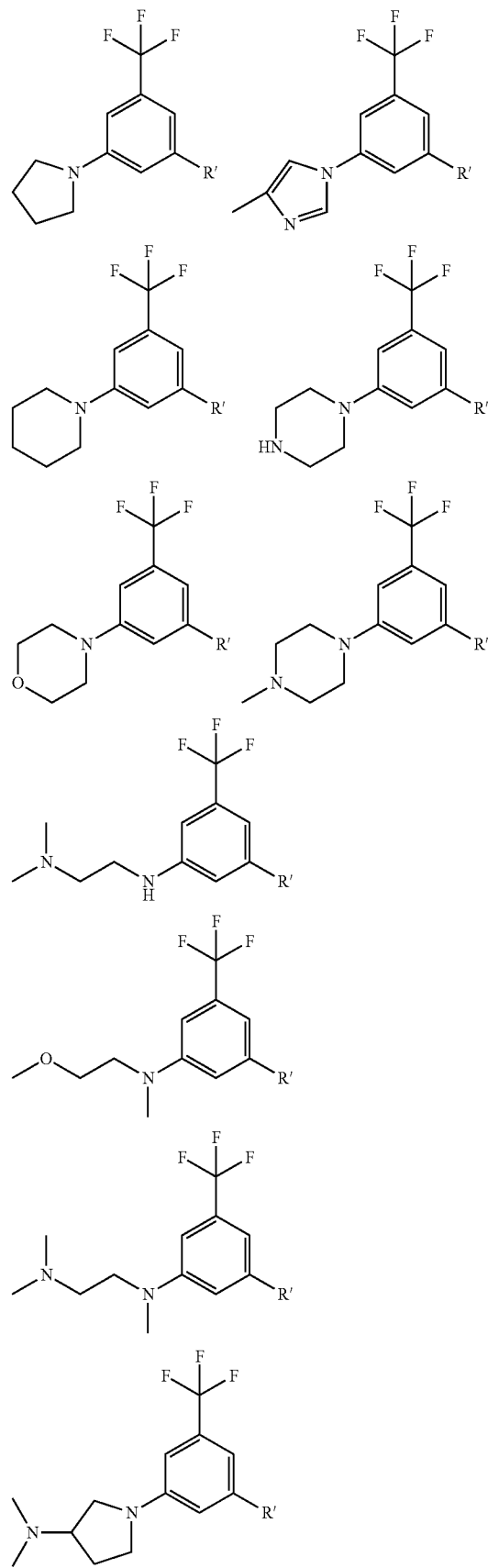
and R' denotes the binding site to the linker unit L¹.
In another aspect (E15) the invention relates to compounds (1), wherein
R² is selected from among

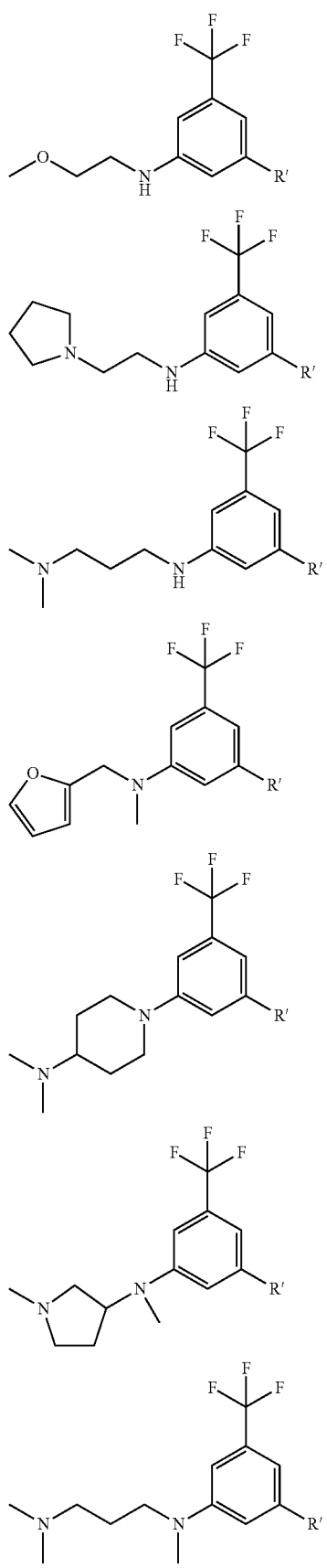
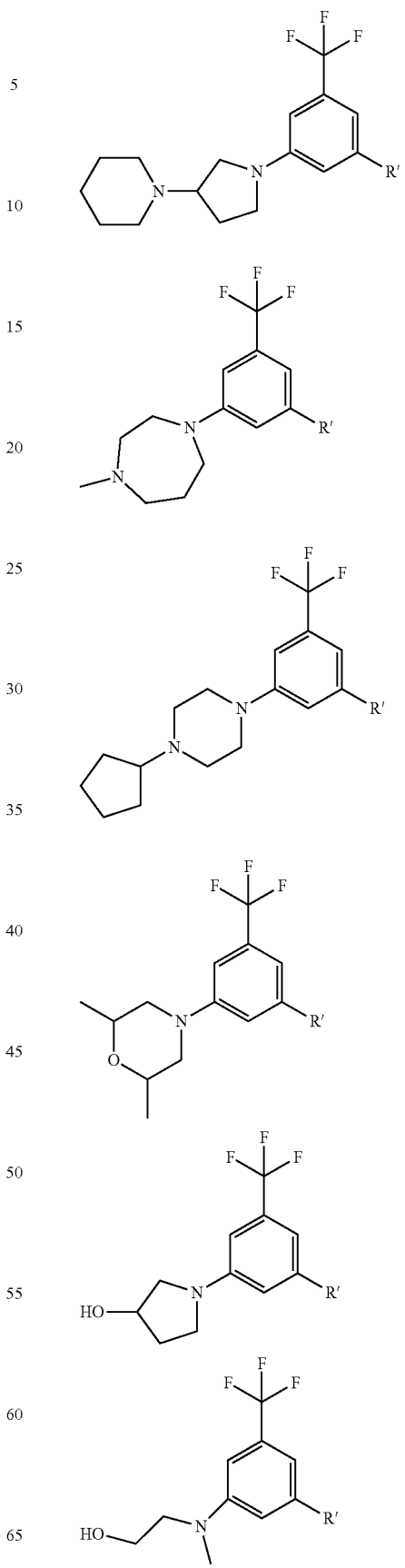

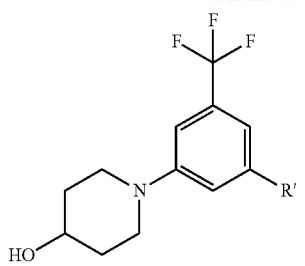
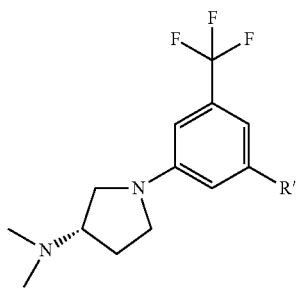
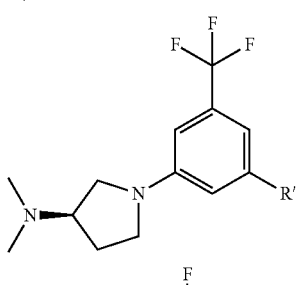
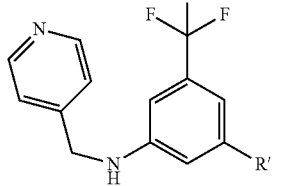
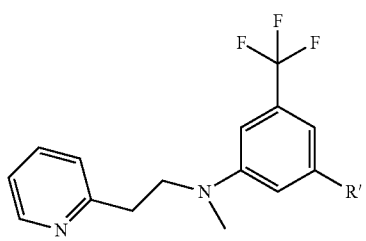
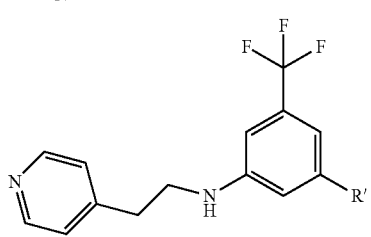
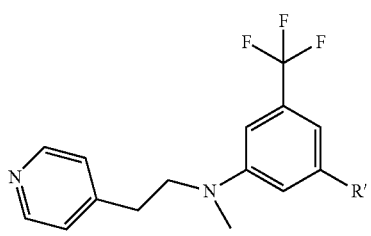
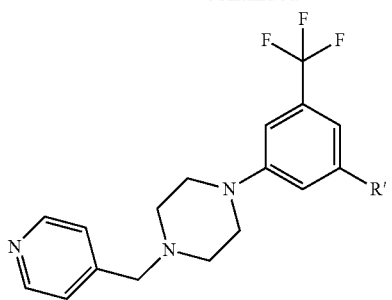
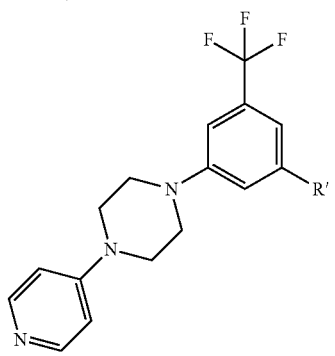
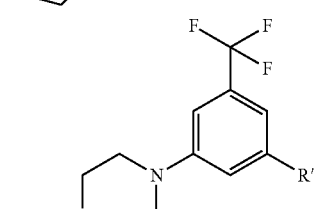
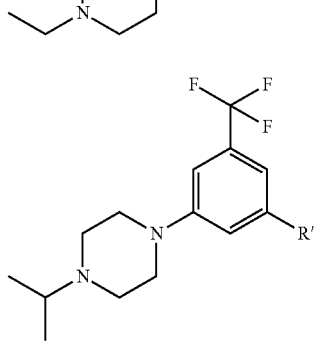
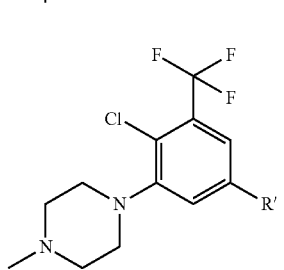
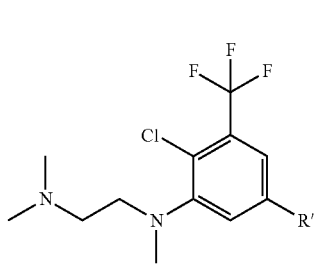

31
-continued
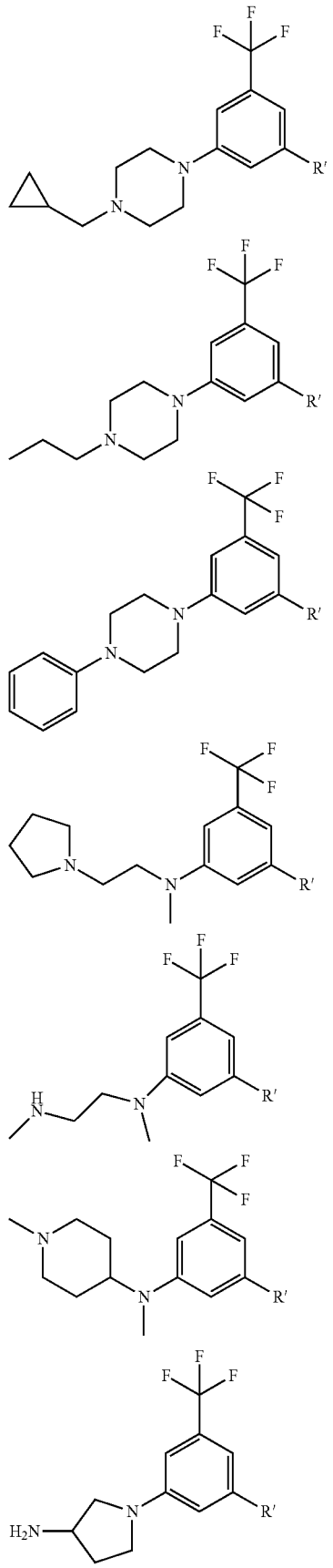
32
-continued
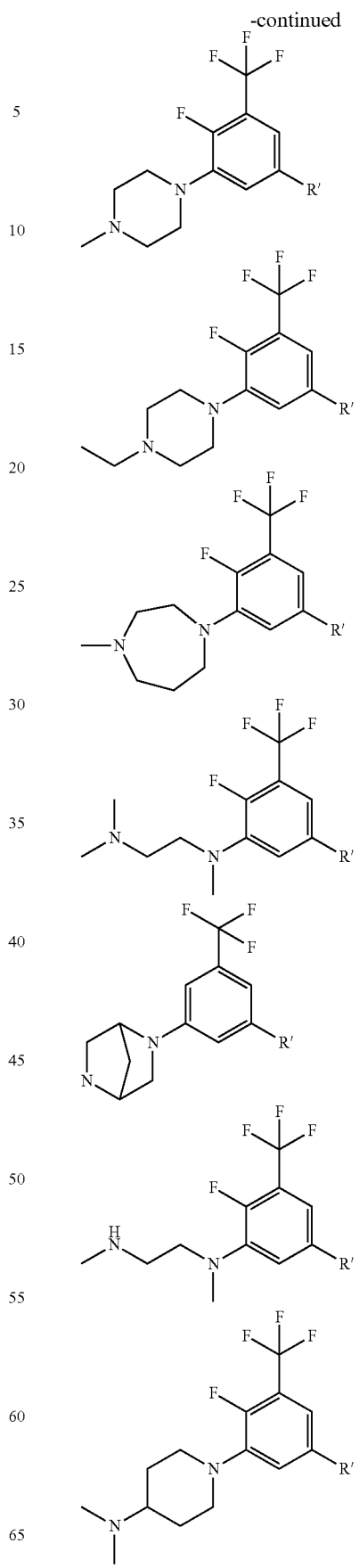

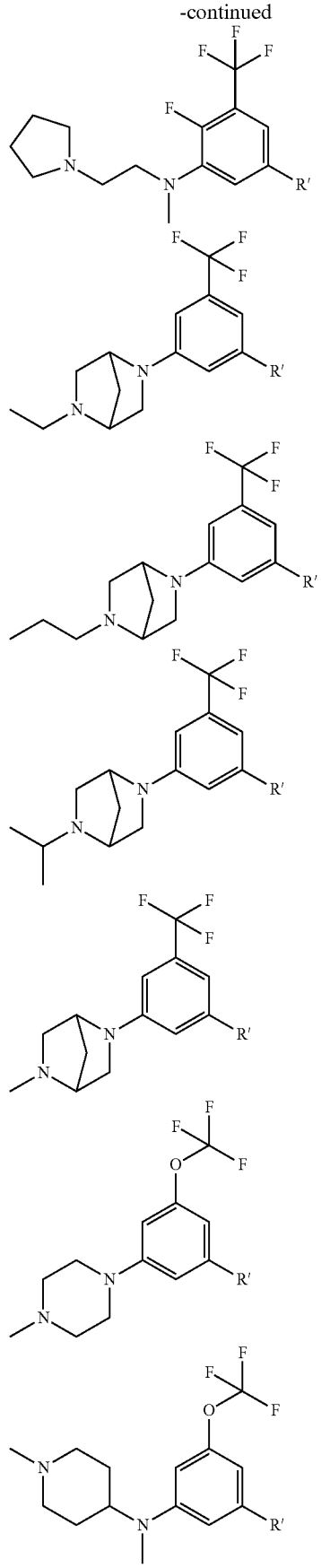
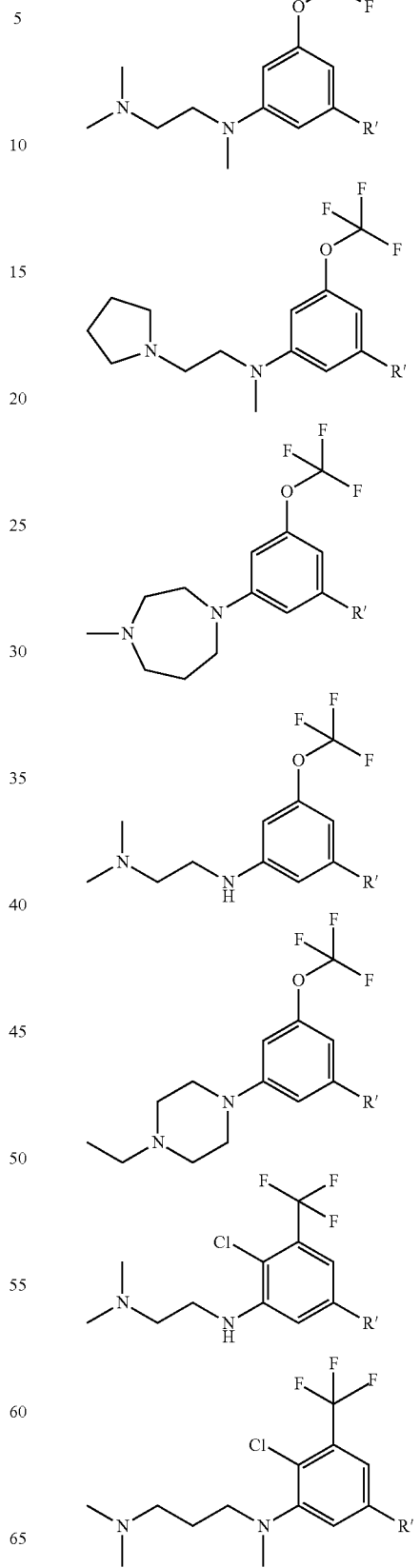

35
-continued
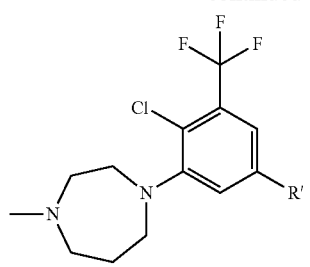
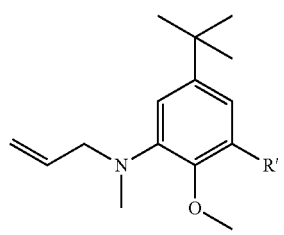
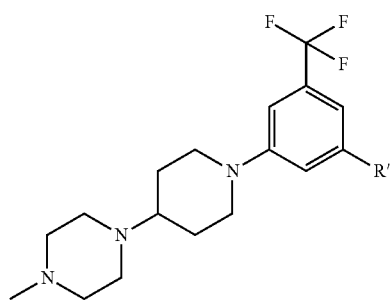
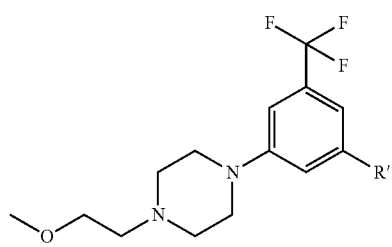
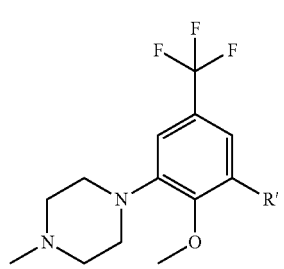
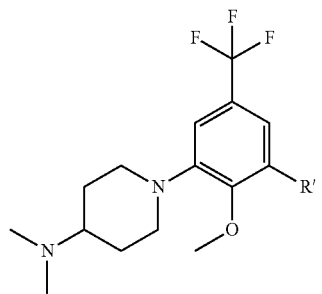
36
-continued
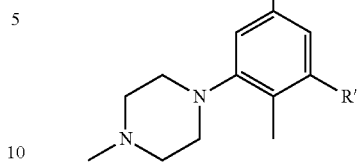
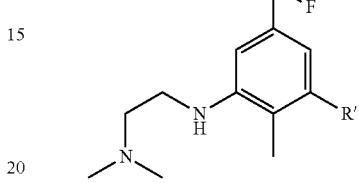
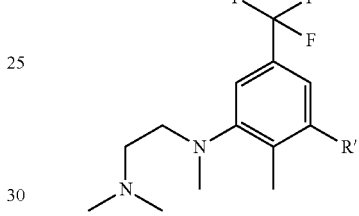
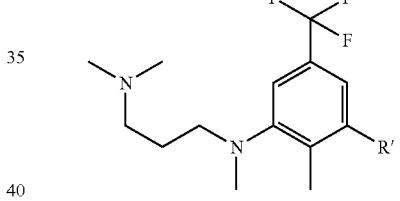
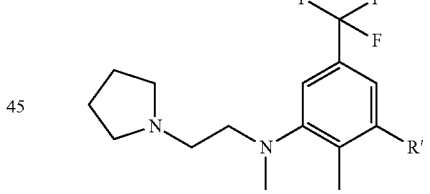
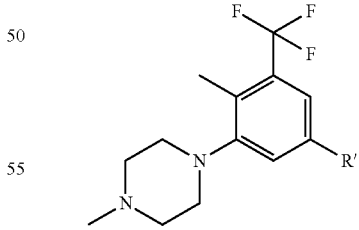
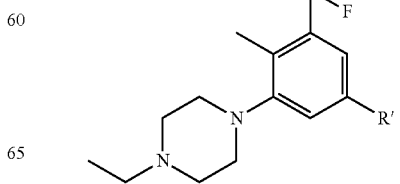

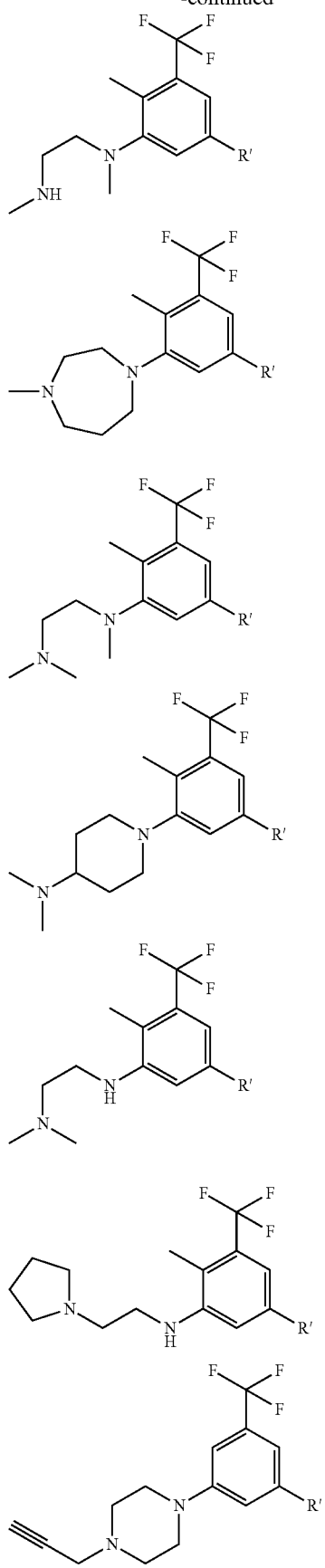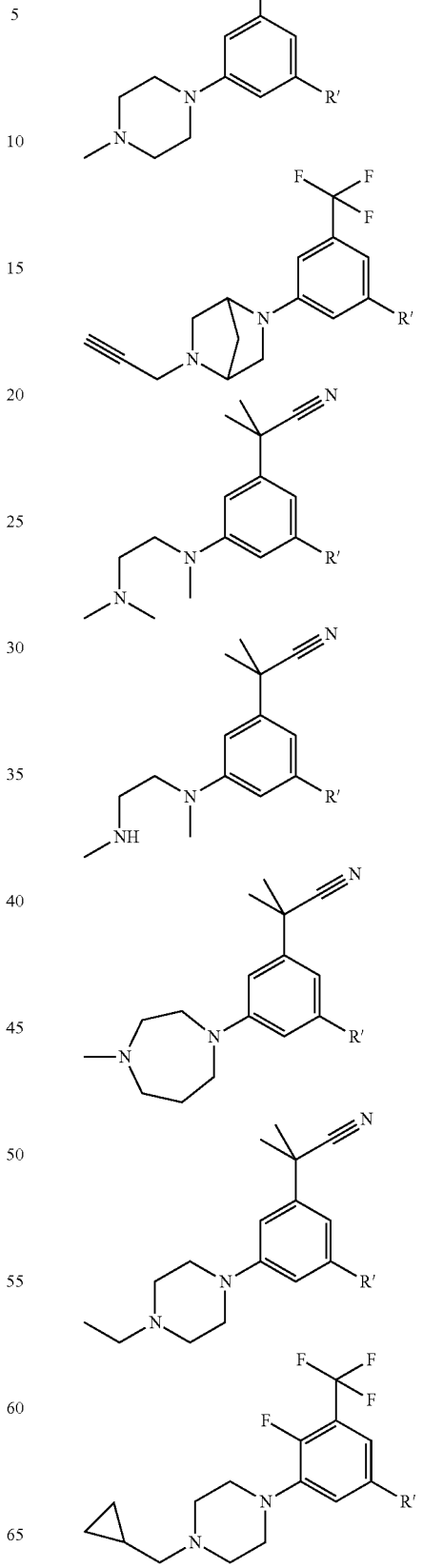

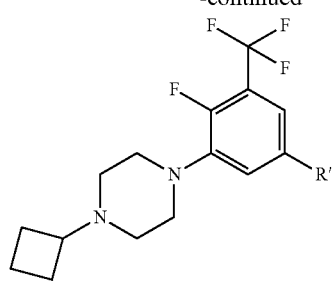
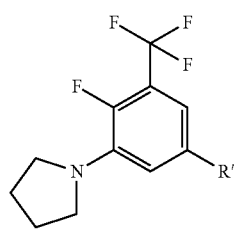
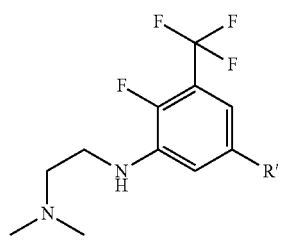
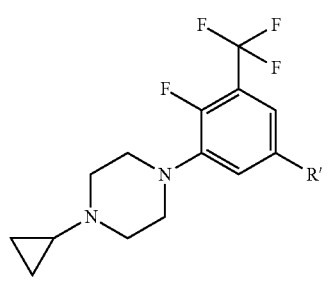
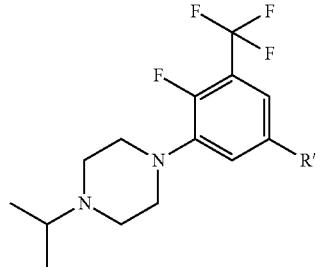
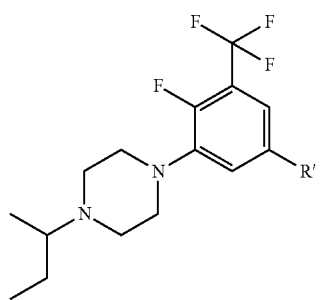
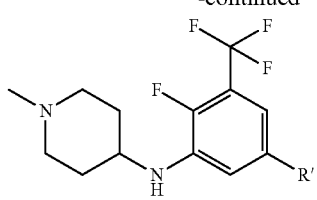
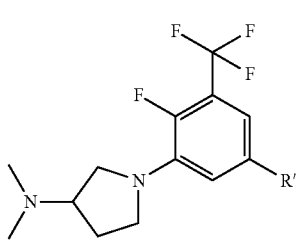
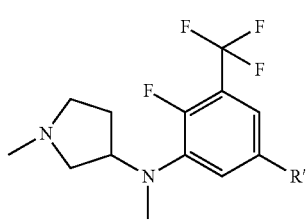
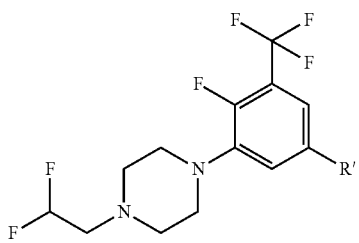
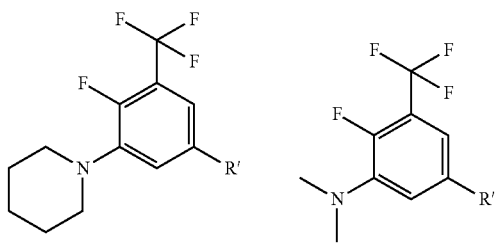
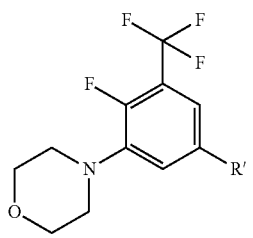
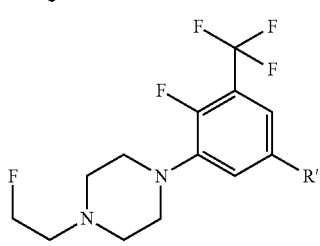

-continued
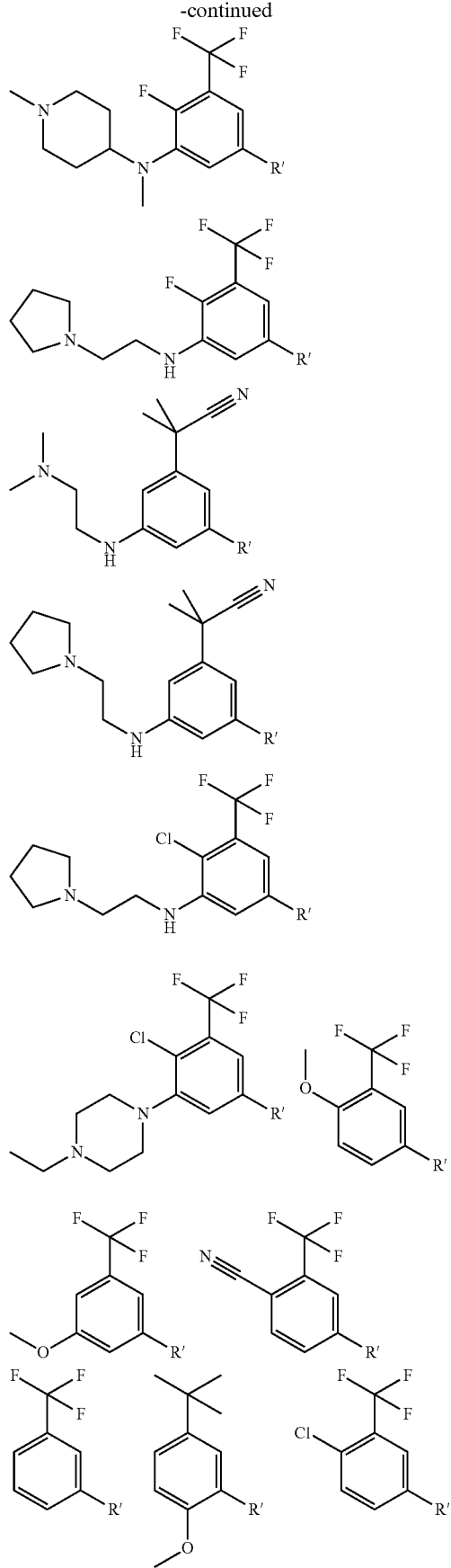
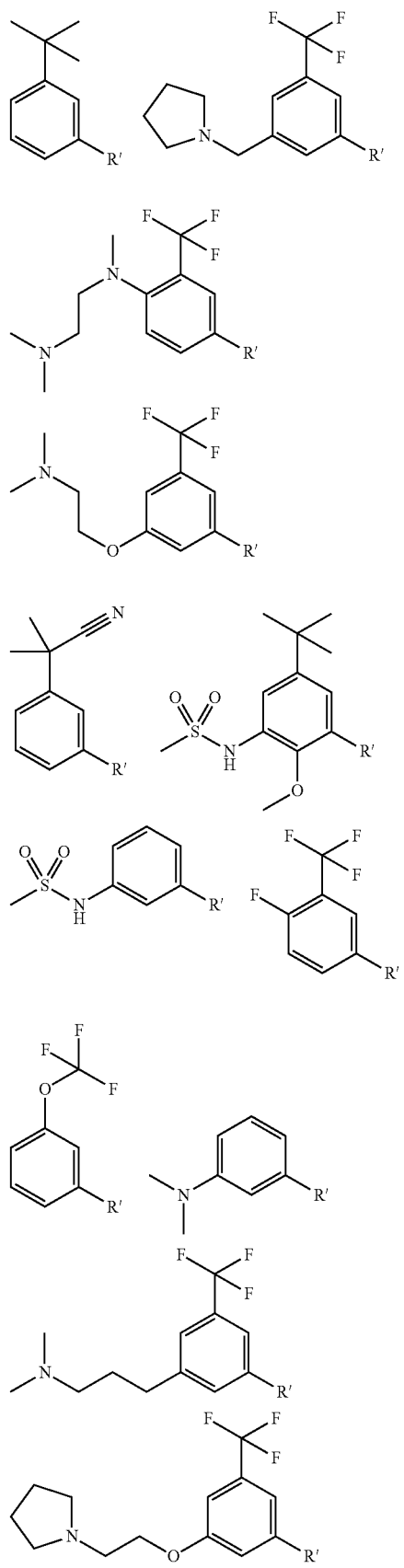

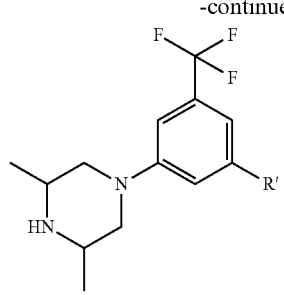
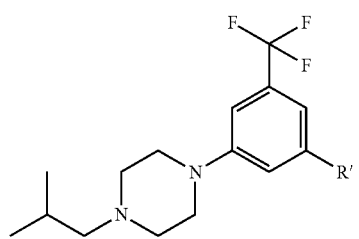
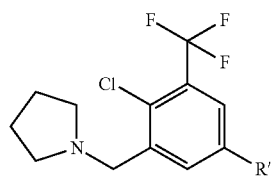
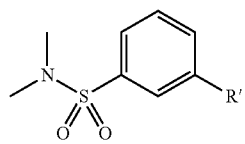
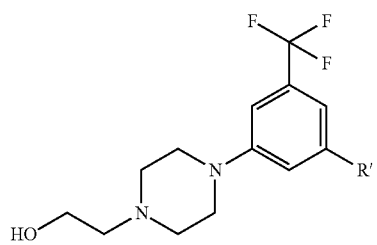
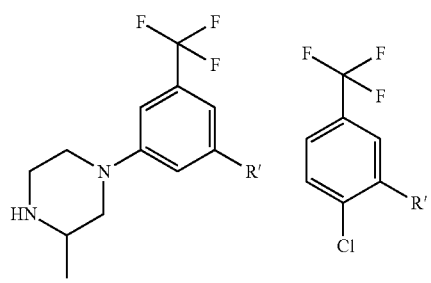
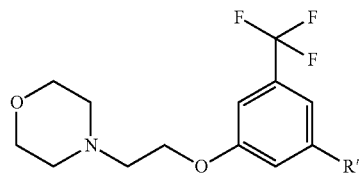
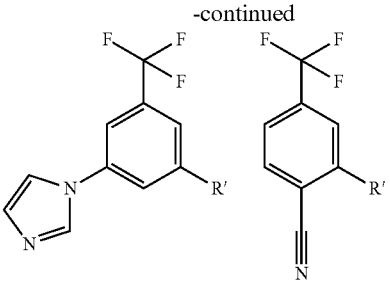
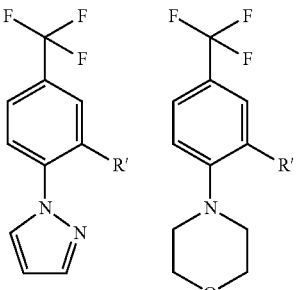
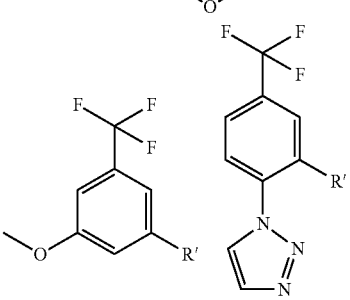
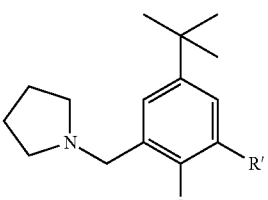
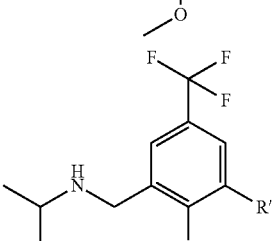
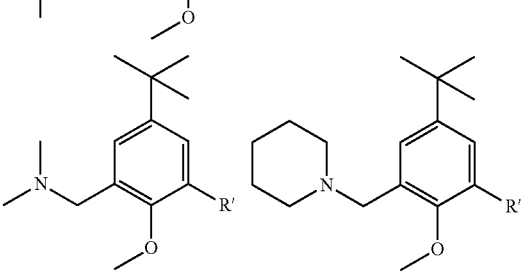
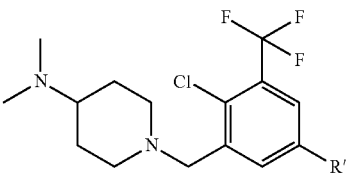

-continued
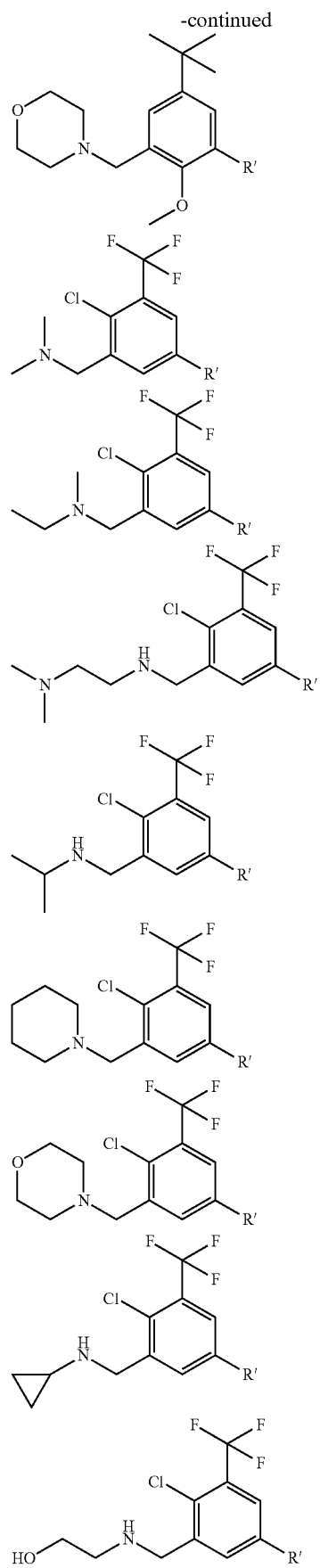
-continued
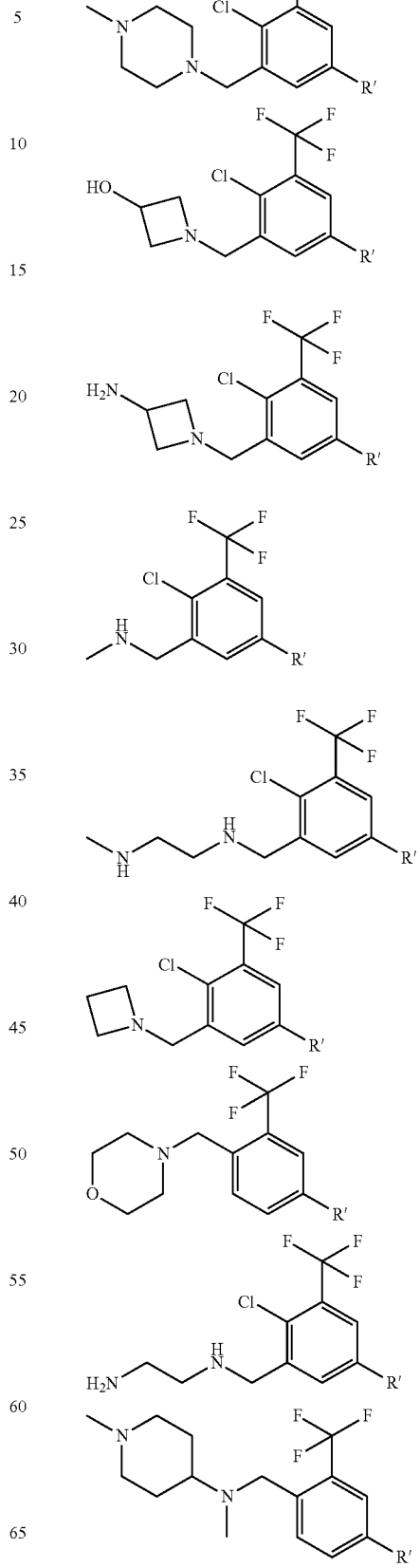

47
-continued
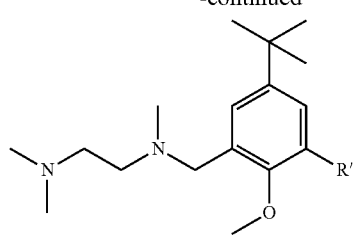
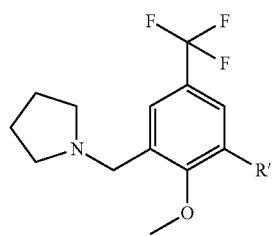
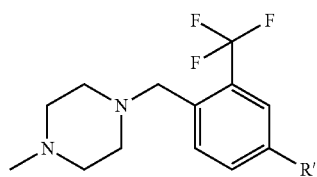
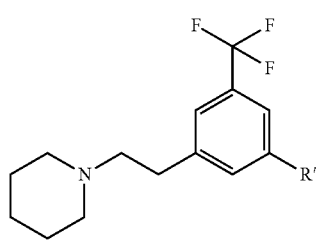
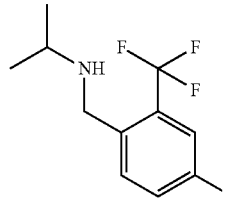
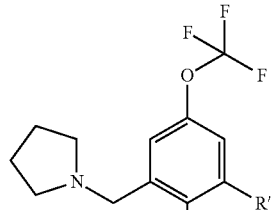
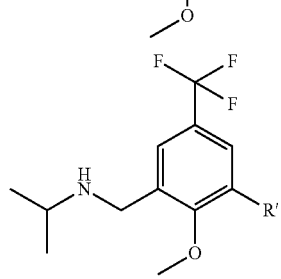
48
-continued
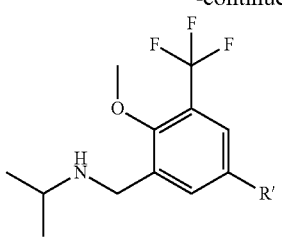
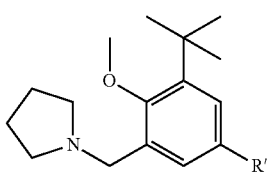
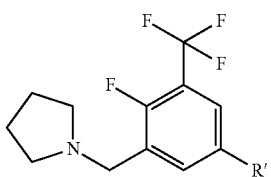
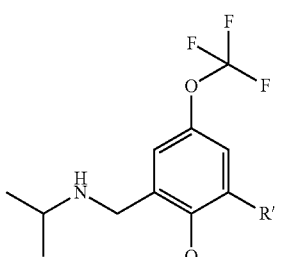
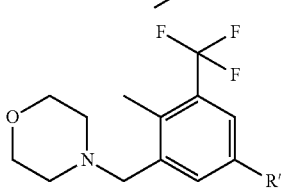
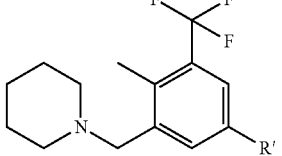
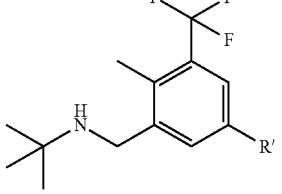
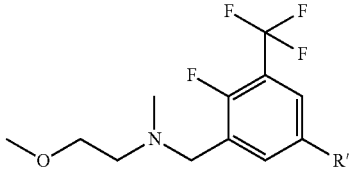

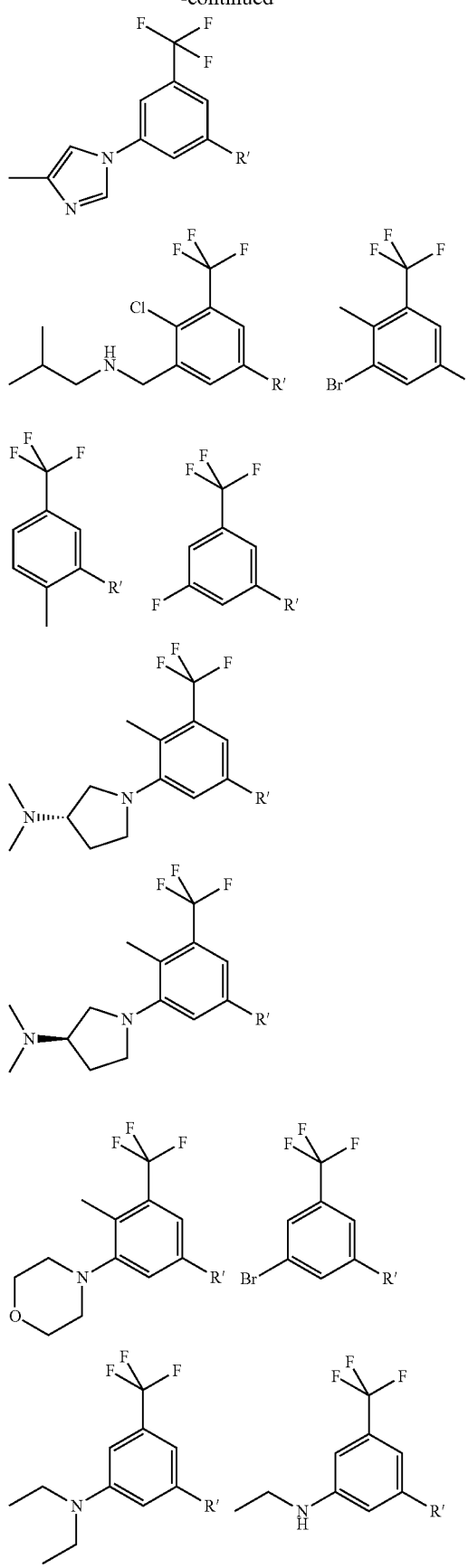
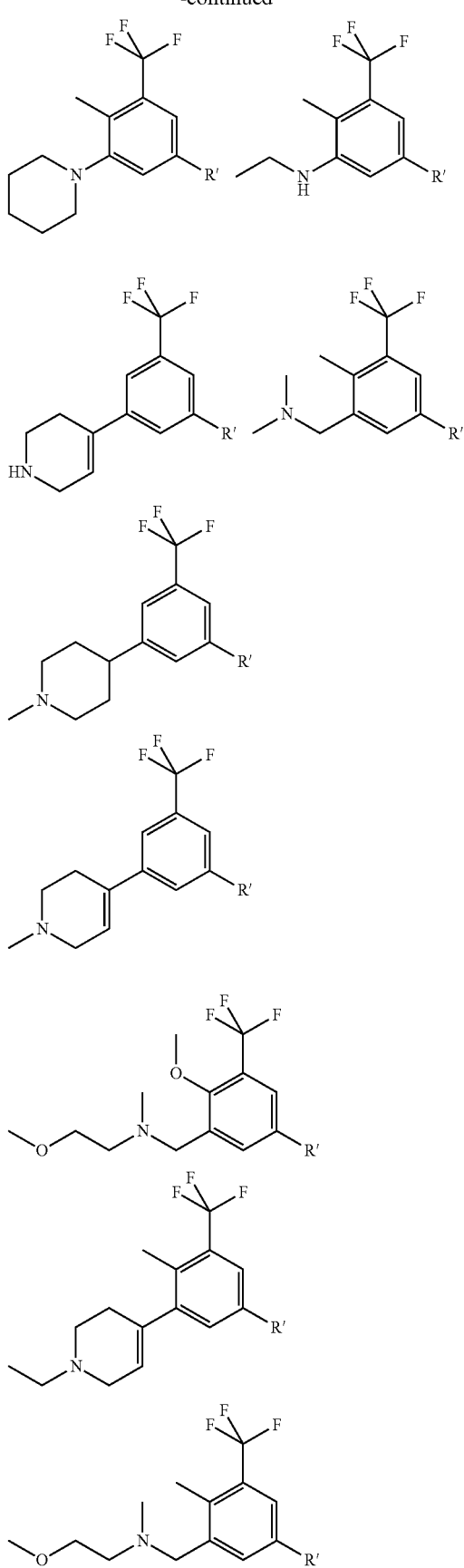

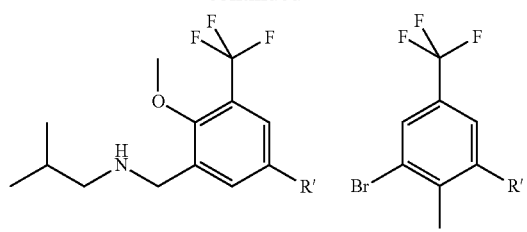
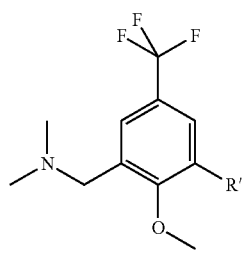
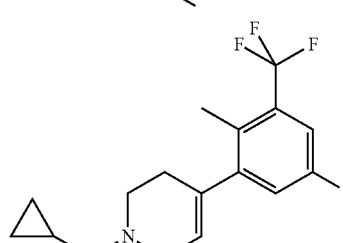
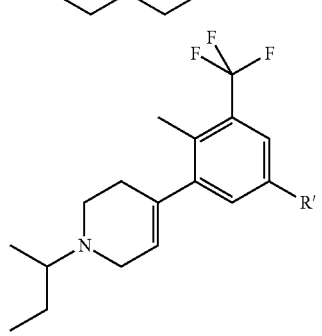
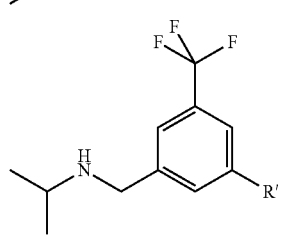
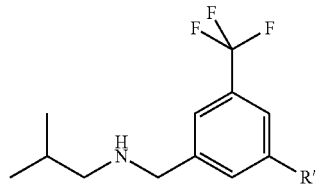
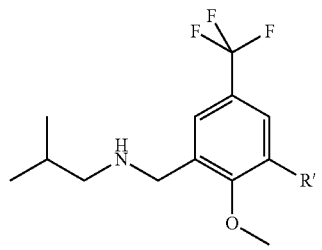
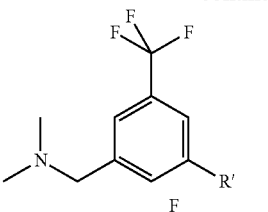
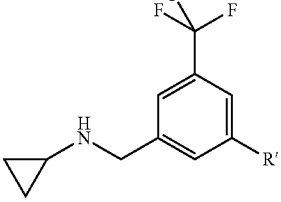
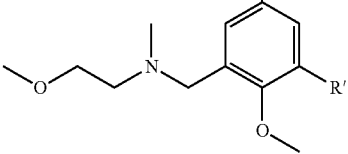
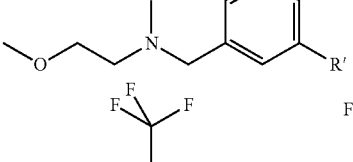
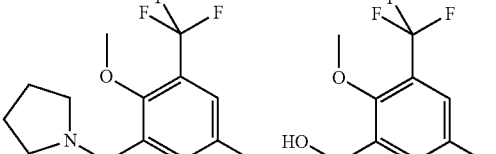
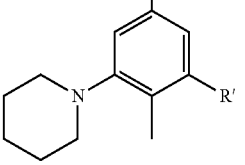
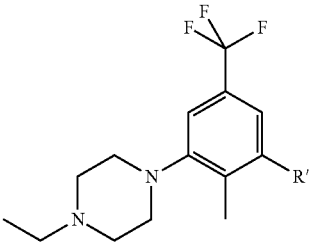

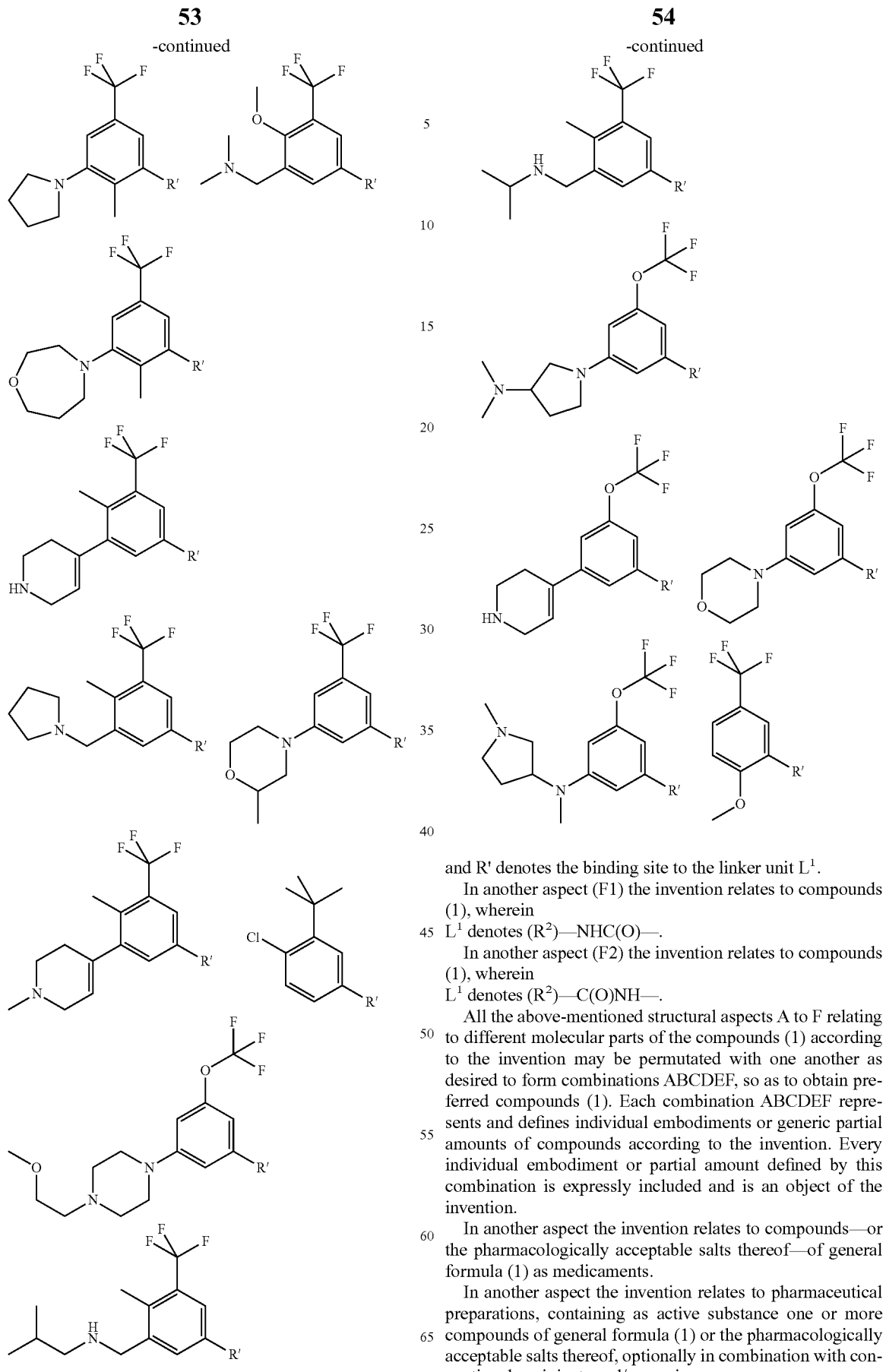

and R' denotes the binding site to the linker unit $L^1$.

In another aspect (F1) the invention relates to compounds (1), wherein
$L^1$ denotes $(R^2)$—NHC(O)—.

In another aspect (F2) the invention relates to compounds (1), wherein
$L^1$ denotes $(R^2)$—C(O)NH—.

All the above-mentioned structural aspects A to F relating to different molecular parts of the compounds (1) according to the invention may be permutated with one another as desired to form combinations ABCDEF, so as to obtain preferred compounds (1). Each combination ABCDEF represents and defines individual embodiments or generic partial amounts of compounds according to the invention. Every individual embodiment or partial amount defined by this combination is expressly included and is an object of the invention.

In another aspect the invention relates to compounds—or the pharmacologically acceptable salts thereof—of general formula (1) as medicaments.

In another aspect the invention relates to pharmaceutical preparations, containing as active substance one or more compounds of general formula (1) or the pharmacologically acceptable salts thereof, optionally in combination with conventional excipients and/or carriers.

In another aspect the invention relates to compounds of general formula (1) for use in the treatment and/or prevention of cancer, infections, inflammations and autoimmune diseases.

In another aspect the invention relates to compounds of general formula (1) for use in the treatment and/or prevention of cancer.

In another aspect the invention relates to a pharmaceutical preparation comprising a compound of general formula (1), while the compounds (1) may optionally also be in the form of the tautomers, racemates, enantiomers, diastereomers and mixtures thereof or as the respective pharmacologically acceptable salts of all the above-mentioned forms, and at least one other cytostatic or cytotoxic active substance different from formula (1).

Definitions

As used herein, the following definitions apply, unless stated otherwise:

The use of the prefix $C_{x-y}$, where x and y in each case denote a natural number (x<y), indicates that the chain or cyclic structure or combination of chain and cyclic structure referred to and mentioned in direction connection may consist in total of a maximum of y and a minimum of x carbon atoms.

The information as to the number of members in groups containing one or more heteroatom(s) (heteroalkyl, heteroaryl, heteroarylalkyl, heterocycloalkyl, heterocycloalkylalkyl) refers to the total atomic number of all the ring members or chain members or the total of all the ring and chain members.

Alkyl is made up of the sub-groups saturated hydrocarbon chains and unsaturated hydrocarbon chains, while the latter may be further subdivided into hydrocarbon chains with a double bond (alkenyl) and hydrocarbon chains with a triple bond (alkynyl). Alkenyl contains at least one double bond, alkynyl at least one triple bond. If a hydrocarbon chain should have both at least one double bond and at least one triple bond, by definition it belongs to the alkynyl sub-group. All the above-mentioned sub-groups may be further subdivided into straight-chain (unbranched) and branched. If an alkyl is substituted, it may be mono- or polysubstituted independently of one another at all the hydrogen-carrying carbon atoms.

Examples of individual sub-groups are listed below:

Straight-Chain (Unbranched) or Branched, Saturated Hydrocarbon Chains:

methyl; ethyl; n-propyl; isopropyl (1-methylethyl); n-butyl; 1-methylpropyl; isobutyl (2-methylpropyl); sec.-butyl (1-methylpropyl); tert.-butyl (1.1-dimethylethyl); n-pentyl; 1-methylbutyl; 1-ethylpropyl; isopentyl (3-methylbutyl); neopentyl (2,2-dimethyl-propyl); n-hexyl; 2,3-dimethylbutyl; 2,2-dimethylbutyl; 3,3-dimethylbutyl; 2-methyl-pentyl; 3-methylpentyl; n-heptyl; 2-methylhexyl; 3-methylhexyl; 2,2-dimethylpentyl; 2,3-dimethylpentyl; 2,4-dimethylpentyl; 3,3-dimethylpentyl; 2,2,3-trimethylbutyl; 3-ethylpentyl; n-octyl; n-nonyl; n-decyl etc.

Straight-Chained (Unbranched) or Branched Alkenyl:

vinyl(ethenyl); prop-1-enyl; allyl(prop-2-enyl); isopropenyl; but-1-enyl; but-2-enyl; but-3-enyl; 2-methyl-prop-2-enyl; 2-methyl-prop-1-enyl; 1-methyl-prop-2-enyl; 1-methyl-prop-1-enyl; 1-methylidenepropyl; pent-1-enyl; pent-2-enyl; pent-3-enyl; pent-4-enyl; 3-methyl-but-3-enyl; 3-methyl-but-2-enyl; 3-methyl-but-1-enyl; hex-1-enyl; hex-2-enyl; hex-3-enyl; hex-4-enyl; hex-5-enyl; 2,3-dimethyl-but-3-enyl; 2,3-dimethyl-but-2-enyl; 2-methylidene-3-methylbutyl; 2,3-dimethyl-but-1-enyl; hexa-1, 3-dienyl; hexa-1,4-dienyl; penta-1,4-dienyl; penta-1,3-dienyl; buta-1,3-dienyl; 2,3-dimethylbuta-1,3-diene etc.

Straight-Chain (Unbranched) or Branched Alkynyl:

ethynyl; prop-1-ynyl; prop-2-ynyl; but-1-ynyl; but-2-ynyl; but-3-ynyl; 1-methyl-prop-2-ynyl etc.

By the terms propyl, butyl, pentyl, hexyl, heptyl, octyl, nonyl, decyl etc. unless otherwise stated are meant saturated hydrocarbon groups with the corresponding number of carbon atoms, including all the isomeric forms.

By the terms propenyl, butenyl, pentenyl, hexenyl, heptenyl, octenyl, nonenyl, decenyl etc. unless otherwise stated are meant unsaturated hydrocarbon groups with the corresponding number of carbon atoms and a double bond, including all the isomeric forms, also (Z)/(E)-isomers, where applicable.

By the terms butadienyl, pentadienyl, hexadienyl, heptadienyl, octadienyl, nonadienyl, decadienyl etc. unless otherwise stated are meant unsaturated hydrocarbon groups with the corresponding number of carbon atoms and two double bonds, including all the isomeric forms, also (Z)/(E)-isomers, where applicable.

By the terms propynyl, butynyl, pentynyl, hexynyl, heptynyl, octynyl, nonynyl, decynyl etc. unless otherwise stated are meant unsaturated hydrocarbon groups with the corresponding number of carbon atoms and a triple bond, including all the isomeric forms.

From alkyl as hereinbefore defined and its subgroups the term alkylene can also be derived. Alkylene unlike alkyl is bivalent and requires two bonding partners. Formally the second valency is produced by removing a hydrogen atom from an alkyl. Corresponding groups are for example —$CH_3$ and —$CH_2$—, —$CH_2CH_3$ and —$CH_2CH_2$— or >$CHCH_3$ etc. For all the subgroups of alkyl there are correspondences for alkylene.

By heteroatoms are meant oxygen, nitrogen and sulphur atoms.

By the term heteroalkyl are meant groups which are derived from the alkyl as hereinbefore defined in its widest sense by replacing, in the hydrocarbon chains, one or more of the groups —$CH_3$ independently of one another by the groups —OH, —SH or —$NH_2$, one or more of the groups —$CH_2$— independently of one another by the groups —O—, —S— or —NH—, one or more of the groups >CH— by the group >N—, one or more of the groups =CH— by the group =N—, one or more of the groups =$CH_2$ by the group =NH or one or more of the groups =CH by the group =N, while a total of not more than three heteroatoms may be present in one heteroalkyl, there must be at least one carbon atom between two oxygen atoms and between two sulphur atoms or between one oxygen and one sulphur atom and the group as a whole must have chemical stability.

A direct result of the indirect definition/derivation from alkyl is that heteroalkyl is made up of the sub-groups saturated hydrocarbon chains with heteroatom(s), heteroalkenyl and heteroalkynyl, and it may be further subdivided into straight-chain (unbranched) and branched. If a heteroalkyl is substituted, it may be mono- or polysubstituted independently of one another at all the hydrogen-carrying oxygen, sulphur, nitrogen and/or carbon atoms. Heteroalkyl itself as a substituent may be attached to the molecule both through a carbon atom and through a heteroatom.

The following are listed by way of example:

dimethylaminomethyl; dimethylaminoethyl (1-dimethylaminoethyl; 2-dimethyl-aminoethyl); dimethylaminopropyl (1-dimethylaminopropyl, 2-dimethylaminopropyl, 3-dimethylaminopropyl); diethylaminomethyl; diethylaminoethyl (1-diethylaminoethyl, 2-diethylaminoethyl); diethylaminopropyl (1-diethylaminopropyl, 2-diethylaminopropyl, 3-diethylaminopropyl); diisopropylaminoethyl (1-diisopropylaminoethyl, 2-di-isopropylaminoethyl);

bis-2-methoxyethylamino; [2-(dimethylamino-ethyl)-ethyl-amino]-methyl; 3-[2-(dimethylamino-ethyl)-ethyl-amino]-propyl; hydroxymethyl; 2-hydroxy-ethyl; 3-hydroxypropyl; methoxy; ethoxy; propoxy; methoxymethyl; 2-methoxyethyl etc.

From heteroalkyl as hereinbefore defined and its subgroups the term heteroalkylene can also be derived. Heteroalkylene unlike heteroalkyl is bivalent and requires two bonding partners. Formally the second valency is produced by removing a hydrogen atom from a heteroalkyl. Corresponding groups are for example —CH$_2$NH$_2$ and —CH$_2$NH— or >CHNH$_2$, —NHCH$_3$ and >NCH$_3$ or —NHCH$_2$—, —CH$_2$OCH$_3$ and —CH$_2$OCH$_2$— or >CHOCH$_3$ etc. For all the subgroups of heteroalkyl there are correspondences for heteroalkylene.

Haloalkyl is derived from alkyl as hereinbefore defined in its broadest sense, by replacing one or more hydrogen atoms of the hydrocarbon chain independently of one another by halogen atoms, which may be identical or different. A direct result of the indirect definition/derivation from alkyl is that haloalkyl is made up of the sub-groups saturated hydrohalogen chains, haloalkenyl and haloalkynyl, and it may be further subdivided into straight-chain (unbranched) and branched. If a haloalkyl is substituted, it may be mono- or polysubstituted independently of one another at all the hydrogen-carrying carbon atoms.

Typical examples are listed below:
—CF$_3$; —CHF$_2$; —CH$_2$F; —CF$_2$CF$_3$; —CHFCF$_3$; —CH$_2$CF$_3$; —CF$_2$CH$_3$; —CHFCH$_3$; —CF$_2$CF$_2$CF$_3$; —CF$_2$CH$_2$CH$_3$; —CF=CF$_2$; —CCl=CH$_2$; —CBr=CH$_2$; —CI=CH$_2$; —C≡C—CF$_3$; —CHFCH$_2$CH$_3$; —CHFCH$_2$CF$_3$ etc.

From haloalkyl as hereinbefore defined and its subgroups the term haloalkylene can also be derived. Haloalkylene unlike haloalkyl is bivalent and requires two bonding partners. Formally the second valency is produced by removing a hydrogen atom from a haloalkyl. Corresponding groups are for example —CH$_2$F and —CHF—, —CHFCH$_2$F and —CHFCHF— or >CFCH$_2$F etc. For all the subgroups of haloalkyl there are correspondences for haloalkylene.

Halogen encompasses fluorine, chlorine, bromine and/or iodine atoms.

Cycloalkyl is made up of the sub-groups monocyclic hydrocarbon rings, bicyclic hydrocarbon rings and spirohydrocarbon rings, while each sub-group may be further subdivided into saturated and unsaturated (cycloalkenyl). By unsaturated is meant that there is at least one double bond in the ring system, but no aromatic system is formed. In bicyclic hydrocarbon rings two rings are linked such that they share at least two carbon atoms. In spirohydrocarbon rings one carbon atom (spiroatom) is shared by two rings. If a cycloalkyl is substituted, it may be mono- or polysubstituted independently of one another at all the hydrogen-carrying carbon atoms. Cycloalkyl itself as a substituent may be attached to the molecule through any suitable position of the ring system.

The following individual sub-groups are listed by way of example:

Monocyclic Hydrocarbon Rings, Saturated:
cyclopropyl; cyclobutyl; cyclopentyl; cyclohexyl; cycloheptyl etc.

Monocyclic Hydrocarbon Rings, Unsaturated:
cycloprop-1-enyl; cycloprop-2-enyl; cyclobut-1-enyl; cyclobut-2-enyl; cyclopent-1-enyl; cyclopent-2-enyl; cyclopent-3-enyl; cyclohex-1-enyl; cyclohex-2-enyl; cyclohex-3-enyl; cyclohept-1-enyl; cyclohept-2-enyl; cyclohept-3-enyl; cyclohept-4-enyl; cyclobuta-1,3-dienyl; cyclopenta-1,4-dienyl; cyclopenta-1,3-dienyl; cyclopenta-2,4-dienyl; cyclohexa-1,3-dienyl; cyclohexa-1,5-dienyl; cyclohexa-2,4-dienyl; cyclohexa-1,4-dienyl; cyclohexa-2,5-dienyl etc.

Bicyclic Hydrocarbon Rings (Saturated and Unsaturated):
bicyclo[2.2.0]hexyl; bicyclo[3.2.0]heptyl; bicyclo[3.2.1]octyl; bicyclo[2.2.2]octyl; bicyclo[4.3.0]nonyl(octahydroindenyl); bicyclo[4.4.0]decyl(decahydronaphthalene); bicyclo[2.2.1]heptyl(norbornyl); (bicyclo[2.2.1]hepta-2,5-dienyl(norborna-2,5-dienyl); bicyclo[2.2.1]hept-2-enyl (norbornenyl); bicyclo[4.1.0]heptyl(norcaranyl); bicyclo-[3.1.1]heptyl(pinanyl) etc.

Spirohydrocarbon Rings (Saturated and Unsaturated):
spiro[2.5]octyl, spiro[3,3]heptyl, spiro[4,5]dec-2-ene, etc.

If the free valency of a cycloalkyl is saturated off, an alicyclic ring is obtained.

From cycloalkyl as hereinbefore defined and its subgroups the term cycloalkylene can also be derived. Cycloalkylene unlike cycloalkyl is bivalent and requires two bonding partners. Formally the second valency is produced by removing a hydrogen atom from a cycloalkyl.

Corresponding groups are for example
cyclohexyl and

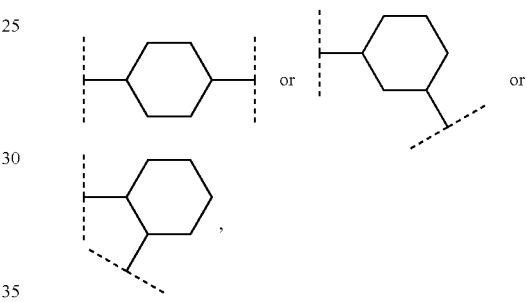

cyclopentenyl and

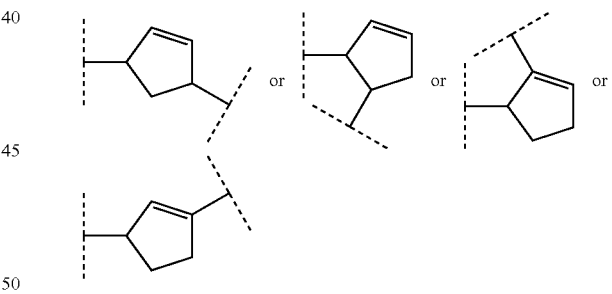

etc.

For all the subgroups of cycloalkyl there are correspondences for cycloalkylene.

Cycloalkylalkyl refers to the combination of the alkyl in question, as hereinbefore defined, with cycloalkyl, both in their widest sense. Alternatively cycloalkylalkyl may also be regarded as a combination of cycloalkyl with alkylene. Formally, cycloalkylalkyl is obtained by first linking an alkyl as substituent directly with the molecule and then substituting with a cycloalkyl. The linking of alkyl and cycloalkyl may be carried out in both groups using carbon atoms that are suitable for this purpose. The respective subgroups of alkyl (alkylene) and cycloalkyl are also included in the combination of the two groups.

Aryl denotes mono-, bi- or tricyclic carbon rings with at least one aromatic ring. If an aryl is substituted, the substitution may be mono- or polysubstitution in each case, at all the hydrogen-carrying carbon atoms, independently of one another. Aryl itself may be linked to the molecule as substituent via any suitable position of the ring system.

Typical examples are listed below:

phenyl, naphthyl, indanyl (2,3-dihydroindenyl), 1,2,3,4-tetrahydronaphthyl, fluorenyl, etc. If the free valency of an aryl is saturated off, an aromatic group is obtained.

From aryl as hereinbefore defined the term arylene can also be derived. Arylene unlike aryl is bivalent and requires two bonding partners. Formally the second valency is produced by removing a hydrogen atom from an aryl. Corresponding groups are for example
phenyl and

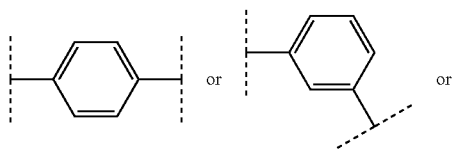

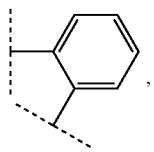

naphthyl and

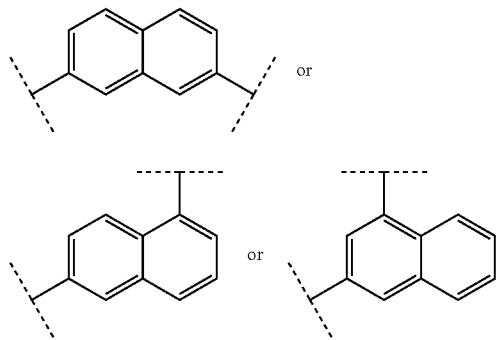

etc.

For all the subgroups of aryl there are correspondences for arylene.

Arylalkyl denotes the combination of the groups alkyl and aryl as hereinbefore defined, in each case in their broadest sense. Alternatively arylalkyl may also be regarded as a combination of aryl with alkylene. Formally, arylalkyl is obtained by first linking an alkyl as substituent directly to the molecule and substituting it with an aryl group. The alkyl and aryl may be linked in both groups via any carbon atoms suitable for this purpose. The respective sub-groups of alkyl (alkylene) and aryl are also included in the combination of the two groups.

Typical examples are listed below:

benzyl; 1-phenylethyl; 2-phenylethyl; phenylvinyl; phenylallyl etc.

Heteroaryl denotes monocyclic aromatic rings or polycyclic rings with at least one aromatic ring, which, compared with corresponding aryl or cycloalkyl, contain instead of one or more carbon atoms one or more identical or different heteroatoms, selected independently of one another from among nitrogen, sulphur and oxygen, while the resulting group must be chemically stable. The prerequisite for the presence of heteroaryl is a heteroatom and an aromatic system, although it need not necessarily be a heteroaromatic system. Thus 2,3-dihydro-1H-indol-6-yl

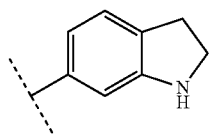

may according to the definition be a heteroaryl.

If a heteroaryl is substituted, the substitution may be mono- or polysubstitution in each case, at all the hydrogen-carrying carbon and/or nitrogen atoms, independently of one another. Heteroaryl itself as substituent may be linked to the molecule via any suitable position of the ring system, both carbon and nitrogen.

Typical examples are listed below:

Monocyclic Heteroaryls furyl; thienyl; pyrrolyl; oxazolyl; thiazolyl; isoxazolyl; isothiazolyl; pyrazolyl; imidazolyl; triazolyl; tetrazolyl; oxadiazolyl; thiadiazolyl; pyridyl; pyrimidyl; pyridazinyl; pyrazinyl; triazinyl; pyridyl-N-oxide; pyrrolyl-N-oxide; pyrimidinyl-N-oxide; pyridazinyl-N-oxide; pyrazinyl-N-oxide; imidazolyl-N-oxide; isoxazolyl-N-oxide; oxazolyl-N-oxide; thiazolyl-N-oxide; oxadiazolyl-N-oxide; thiadiazolyl-N-oxide; triazolyl-N-oxide; tetrazolyl-N-oxide etc.

Polycyclic Heteroaryls indolyl; isoindolyl; benzofuryl; benzothienyl; benzoxazolyl; benzothiazolyl; benz-isoxazolyl; dihydroindolyl; benzisothiazolyl; benzimidazolyl; indazolyl; isoquinolinyl; quinolinyl; quinoxalinyl; cinnolinyl; phthalazinyl; quinazolinyl; benzotriazinyl; indolizinyl; oxazolopyridyl; imidazopyridyl; naphthyridinyl; indolinyl; isochromanyl; chromanyl; tetrahydroisoquinolinyl; isoindolinyl; isobenzotetrahydrofuryl; isobenzotetra-hydrothienyl; isobenzothienyl; benzoxazolyl; pyridopyridyl; benzotetrahydrofuryl; benzotetrahydro-thienyl; purinyl; benzodioxolyl; phenoxazinyl; phenothiazinyl; pteridinyl; benzothiazolyl; imidazopyridyl; imidazothiazolyl; dihydrobenzisoxazinyl; benzisoxazinyl; benzoxazinyl; dihydrobenzisothiazinyl; benzopyranyl; benzothiopyranyl; coumarinyl; isocoumarinyl; chromonyl; chromanonyl; tetrahydroquinolinyl; dihydroquinolinyl; dihydroquinolinonyl; dihydroisoquinolinonyl; dihydrocoumarinyl; dihydroisocoumarinyl; isoindolinonyl; benzodioxanyl; benzoxazolinonyl; quinolinyl-N-oxide; indolyl-N-oxide; indolinyl-N-oxide; isoquinolyl-N-oxide; quinazolinyl-N-oxide; quinoxalinyl-N-oxide; phthalazinyl-N-oxide; indolizinyl-N-oxide; indazolyl-N-oxide; benzothiazolyl-N-oxide; benzimidazolyl-N-oxide; benzothiopyranyl-S-oxide and benzothiopyranyl-S,S-dioxide etc.

If the free valency of a heteroaryl is saturated off, a heteroaromatic group is obtained. From heteroaryl as hereinbefore defined the term heteroarylene can also be derived. Heteroarylene unlike heteroaryl is bivalent and requires two bonding partners. Formally the second valency is produced by removing a hydrogen atom from a heteroaryl.

Corresponding groups are for example pyrrolyl and

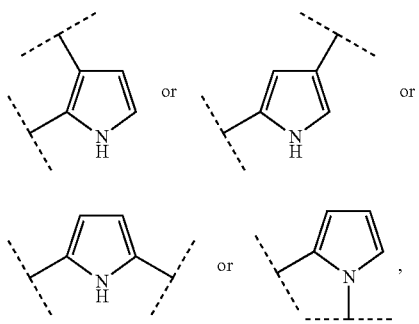

2,3-dihydro-1H-indolyl and

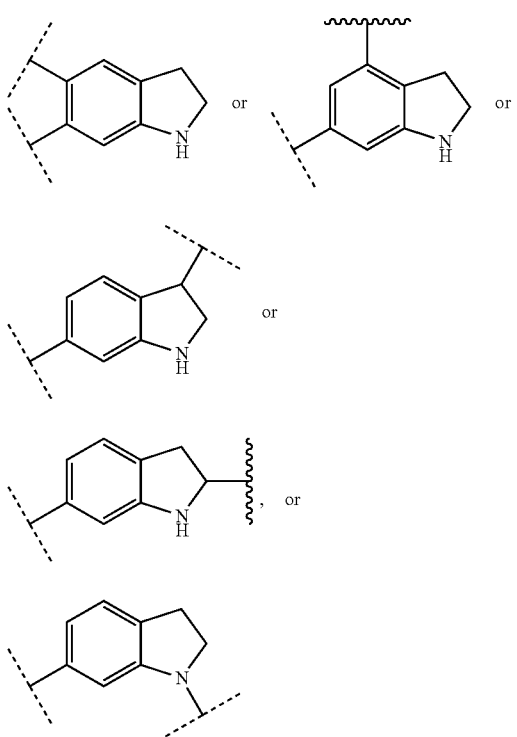

etc.

For all the subgroups of heteroaryl there are correspondences for heteroarylene.

Heteroarylalkyl denotes the combination of the alkyl in question as hereinbefore defined with heteroaryl, both in their broadest sense. Alternatively heteroarylalkyl may also be regarded as a combination of heteroaryl with alkylene. Formally heteroarylalkyl is obtained by first linking an alkyl as substituent directly with the molecule and then substituting it with a heteroaryl. The linking of the alkyl and heteroaryl may be achieved on the alkyl side via any carbon atoms suitable for this purpose and on the heteroaryl side via any carbon or nitrogen atoms suitable for this purpose. The respective subgroups of alkyl (alkylene) and heteroaryl are also included in the combination of the two groups.

By the term heterocycloalkyl are meant groups which are derived from the cycloalkyl as hereinbefore defined if in the hydrocarbon rings one or more of the groups —CH$_2$— are replaced independently of one another by the groups —O—, —S— or —NH— or one or more of the groups =CH— are replaced by the group =N—, while not more than five heteroatoms may be present in total, there must be at least one carbon atom between two oxygen atoms and between two sulphur atoms or between one oxygen and one sulphur atom and the group as a whole must be chemically stable. Heteroatoms may simultaneously be present in all the possible oxidation stages (sulphur→sulphoxide —SO—, sulphone —SO$_2$—; nitrogen→N-oxide). It is immediately apparent from the indirect definition/derivation from cycloalkyl that heterocycloalkyl is made up of the sub-groups monocyclic hetero-rings, bicyclic hetero-rings and spirohetero-rings, while each sub-group can also be further subdivided into saturated and unsaturated (heterocycloalkenyl). The term unsaturated means that in the ring system in question there is at least one double bond, but no aromatic system is formed. In bicyclic hetero-rings two rings are linked such that they have at least two atoms in common. In spirohetero-rings one carbon atom (spiroatom) is shared by two rings. If a heterocycloalkyl is substituted, the substitution may be mono- or polysubstitution in each case, at all the hydrogen-carrying carbon and/or nitrogen atoms, independently of one another. Heterocycloalkyl itself as substituent may be linked to the molecule via any suitable position of the ring system.

Typical examples of individual sub-groups are listed below.

Monocyclic Heterorings (Saturated and Unsaturated)
tetrahydrofuryl; pyrrolidinyl; pyrrolinyl; imidazolidinyl; thiazolidinyl; imidazolinyl; pyrazolidinyl; pyrazolinyl; piperidinyl; piperazinyl; oxiranyl; aziridinyl; azetidinyl; 1,4-dioxanyl; azepanyl; diazepanyl; morpholinyl; thiomorpholinyl; homomorpholinyl; homopiperidinyl; homopiperazinyl; homothiomorpholinyl; thiomorpholinyl-S-oxide; thiomorpholinyl-S,S-dioxide; 1,3-dioxolanyl; tetrahydropyranyl; tetrahydrothiopyranyl; [1,4]-oxazepanyl; tetrahydrothienyl; homothiomorpholinyl-S,S-dioxide; oxazolidinonyl; dihydropyrazolyl; dihydropyrrolyl; dihydropyrazinyl; dihydropyridyl; dihydro-pyrimidinyl; dihydrofuryl; dihydropyranyl; tetrahydrothienyl-S-oxide; tetrahydrothienyl-S,S-dioxide; homothiomorpholinyl-S-oxide; 2,3-dihydroazet; 2H-pyrrolyl; 4H-pyranyl; 1,4-dihydropyridinyl etc.

Bicyclic Heterorings (Saturated and Unsaturated)
8-azabicyclo[3.2.1]octyl; 8-azabicyclo[5.1.0]octyl; 2-oxa-5-azabicyclo[2.2.1]heptyl; 8-oxa-3-aza-bicyclo[3.2.1]octyl; 3,8-diaza-bicyclo[3.2.1]octyl; 2,5-diaza-bicyclo-[2.2.1]heptyl; 1-aza-bicyclo[2.2.2]octyl; 3,8-diaza-bicyclo[3.2.1]octyl; 3,9-diaza-bicyclo[4.2.1]nonyl; 2,6-diaza-bicyclo[3.2.2]nonyl etc.

Spiro-Heterorings (Saturated and Unsaturated)
1,4-dioxa-spiro[4.5]decyl; 1-oxa-3.8-diaza-spiro[4.5]decyl; 2,6-diaza-spiro[3.3]heptyl; 2,7-diaza-spiro[4.4]nonyl; 2,6-diaza-spiro[3.4]octyl; 3,9-diaza-spiro[5.5]undecyl; 2,8-diaza-spiro[4.5]decyl etc.

If the free valency of a heterocycloalkyl is saturated off, then a heterocyclic ring is obtained.

From heterocycloalkyl as hereinbefore defined the term heterocycloalkylene can also be derived. Heterocycloalkylene unlike heterocycloalkyl is bivalent and requires two bonding partners. Formally the second valency is produced by removing a hydrogen atom from a heterocycloalkyl. Corresponding groups are for example piperidinyl and

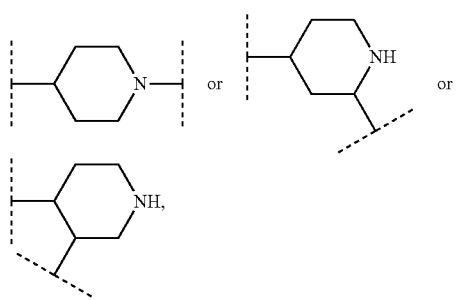

2,3-dihydro-1H-pyrrolyl and

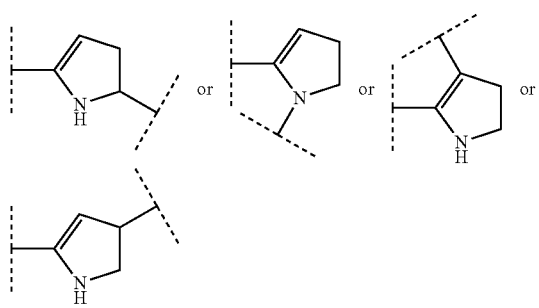

etc.

For all the subgroups of heterocycloalkyl there are correspondences for heterocycloalkylene.

Heterocycloalkylalkyl denotes the combination of the alkyl in question as hereinbefore defined with heterocycloalkyl, both in their broadest sense. Alternatively heterocycloalkylalkyl may also be regarded as a combination of heterocycloalkyl with alkylene. Formally, heterocycloalkyl is obtained by first linking an alkyl as substituent directly with the molecule and then substituting it with a heterocycloalkyl. The linking of the alkyl and heterocycloalkyl may be achieved on the alkyl side via any carbon atoms suitable for this purpose and on the heterocycloalkyl side via any carbon or nitrogen atoms suitable for this purpose. The respective sub-groups of alkyl and heterocycloalkyl are also included in the combination of the two groups.

By is substituted is meant that a hydrogen atom that is bound directly to the atom under consideration is replaced by another atom or another group of atoms (substituent). Depending on the starting conditions (number of hydrogen atoms) mono- or polysubstitution may take place at an atom.

Bivalent substituents such as for example =S, =NR, =NOR, =NNRR, =NN(R)C(O)NRR, =N$_2$ or the like may only be substituents at carbon atoms, while the bivalent substituent =O may also be a substituent of sulphur. Generally speaking, substitution by a bivalent substituent may only take place at ring systems and requires exchange for two geminal hydrogen atoms, i.e. hydrogen atoms that are bound to the same carbon atom saturated before the substitution. Substitution by a bivalent substituent is therefore only possible at the group —CH$_2$— or sulphur atoms of a ring system.

In addition to this, the term "suitable substituent" denotes a substituent which on the one hand is suitable on account of its valency and on the other hand leads to a system with chemical stability.

The following are some abbreviated notations and their structural correspondences:

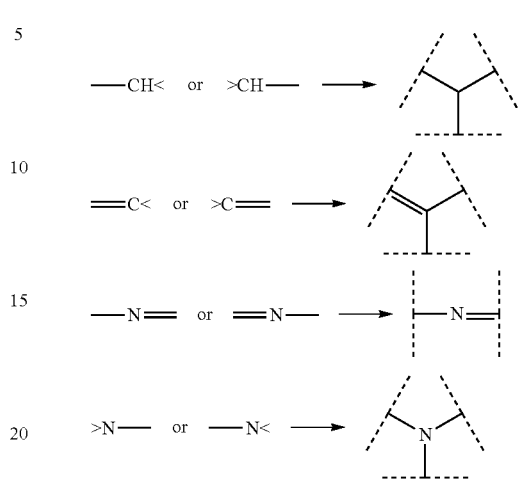

If for example in the sequence A-B-C the member B were to correspond to the structural detail —N=, this is to be understood as both A=N—C and A-N=C If for example in the sequence

the member A were to correspond to the structural detail >C= this is to be understood as being

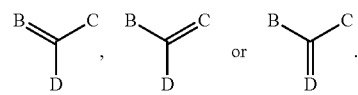

In a diagram such as for example

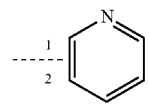

the dotted line indicates that the ring system may be attached to the molecule via the carbon 1 or 2, i.e. is equivalent to the following diagram

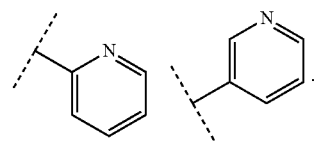

In the partial structure (i)

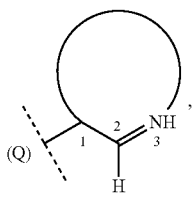

the ring system of which is in total a heteroaryl according to the preceding definition and wherein (in the case of a bicyclic group) the ring that binds directly to Q is heteroaromatic, the atoms 1, 2 (unsaturated carbon in each case) and 3 (unsaturated nitrogen) are fixed. The ring is completed by the linking of the atoms 1 and 3 through at least two further atoms. Examples of ring systems with the partial structure (i) are

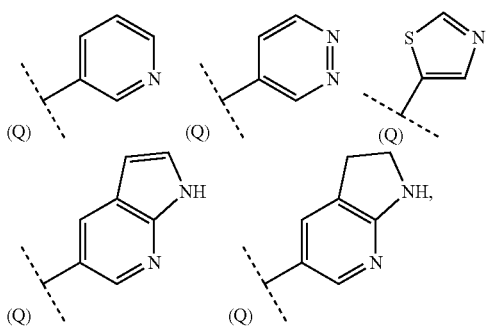

wherein the ring system in question may optionally also be substituted by one or more identical or different substituents $R^b$ and/or $R^c$.

In a diagram such as for example

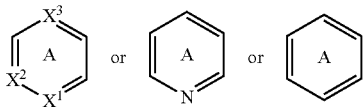

the letter A has the function of a cyclic designation in order to describe the linking of the ring in question to other rings more easily, for example.

For bivalent groups where the valency with which they bind which adjacent group is critical, the corresponding binding partners are given in brackets, wherever it is necessary for clarification, as in the following formulae:

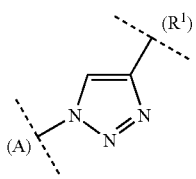

or $(R^2)$—C(O)NH— or $(R^2)$—NHC(O)—;

Groups or substituents are frequently selected from among alternative groups/substituents with a corresponding group designation (e.g. $R^a$, $R^b$ etc). If a group of this kind is used repeatedly to define a compound according to the invention in different parts of the molecule, it should always be borne in mind that the respective uses are to be regarded as being totally independent of one another.

List of Abbreviations

| | |
|---|---|
| Ac | acetyl |
| aq. | aquatic, aqueous |
| ATP | adenosine triphosphate |
| BiPh | biphenyl |
| Bn | benzyl |
| Boc | tert-butyloxycarbonyl |
| Bu | butyl |
| c | concentration |
| CDI | carbonyldiimidazole |
| chex | cyclohexane |
| d | day(s) |
| dba | dibenzylideneacetone |
| TLC | thin layer chromatography |
| DCC | dicyclohexylcarbodiimide |
| DCM | dichloromethane |
| DEA | diethylamine |
| DIPEA | N-ethyl-N,N-diisopropylamine (Hünig base) |
| DMAP | 4-N,N-dimethylaminopyridine |
| DME | 1,2-dimethoxyethane |
| DMF | N,N-dimethylformamide |
| DMSO | dimethylsulphoxide |
| DPPA | diphenylphosphorylazide |
| dppf | 1.1'-bis(diphenylphosphino)ferrocene |
| EDC | 1-ethyl-3-(3-dimethylaminopropyl)-carbodiimide |
| EDTA | ethylenediaminetetraacetic acid |
| EE | ethyl acetate |
| EGTA | ethyleneglycoltetraacetic acid |
| eq | equivalent(s) |
| ESI | electron spray ionization |
| Et | ethyl |
| $Et_2O$ | diethyl ether |
| EtOAc | ethyl acetate |
| EtOH | ethanol |
| h | hour |
| HATU | O-(7-azabenzotriazol-1-yl)-N,N,N',N'-tetramethyl-uronium hexafluorophosphate |
| hex | hexyl |
| HPLC | high performance liquid chromatography |
| Hünig-base | N-ethyl-N,N-diisopropylamine |
| i | iso |
| Kat., kat. | catalyst, catalytic |
| conc. | concentrated |
| LC | liquid chromatography |
| sln. | solution |
| mCPBA | m-chloroperbenzoic acid |
| Me | methyl |
| MeOH | methanol |
| min | minutes |
| MPLC | medium pressure liquid chromatography |
| MS | mass spectrometry |
| NMM | N-methylmorpholine |
| NMP | N-methylpyrrolidone |
| NP | normal phase |
| n.a. | not available |
| PBS | phosphate-buffered saline |
| Ph | phenyl |
| PMSF | benzylsulphonic acid fluoride |
| PPCA | propanephosphonic acid cycloanhydride |
| Pr | propyl |
| Py | pyridine |
| pyBOP | benzotriazol-1-yl-oxy-tris-pyrrolidino-phosphonium hexafluorophosphate |
| rac | racemic |
| red. | reduction |
| $R_f$(Rf) | retention factor |
| RP | reversed phase |
| RT | ambient temperature |
| $S_N$ | nucleophilic substitution |
| TBAF | tetrabutylammonium fluoride |
| TBME | tert-butylmethylether |
| TBTU | O-(benzotriazol-1-yl)-N,N,N',N'-tetramethyl-uronium tetrafluoroborate |

| | |
|---|---|
| TEA | triethylamine |
| temp. | temperature |
| tert. | tertiary |
| Tf | triflate |
| TFA | trifluoroacetic acid |
| THF | tetrahydrofuran |
| TMS | trimethylsilyl |
| $t_{Ret.}$ | retention time (HPLC) |
| TRIS | tris(hydroxymethyl)-aminomethane |
| TsOH | p-toluenesulphonic acid |
| UV | ultraviolet |

Features and advantages of the present invention will become apparent from the following detailed Examples, which illustrate the fundamentals of the invention by way of example, without restricting its scope:

Preparation of the Compounds According to the Invention

General

Unless stated otherwise, all the reactions are carried out in commercially obtainable apparatus using methods that are commonly used in chemical laboratories. Starting materials that are sensitive to air and/or moisture are stored under protective gas and corresponding reactions and manipulations therewith are carried out under protective gas (nitrogen or argon).

The compounds according to the invention are named in accordance with CAS rules using the software Autonom (Beilstein).

Microwave reactions are carried out in an initiator/reactor made by Biotage or in an Explorer made by CEM in sealed containers (preferably 2, 5 or 20 mL), preferably with stirring.

Chromatography

For preparative medium pressure chromatography (MPLC) silica gel made by Millipore (name: Granula Silica Si-60A 35-70 µm, NP phase) or C-18 RP-silica gel (RP-phase) made by Macherey Nagel (name: Polygoprep 100-50 C18) is used.

Automated normal phase chromatography is also carried out on a CombiFlash Companion XL apparatus in combination with a CombiFlash Foxy 200 fraction collector made by Isco. For this, commercially obtainable RediSepRf (120 g silica gel) one-way columns are used. The thin layer chromatography is carried out on ready-made silica gel 60 TLC plates on glass (with fluorescence indicator F-254) made by Merck.

The preparative high pressure chromatography (HPLC) of the example compounds according to the invention is carried out with columns made by Waters (names: XTerra Prep. MS C18, 5 µm, 30×100 mm or XTerra Prep. MS C18, 5 µm, 50×100 mm OBD or Symmetrie C18, 5 µm, 19×100 mm or Sunfire C18 OBD, 19×100 mm, 5 µm or Sunfire Prep C 10 µm OBD 50×150 mm or X-Bridge Prep C18, 5 µm OBD 19×50 mm), Agilent (name: Zorbax SB-C8 5 µm PrepHT 21.2×50 mm) and Phenomenex (names: Gemini C18 5 µm AXIA 21.2×50 mm or Gemini C18 10 µm 50×150 mm). Different gradients of $H_2O$/acetonitrile or $H_2O$/MeOH are used to elute the compounds, while 0.1% HCOOH is added to the water.

The preparative high pressure chromatography (HPLC) on normal phase of the example compounds according to the invention is carried out with columns made by Macherey & Nagel (name: Nucleosil, 50-7, 40×250 mm) and VDSoptilab (name: Kromasil 100 $NH_2$, 10 µM, 50×250 mm). Different gradients of DCM/MeOH are used to elute the compounds, while 0.1% $NH_3$ is added to the MeOH.

The analytical HPLC (reaction control) of intermediate compounds is carried out using columns made by Agilent (names: Zorbax SB-C8, 5 µm, 21.2×50 mm or Zorbax SB-C8 3.5 µm 2.1×50 mm) and Phenomenex (name: Gemini C18 3 µm 2×30 mm). The analytical equipment is also equipped with a mass detector in each case.

HPLC-Mass Spectroscopy/UV-Spectrometry

The retention times/MS-ESI$^+$ for characterising the example compounds according to the invention are produced using an HPLC-MS apparatus (high performance liquid chromatography with mass detector). Compounds that elute at the injection peak are given the retention time $t_{Ret.}$=0.00.

HPLC-MS Method 1

HPLC: Agilent 1100 Series

MS: Agilent LC/MSD SL

Column: Waters, Xterra MS C18, 2.5 µm, 2.1×30 mm, Part. No. 186000592

Eluant: A: $H_2O$ with 0.1% HCOOH; B: acetonitrile (HPLC grade)

Detection: MS: positive and negative mode

Mass range: 20-900 m/z

Flow 1.10 mL/min

Column temp.: 40° C.

Gradient: 0.00 min: 5% eluant B 0.00-2.50 min: 5%→95% eluant B 2.50-2.80 min: 95% eluant B 2.81-3.10 min: 95%→5% eluant B The compounds according to the invention are prepared by the methods of synthesis described hereinafter, in which the substituents of the general formulae have the meanings given hereinbefore. These methods are intended as an illustration of the invention, without restricting its subject matter and the scope of the compounds claimed to these examples. Where the preparation of starting compounds is not described, they are commercially obtainable or may be prepared analogously to known compounds or methods described herein. Substances described in the literature are prepared according to the published methods of synthesis.

Reaction scheme A

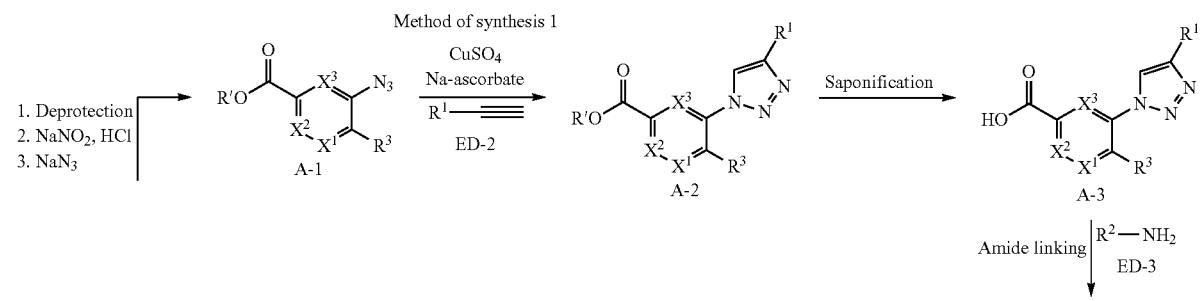

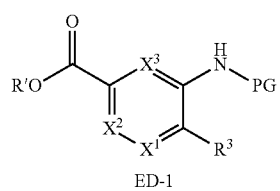

ED-1

(R' = common carboxyl protecting
group, e.g. $C_{1-6}$Alkyl, Benzyl)
PG = common amino protecting
group, e.g. Boc)

Method of synthesis 2
1. Saponification
2. Amide linking $R^2$—$NH_2$

ED-3

-continued

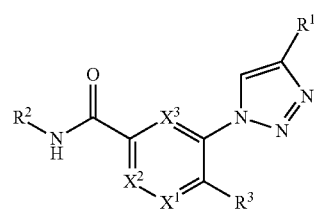

I

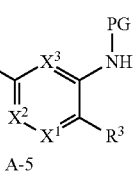

ED-2

$R^1$—≡ | $CuSO_4$
        | Na-ascorbate

Saponification

Method of synthesis 3

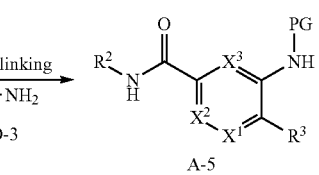

A-4

Amide linking $R^2$—$NH_2$

ED-3

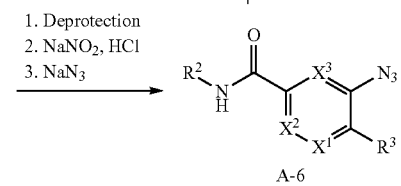

A-5

1. Deprotection
2. $NaNO_2$, HCl
3. $NaN_3$

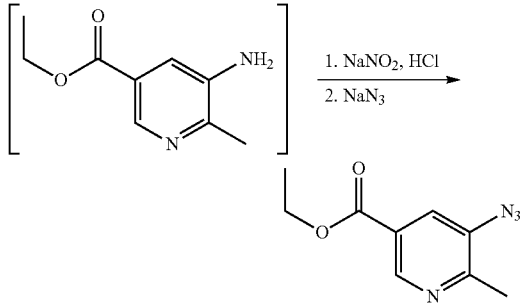

A-6

Example Compounds of Type I:

Compounds according to the invention with an N-linked triazole ring (type I) may be prepared for example by one of the synthesis routes (synthesis methods 1-3) shown in Reaction scheme A.

Starting from heteroaromatic, protected amino acid esters ED-1 the azide intermediates A-1 are obtained after elimination of the amino protecting group (for Boc e.g. TFA or HCl), diazotisation with sodium nitrite in hydrochloric acid solution and reaction of the diazonium salt formed with sodium azide.

These are reacted (synthesis method 1) in a copper-catalysed, 1,3-dipolar cycloaddition reaction with heteroarylalkynes ED-2 and in this way the triazole ring substituted by $R^1$ is prepared (A-2). Finally the ester A-2 obtained is saponified to form the free acid A-3 (the ethyl ester with LiOH or NaOH, for example) and the amide coupling is carried out with an amino component ED-3.

Alternatively (synthesis method 2) first of all the saponification and amide coupling to form the azide A-6 may also take place starting from azide A-1, the example compounds I then being obtained by final 1,3-dipolar cycloaddition with alkyne ED-2.

Starting from ED-1 first of all the saponification to form the free acid A-4 and then the amide coupling with ED-3 to form the amide A-5 may also be carried out (synthesis method 3) before the reaction sequence is completed by the formation of the triazole ring via the intermediate A-6.

Synthesis of Examples I-1-I-207 a) Method of Synthesising A-1a

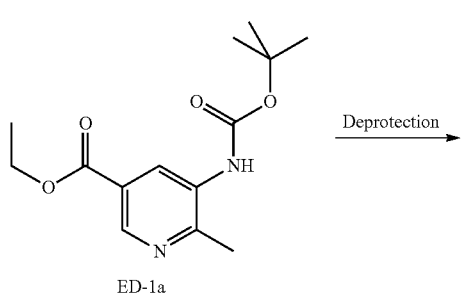

ED-1a

Deprotection

-continued

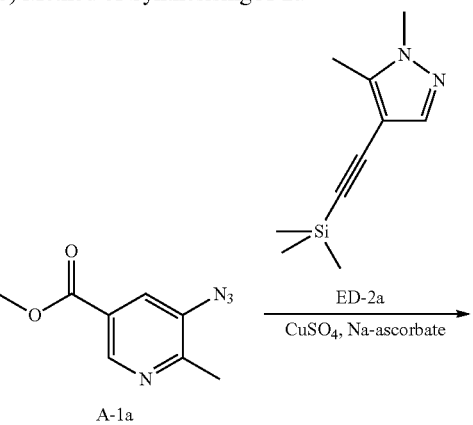

A-1a

Ester ED-1a (743 mg, 2.65 mmol) is suspended in 12.5 N aqueous hydrochloric acid (2.5 mL) and at RT the mixture is stirred for 2 h. 13 mL of $H_2O$ are added, the mixture is cooled to 0° C., a cooled aqueous $NaNO_2$ solution (219 mg, 3.18 mmol in 3.5 mL $H_2O$) is slowly added thereto and the mixture is stirred for 30 min. At 0° C. an aqueous $NaN_3$ solution (209 mg, 31.8 mmol in 3.5 mL $H_2O$) is added and the mixture is stirred for a further 30 min. It is diluted with water and extracted 3× with DCM (30 mL each time). The combined organic phases are dried on $MgSO_4$, filtered and evaporated down. The azide A-1a thus obtained (HPLC-MS: $t_{Ret.}$=1.42 min; MS $(M+H)^+$=207) is further reacted directly without any additional cleaning step.

Analogously to the method of synthesising A-1a further azides A-1 are obtained from the corresponding educts ED-1.

b) Method of Synthesising A-2a

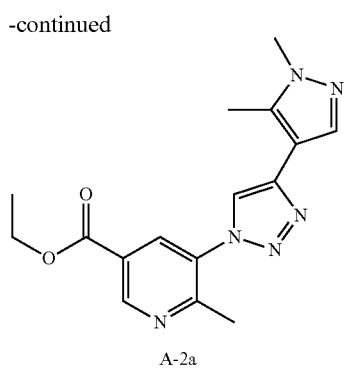

A-2a

In order to cleave the trimethylsilyl group 1,5-dimethyl-4-trimethylsilanylethynyl-1H-pyrazole ED-2a (760 mg, 3.95 mmol) is placed in MeOH (10 mL) and stirred overnight at RT together with KF (374 mg, 6.43 mmol). Then A-1a (546 mg, 2.65 mmol), sodium ascorbate (577 mg, 2.91 mmol in 2 mL H$_2$O) and 1.2 mL of a 0.8 M aqueous CuSO$_4$ solution are added and the mixture is stirred overnight at RT. The reaction mixture is evaporated down using the rotary evaporator, taken up in H$_2$O and extracted 3× with DCM. The combined organic phases are dried on MgSO$_4$, filtered and evaporated down. The residue is taken up in a little DMF and purified by preparative HPLC. The product-containing fractions of A-2a are freeze-dried.

Analogously to the method of synthesising A-2a further intermediates A-2 are obtained from the corresponding components A-1 and ED-2.

c) Method of Synthesising A-3a

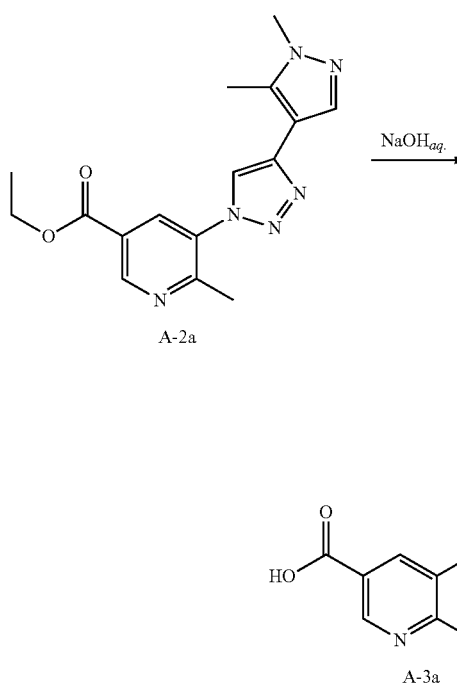

A-2a (530 mg, 1.70 mmol) is taken up in H$_2$O (3 mL) and MeOH (1.5 mL), combined with 1.0 M sodium hydroxide solution (6.0 mL) and stirred for 2 h at 40° C. The mixture is neutralised with hydrochloric acid and evaporated down using the rotary evaporator. The residue is taken up in a little DMF and purified by preparative HPLC. The product-containing fractions of A-3a (HPLC-MS: $t_{Ret.}$=0.36 min; MS (M+H)$^+$=299) are freeze-dried.

Analogously to this method other free acids A-3 are obtained from the corresponding esters A-2.

d) Method of Synthesising Example Compound I-1 (Method A—Activation Using GHOSEZ Reagent)

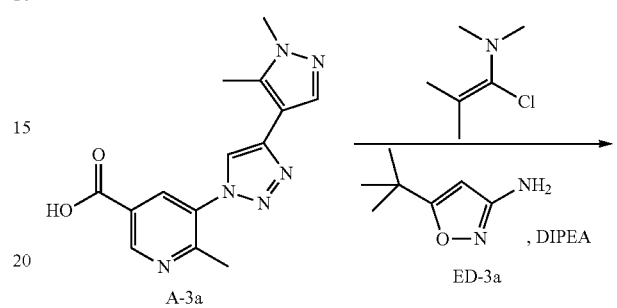

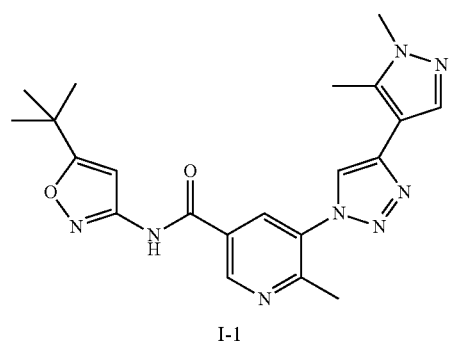

I-1

A-3a (55.8 mg, 0.19 mmol) is placed in DCM (3 mL), combined with 1-chloro-N,N.2-trimethylpropenylamine (43 µL, 0.19 mmol) and stirred overnight at RT. 5-tert-butyl-isoxazol-3-ylamine ED-3a (25.5 mg, 0.18 mmol) dissolved in DCM and DIPEA (79 µL, 0.46 mmol) are added and the mixture is stirred for 3 h at RT. Then it is evaporated down using the rotary evaporator, the residue is taken up in a little DMF and purified by preparative HPLC. The product-containing fractions of I-1 (HPLC-MS: $t_{Ret.}$=1.47 min; MS (M+H)$^+$=421) are freeze-dried.

e) Method of Synthesising Example Compound I-4 (Method B—Activation with HATU)

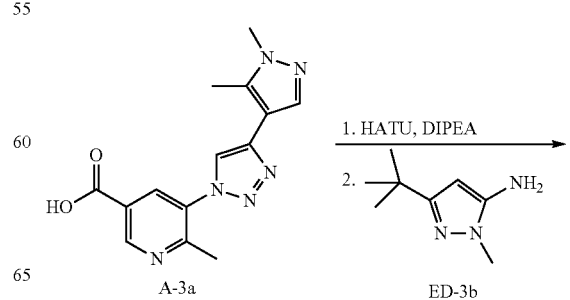

-continued

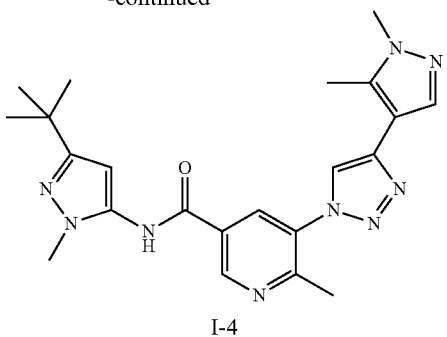

I-4

A-3a (75.2 mg, 0.25 mmol) is placed in THF (3 mL), mixed with HATU (112 mg, 0.35 mmol) and DIPEA (50 µL, 0.30 mmol) and stirred for 30 min at RT. Then 5-tert-butyl-2-methyl-2H-pyrazol-3-ylamine ED-3b (47.1 mg, 0.31 mmol) are added and the mixture is left overnight at RT and stirred for a further 24 h at 50° C. Then it is evaporated down using the rotary evaporator, the residue is taken up in a little DMF and purified by preparative HPLC. The product-containing fractions of I-4 (HPLC-MS: $t_{Ret.}$=1.38 min; MS $(M+H)^+$= 434) are freeze-dried.

f) Method of Synthesising the Example Compounds I-56 and I-61

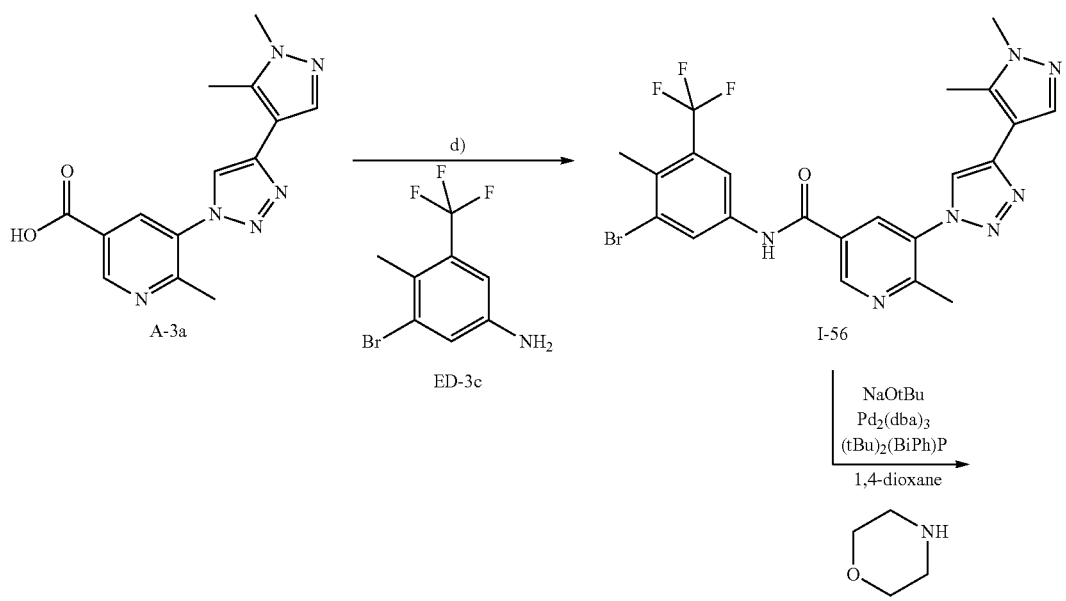

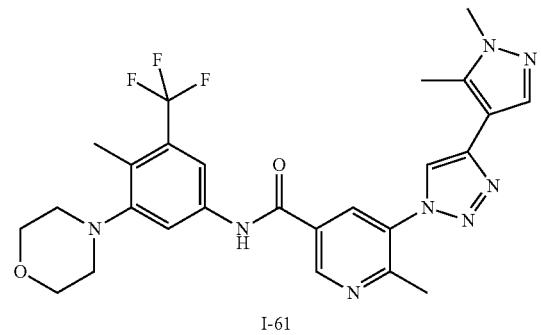

I-61

A-3a (1.30 g, 3.05 mmol) is activated as described in reaction method d) and reacted with ED-3c (1.00 g, 3.07 mmol). The product-containing fractions of I-56 (HPLC-MS: $t_{Ret.}$=2.02 min; MS (M+H)$^+$=534/536) are freeze-dried.

I-56 (75 mg, 0.14 mmol) is placed in 1,4-dioxane (2 mL) with NaOtBu (55 mg, 0.56 mmol), Pd$_2$(dba)$_3$ (25 mg, 0.03 mmol) and biphenyl-2-yl-di-tert.-butyl-phosphane (19 mg, 0.06 mmol), mixed with morpholine (50 µL, 0.57 mmol) and stirred overnight at 45° C. under argon in a sealed vial. Then the reaction mixture is filtered, diluted with DMF and H$_2$O and purified by preparative HPLC. The product-containing fractions of I-61 (HPLC-MS: $t_{Ret.}$=1.86 min; MS (M+H)$^+$= 541) are freeze-dried.

g) Method of Synthesising the Example Compounds I-126 and I-97

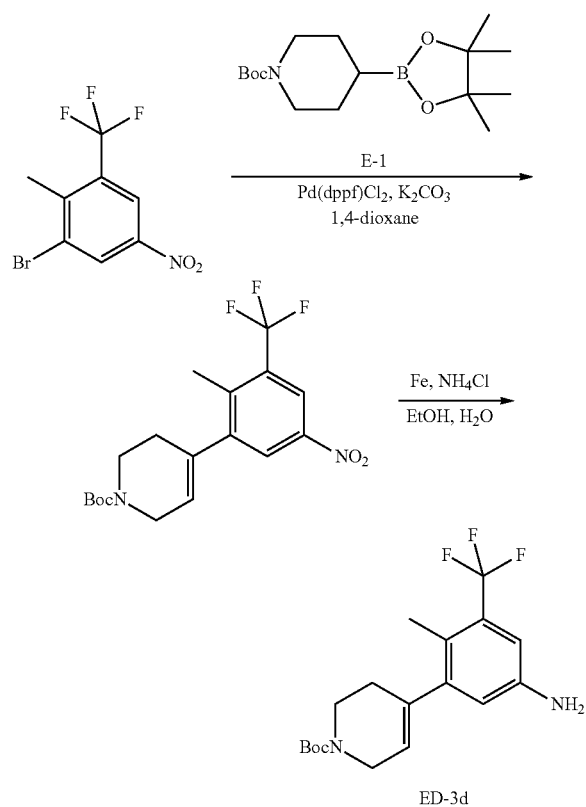

3-bromo-5-trifluoromethyl-4-methyl-nitrobenzene (1.01 g, 3.55 mmol), tert. butyl 4-(4,4,5,5-tetramethyl-1,3,2-dioxaborolan-2-yl)-3,6-dihydro-2H-pyridine-1-carboxylate (1.38 g, 4.45 mmol), Pd(dppf)Cl$_2$.CH$_2$Cl$_2$ (434 mg, 0.53 mmol) and K$_2$CO$_3$ (1.61 g, 11.6 mmol) are placed in 1,4-dioxane (10 mL) and H$_2$O (3 mL) under protective gas and stirred for 1.5 h at 100° C. After cooling the reaction mixture is diluted with DCM and H$_2$O and the aqueous phase is separated off. The organic phase is filtered through silica gel, evaporated down using the rotary evaporator, the residue is taken up in EtOAc and washed with saturated NaCl solution. The organic phase is dried on MgSO$_4$, filtered and evaporated down using the rotary evaporator. The intermediate compound thus obtained (HPLC-MS: $t_{Ret.}$=2.34 min) is used further without any further purification steps. The intermediate compound obtained (1.30 g, 2.36 mmol) is placed in EtOH (15 mL), combined with NH$_4$Cl solution (67 mg, 1.26 mmol in 20 mL H$_2$O) and heated to 75° C. Fe chips are added batchwise (1.36 g, 24.4 mmol) and the mixture is stirred for 30 min at 75° C. The reaction mixture is filtered through a glass fibre filter, washed with MeOH and the filtrate is evaporated down using the rotary evaporator. The ED-3d thus obtained is further used without any further purification steps.

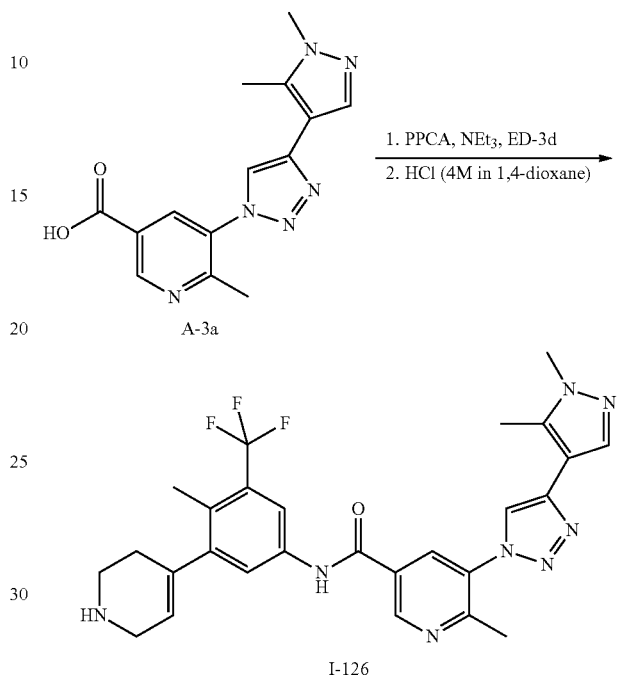

A-3a (839 mg, 2.35 mmol) and ED-3d (609 mg, 2.04 mmol) are placed in THF (8 mL) and combined with NEt$_3$ (1.6 mL, 11.5 mmol). Propanephosphonic acid cycloanhydride (3.1 mL, 50% in DMF, 5.31 mmol) is added and the mixture is stirred for 2.5 h at RT. The reaction mixture is evaporated down using the rotary evaporator, the residue is taken up in a little DMF and purified by preparative HPLC. The product-containing fractions of the still Boc-protected example compound I-126 (HPLC-MS: $t_{Ret.}$=2.20 min; MS (M+H)$^+$=635) are freeze-dried.

The still Boc-protected example compound (241 mg, 0.38 mmol) is placed in 1,4-dioxane (5 mL), combined with conc. HCl (1 mL) and stirred for 2 h at RT. The reaction mixture is evaporated down using the rotary evaporator, the residue is taken up in a little DMF and H$_2$O and purified by preparative HPLC. The product-containing fractions of I-126 (HPLC-MS: $t_{Ret.}$=1.79 min; MS (M+H)$^+$=537) are freeze-dried.

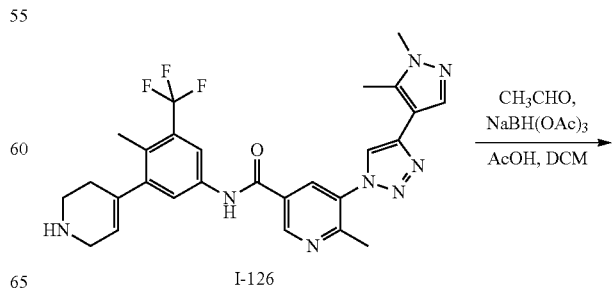

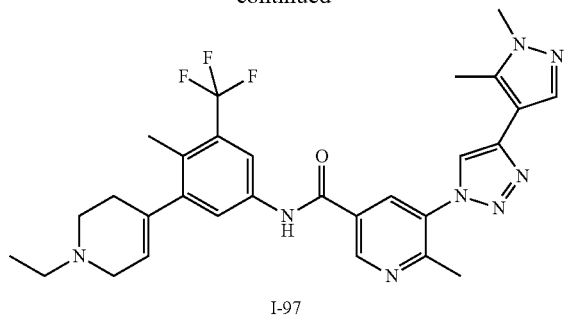

I-126 (75 mg, 0.14 mmol) is placed in DCM (1.5 mL), combined with AcOH (40 µL, 0.70 mmol) and acetaldehyde (16 µL, 0.28 mmol) and stirred for 30 min. Then sodium trisacetoxyborohydride (51 mg, 0.24 mmol) is added and the mixture is stirred for 2 d at RT. The reaction mixture is evaporated down using the rotary evaporator, the residue is taken up in a little MeOH and H$_2$O and purified by preparative HPLC. The product-containing fractions of I-97 (HPLC-MS: $t_{Ret.}$=1.98 min; MS (M+H)$^+$=565) are freeze-dried.

h) Method of Synthesising A-6a

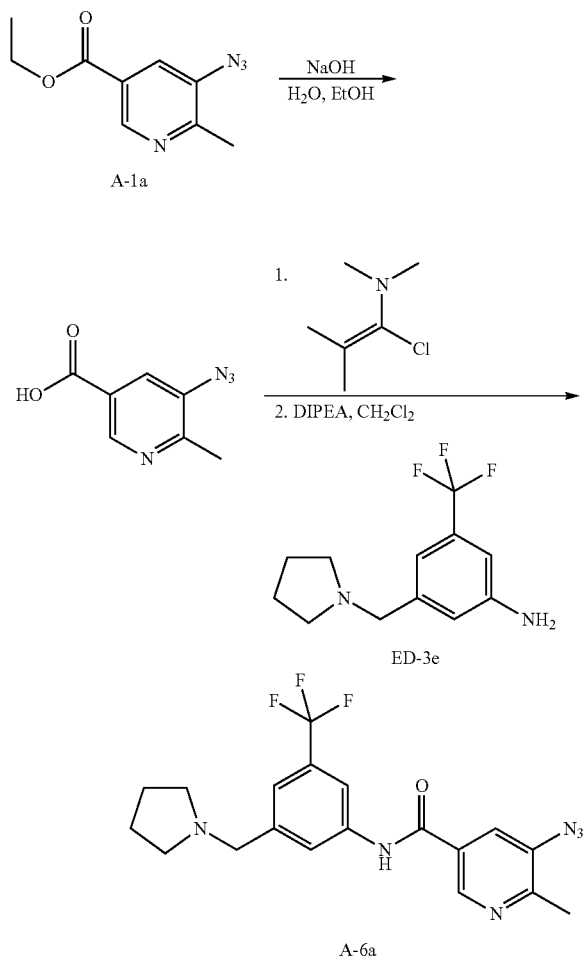

A-1a (1.49 g, 7.08 mmol) is taken up in water (1 mL) and EtOH (7.5 mL), combined with sodium hydroxide solution (8 M, 3.5 mL) and stirred for 2 h at 40° C. The reaction mixture is evaporated down, the still moist residue is taken up in hydrochloric acid and filtered. The filtrate is evaporated down again, taken up in a little DMF and purified by preparative HPLC. The product-containing fractions of the free carboxylic acid are freeze-dried.

The free nicotinic acid (75 mg, 0.42 mmol) is placed in DCM (2.5 mL), mixed with 1-chloro-N,N,2-trimethylpropenylamine (145 µL, 1.10 mmol) and stirred for 3.5 h at RT. Aniline ED-3e (104 mg, 0.43 mmol) and DIPEA (108 µL, 0.63 mmol) are added and the mixture is stirred for 1 h at RT. The reaction mixture is evaporated down, taken up in a little DMF and purified by preparative HPLC. The product-containing fractions of A-6a (HPLC-MS: $t_{Ret.}$=2.10 min; MS (M+H)$^+$=405) are freeze-dried.

Analogously to this method other azides A-6 may be obtained from the corresponding azides A-1.

i) Method of Synthesising Example Compound I-15

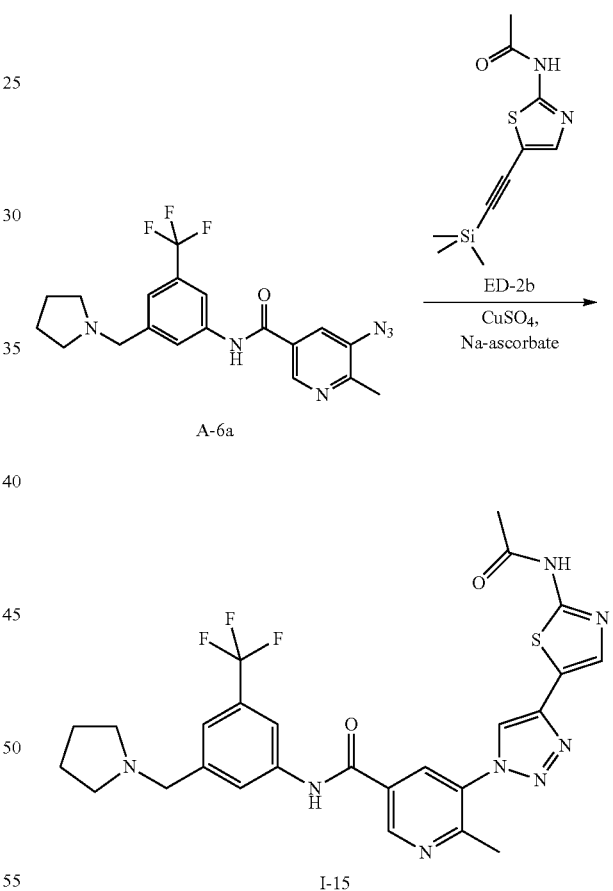

ED-2b (66.2 mg, 0.26 mmol) is taken up in MeOH (3 mL), mixed with KF (29.4 mg, 0.51 mmol) and stirred for 3 h at 30° C. Then A-6a (71.0 mg, 0.18 mmol), 0.8 M aqueous CuSO$_4$ solution (22 µL, 0.02 mmol) and Na-ascorbate (36.3 mg, 0.18 mmol) are added and the mixture is stirred for a further 4 d at 40° C. The reaction mixture is evaporated down using the rotary evaporator, the residue is taken up in a little DMF and purified by preparative HPLC. The product-containing fractions of I-15 (HPLC-MS: $t_{Ret.}$=1.84 min; MS (M+H)$^+$=571) are freeze-dried.

j) Method of Synthesising A-4a

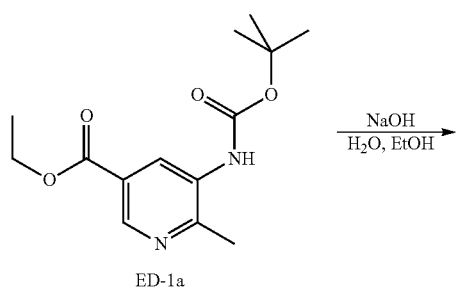

ED-1a

ED-1a (28.4 g, 101 mmol) is taken up in MeOH (120 mL) and H$_2$O (100 mL), mixed with sodium hydroxide solution (80 mL, 2 M in H$_2$O) and stirred for 8 h at 120° C. Then the volatile constituents are eliminated using the rotary evaporator and the residue is slowly acidified to pH 4 with hydrochloric acid (2 N), during which time a partial quantity of A-4a (HPLC-MS: t$_{Ret.}$=0.34 min; MS (M+H)$^+$=253) is precipitated as a solid which is isolated by filtration. The filtrate is extracted three times with EtOAc, dried on MgSO$_4$, filtered and evaporated down using the rotary evaporator, while further product A-4a is isolated.

k) Method of Synthesising A-5a

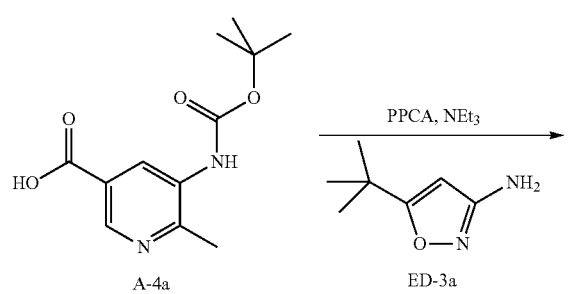

Propanephosphonic cycloanhydride (52.5 mL, 50% in EtOAc) is slowly added dropwise to A-4a (14.7 g, 58.4 mmol), ED-3a (9.06 g, 62.7 mmol) and NEt$_3$ (27 mL, 195 mmol) in THF (159 mL) and the mixture is stirred overnight at RT. After filtration of the reaction mixture the filtrate is evaporated down using the rotary evaporator and the residue is combined with H$_2$O, during which time A-5a (HPLC-MS: t$_{Ret.}$=1.83 min; MS (M+H)$^+$=375) is precipitated as a solid which is filtered off and is used further without any additional purification steps.

l) Method of Synthesising A-6b

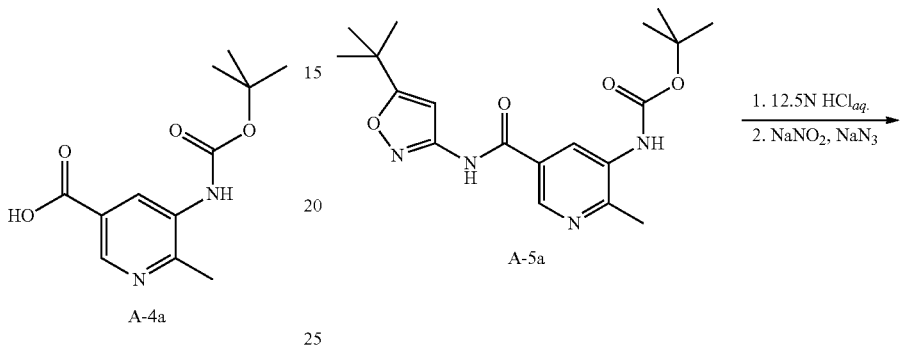

In order to cleave the Boc protective group A-5a (20.5 g, 54.8 mmol) is placed in 12.5 N hydrochloric acid (15 mL) and stirred overnight at RT. Then the reaction mixture is cooled to 0° C., a pre-chilled solution of NaNO$_2$ (4.88 g, 70.8 mmol) in H$_2$O is slowly added dropwise thereto and the mixture is stirred for another 90 min. Then at 0° C. NaN$_3$ (4.39 g, 66.9 mmol) dissolved in H$_2$O is slowly added and the reaction mixture is stirred for 30 min. By diluting with H$_2$O a precipitate is formed which is filtered off and dissolved in DCM. The organic phase is extracted twice with H$_2$O and evaporated down using the rotary evaporator. A-6b (HPLC-MS: t$_{Ret.}$=1.70 min; MS (M+H)$^+$=301) is recrystallised from a little isopropanol to purify it.

Analogously to methods k) and l) further azides A-6 are obtained from the corresponding carboxylic acids A-4 and the amines ED-3 with the amides A-5 as intermediate compounds.

m) Method of Synthesising Example Compound I-34

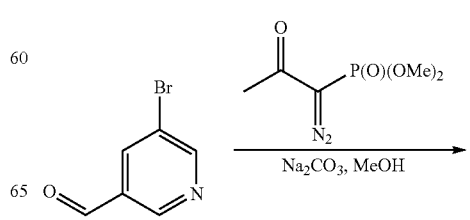

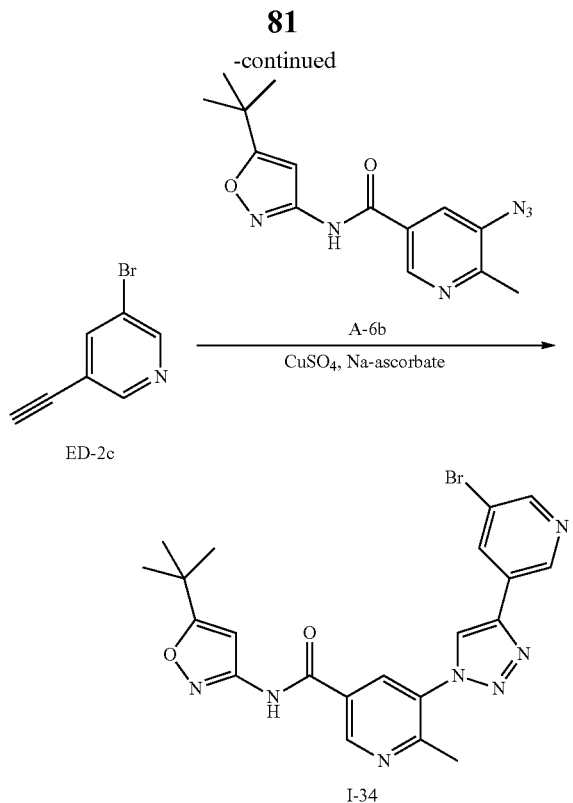

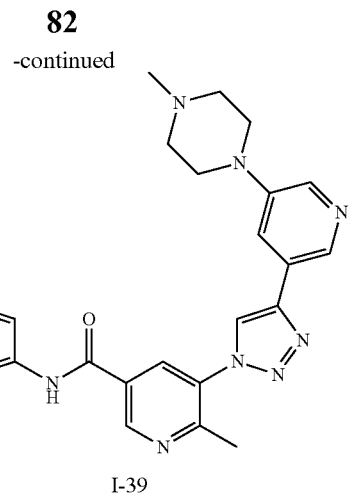

I-39

I-34 (66 mg, 0.14 mmol), NaOtBu (65 mg, 0.65 mmol), biphenyl-2-yl-di-tert-butyl-phosphane (16 mg, 0.06 mmol) and Pd$_2$(dba)$_3$ (35 mg, 0.04 mmol) are placed in 1,4-dioxane (2 mL) under a protective gas atmosphere, combined with N-methylpiperazine (60 mg, 0.60 mmol) and stirred overnight at 45° C. in a sealed reaction vessel. Then the reaction mixture is diluted with H$_2$O and DMF and purified by preparative HPLC. The product-containing fractions of I-39 (HPLC-MS: t$_{Ret.}$=1.62 min; MS (M+H)$^+$=502) are freeze-dried.

o) Method of Synthesising Example Compound I-187

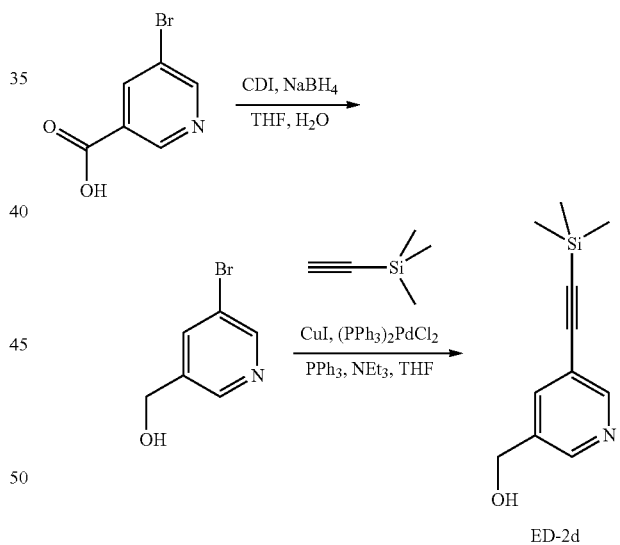

5-bromo-pyridine-3-carbaldehyde (1.48 g, 7.71 mmol) and das BESTMANN-OHIRA reagent (2.03 g, 10.6 mmol) are placed in MeOH (20 mL), combined with K$_2$CO$_3$ (1.16 g, 8.37 mmol) and stirred for 12 h at RT. Then the reaction mixture is evaporated down using the rotary evaporator, the residue is taken up in DCM and extracted three times with H$_2$O. The organic phase is dried on MgSO$_4$, filtered and evaporated down using the rotary evaporator. ED-2c (HPLC-MS: t$_{Ret.}$=1.37 min) is obtained which is used further without any additional purification steps.

ED-2c (1.67 g, 9.15 mmol) is placed in MeOH (40 mL), combined first of all with A-6b (2.00 g, 6.66 mmol) and after 5 min successively with an aqueous sodium ascorbate solution (6.0 mL, 1 M) and an aqueous CuSO$_4$ solution (14 mL, 0.1 M) and stirred for 48 h at 45° C. Then the reaction mixture is evaporated down using the rotary evaporator, the residue is taken up in H$_2$O and the precipitate formed is filtered off. The solid is stirred with saturated EDTA solution, filtered off again and I-34 (HPLC-MS: t$_{Ret.}$=1.79 min; MS (M+H)$^+$=482/484) is obtained. For further purification some of the solid is taken up in DMF and purified by preparative HPLC. The product-containing fractions of I-34 are freeze-dried.

n) Method of Synthesising Example Compound I-39

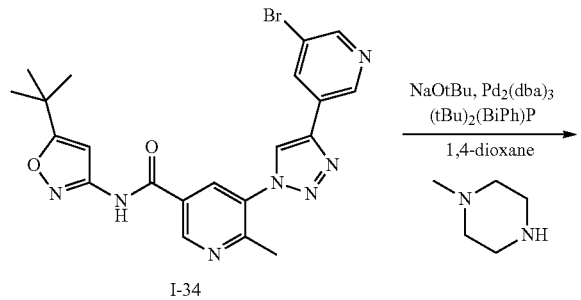

5-Bromonicotinic acid (3.44 g, 17.0 mmol) is placed in THF (40 mL), combined with CDI (3.00 g, 18.5 mmol) and stirred for 2 h at 50° C. Then while cooling with ice the reaction mixture is poured onto an aqueous NaBH$_4$ solution (600 mg, 15.9 mmol in 100 mL H$_2$O), stirred for 3 d at RT and extracted 7× with DCM. The combined organic phases are dried on Na$_2$SO$_4$, filtered and evaporated down using the rotary evaporator. The (5-bromo-pyridin-3-yl)-methanol thus obtained (HPLC-MS: t$_{Ret.}$=0.21 min; MS (M+H)$^+$=188/190) is further used without any further purification steps.

(5-bromo-pyridin-3-yl)-methanol (3.00 g, 16.0 mmol) is placed in THF (60 mL) and NEt$_3$ (6 mL) under protective gas, combined with CuI (100 mg, 0.53 mmol), (PPh$_3$)$_2$Cl$_2$ (430 mg, 0.61 mmol), PPh₃ (180 mg, 0.69 mmol) and TMS-acetylene (2.9 mL, 20.9 mmol) and stirred for 1 h at 80° C. The reaction mixture is evaporated down using the rotary evaporator and purified by normal phase chromatography (DCM/MeOH; 90:10). The product-containing fractions of ED-2d (HPLC-MS: $t_{Ret.}$=1.81 min; MS (M+H)$^+$=206) are evaporated down using the rotary evaporator.

ED-2d (1.00 g, 3.30 mmol) is placed in MeOH (20 mL), mixed with KF (310 mg, 5.33 mmol) and stirred for 2 h at RT. Then A-6b (300 mg, 1.00 mmol) in MeOH (20 mL), aqueous sodium ascorbate solution (2.5 mL, 1 M) and aqueous CuSO₄ solution (788 µL, 0.8 M) are added successively and the mixture is stirred for 4 h at 50° C. MeOH is eliminated using the rotary evaporator and the residue is combined with H₂O. The resulting precipitate of the hydroxymethyl compound formed is filtered off, dried in the vacuum dryer and further used without any further purification steps.

The crude product of the hydroxymethyl compound (1.4 g, 3.23 mmol) is placed in DCM (30 mL) and DMF (3 mL), combined with SOCl₂ (3.0 mL) and refluxed for 1 h. Then the reaction mixture is evaporated down using the rotary evaporator, taken up in DCM/MeOH, the resulting precipitate of the product is filtered off and purified by normal phase chromatography (DCM/MeOH; gradient from 100:0 to 40:60). The product-containing fractions of the chloromethyl compound initially obtained as a further intermediate product (HPLC-MS: $t_{Ret.}$=1.68 min; MS (M+H)$^+$=452) are evaporated down using the rotary evaporator.

The chloromethyl compound obtained (80.0 mg, 0.18 mmol) is placed in DCM (3 mL) and DMF (1 mL), combined with dimethylamine (17 mg, 0.35 mmol) and stirred overnight at 50° C. Then the reaction mixture is evaporated down using the rotary evaporator and purified by preparative HPLC. The product-containing fractions of I-187 (HPLC-MS: $t_{Ret.}$=1.57 min; MS (M+H)$^+$=461) are freeze-dried.

Analogously to reaction methods a) to g) described above (synthesis method 1) for synthesising the example compounds I-1, I-4, I-56, I-61, I-97 and I-126 or a), h) and i) (synthesis method 2) for synthesising the example compound I-15 or j) to o) (synthesis method 3) for synthesising the example compounds I-34, I-39 and I-187, the other example compounds of type I in the following Table 1 (Examples I-1 to I-207) or comparable other Examples may be obtained from the corresponding precursors which are either commercially obtainable or are prepared by methods known from the literature.

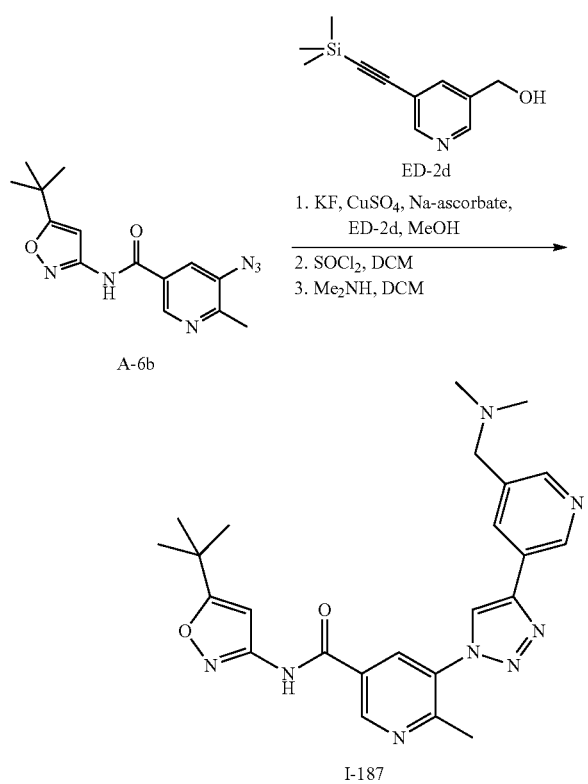 [SMILES: C[Si](C)(C)C#Cc1cncc(CO)c1 ; Cc1ncc(C(=O)Nc2cc(C(C)(C)C)on2)cc1N=[N+]=[N-] ; Cc1ncc(C(=O)Nc2cc(C(C)(C)C)on2)cc1-n1cc(-c2cncc(CN(C)C)c2)nn1]

TABLE 1

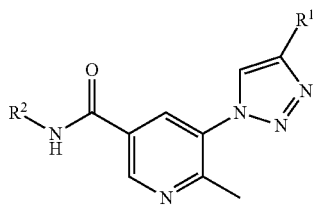

Example compounds I-1 to I-207

| # | Structure | $t_{Ret.}$ (HPLC) [min] | MS (M + H)$^+$ |
|---|---|---|---|
| I-1 | 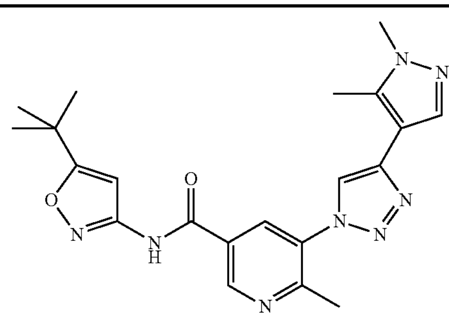 | 1.47 | 421 |

TABLE 1-continued

Example compounds I-1 to I-207

| # | Structure | $t_{Ret.}$ (HPLC) [min] | MS (M + H)+ |
|---|---|---|---|
| I-2 | 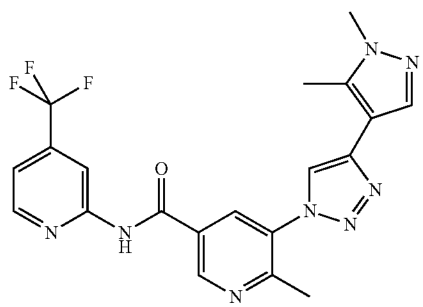 [SMILES: Cc1ncc(C(=O)Nc2cc(C(F)(F)F)ccn2)cc1-n1cc(-c2cnn(C)c2C)nn1] | 1.57 | 443 |
| I-3 | 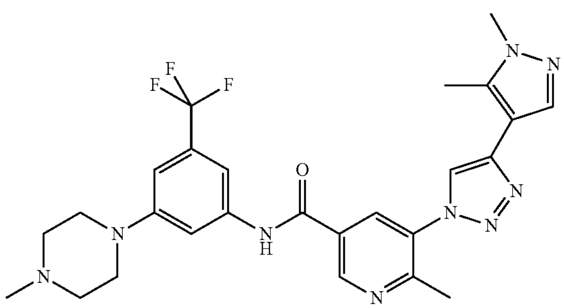 | 1.80 | 540 |
| I-4 | 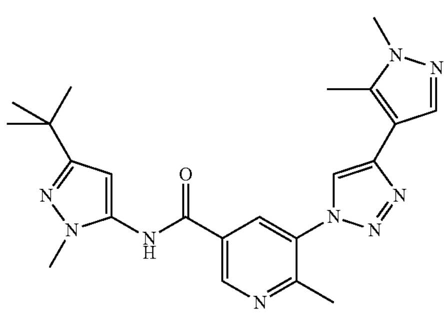 [SMILES: Cc1ncc(C(=O)Nc2cc(C(C)(C)C)nn2C)cc1-n1cc(-c2cnn(C)c2C)nn1] | 1.38 | 434 |
| I-5 | 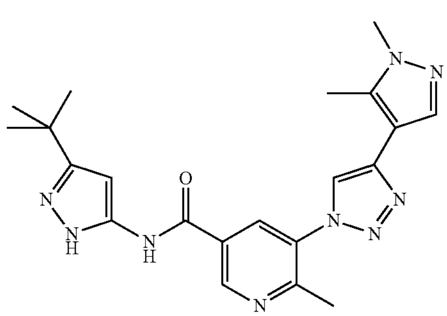 [SMILES: Cc1ncc(C(=O)Nc2cc(C(C)(C)C)n[nH]2)cc1-n1cc(-c2cnn(C)c2C)nn1] | | |

TABLE 1-continued
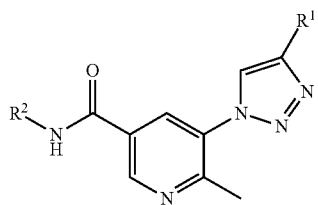
Example compounds I-1 to I-207
| # | Structure | $t_{Ret.}$ (HPLC) [min] | MS (M + H)⁺ |
|---|---|---|---|
| I-6 | 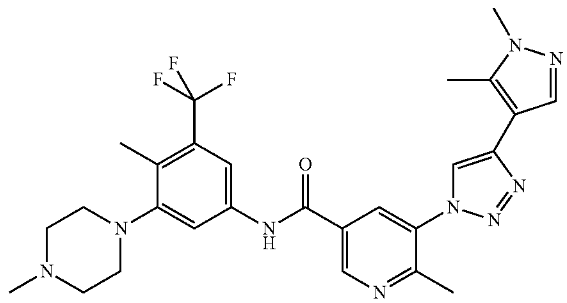 [SMILES: Cc1ncc(C(=O)Nc2cc(N3CCN(C)CC3)c(C)c(C(F)(F)F)c2)cc1-n1cc(-c2cnn(C)c2C)nn1] | 1.98 | 554 |
| I-7 | 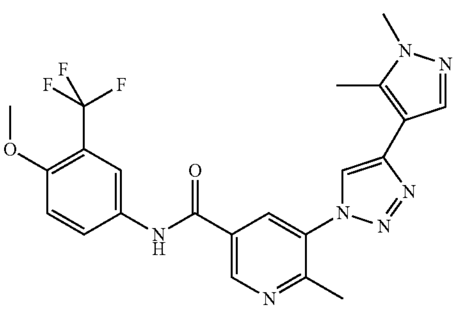 [SMILES: COc1ccc(NC(=O)c2cnc(C)c(-n3cc(-c4cnn(C)c4C)nn3)c2)cc1C(F)(F)F] | 1.84 | 472 |
| I-8 | 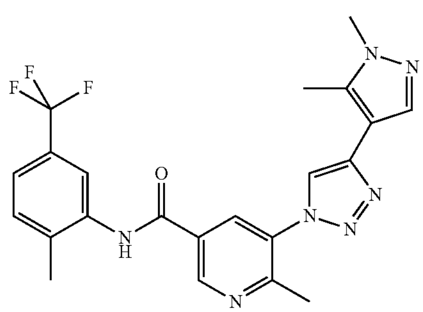 [SMILES: Cc1ccc(C(F)(F)F)cc1NC(=O)c1cnc(C)c(-n2cc(-c3cnn(C)c3C)nn2)c1] | 1.73 | 456 |
| I-9 | 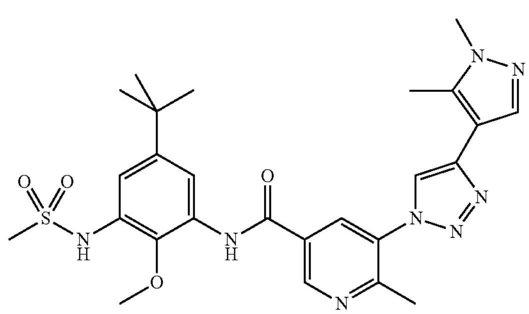 [SMILES: COc1c(NC(=O)c2cnc(C)c(-n3cc(-c4cnn(C)c4C)nn3)c2)cc(C(C)(C)C)cc1NS(C)(=O)=O] | 1.37 | 553 |

TABLE 1-continued
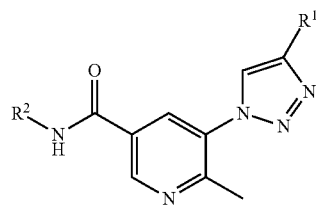
Example compounds I-1 to I-207
| # | Structure | t_Ret. (HPLC) [min] | MS (M + H)+ |
|---|---|---|---|
| I-10 | 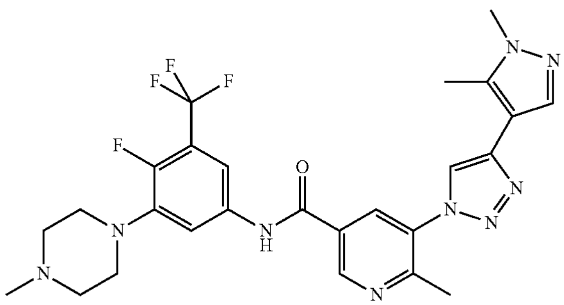 [SMILES: Cc1ncc(C(=O)Nc2cc(N3CCN(C)CC3)c(F)c(C(F)(F)F)c2)cc1-n1cc(-c2cnn(C)c2C)nn1] | 1.89 | 558 |
| I-11 | 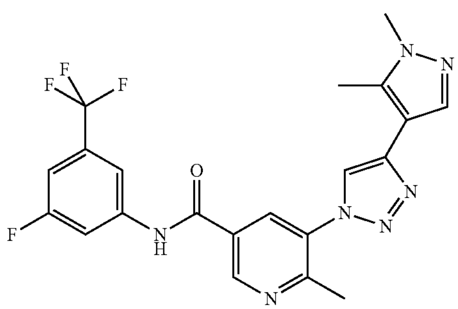 [SMILES: Cc1ncc(C(=O)Nc2cc(F)cc(C(F)(F)F)c2)cc1-n1cc(-c2cnn(C)c2C)nn1] | | |
| I-12 | 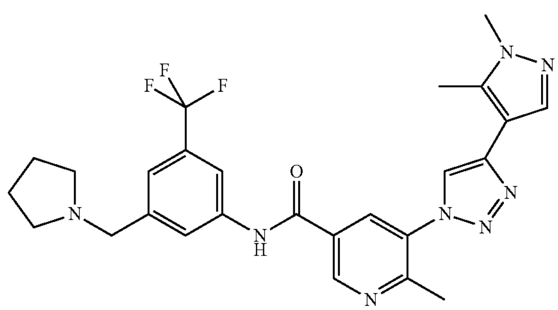 [SMILES: Cc1ncc(C(=O)Nc2cc(CN3CCCC3)cc(C(F)(F)F)c2)cc1-n1cc(-c2cnn(C)c2C)nn1] | 1.96 | 525 |
| I-13 | 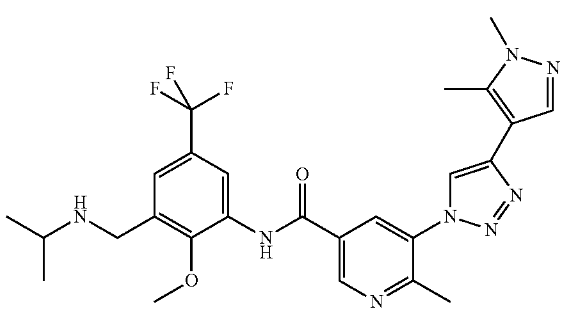 [SMILES: COc1c(CNC(C)C)cc(C(F)(F)F)cc1NC(=O)c1cnc(C)c(-n2cc(-c3cnn(C)c3C)nn2)c1] | 1.80 | 543 |

TABLE 1-continued
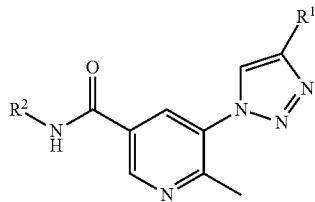
Example compounds I-1 to I-207
| # | Structure | $t_{Ret.}$ (HPLC) [min] | MS (M + H)$^+$ |
|---|---|---|---|
| I-14 | 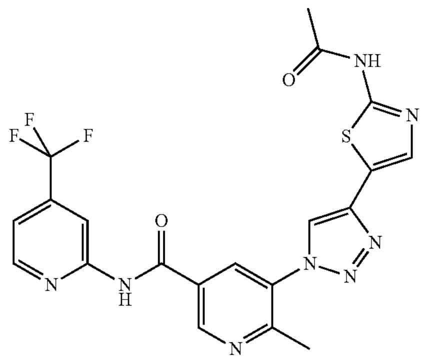 [SMILES: CC(=O)Nc1ncc(-c2cn(-c3cc(C(=O)Nc4cc(C(F)(F)F)ccn4)cnc3C)nn2)s1] | 1.54 | 489 |
| I-15 | 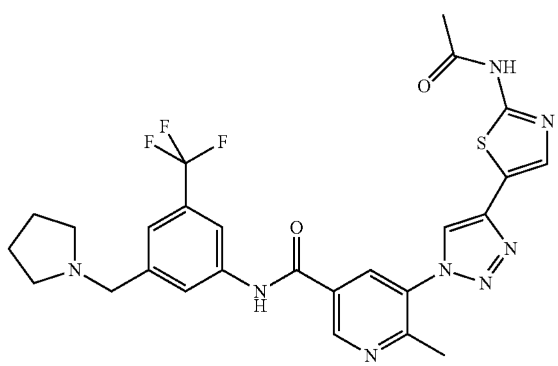 [SMILES: CC(=O)Nc1ncc(-c2cn(-c3cc(C(=O)Nc4cc(CN5CCCC5)cc(C(F)(F)F)c4)cnc3C)nn2)s1] | 1.84 | 571 |
| I-16 | 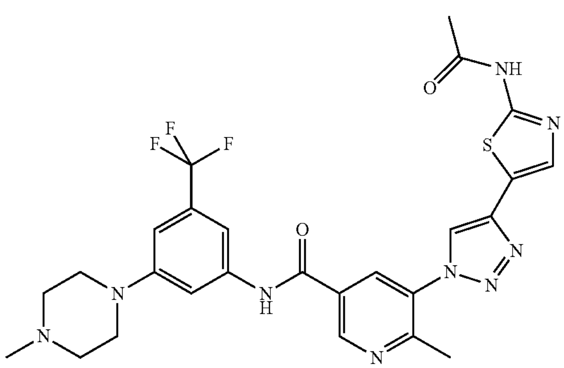 [SMILES: CC(=O)Nc1ncc(-c2cn(-c3cc(C(=O)Nc4cc(N5CCN(C)CC5)cc(C(F)(F)F)c4)cnc3C)nn2)s1] | 1.69 | 586 |

TABLE 1-continued
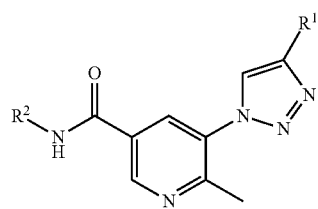
Example compounds I-1 to I-207
| # | Structure | t$_{Ret.}$ (HPLC) [min] | MS (M + H)$^+$ |
|---|---|---|---|
| I-17 | 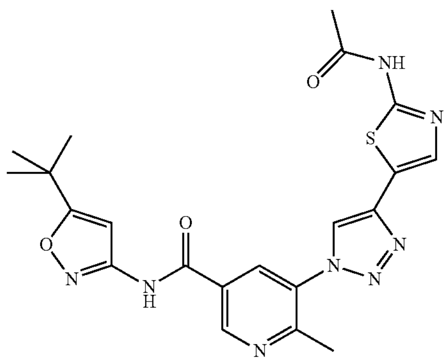 [SMILES: CC(=O)Nc1ncc(-c2cn(-c3cc(C(=O)Nc4cc(C(C)(C)C)on4)cnc3C)nn2)s1] | | |
| I-18 | 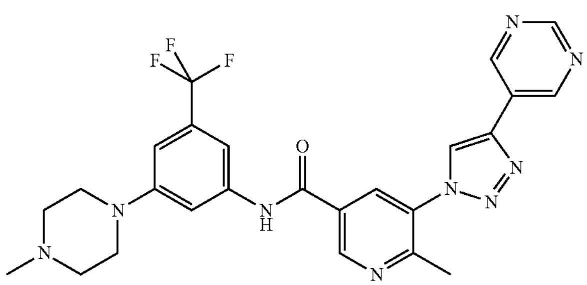 [SMILES: Cc1ncc(C(=O)Nc2cc(N3CCN(C)CC3)cc(C(F)(F)F)c2)cc1-n1cc(-c2cncnc2)nn1] | 1.65 | 524 |
| I-19 | 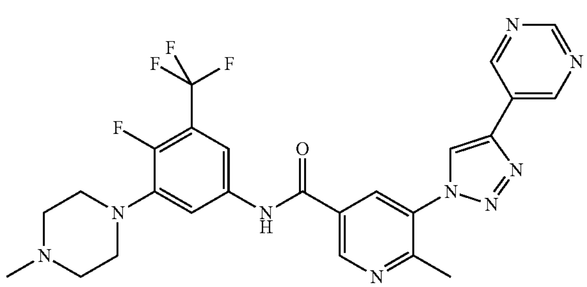 | | |
| I-20 | 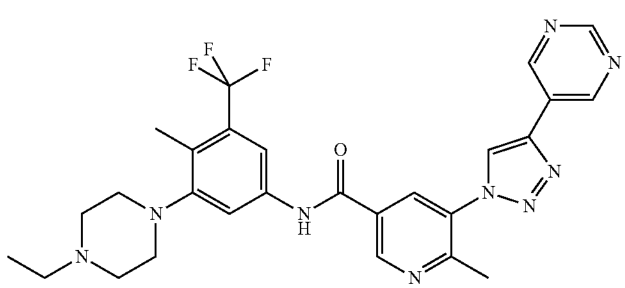 [SMILES: CCN1CCN(c2cc(NC(=O)c3cnc(C)c(-n4cc(-c5cncnc5)nn4)c3)cc(C(F)(F)F)c2C)CC1] | 1.98 | 552 |

TABLE 1-continued
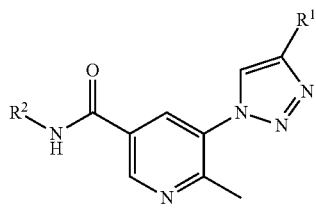
Example compounds I-1 to I-207
| # | Structure | t$_{Ret.}$ (HPLC) [min] | MS (M + H)$^+$ |
|---|---|---|---|
| I-21 | 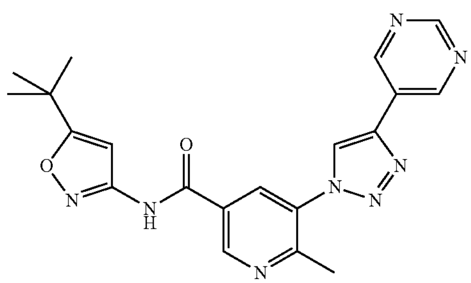 [SMILES: Cc1ncc(C(=O)Nc2cc(C(C)(C)C)on2)cc1-n1cc(-c2cncnc2)nn1] | 1.52 | 405 |
| I-22 | 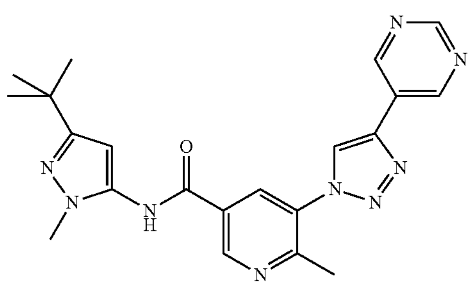 [SMILES: Cc1ncc(C(=O)Nc2cc(C(C)(C)C)nn2C)cc1-n1cc(-c2cncnc2)nn1] | | |
| I-23 | 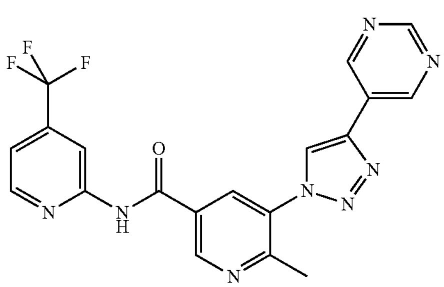 [SMILES: Cc1ncc(C(=O)Nc2cc(C(F)(F)F)ccn2)cc1-n1cc(-c2cncnc2)nn1] | 1.42 | 427 |
| I-24 | 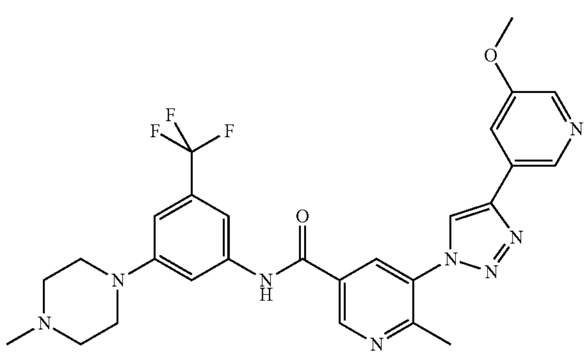 [SMILES: COc1cncc(-c2cn(-c3cc(C(=O)Nc4cc(N5CCN(C)CC5)cc(C(F)(F)F)c4)cnc3C)nn2)c1] | 1.85 | 553 |

TABLE 1-continued
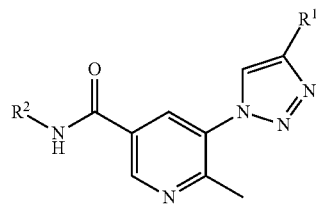
Example compounds I-1 to I-207
| # | Structure | $t_{Ret.}$ (HPLC) [min] | MS (M + H)⁺ |
|---|---|---|---|
| I-25 | 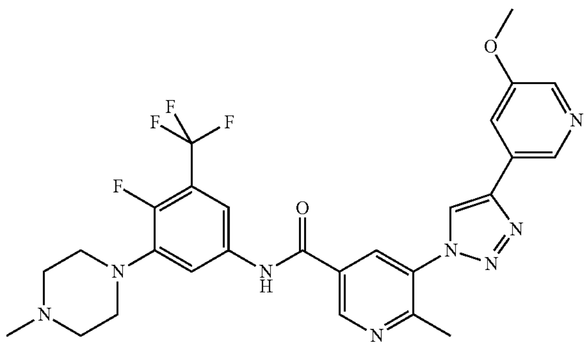 [SMILES: COc1cncc(-c2cn(-c3cc(C(=O)Nc4cc(N5CCN(C)CC5)c(F)c(C(F)(F)F)c4)cnc3C)nn2)c1] | 1.91 | 571 |
| I-26 | 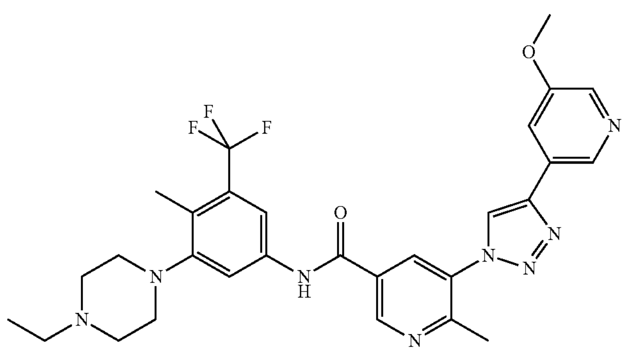 [SMILES: CCN1CCN(c2cc(NC(=O)c3cnc(C)c(-n4cc(-c5cncc(OC)c5)nn4)c3)cc(C(F)(F)F)c2C)CC1] | 2.21 | 581 |
| I-27 | 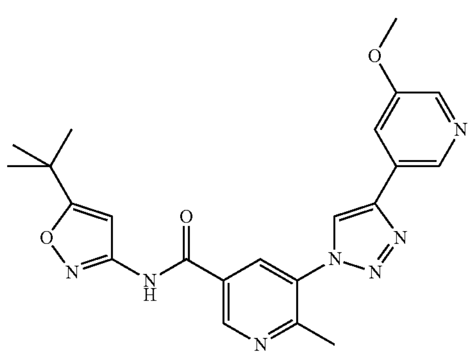 [SMILES: COc1cncc(-c2cn(-c3cc(C(=O)Nc4cc(C(C)(C)C)on4)cnc3C)nn2)c1] | 1.59 | 434 |

TABLE 1-continued
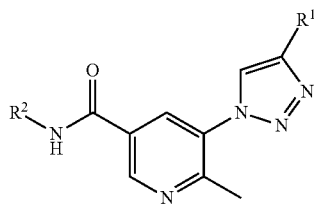
Example compounds I-1 to I-207
| # | Structure | $t_{Ret.}$ (HPLC) [min] | MS (M + H)⁺ |
|---|---|---|---|
| I-28 | 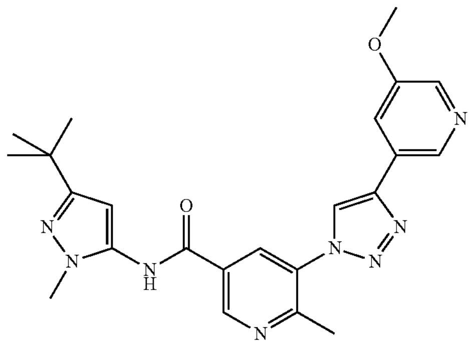 [SMILES: COc1cncc(-c2cn(-c3cc(C(=O)Nc4cc(C(C)(C)C)nn4C)cnc3C)nn2)c1] | | |
| I-29 | 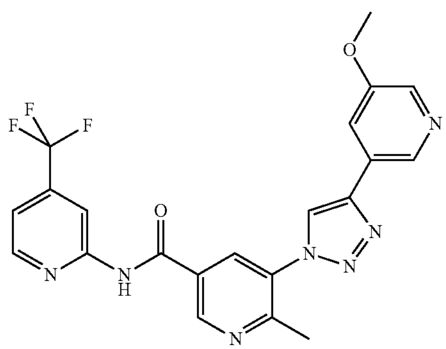 [SMILES: COc1cncc(-c2cn(-c3cc(C(=O)Nc4cc(C(F)(F)F)ccn4)cnc3C)nn2)c1] | 1.72 | 456 |
| I-30 | 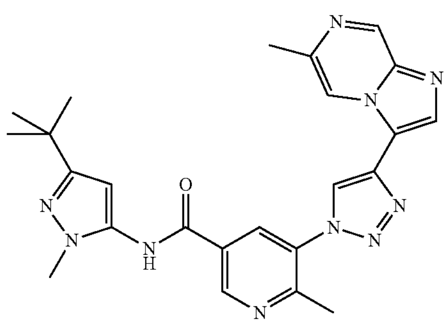 [SMILES: Cc1cn2c(-c3cn(-c4cc(C(=O)Nc5cc(C(C)(C)C)nn5C)cnc4C)nn3)cnc2cn1] | 1.42 | 471 |
| I-31 | 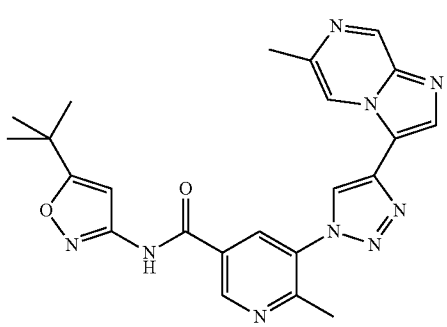 [SMILES: Cc1cn2c(-c3cn(-c4cc(C(=O)Nc5cc(C(C)(C)C)on5)cnc4C)nn3)cnc2cn1] | | |

TABLE 1-continued
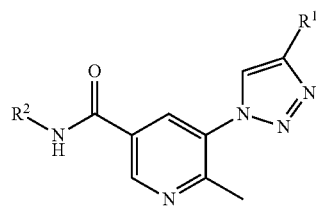
Example compounds I-1 to I-207
| # | Structure | $t_{Ret.}$ (HPLC) [min] | MS (M + H)$^+$ |
|---|---|---|---|
| I-32 | 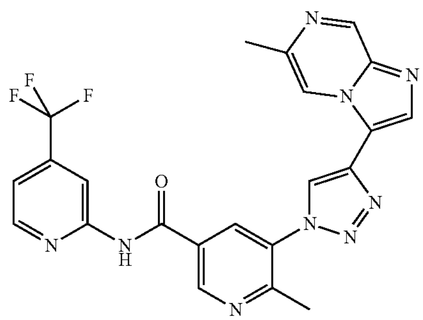 [SMILES: Cc1cn2c(-c3cn(-c4cc(C(=O)Nc5cc(C(F)(F)F)ccn5)cnc4C)nn3)cnc2cn1] | 1.71 | 480 |
| I-33 | 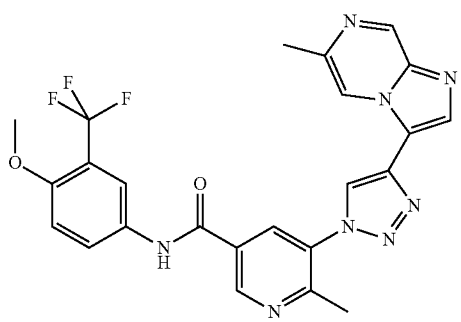 [SMILES: COc1ccc(NC(=O)c2cnc(C)c(-n3cc(-c4cnc5cnc(C)cn45)nn3)c2)cc1C(F)(F)F] | 1.78 | 509 |
| I-34 | 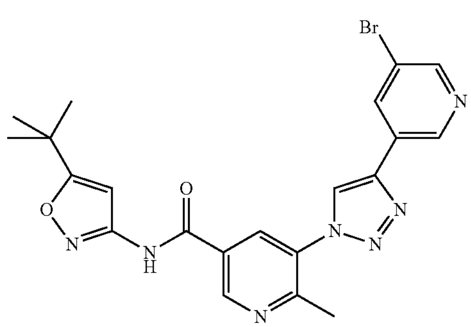 [SMILES: Cc1ncc(C(=O)Nc2cc(C(C)(C)C)on2)cc1-n1cc(-c2cncc(Br)c2)nn1] | 1.85 | 482/484 |

TABLE 1-continued

Example compounds I-1 to I-207

| # | Structure | t_{Ret.} (HPLC) [min] | MS (M + H)⁺ |
|---|---|---|---|
| I-35 | 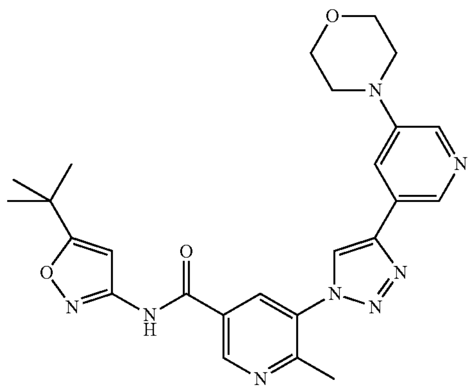 [SMILES: Cc1ncc(C(=O)Nc2cc(C(C)(C)C)on2)cc1-n1cc(-c2cncc(N3CCOCC3)c2)nn1] | 1.63 | 489 |
| I-36 | 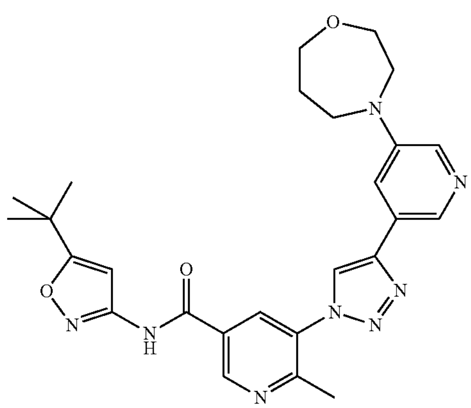 [SMILES: Cc1ncc(C(=O)Nc2cc(C(C)(C)C)on2)cc1-n1cc(-c2cncc(N3CCCOCC3)c2)nn1] | 1.67 | 503 |
| I-37 | 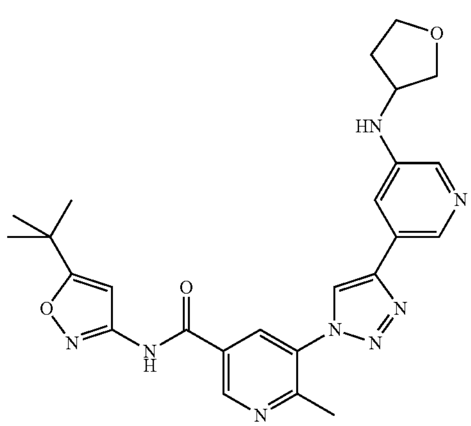 [SMILES: Cc1ncc(C(=O)Nc2cc(C(C)(C)C)on2)cc1-n1cc(-c2cncc(NC3CCOC3)c2)nn1] | 1.59 | 489 |

TABLE 1-continued

Example compounds I-1 to I-207

| # | Structure | t<sub>Ret.</sub> (HPLC) [min] | MS (M + H)⁺ |
|---|---|---|---|
| I-38 | 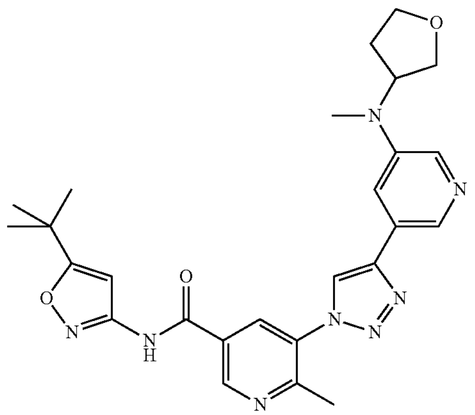 [SMILES: Cc1ncc(C(=O)Nc2cc(C(C)(C)C)on2)cc1-n1cc(-c2cncc(N(C)C3CCOC3)c2)nn1] | 1.68 | 503 |
| I-39 | 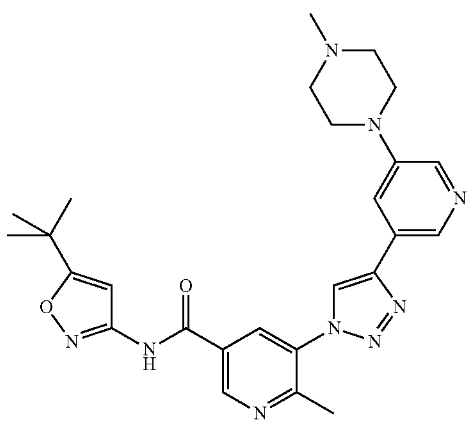 [SMILES: Cc1ncc(C(=O)Nc2cc(C(C)(C)C)on2)cc1-n1cc(-c2cncc(N3CCN(C)CC3)c2)nn1] | 1.62 | 502 |
| I-40 | 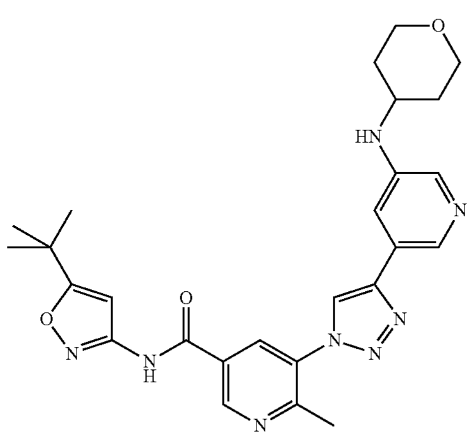 [SMILES: Cc1ncc(C(=O)Nc2cc(C(C)(C)C)on2)cc1-n1cc(-c2cncc(NC3CCOCC3)c2)nn1] | 1.62 | 503 |

TABLE 1-continued

Example compounds I-1 to I-207

| # | Structure | $t_{Ret.}$ (HPLC) [min] | MS (M + H)⁺ |
|---|---|---|---|
| I-41 | 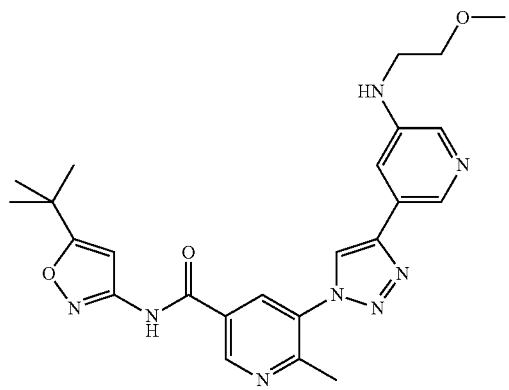 [SMILES: COCCNc1cncc(-c2cn(-c3cc(C(=O)Nc4cc(C(C)(C)C)on4)cnc3C)nn2)c1] | 1.61 | 477 |
| I-42 | 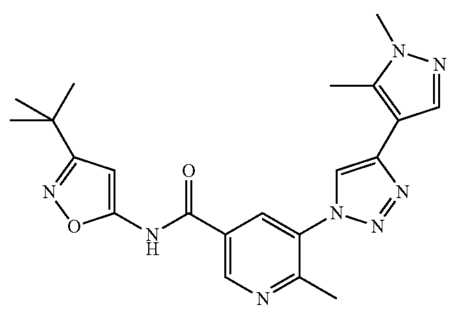 [SMILES: Cc1ncc(C(=O)Nc2cc(C(C)(C)C)no2)cc1-n1cc(-c2cnn(C)c2C)nn1] | 1.13 | 421 |
| I-43 | 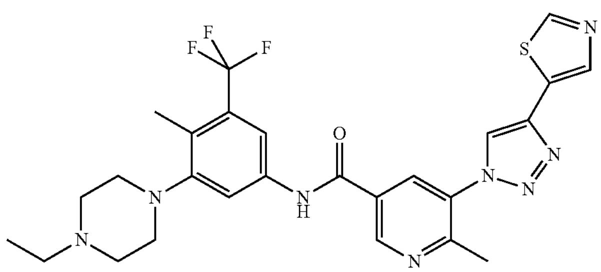 [SMILES: CCN1CCN(c2cc(NC(=O)c3cnc(C)c(-n4cc(-c5cncs5)nn4)c3)cc(C(F)(F)F)c2C)CC1] | 2.04 | 557 |
| I-44 | 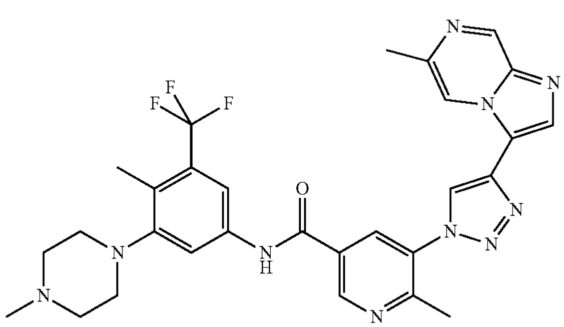 [SMILES: Cc1cn2c(-c3cn(-c4cc(C(=O)Nc5cc(N6CCN(C)CC6)c(C)c(C(F)(F)F)c5)cnc4C)nn3)cnc2cn1] | 1.95 | 591 |

TABLE 1-continued
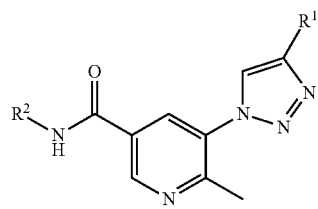
Example compounds I-1 to I-207
| # | Structure | $t_{Ret.}$ (HPLC) [min] | MS (M + H)$^+$ |
|---|---|---|---|
| I-45 | 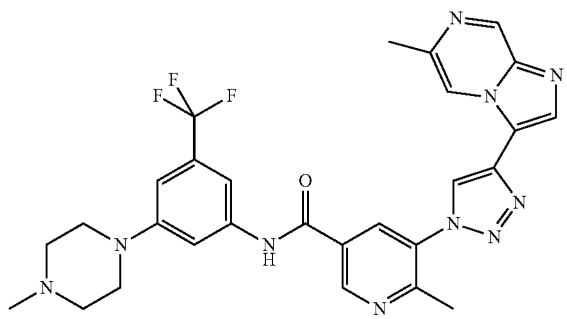 [SMILES: Cc1cn2c(-c3cn(-c4cc(C(=O)Nc5cc(N6CCN(C)CC6)cc(C(F)(F)F)c5)cnc4C)nn3)cnc2cn1] | 1.79 | 577 |
| I-46 | 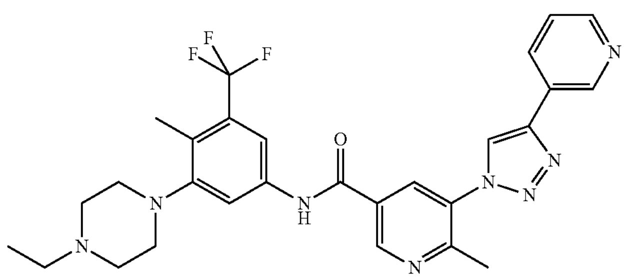 [SMILES: CCN1CCN(c2cc(NC(=O)c3cnc(C)c(-n4cc(-c5cccnc5)nn4)c3)cc(C(F)(F)F)c2C)CC1] | 2.05 | 551 |
| I-47 | 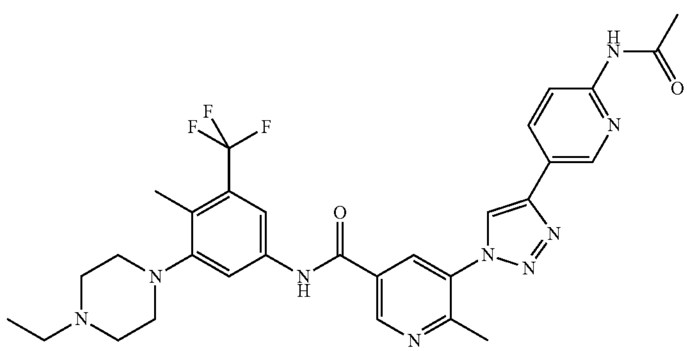 [SMILES: CCN1CCN(c2cc(NC(=O)c3cnc(C)c(-n4cc(-c5ccc(NC(C)=O)nc5)nn4)c3)cc(C(F)(F)F)c2C)CC1] | 2.03 | 608 |
| I-48 | 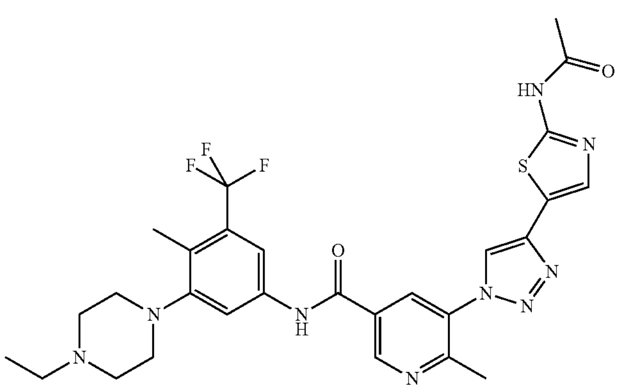 [SMILES: CCN1CCN(c2cc(NC(=O)c3cnc(C)c(-n4cc(-c5cnc(NC(C)=O)s5)nn4)c3)cc(C(F)(F)F)c2C)CC1] | 1.91 | 614 |

TABLE 1-continued
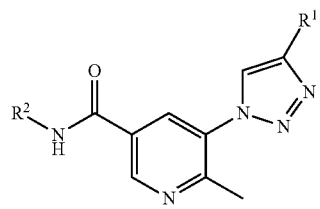
Example compounds I-1 to I-207
| # | Structure | $t_{Ret.}$ (HPLC) [min] | MS (M + H)$^+$ |
|---|---|---|---|
| I-49 | 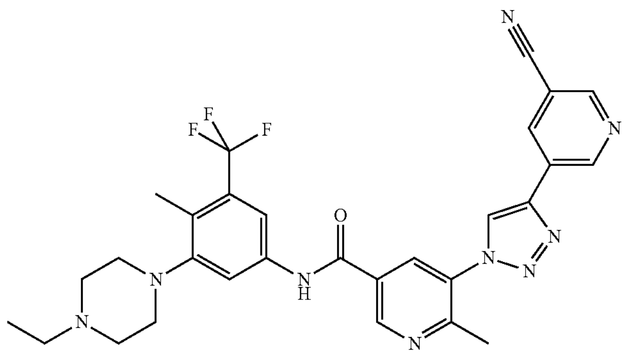 [SMILES: CCN1CCN(c2cc(NC(=O)c3cnc(C)c(-n4cc(-c5cncc(C#N)c5)nn4)c3)cc(C(F)(F)F)c2C)CC1] | 2.10 | 576 |
| I-50 | 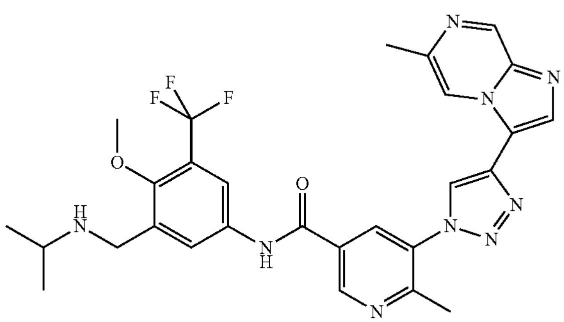 [SMILES: COc1c(CNC(C)C)cc(NC(=O)c2cnc(C)c(-n3cc(-c4cnc5cnc(C)cn45)nn3)c2)cc1C(F)(F)F] | 1.87 | 580 |
| I-51 | 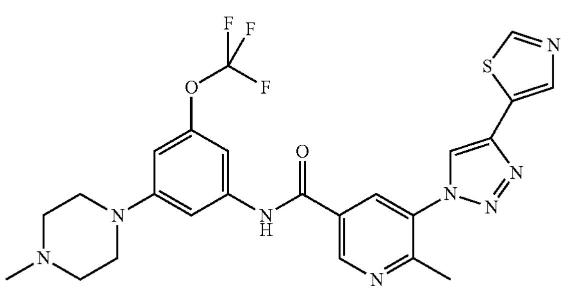 [SMILES: Cc1ncc(C(=O)Nc2cc(OC(F)(F)F)cc(N3CCN(C)CC3)c2)cc1-n1cc(-c2cncs2)nn1] | 1.82 | 545 |
| I-52 | 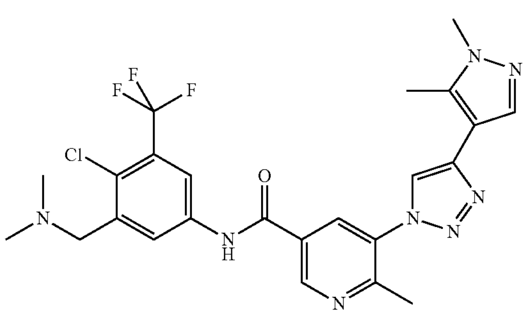 | 1.94 | 533 |

TABLE 1-continued

Example compounds I-1 to I-207

| # | Structure | t$_{Ret.}$ (HPLC) [min] | MS (M + H)$^+$ |
|---|---|---|---|
| I-53 | 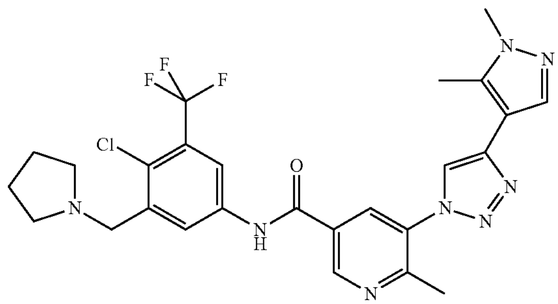 [SMILES: Cc1ncc(C(=O)Nc2cc(CN3CCCC3)c(Cl)c(C(F)(F)F)c2)cc1-n1cc(-c2cnn(C)c2C)nn1] | 2.09 | 559 |
| I-54 | 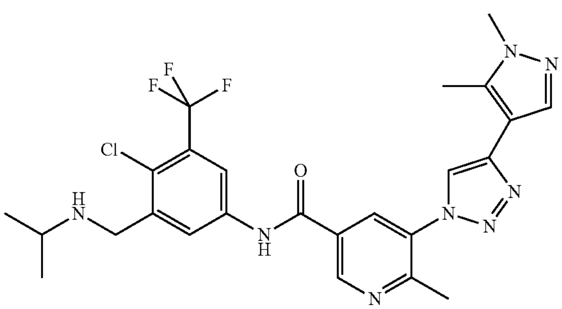 [SMILES: Cc1ncc(C(=O)Nc2cc(CNC(C)C)c(Cl)c(C(F)(F)F)c2)cc1-n1cc(-c2cnn(C)c2C)nn1] | 1.96 | 547 |
| I-55 | 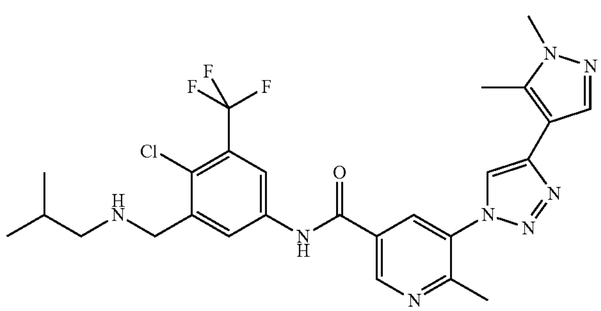 [SMILES: Cc1ncc(C(=O)Nc2cc(CNCC(C)C)c(Cl)c(C(F)(F)F)c2)cc1-n1cc(-c2cnn(C)c2C)nn1] | 2.10 | 561 |
| I-56 | 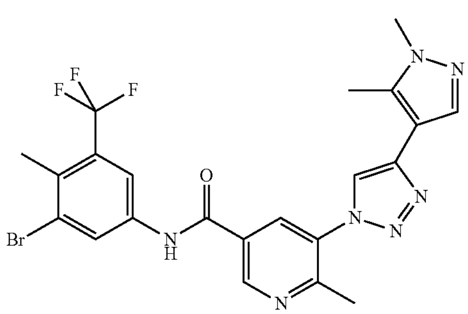 [SMILES: Cc1ncc(C(=O)Nc2cc(Br)c(C)c(C(F)(F)F)c2)cc1-n1cc(-c2cnn(C)c2C)nn1] | 2.02 | 534/536 |

TABLE 1-continued

Example compounds I-1 to I-207

| # | Structure | t$_{Ret.}$ (HPLC) [min] | MS (M + H)$^+$ |
|---|---|---|---|
| I-57 | 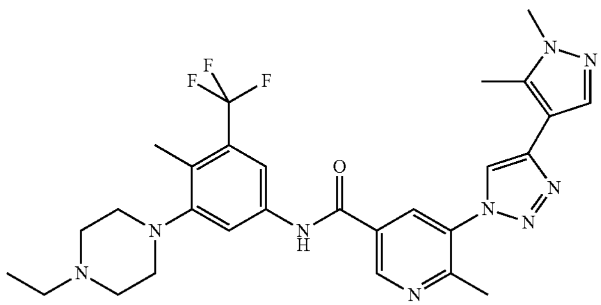 [SMILES: CCN1CCN(c2cc(NC(=O)c3cnc(C)c(-n4cc(-c5cnn(C)c5C)nn4)c3)cc(C(F)(F)F)c2C)CC1] | 2.03 | 568 |
| I-58 | 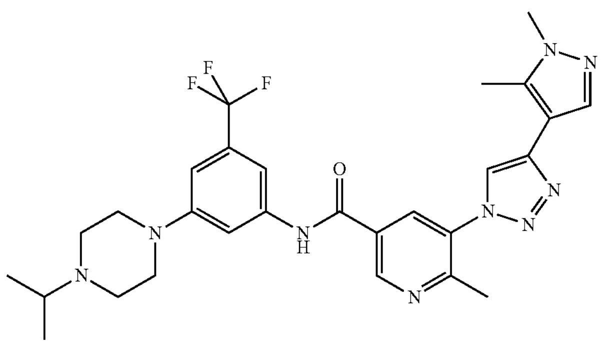 [SMILES: Cc1ncc(C(=O)Nc2cc(N3CCN(C(C)C)CC3)cc(C(F)(F)F)c2)cc1-n1cc(-c2cnn(C)c2C)nn1] | 1.92 | 568 |
| I-59 | 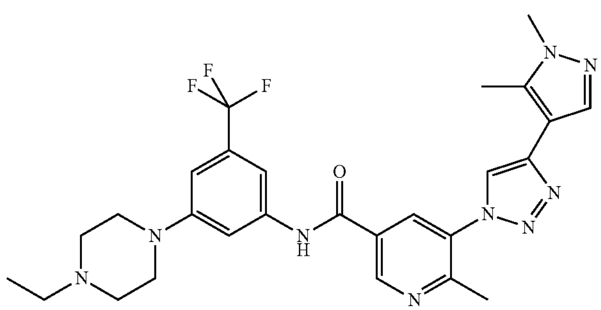 [SMILES: CCN1CCN(c2cc(NC(=O)c3cnc(C)c(-n4cc(-c5cnn(C)c5C)nn4)c3)cc(C(F)(F)F)c2)CC1] | 1.85 | 554 |
| I-60 | 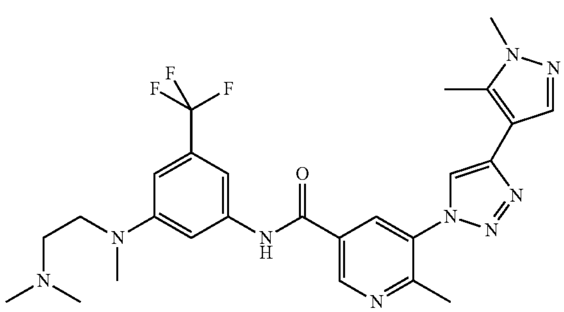 [SMILES: Cc1ncc(C(=O)Nc2cc(N(C)CCN(C)C)cc(C(F)(F)F)c2)cc1-n1cc(-c2cnn(C)c2C)nn1] | 1.86 | 542 |

TABLE 1-continued
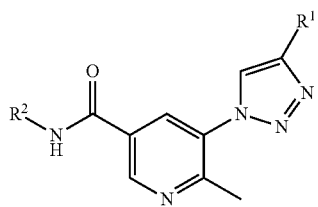
Example compounds I-1 to I-207
| # | Structure | $t_{Ret.}$ (HPLC) [min] | MS (M + H)$^+$ |
|---|---|---|---|
| I-61 | 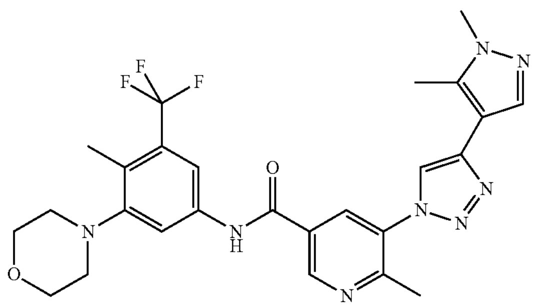 [SMILES: Cc1ncc(C(=O)Nc2cc(N3CCOCC3)c(C)c(C(F)(F)F)c2)cc1-n1cc(-c2cnn(C)c2C)nn1] | 1.86 | 541 |
| I-62 | 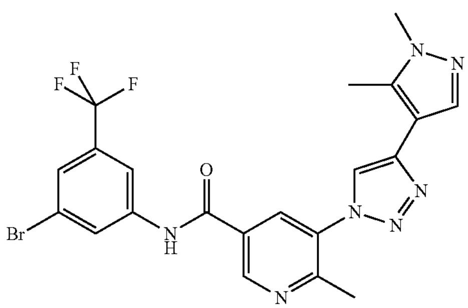 [SMILES: Cc1ncc(C(=O)Nc2cc(Br)cc(C(F)(F)F)c2)cc1-n1cc(-c2cnn(C)c2C)nn1] | 1.97 | 520/522 |
| I-63 | 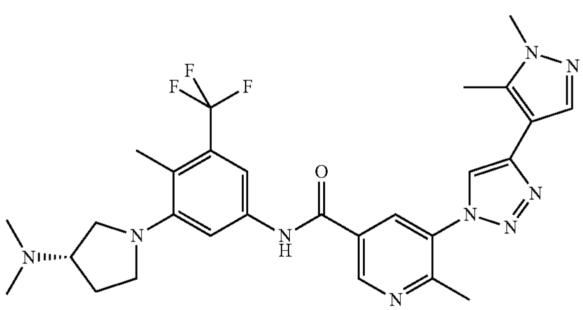 [SMILES: Cc1ncc(C(=O)Nc2cc(N3CC[C@H](N(C)C)C3)c(C)c(C(F)(F)F)c2)cc1-n1cc(-c2cnn(C)c2C)nn1] | 1.93 | 568 |
| I-64 | 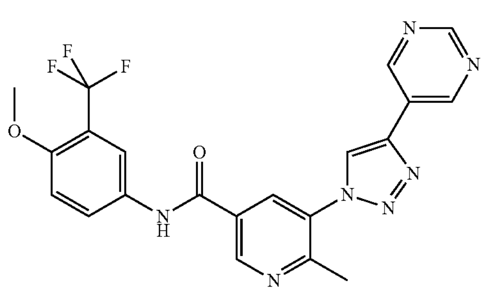 [SMILES: COc1ccc(NC(=O)c2cnc(C)c(-n3cc(-c4cncnc4)nn3)c2)cc1C(F)(F)F] | 1.59 | 456 |

TABLE 1-continued
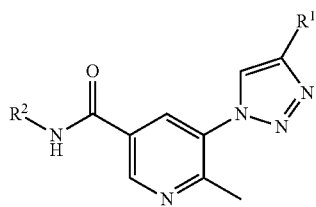
Example compounds I-1 to I-207
| # | Structure | t_Ret. (HPLC) [min] | MS (M + H)+ |
|---|---|---|---|
| I-65 | 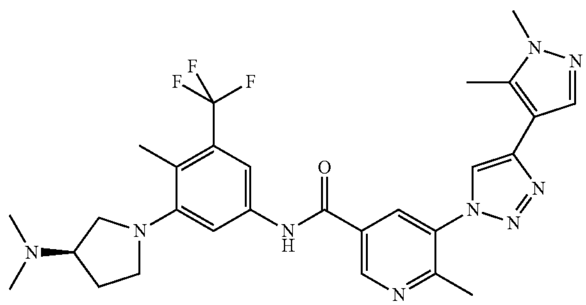 [SMILES: Cc1ncc(C(=O)Nc2cc(N3CC[C@@H](N(C)C)C3)c(C)c(C(F)(F)F)c2)cc1-n1cc(-c2cnn(C)c2C)nn1] | 1.89 | 568 |
| I-66 | 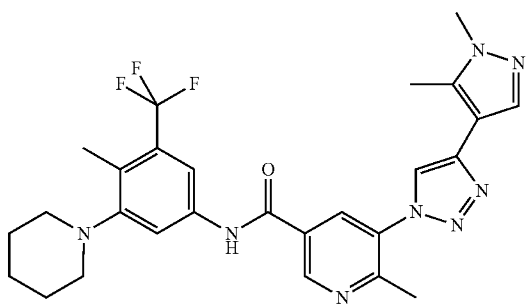 [SMILES: Cc1ncc(C(=O)Nc2cc(N3CCCCC3)c(C)c(C(F)(F)F)c2)cc1-n1cc(-c2cnn(C)c2C)nn1] | 2.20 | 539 |
| I-67 | 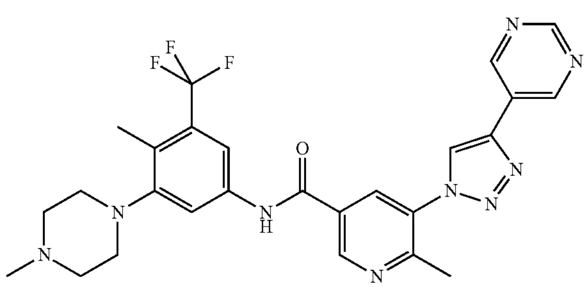 [SMILES: Cc1ncc(C(=O)Nc2cc(N3CCN(C)CC3)c(C)c(C(F)(F)F)c2)cc1-n1cc(-c2cncnc2)nn1] | 1.87 | 538 |
| I-68 | 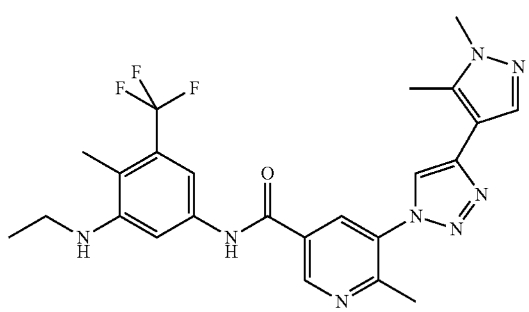 [SMILES: CCNc1cc(NC(=O)c2cnc(C)c(-n3cc(-c4cnn(C)c4C)nn3)c2)cc(C(F)(F)F)c1C] | 1.84 | 499 |

TABLE 1-continued
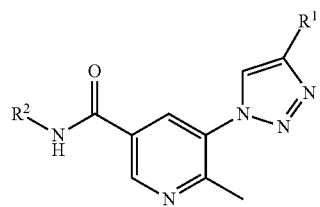
Example compounds I-1 to I-207
| # | Structure | $t_{Ret.}$ (HPLC) [min] | MS (M + H)$^+$ |
|---|---|---|---|
| I-69 | 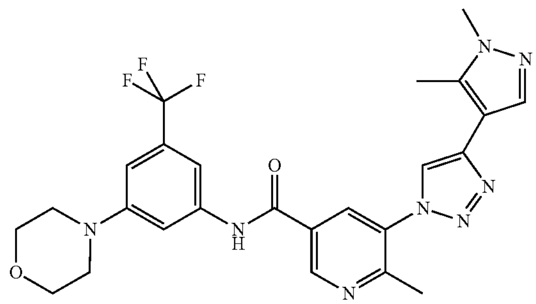 [SMILES: Cc1ncc(C(=O)Nc2cc(N3CCOCC3)cc(C(F)(F)F)c2)cc1-n1cc(-c2cnn(C)c2C)nn1] | 1.72 | 527 |
| I-70 | 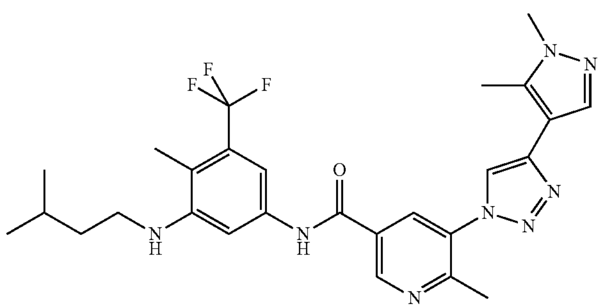 [SMILES: Cc1ncc(C(=O)Nc2cc(NCCC(C)C)c(C)c(C(F)(F)F)c2)cc1-n1cc(-c2cnn(C)c2C)nn1] | 1.81 | 542 |
| I-71 | 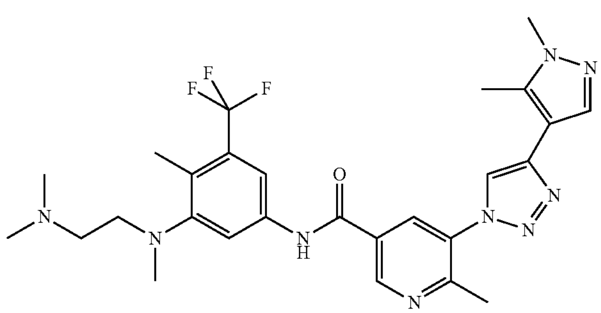 [SMILES: Cc1ncc(C(=O)Nc2cc(N(C)CCN(C)C)c(C)c(C(F)(F)F)c2)cc1-n1cc(-c2cnn(C)c2C)nn1] | 1.92 | 556 |
| I-72 | 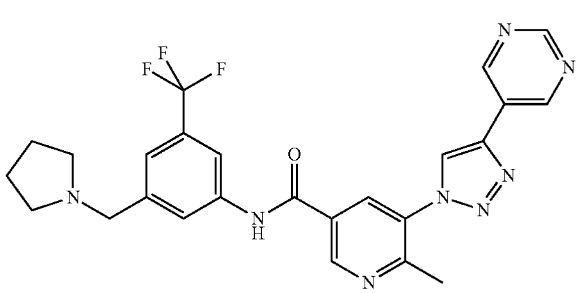 [SMILES: Cc1ncc(C(=O)Nc2cc(CN3CCCC3)cc(C(F)(F)F)c2)cc1-n1cc(-c2cncnc2)nn1] | 1.82 | 509 |

TABLE 1-continued
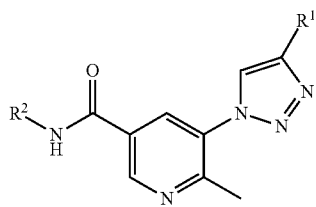
Example compounds I-1 to I-207
| # | Structure | t$_{Ret.}$ (HPLC) [min] | MS (M + H)$^+$ |
|---|---|---|---|
| I-73 | 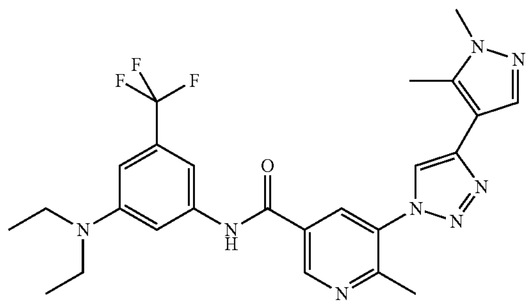 [SMILES: CCN(CC)c1cc(NC(=O)c2cnc(C)c(-n3cc(-c4cnn(C)c4C)nn3)c2)cc(C(F)(F)F)c1] | 2.01 | 513 |
| I-74 | 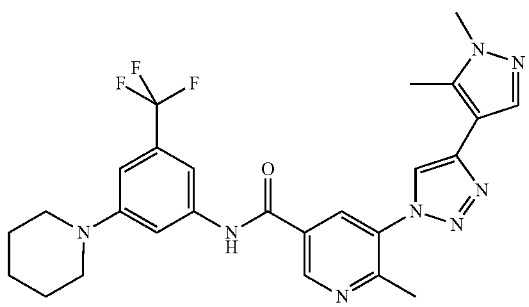 [SMILES: Cc1ncc(C(=O)Nc2cc(N3CCCCC3)cc(C(F)(F)F)c2)cc1-n1cc(-c2cnn(C)c2C)nn1] | 2.03 | 525 |
| I-75 | 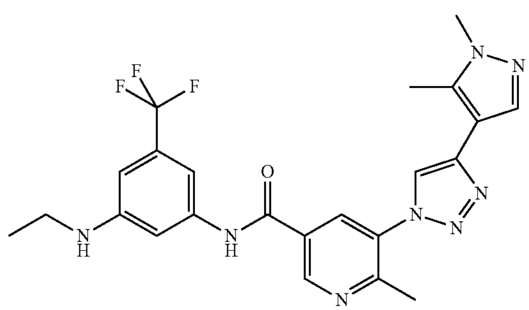 [SMILES: CCNc1cc(NC(=O)c2cnc(C)c(-n3cc(-c4cnn(C)c4C)nn3)c2)cc(C(F)(F)F)c1] | 1.78 | 485 |
| I-76 | 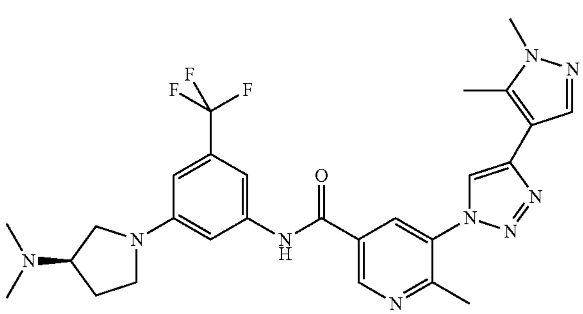 [SMILES: Cc1ncc(C(=O)Nc2cc(N3CC[C@@H](N(C)C)C3)cc(C(F)(F)F)c2)cc1-n1cc(-c2cnn(C)c2C)nn1] | 1.81 | 554 |

TABLE 1-continued
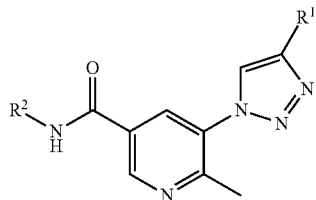
Example compounds I-1 to I-207
| # | Structure | t_{Ret.} (HPLC) [min] | MS (M + H)+ |
|---|---|---|---|
| I-77 | 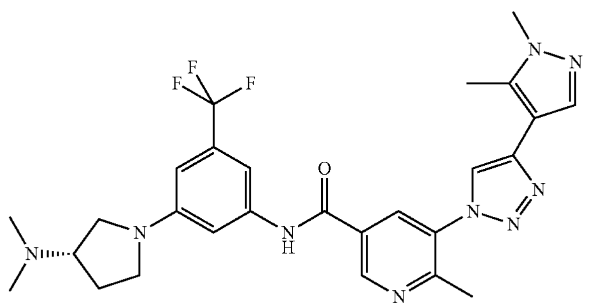 [SMILES: Cc1ncc(C(=O)Nc2cc(N3CC[C@H](N(C)C)C3)cc(C(F)(F)F)c2)cc1-n1cc(-c2cnn(C)c2C)nn1] | 1.81 | 554 |
| I-78 | 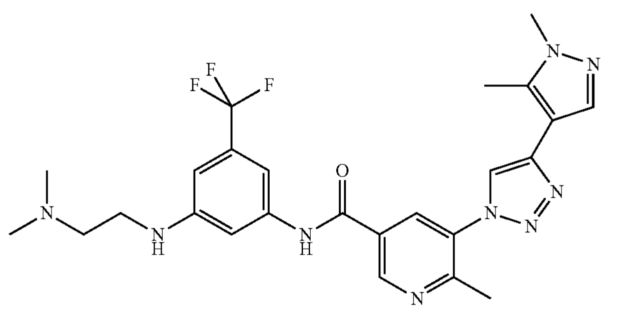 [SMILES: Cc1ncc(C(=O)Nc2cc(NCCN(C)C)cc(C(F)(F)F)c2)cc1-n1cc(-c2cnn(C)c2C)nn1] | 1.77 | 528 |
| I-79 | 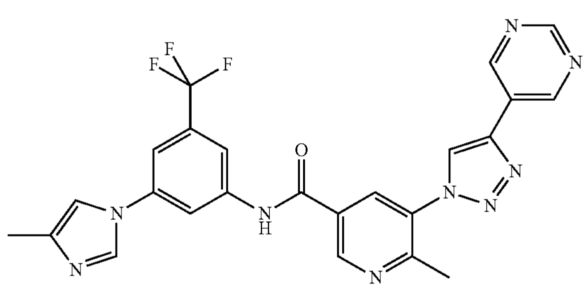 [SMILES: Cc1cn(-c2cc(NC(=O)c3cnc(C)c(-n4cc(-c5cncnc5)nn4)c3)cc(C(F)(F)F)c2)cn1] | 1.65 | 506 |
| I-80 | 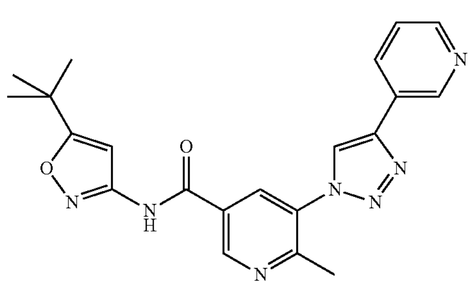 [SMILES: Cc1ncc(C(=O)Nc2cc(C(C)(C)C)on2)cc1-n1cc(-c2cccnc2)nn1] | 1.50 | 404 |

TABLE 1-continued
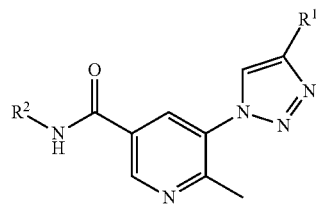
Example compounds I-1 to I-207
| # | Structure | $t_{Ret.}$ (HPLC) [min] | MS (M + H)⁺ |
|---|---|---|---|
| I-81 | 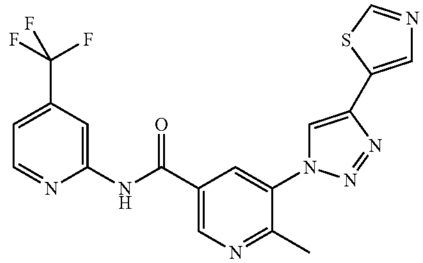 [SMILES: Cc1ncc(C(=O)Nc2cc(C(F)(F)F)ccn2)cc1-n1cc(-c2cncs2)nn1] | 1.62 | 432 |
| I-82 | 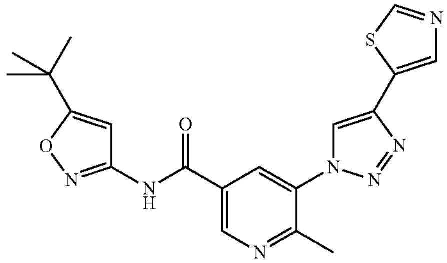 [SMILES: Cc1ncc(C(=O)Nc2cc(C(C)(C)C)on2)cc1-n1cc(-c2cncs2)nn1] | 1.48 | 410 |
| I-83 | 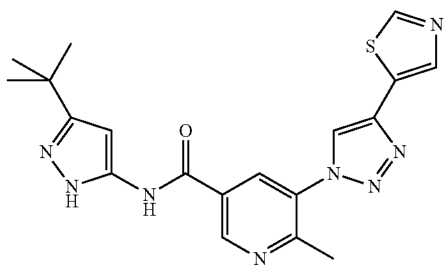 [SMILES: Cc1ncc(C(=O)Nc2cc(C(C)(C)C)n[nH]2)cc1-n1cc(-c2cncs2)nn1] | 1.49 | 409 |
| I-84 | 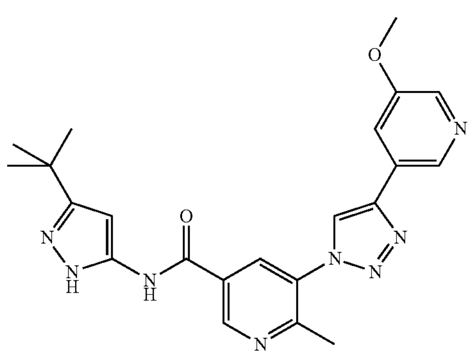 | 1.60 | 433 |

TABLE 1-continued
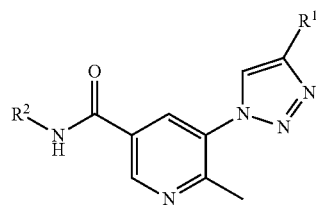
Example compounds I-1 to I-207
| # | Structure | $t_{Ret.}$ (HPLC) [min] | MS (M + H)+ |
|---|---|---|---|
| I-85 | 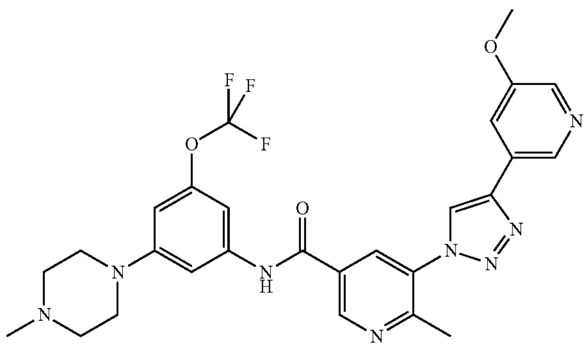 [SMILES: COc1cncc(-c2cn(-c3cc(C(=O)Nc4cc(OC(F)(F)F)cc(N5CCN(C)CC5)c4)cnc3C)nn2)c1] | 1.89 | 569 |
| I-86 | 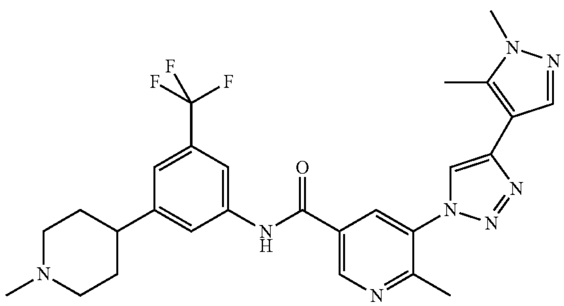 [SMILES: Cc1ncc(C(=O)Nc2cc(C3CCN(C)CC3)cc(C(F)(F)F)c2)cc1-n1cc(-c2cnn(C)c2C)nn1] | 1.88 | 539 |
| I-87 | 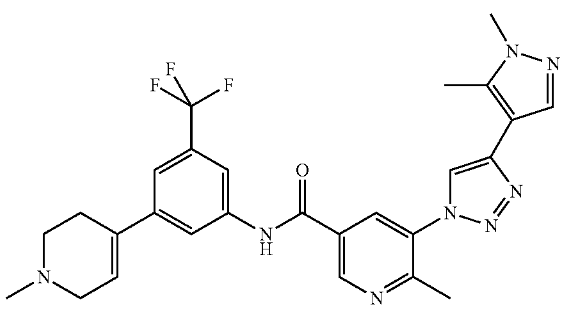 [SMILES: Cc1ncc(C(=O)Nc2cc(C3=CCN(C)CC3)cc(C(F)(F)F)c2)cc1-n1cc(-c2cnn(C)c2C)nn1] | 1.86 | 537 |
| I-88 | 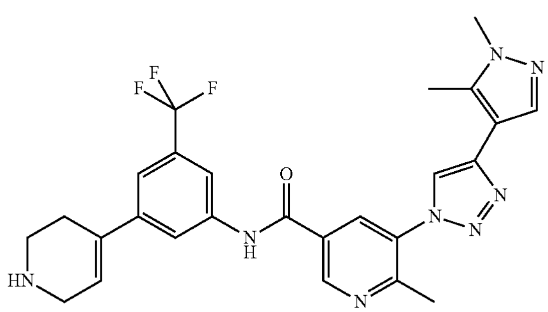 [SMILES: Cc1ncc(C(=O)Nc2cc(C3=CCNCC3)cc(C(F)(F)F)c2)cc1-n1cc(-c2cnn(C)c2C)nn1] | 1.81 | 523 |

TABLE 1-continued
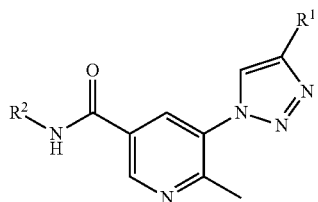
Example compounds I-1 to I-207
| # | Structure | $t_{Ret.}$ (HPLC) [min] | MS (M + H)$^+$ |
|---|---|---|---|
| I-89 | 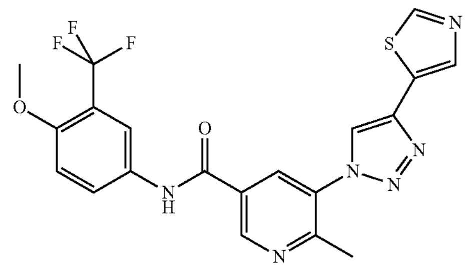 [SMILES: COc1ccc(NC(=O)c2cnc(C)c(-n3cc(-c4cncs4)nn3)c2)cc1C(F)(F)F] | 1.73 | 459 |
| I-90 | 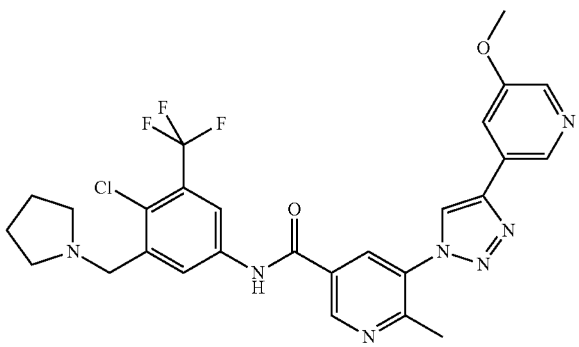 [SMILES: COc1cncc(-c2cn(-c3cc(C(=O)Nc4cc(CN5CCCC5)c(Cl)c(C(F)(F)F)c4)cnc3C)nn2)c1] | 2.13 | 572 |
| I-91 | 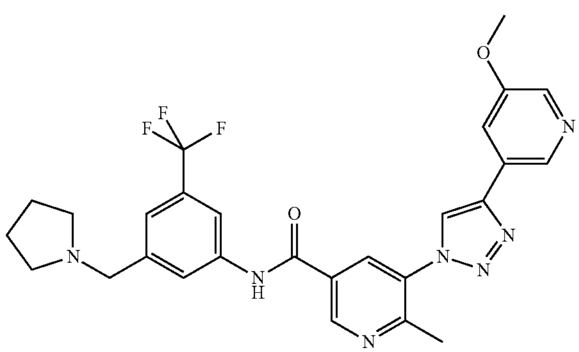 [SMILES: COc1cncc(-c2cn(-c3cc(C(=O)Nc4cc(CN5CCCC5)cc(C(F)(F)F)c4)cnc3C)nn2)c1] | 2.00 | 538 |
| I-92 | 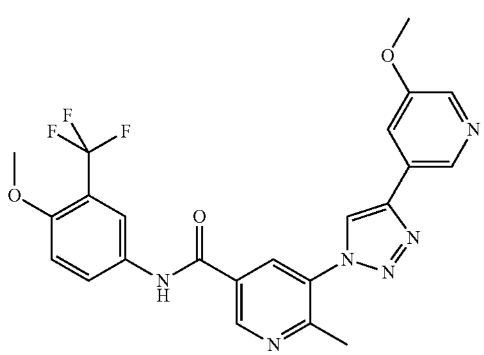 [SMILES: COc1cncc(-c2cn(-c3cc(C(=O)Nc4ccc(OC)c(C(F)(F)F)c4)cnc3C)nn2)c1] | 1.80 | 485 |

TABLE 1-continued
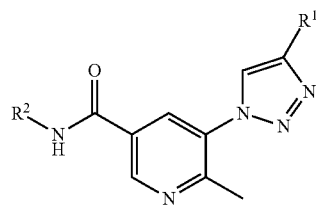
Example compounds I-1 to I-207
| # | Structure | $t_{Ret.}$ (HPLC) [min] | MS (M + H)$^+$ |
|---|---|---|---|
| I-93 | 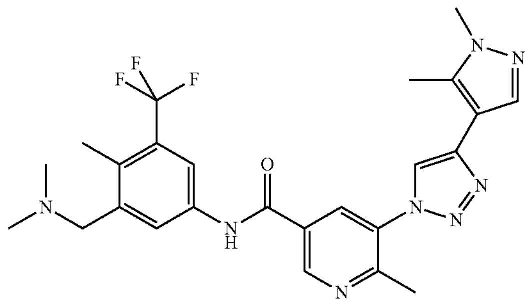 [SMILES: Cc1ncc(C(=O)Nc2cc(CN(C)C)c(C)c(C(F)(F)F)c2)cc1-n1cc(-c2cnn(C)c2C)nn1] | 2.01 | 513 |
| I-94 | 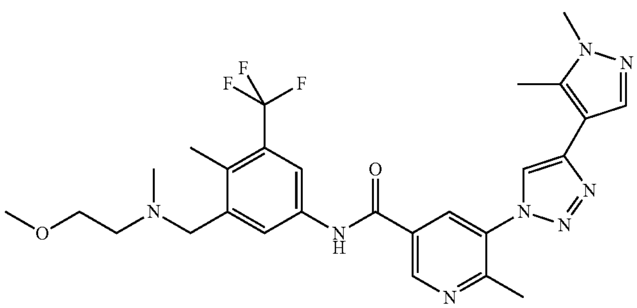 [SMILES: COCCN(C)Cc1cc(NC(=O)c2cnc(C)c(-n3cc(-c4cnn(C)c4C)nn3)c2)cc(C(F)(F)F)c1C] | 1.90 | 557 |
| I-95 | 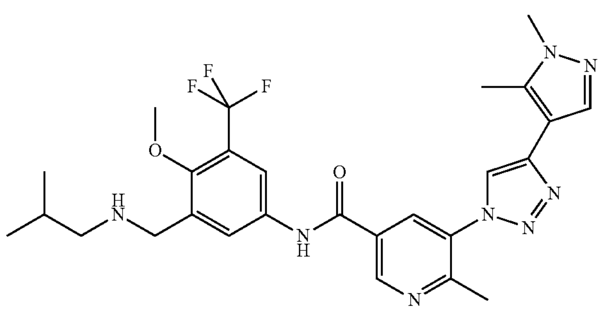 [SMILES: COc1c(CNCC(C)C)cc(NC(=O)c2cnc(C)c(-n3cc(-c4cnn(C)c4C)nn3)c2)cc1C(F)(F)F] | 1.90 | 557 |
| I-96 | 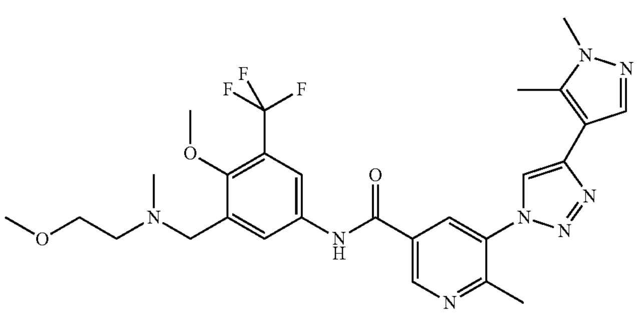 [SMILES: COCCN(C)Cc1cc(NC(=O)c2cnc(C)c(-n3cc(-c4cnn(C)c4C)nn3)c2)cc(C(F)(F)F)c1OC] | 1.79 | 573 |

TABLE 1-continued
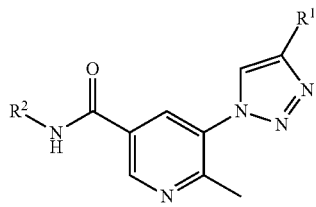
Example compounds I-1 to I-207
| # | Structure | $t_{Ret.}$ (HPLC) [min] | MS (M + H)$^+$ |
|---|---|---|---|
| I-97 | 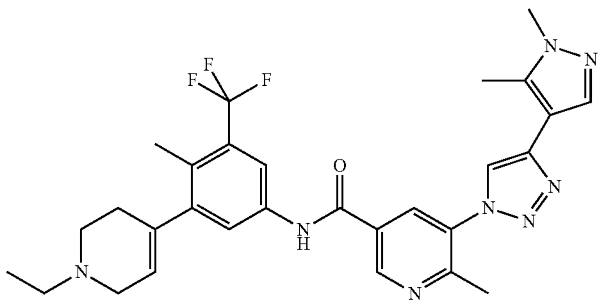 [SMILES: CCN1CC=C(c2cc(NC(=O)c3cnc(C)c(-n4cc(-c5cnn(C)c5C)nn4)c3)cc(C(F)(F)F)c2C)CC1] | 1.98 | 565 |
| I-98 | 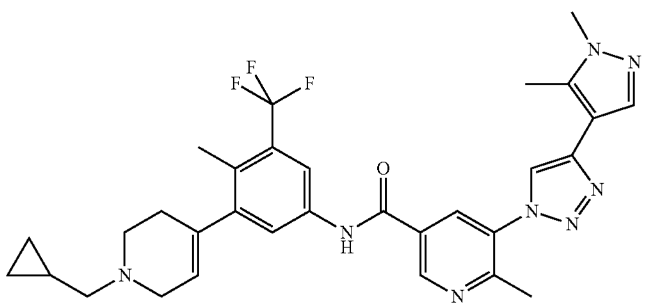 [SMILES: Cc1ncc(C(=O)Nc2cc(C3=CCN(CC4CC4)CC3)c(C)c(C(F)(F)F)c2)cc1-n1cc(-c2cnn(C)c2C)nn1] | 2.09 | 591 |
| I-99 | 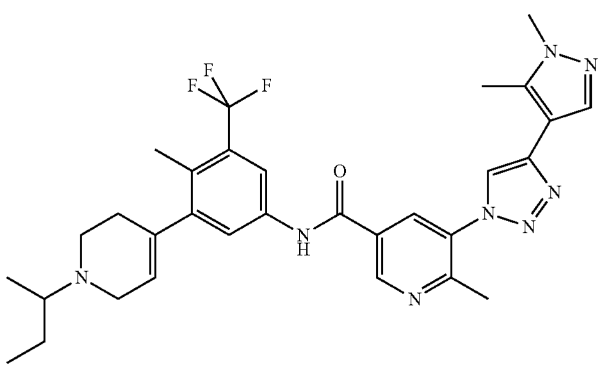 [SMILES: CCC(C)N1CC=C(c2cc(NC(=O)c3cnc(C)c(-n4cc(-c5cnn(C)c5C)nn4)c3)cc(C(F)(F)F)c2C)CC1] | 2.21 | 593 |
| I-100 | 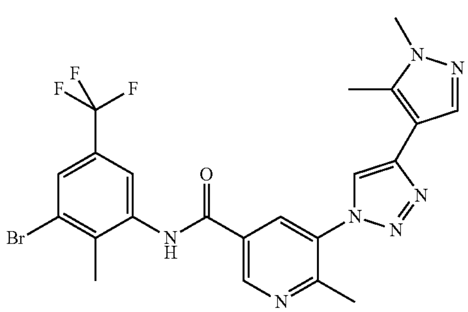 [SMILES: Cc1ncc(C(=O)Nc2cc(C(F)(F)F)cc(Br)c2C)cc1-n1cc(-c2cnn(C)c2C)nn1] | 1.87 | 534 |

TABLE 1-continued
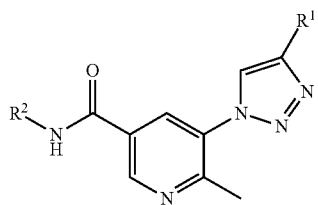
Example compounds I-1 to I-207
| # | Structure | t_Ret. (HPLC) [min] | MS (M + H)+ |
|---|---|---|---|
| I-101 | 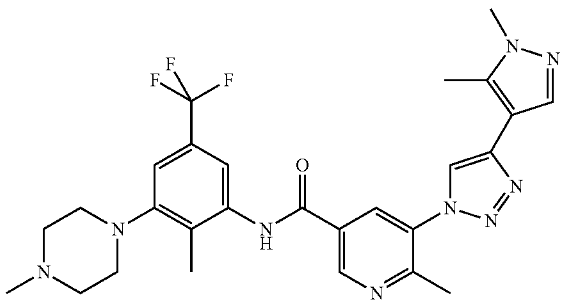 [SMILES: Cc1ncc(C(=O)Nc2cc(C(F)(F)F)cc(N3CCN(C)CC3)c2C)cc1-n1cc(-c2cnn(C)c2C)nn1] | 1.71 | 554 |
| I-102 | 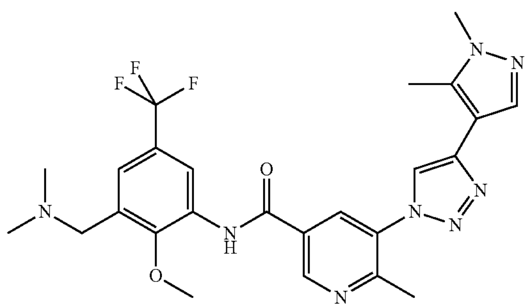 [SMILES: COc1c(CN(C)C)cc(C(F)(F)F)cc1NC(=O)c1cnc(C)c(-n2cc(-c3cnn(C)c3C)nn2)c1] | 1.88 | 529 |
| I-103 | 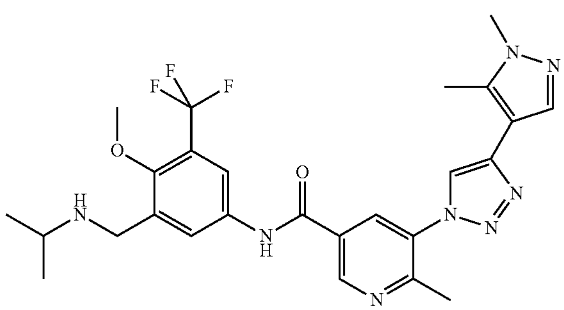 [SMILES: COc1c(CNC(C)C)cc(NC(=O)c2cnc(C)c(-n3cc(-c4cnn(C)c4C)nn3)c2)cc1C(F)(F)F] | 1.82 | 543 |
| I-104 | 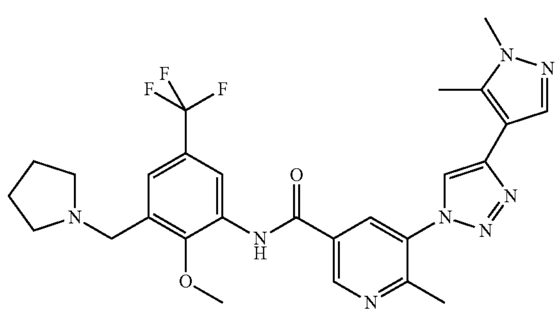 [SMILES: COc1c(CN2CCCC2)cc(C(F)(F)F)cc1NC(=O)c1cnc(C)c(-n2cc(-c3cnn(C)c3C)nn2)c1] | 1.93 | 555 |

TABLE 1-continued
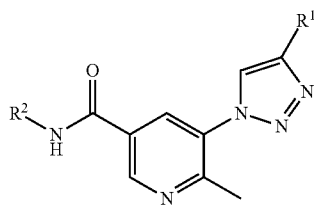
Example compounds I-1 to I-207
| # | Structure | t_Ret. (HPLC) [min] | MS (M + H)+ |
|---|---|---|---|
| I-105 | 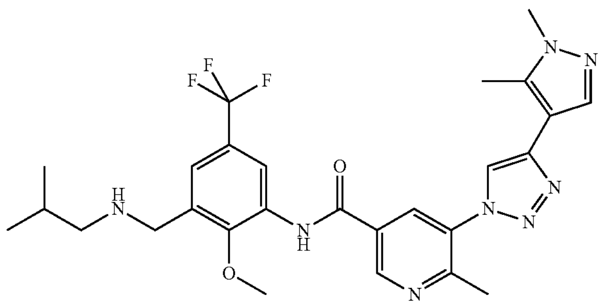 [SMILES: COc1c(CNCC(C)C)cc(C(F)(F)F)cc1NC(=O)c1cnc(C)c(-n2cc(-c3cnn(C)c3C)nn2)c1] | 1.94 | 557 |
| I-106 | 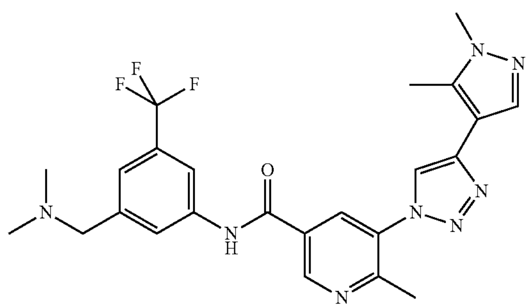 | 1.76 | 499 |
| I-107 | 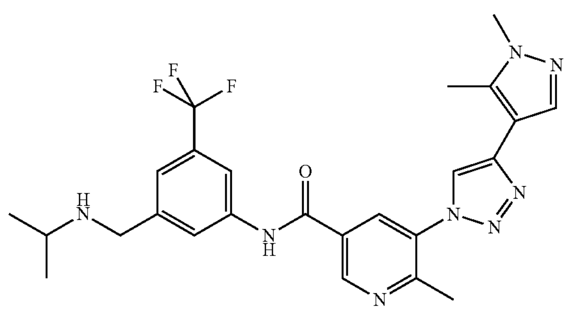 [SMILES: Cc1ncc(C(=O)Nc2cc(CNC(C)C)cc(C(F)(F)F)c2)cc1-n1cc(-c2cnn(C)c2C)nn1] | 1.79 | 513 |
| I-108 | 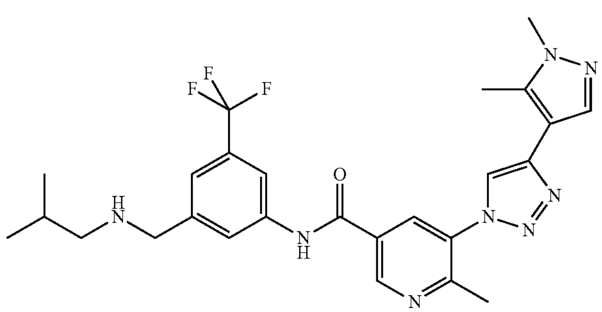 [SMILES: Cc1ncc(C(=O)Nc2cc(CNCC(C)C)cc(C(F)(F)F)c2)cc1-n1cc(-c2cnn(C)c2C)nn1] | 1.93 | 527 |

TABLE 1-continued
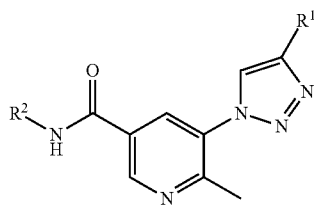
Example compounds I-1 to I-207
| # | Structure | t$_{Ret.}$ (HPLC) [min] | MS (M + H)$^+$ |
|---|---|---|---|
| I-109 | 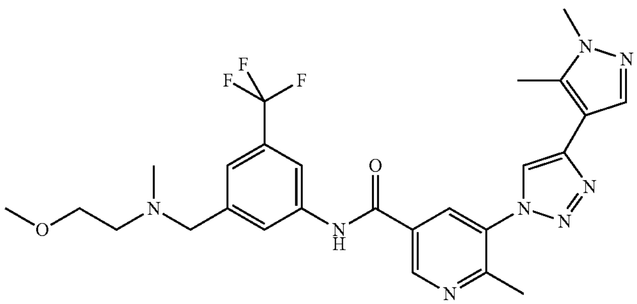 [SMILES: COCCN(C)Cc1cc(NC(=O)c2cnc(C)c(-n3cc(-c4cnn(C)c4C)nn3)c2)cc(C(F)(F)F)c1] | 1.80 | 543 |
| I-110 | 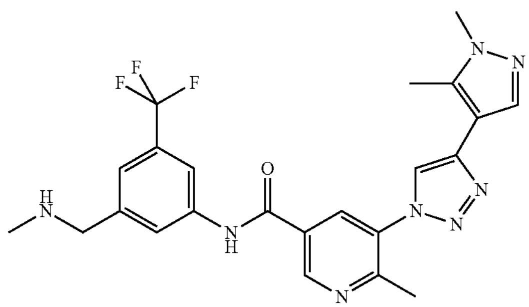 [SMILES: CNCc1cc(NC(=O)c2cnc(C)c(-n3cc(-c4cnn(C)c4C)nn3)c2)cc(C(F)(F)F)c1] | 1.59 | 485 |
| I-111 | 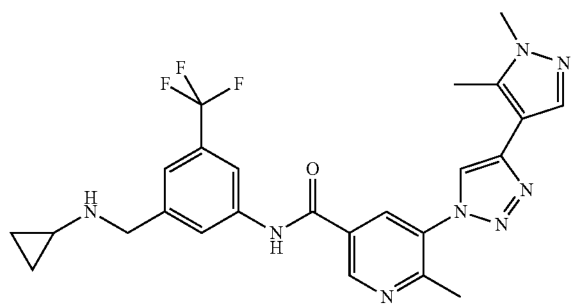 [SMILES: Cc1ncc(C(=O)Nc2cc(CNC3CC3)cc(C(F)(F)F)c2)cc1-n1cc(-c2cnn(C)c2C)nn1] | 1.77 | 511 |
| I-112 | 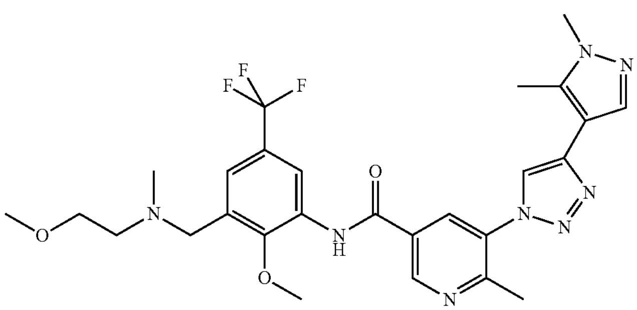 [SMILES: COCCN(C)Cc1cc(C(F)(F)F)cc(NC(=O)c2cnc(C)c(-n3cc(-c4cnn(C)c4C)nn3)c2)c1OC] | 1.82 | 573 |

TABLE 1-continued
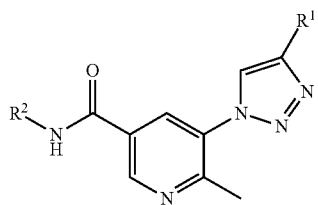
Example compounds I-1 to I-207
| # | Structure | t$_{Ret.}$ (HPLC) [min] | MS (M + H)$^+$ |
|---|---|---|---|
| I-113 | 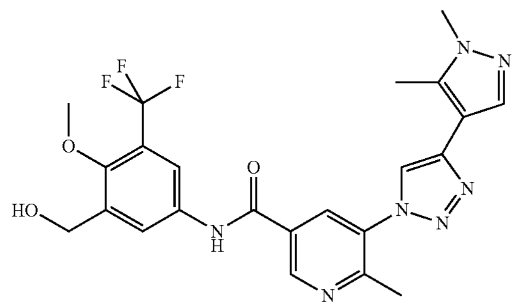 [SMILES: COc1c(CO)cc(NC(=O)c2cnc(C)c(-n3cc(-c4cnn(C)c4C)nn3)c2)cc1C(F)(F)F] | 1.56 | 502 |
| I-114 | 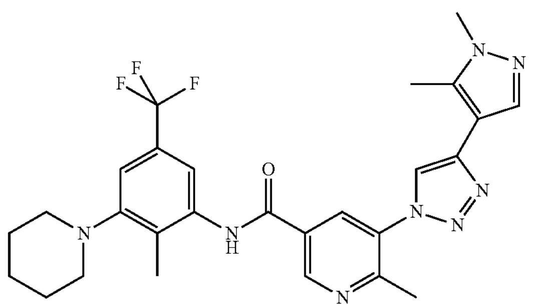 [SMILES: Cc1ncc(C(=O)Nc2cc(C(F)(F)F)cc(N3CCCCC3)c2C)cc1-n1cc(-c2cnn(C)c2C)nn1] | 2.10 | 537 |
| I-115 | 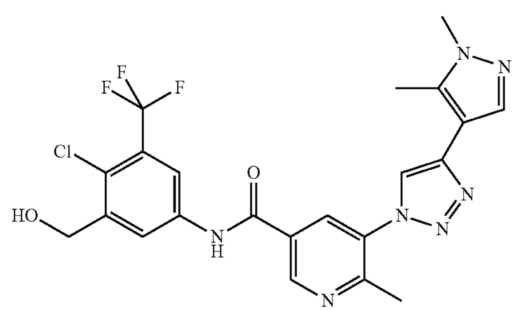 [SMILES: Cc1ncc(C(=O)Nc2cc(CO)c(Cl)c(C(F)(F)F)c2)cc1-n1cc(-c2cnn(C)c2C)nn1] | 1.71 | 506 |
| I-116 | 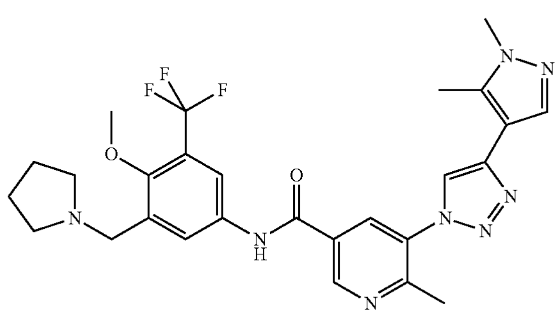 [SMILES: COc1c(CN2CCCC2)cc(NC(=O)c2cnc(C)c(-n3cc(-c4cnn(C)c4C)nn3)c2)cc1C(F)(F)F] | 1.89 | 555 |

US 8,778,929 B2
145                                                                                                              146
TABLE 1-continued
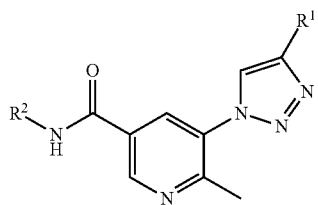
Example compounds I-1 to I-207
| # | Structure | t$_{Ret.}$ (HPLC) [min] | MS (M + H)$^+$ |
|---|---|---|---|
| I-117 | 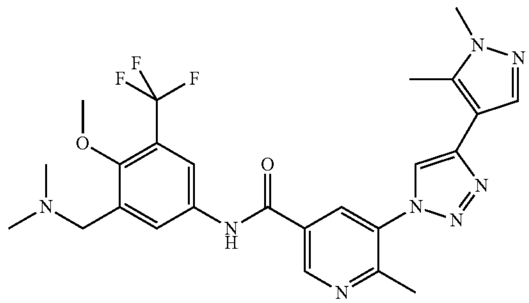 [SMILES: COc1c(CN(C)C)cc(NC(=O)c2cnc(C)c(-n3cc(-c4cnn(C)c4C)nn3)c2)cc1C(F)(F)F] | 1.83 | 519 |
| I-118 | 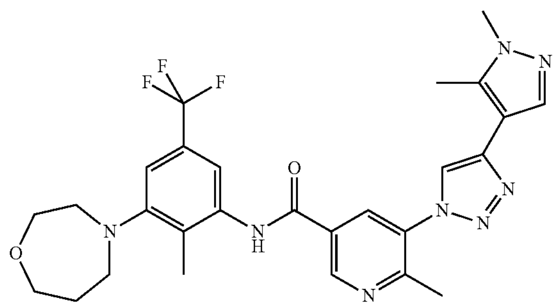 [SMILES: Cc1ncc(C(=O)Nc2cc(C(F)(F)F)cc(N3CCCOCC3)c2C)cc1-n1cc(-c2cnn(C)c2C)nn1] | 1.79 | 553 |
| I-119 | 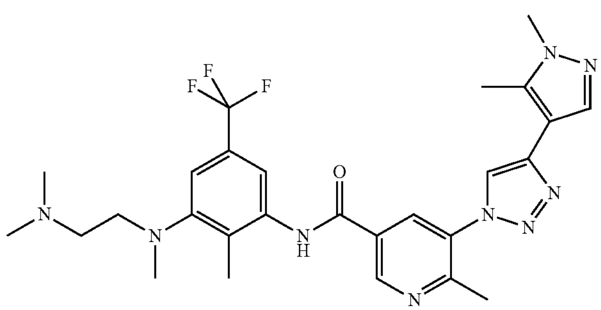 [SMILES: Cc1ncc(C(=O)Nc2cc(C(F)(F)F)cc(N(C)CCN(C)C)c2C)cc1-n1cc(-c2cnn(C)c2C)nn1] | 1.80 | 556 |
| I-120 | 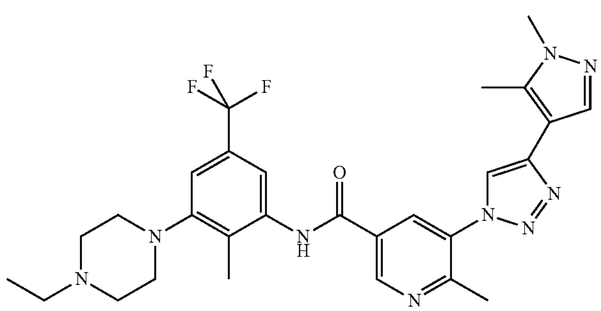 [SMILES: CCN1CCN(c2cc(C(F)(F)F)cc(NC(=O)c3cnc(C)c(-n4cc(-c5cnn(C)c5C)nn4)c3)c2C)CC1] | 1.80 | 568 |

TABLE 1-continued
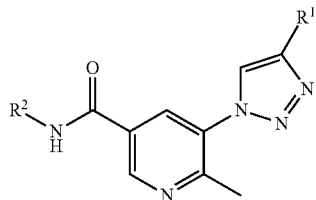
Example compounds I-1 to I-207
| # | Structure | $t_{Ret.}$ (HPLC) [min] | MS (M + H)+ |
|---|---|---|---|
| I-121 | 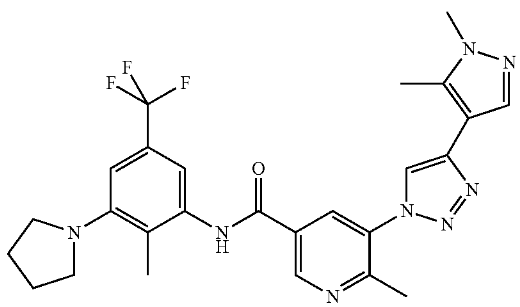 [SMILES: Cc1ncc(C(=O)Nc2cc(C(F)(F)F)cc(N3CCCC3)c2C)cc1-n1cc(-c2cnn(C)c2C)nn1] | 1.95 | 525 |
| I-122 | 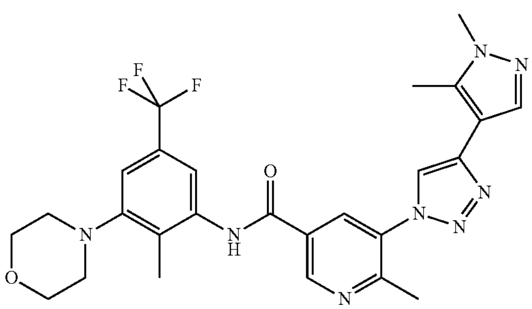 [SMILES: Cc1ncc(C(=O)Nc2cc(C(F)(F)F)cc(N3CCOCC3)c2C)cc1-n1cc(-c2cnn(C)c2C)nn1] | 1.73 | 541 |
| I-123 | 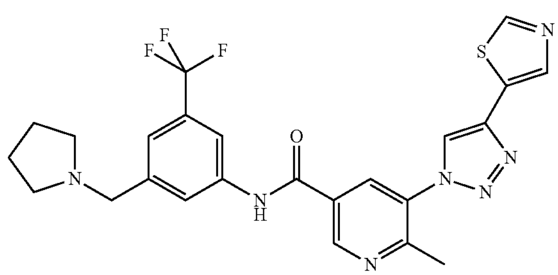 [SMILES: Cc1ncc(C(=O)Nc2cc(CN3CCCC3)cc(C(F)(F)F)c2)cc1-n1cc(-c2cncs2)nn1] | 1.93 | 514 |
| I-124 | 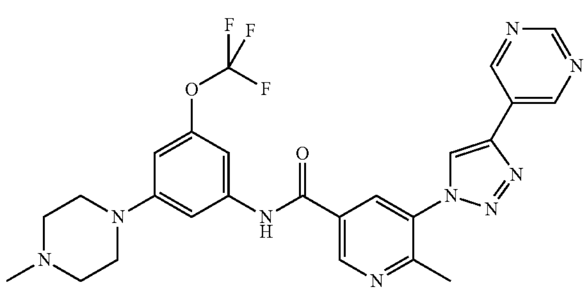 [SMILES: Cc1ncc(C(=O)Nc2cc(OC(F)(F)F)cc(N3CCN(C)CC3)c2)cc1-n1cc(-c2cncnc2)nn1] | 1.74 | 540 |

TABLE 1-continued
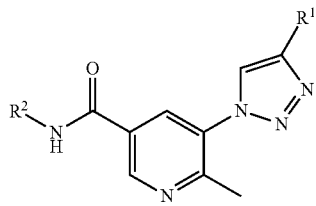
Example compounds I-1 to I-207
| # | Structure | $t_{Ret.}$ (HPLC) [min] | MS (M + H)$^+$ |
|---|---|---|---|
| I-125 | 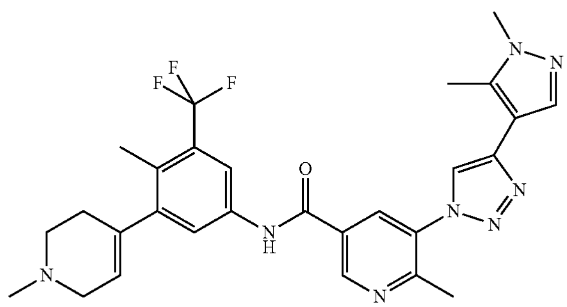 [SMILES: Cc1ncc(C(=O)Nc2cc(C3=CCN(C)CC3)c(C)c(C(F)(F)F)c2)cc1-n1cc(-c2cnn(C)c2C)nn1] | 1.90 | 551 |
| I-126 | 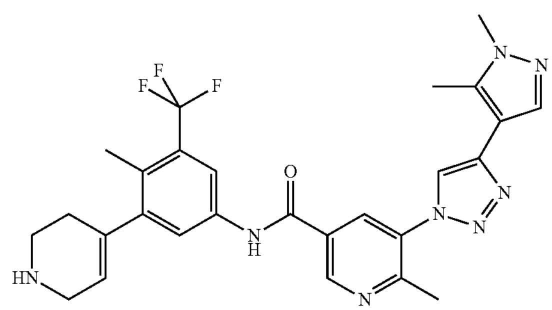 [SMILES: Cc1ncc(C(=O)Nc2cc(C3=CCNCC3)c(C)c(C(F)(F)F)c2)cc1-n1cc(-c2cnn(C)c2C)nn1] | 1.79 | 537 |
| I-127 | 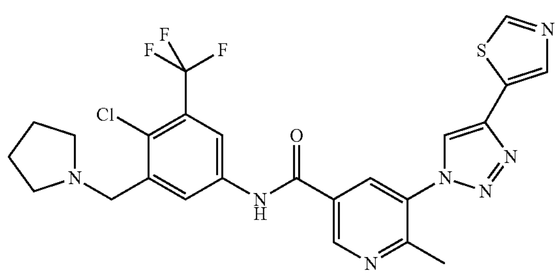 [SMILES: Cc1ncc(C(=O)Nc2cc(CN3CCCC3)c(Cl)c(C(F)(F)F)c2)cc1-n1cc(-c2cncs2)nn1] | 2.09 | 548 |
| I-128 | 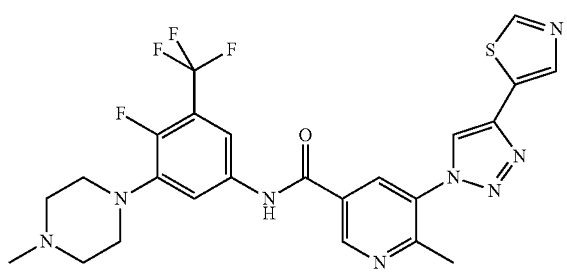 [SMILES: Cc1ncc(C(=O)Nc2cc(N3CCN(C)CC3)c(F)c(C(F)(F)F)c2)cc1-n1cc(-c2cncs2)nn1] | 1.85 | 547 |

TABLE 1-continued
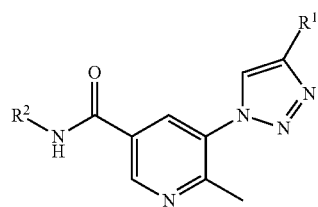
Example compounds I-1 to I-207
| # | Structure | $t_{Ret.}$ (HPLC) [min] | MS (M + H)$^+$ |
|---|---|---|---|
| I-129 | 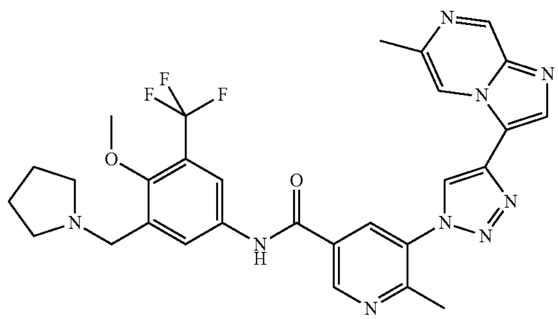 [SMILES: COc1c(CN2CCCC2)cc(NC(=O)c2cnc(C)c(-n3cc(-c4cnc5cnc(C)cn45)nn3)c2)cc1C(F)(F)F] | | |
| I-130 | 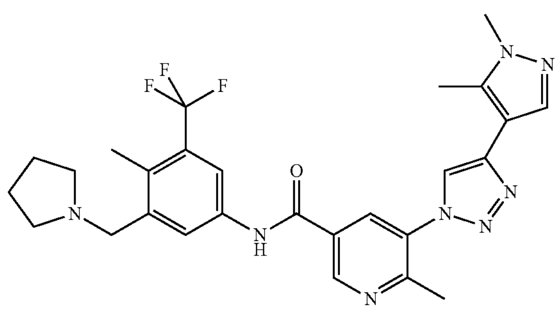 [SMILES: Cc1ncc(C(=O)Nc2cc(CN3CCCC3)c(C)c(C(F)(F)F)c2)cc1-n1cc(-c2cnn(C)c2C)nn1] | 2.03 | 539 |
| I-131 | 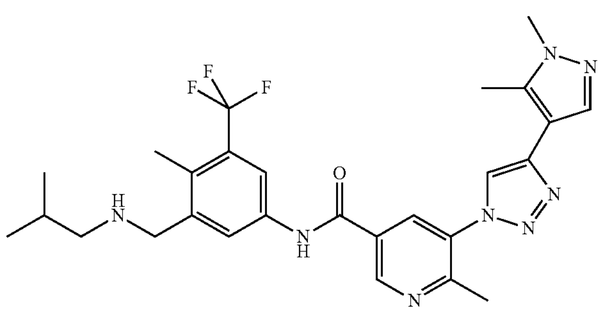 [SMILES: Cc1ncc(C(=O)Nc2cc(CNCC(C)C)c(C)c(C(F)(F)F)c2)cc1-n1cc(-c2cnn(C)c2C)nn1] | 2.05 | 541 |
| I-132 | 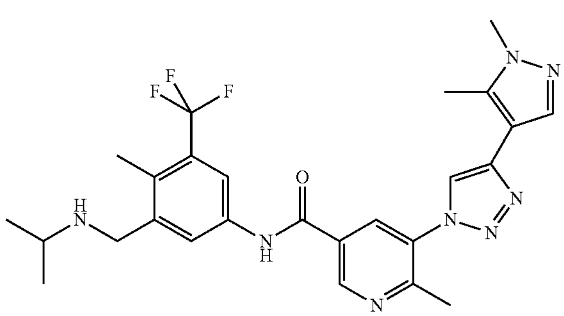 [SMILES: Cc1ncc(C(=O)Nc2cc(CNC(C)C)c(C)c(C(F)(F)F)c2)cc1-n1cc(-c2cnn(C)c2C)nn1] | 1.89 | 527 |

TABLE 1-continued
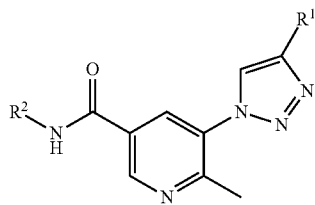
Example compounds I-1 to I-207
| # | Structure | $t_{Ret.}$ (HPLC) [min] | MS (M + H)+ |
|---|---|---|---|
| I-133 | 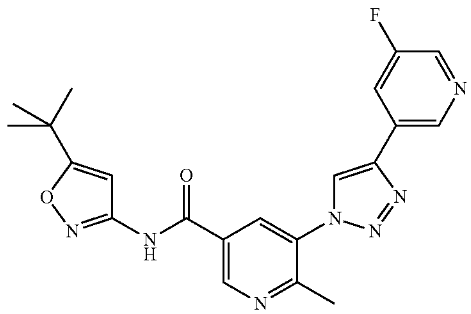 [SMILES: Cc1ncc(C(=O)Nc2cc(C(C)(C)C)on2)cc1-n1cc(-c2cncc(F)c2)nn1] | | |
| I-134 | 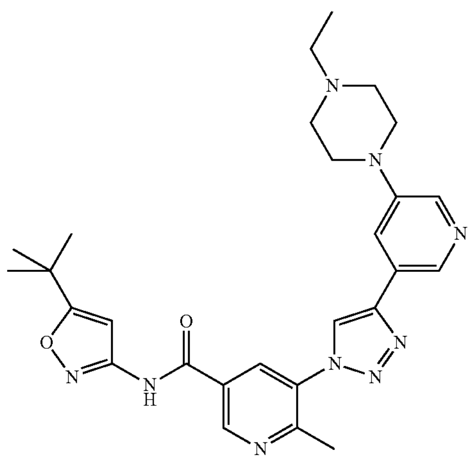 [SMILES: CCN1CCN(c2cncc(-c3cn(-c4cc(C(=O)Nc5cc(C(C)(C)C)on5)cnc4C)nn3)c2)CC1] | 1.75 | 516 |
| I-135 | 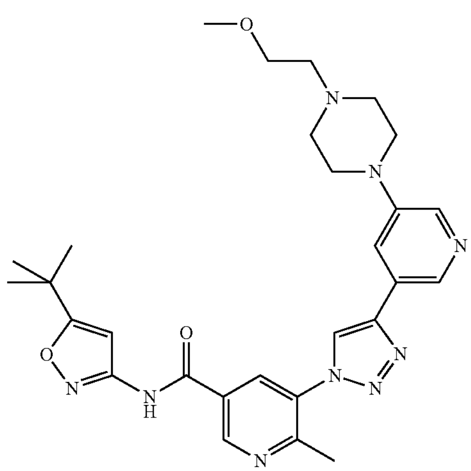 [SMILES: COCCN1CCN(c2cncc(-c3cn(-c4cc(C(=O)Nc5cc(C(C)(C)C)on5)cnc4C)nn3)c2)CC1] | 1.69 | 546 |

TABLE 1-continued
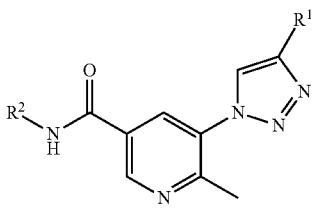
Example compounds I-1 to I-207
| # | Structure | $t_{Ret.}$ (HPLC) [min] | MS (M + H)+ |
|---|---|---|---|
| I-136 | 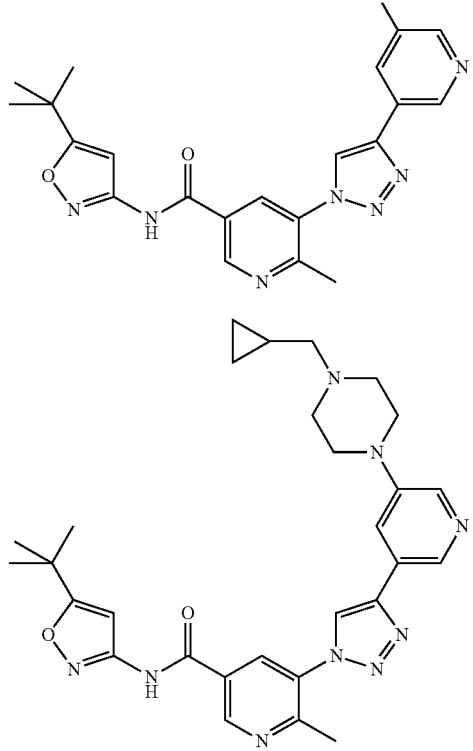 | 1.68 | 572 |
| I-137 | 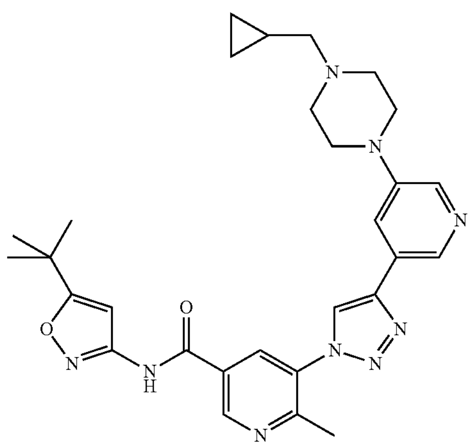 [SMILES: Cc1ncc(C(=O)Nc2cc(C(C)(C)C)on2)cc1-n1cc(-c2cncc(N3CCN(CC4CC4)CC3)c2)nn1] | 1.81 | 542 |
| I-138 | 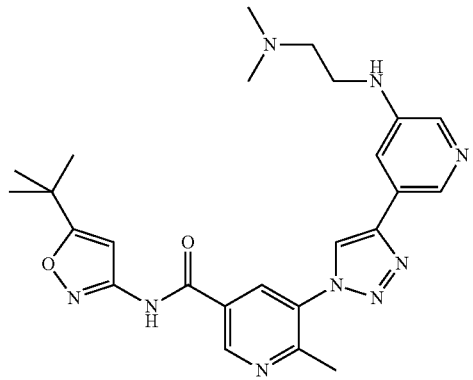 [SMILES: Cc1ncc(C(=O)Nc2cc(C(C)(C)C)on2)cc1-n1cc(-c2cncc(NCCN(C)C)c2)nn1] | 1.68 | 490 |

TABLE 1-continued
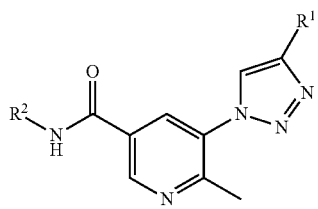
Example compounds I-1 to I-207
| # | Structure | $t_{Ret.}$ (HPLC) [min] | MS (M + H)+ |
|---|---|---|---|
| I-139 | 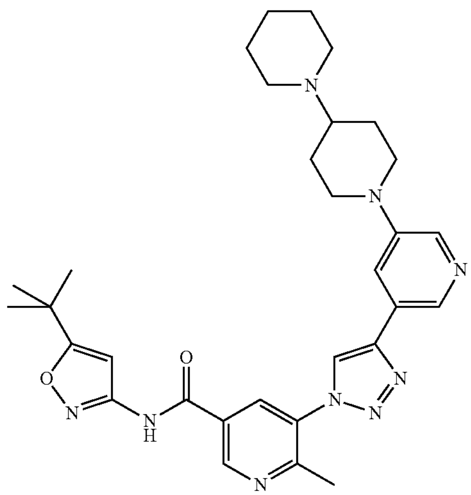 [SMILES: Cc1ncc(C(=O)Nc2cc(C(C)(C)C)on2)cc1-n1cc(-c2cncc(N3CCC(N4CCCCC4)CC3)c2)nn1] | 2.01 | 570 |
| I-140 | 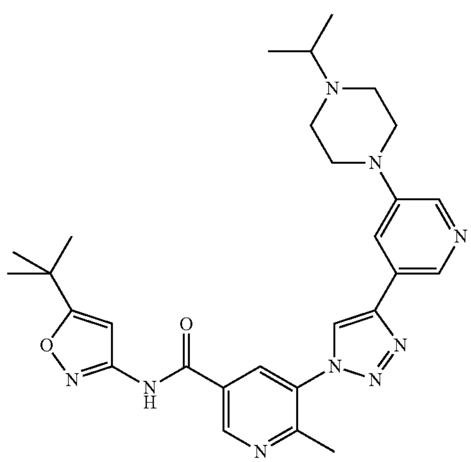 [SMILES: Cc1ncc(C(=O)Nc2cc(C(C)(C)C)on2)cc1-n1cc(-c2cncc(N3CCN(C(C)C)CC3)c2)nn1] | 1.75 | 530 |
| I-141 | 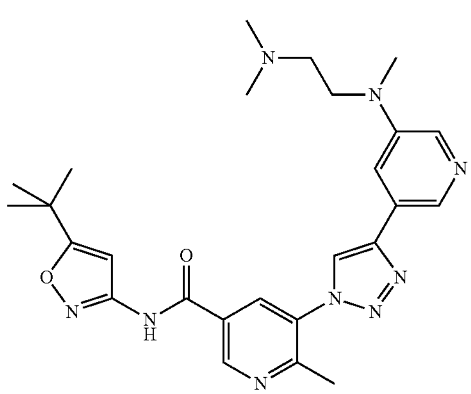 [SMILES: Cc1ncc(C(=O)Nc2cc(C(C)(C)C)on2)cc1-n1cc(-c2cncc(N(C)CCN(C)C)c2)nn1] | 1.76 | 504 |

TABLE 1-continued
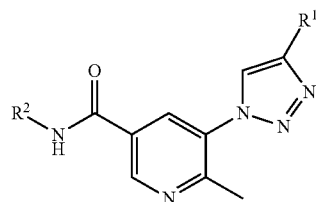
Example compounds I-1 to I-207
| # | Structure | t_Ret. (HPLC) [min] | MS (M + H)+ |
|---|---|---|---|
| I-142 | 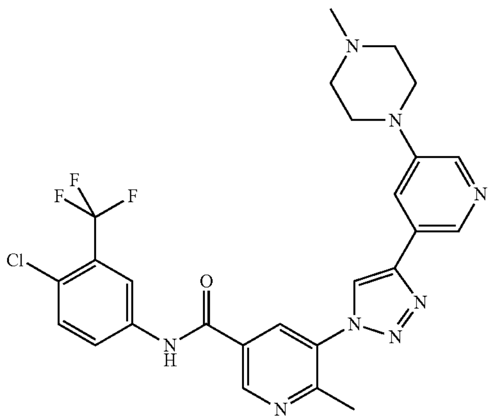 [SMILES: Cc1ncc(C(=O)Nc2ccc(Cl)c(C(F)(F)F)c2)cc1-n1cc(-c2cncc(N3CCN(C)CC3)c2)nn1] | 1.93 | 557 |
| I-143 | 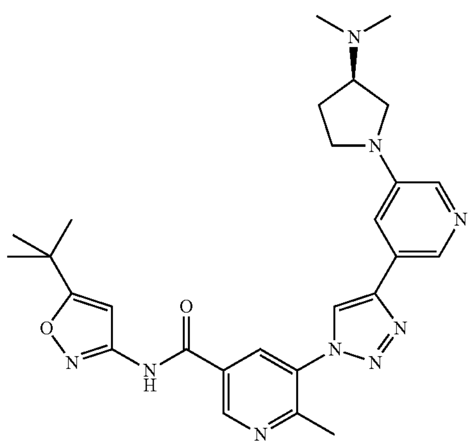 [SMILES: Cc1ncc(C(=O)Nc2cc(C(C)(C)C)on2)cc1-n1cc(-c2cncc(N3CC[C@@H](N(C)C)C3)c2)nn1] | 1.75 | 516 |
| I-144 | 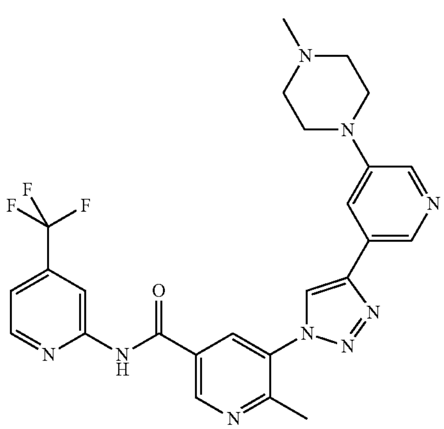 [SMILES: Cc1ncc(C(=O)Nc2cc(C(F)(F)F)ccn2)cc1-n1cc(-c2cncc(N3CCN(C)CC3)c2)nn1] | 1.72 | 524 |

TABLE 1-continued

Example compounds I-1 to I-207

| # | Structure | t_Ret. (HPLC) [min] | MS (M + H)+ |
|---|---|---|---|
| I-145 | 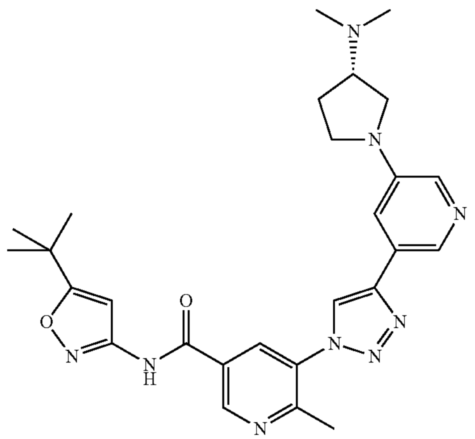 [SMILES: Cc1ncc(C(=O)Nc2cc(C(C)(C)C)on2)cc1-n1cc(-c2cncc(N3CC[C@H](N(C)C)C3)c2)nn1] | 1.74 | 516 |
| I-146 | 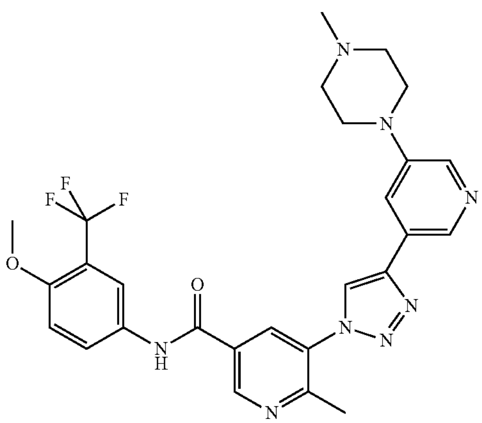 [SMILES: COc1ccc(NC(=O)c2cnc(C)c(-n3cc(-c4cncc(N5CCN(C)CC5)c4)nn3)c2)cc1C(F)(F)F] | 1.75 | 553 |
| I-147 | 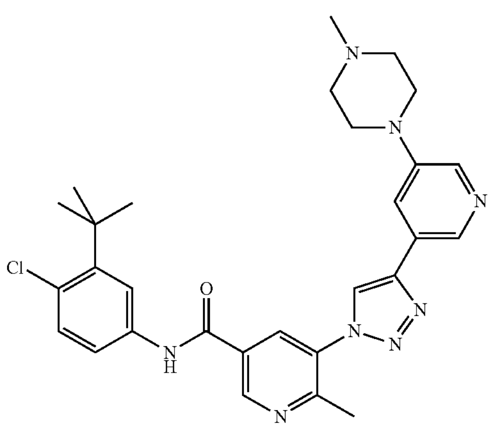 [SMILES: Cc1ncc(C(=O)Nc2ccc(Cl)c(C(C)(C)C)c2)cc1-n1cc(-c2cncc(N3CCN(C)CC3)c2)nn1] | 2.04 | 545 |

TABLE 1-continued
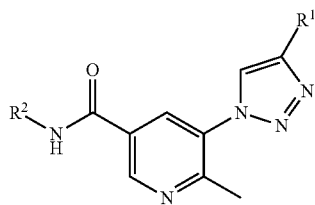
Example compounds I-1 to I-207
| # | Structure | t_{Ret.} (HPLC) [min] | MS (M + H)⁺ |
|---|---|---|---|
| I-148 | 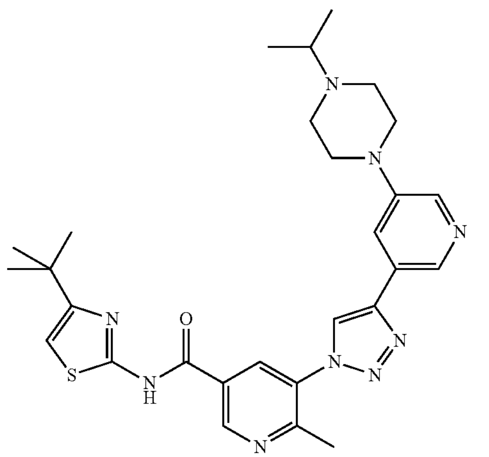 [SMILES: Cc1ncc(C(=O)Nc2nc(C(C)(C)C)cs2)cc1-n1cc(-c2cncc(N3CCN(C(C)C)CC3)c2)nn1] | 1.46 | 546 |
| I-149 | 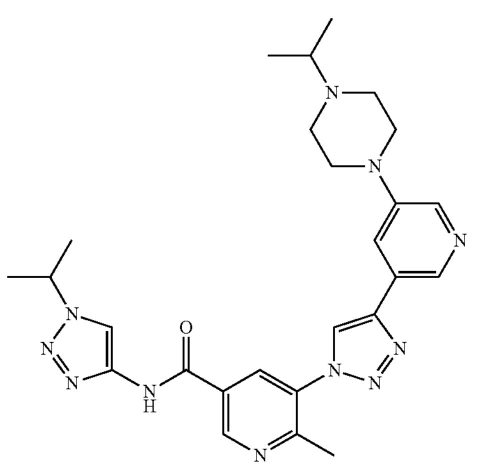 [SMILES: Cc1ncc(C(=O)Nc2cn(C(C)C)nn2)cc1-n1cc(-c2cncc(N3CCN(C(C)C)CC3)c2)nn1] | 1.53 | 516 |

TABLE 1-continued
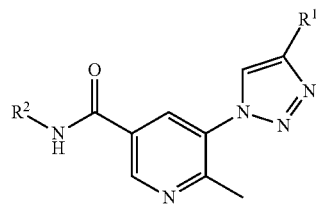
Example compounds I-1 to I-207
| # | Structure | t$_{Ret.}$ (HPLC) [min] | MS (M + H)$^+$ |
|---|---|---|---|
| I-150 | 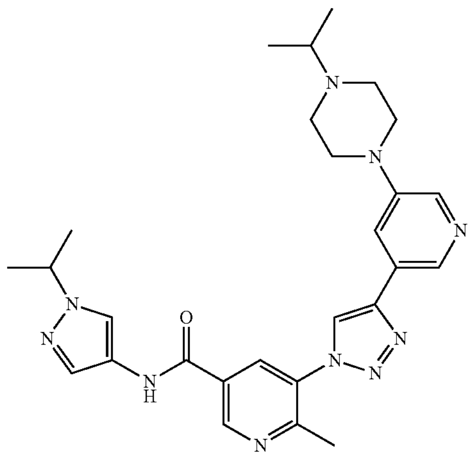 [SMILES: Cc1ncc(C(=O)Nc2cnn(C(C)C)c2)cc1-n1cc(-c2cncc(N3CCN(C(C)C)CC3)c2)nn1] | 1.58 | 515 |
| I-151 | 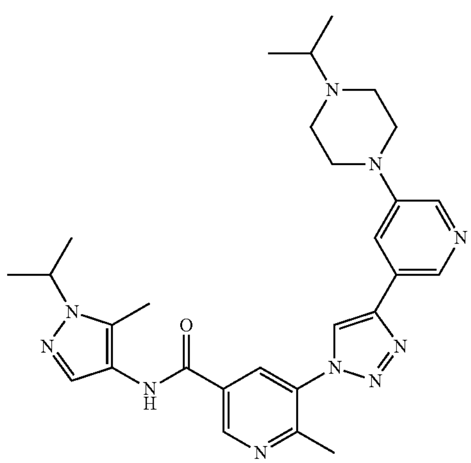 [SMILES: Cc1ncc(C(=O)Nc2cnn(C(C)C)c2C)cc1-n1cc(-c2cncc(N3CCN(C(C)C)CC3)c2)nn1] | 1.58 | 529 |

TABLE 1-continued
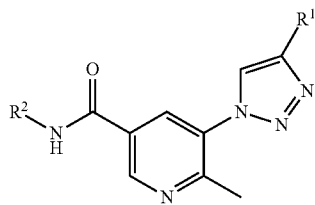
Example compounds I-1 to I-207
| # | Structure | t<sub>Ret.</sub> (HPLC) [min] | MS (M + H)<sup>+</sup> |
|---|---|---|---|
| I-152 | 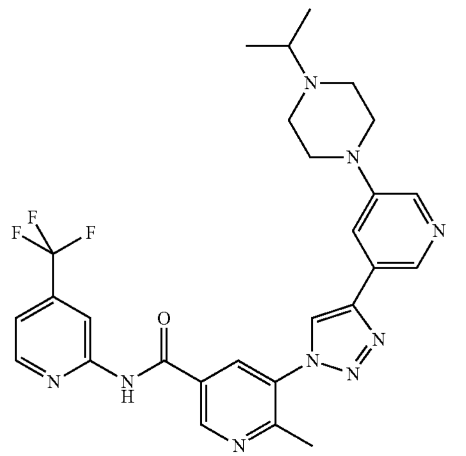 [SMILES: Cc1ncc(C(=O)Nc2cc(C(F)(F)F)ccn2)cc1-n1cc(-c2cncc(N3CCN(C(C)C)CC3)c2)nn1] | 1.89 | 552 |
| I-153 | 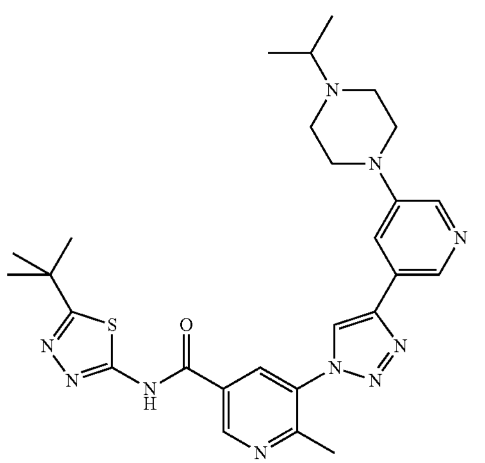 [SMILES: Cc1ncc(C(=O)Nc2nnc(C(C)(C)C)s2)cc1-n1cc(-c2cncc(N3CCN(C(C)C)CC3)c2)nn1] | 1.21 | 547 |

TABLE 1-continued
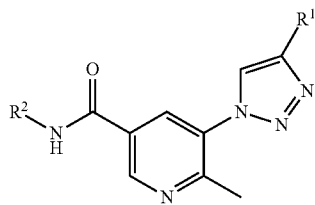
Example compounds I-1 to I-207
| # | Structure | t$_{Ret.}$ (HPLC) [min] | MS (M + H)$^+$ |
|---|---|---|---|
| I-154 | 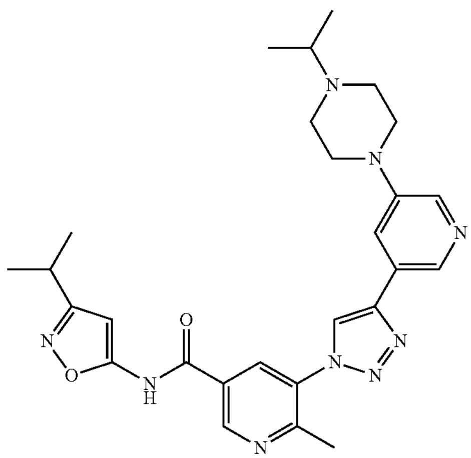 [SMILES: Cc1ncc(C(=O)Nc2cc(C(C)C)no2)cc1-n1cc(-c2cncc(N3CCN(C(C)C)CC3)c2)nn1] | 1.19 | 516 |
| I-155 | 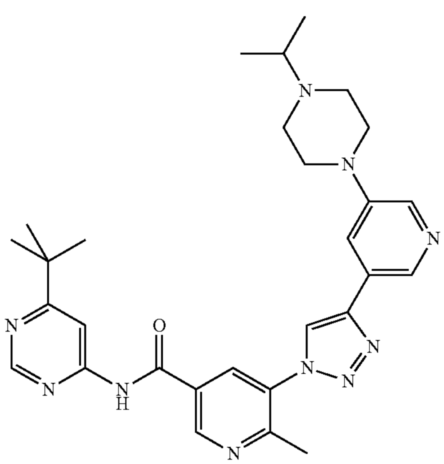 [SMILES: Cc1ncc(C(=O)Nc2cc(C(C)(C)C)ncn2)cc1-n1cc(-c2cncc(N3CCN(C(C)C)CC3)c2)nn1] | 1.82 | 541 |

TABLE 1-continued
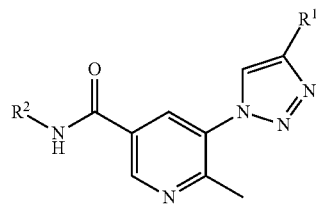
Example compounds I-1 to I-207
| # | Structure | t$_{Ret.}$ (HPLC) [min] | MS (M + H)$^+$ |
|---|---|---|---|
| I-156 | 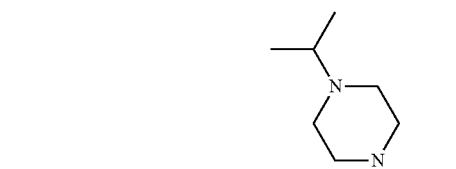 | | |
| I-157 | 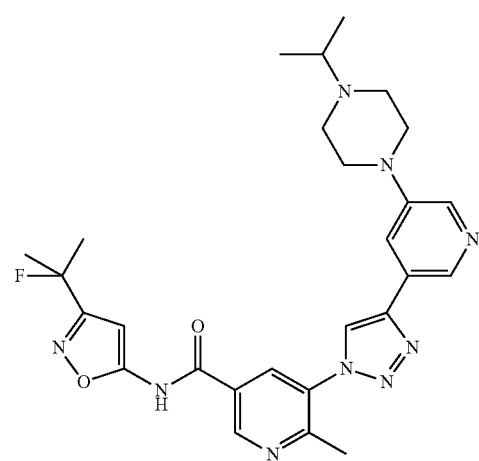 [SMILES: Cc1ncc(C(=O)Nc2cc(C(C)(C)F)no2)cc1-n1cc(-c2cncc(N3CCN(C(C)C)CC3)c2)nn1] | | |

TABLE 1-continued
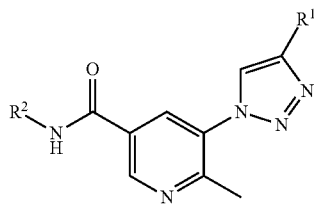
Example compounds I-1 to I-207
| # | Structure | t_Ret. (HPLC) [min] | MS (M + H)+ |
|---|---|---|---|
I-158
I-159

TABLE 1-continued
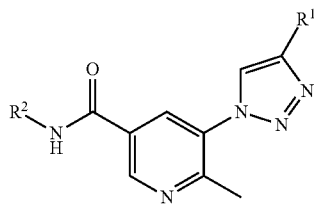
Example compounds I-1 to I-207
| # | Structure | t$_{Ret.}$ (HPLC) [min] | MS (M + H)$^+$ |
|---|---|---|---|
| I-160 | 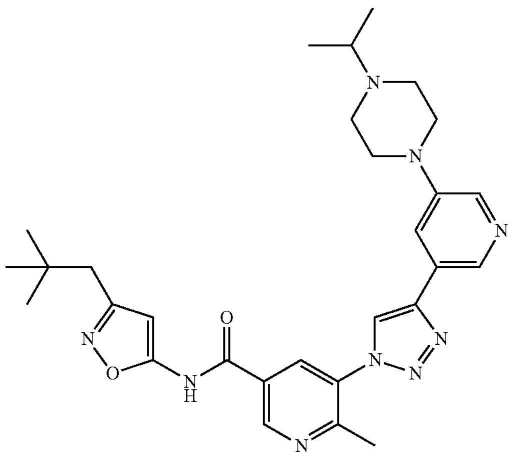 [SMILES: Cc1ncc(C(=O)Nc2cc(CC(C)(C)C)no2)cc1-n1cc(-c2cncc(N3CCN(C(C)C)CC3)c2)nn1] | | |
| I-161 | 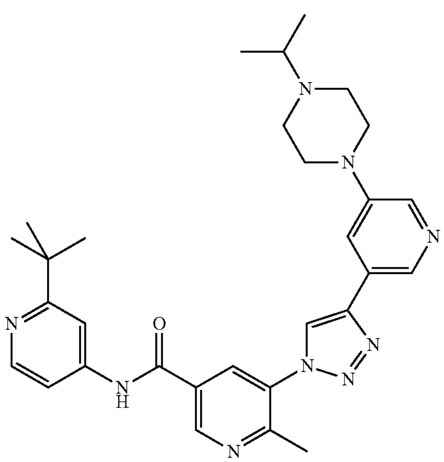 [SMILES: Cc1ncc(C(=O)Nc2ccnc(C(C)(C)C)c2)cc1-n1cc(-c2cncc(N3CCN(C(C)C)CC3)c2)nn1] | | |

US 8,778,929 B2
TABLE 1-continued
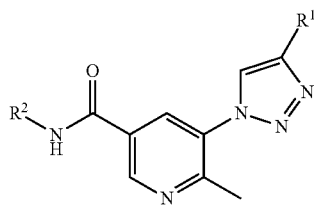
Example compounds I-1 to I-207
| # | Structure | t$_{Ret.}$ (HPLC) [min] | MS (M + H)$^+$ |
|---|---|---|---|
| I-162 | 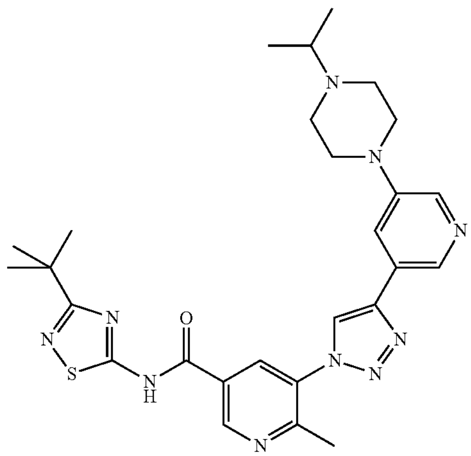 [SMILES: Cc1ncc(C(=O)Nc2nc(C(C)(C)C)ns2)cc1-n1cc(-c2cncc(N3CCN(C(C)C)CC3)c2)nn1] | | |
| I-163 | 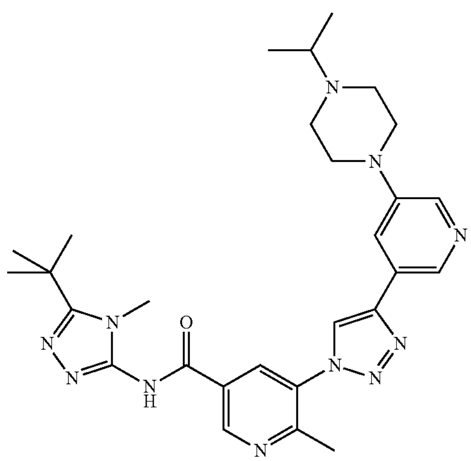 [SMILES: Cc1ncc(C(=O)Nc2nnc(C(C)(C)C)n2C)cc1-n1cc(-c2cncc(N3CCN(C(C)C)CC3)c2)nn1] | | |
| I-164 | 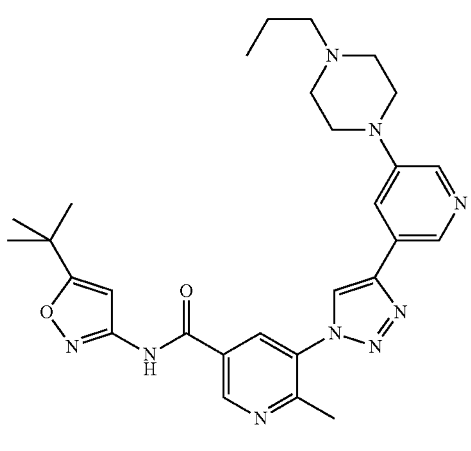 [SMILES: CCCN1CCN(c2cncc(-c3cn(-c4cc(C(=O)Nc5cc(C(C)(C)C)on5)cnc4C)nn3)c2)CC1] | 1.81 | 530 |

TABLE 1-continued
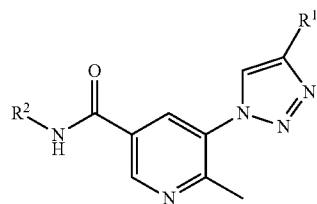
Example compounds I-1 to I-207
| # | Structure | $t_{Ret.}$ (HPLC) [min] | MS (M + H)$^+$ |
|---|---|---|---|
| I-165 | 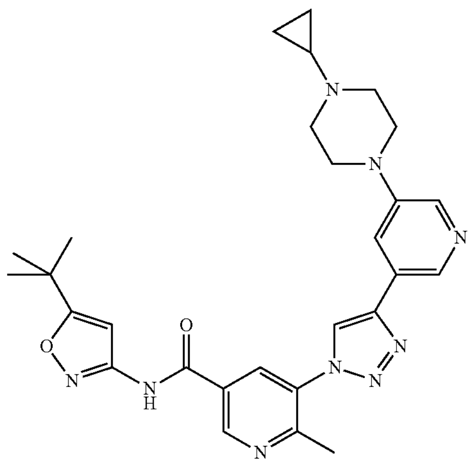 [SMILES: Cc1ncc(C(=O)Nc2cc(C(C)(C)C)on2)cc1-n1cc(-c2cncc(N3CCN(C4CC4)CC3)c2)nn1] | 1.81 | 528 |
| I-166 | 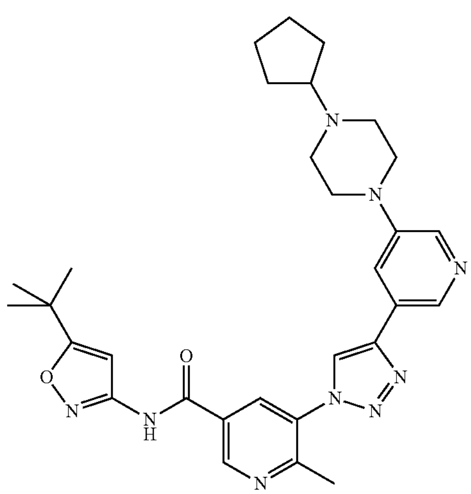 [SMILES: Cc1ncc(C(=O)Nc2cc(C(C)(C)C)on2)cc1-n1cc(-c2cncc(N3CCN(C4CCCC4)CC3)c2)nn1] | 1.93 | 556 |

TABLE 1-continued
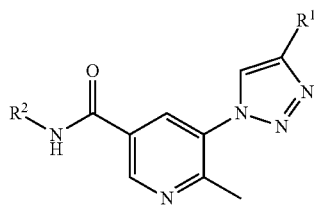
Example compounds I-1 to I-207
| # | Structure | $t_{Ret.}$ (HPLC) [min] | MS (M + H)$^+$ |
|---|---|---|---|
| I-167 | 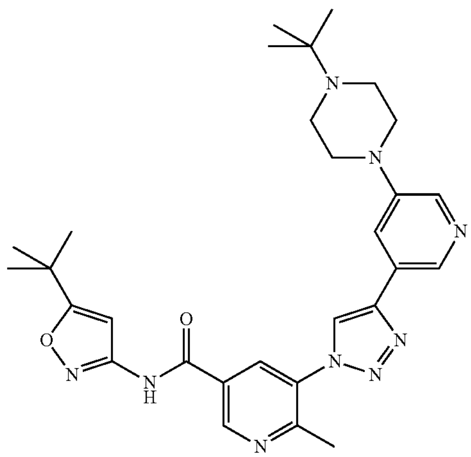 [SMILES: Cc1ncc(C(=O)Nc2cc(C(C)(C)C)on2)cc1-n1cc(-c2cncc(N3CCN(C(C)(C)C)CC3)c2)nn1] | 1.81 | 544 |
| I-168 | 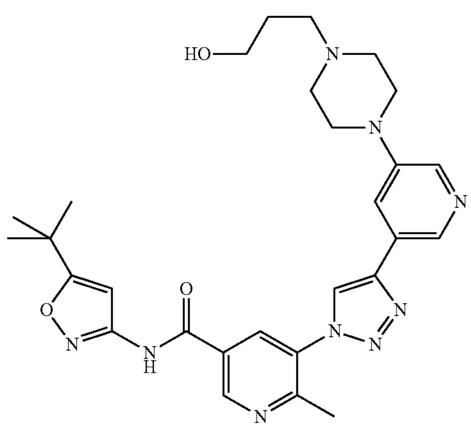 [SMILES: Cc1ncc(C(=O)Nc2cc(C(C)(C)C)on2)cc1-n1cc(-c2cncc(N3CCN(CCCO)CC3)c2)nn1] | 1.52 | 546 |
| I-169 | 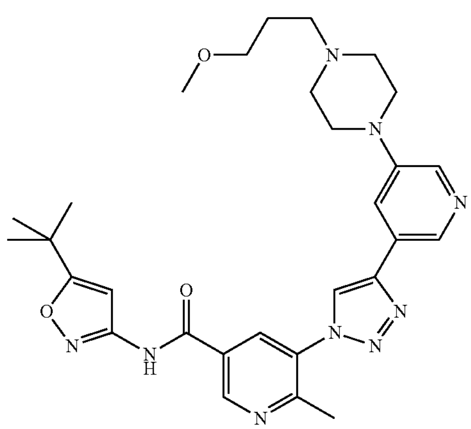 [SMILES: COCCCN1CCN(c2cncc(-c3cn(-c4cc(C(=O)Nc5cc(C(C)(C)C)on5)cnc4C)nn3)c2)CC1] | 1.70 | 560 |

US 8,778,929 B2

TABLE 1-continued

Example compounds I-1 to I-207

| # | Structure | t$_{Ret.}$ (HPLC) [min] | MS (M + H)$^+$ |
|---|---|---|---|
| I-170 | 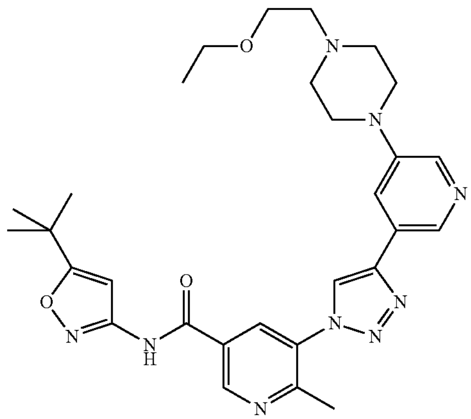 [SMILES: CCOCCN1CCN(c2cncc(-c3cn(-c4cc(C(=O)Nc5cc(C(C)(C)C)on5)cnc4C)nn3)c2)CC1] | 1.65 | 560 |
| I-171 | 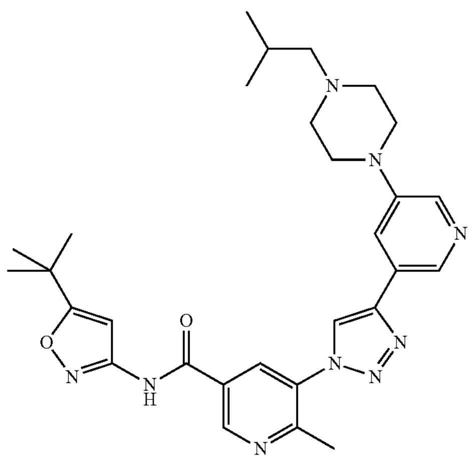 [SMILES: Cc1ncc(C(=O)Nc2cc(C(C)(C)C)on2)cc1-n1cc(-c2cncc(N3CCN(CC(C)C)CC3)c2)nn1] | 2.14 | 544 |
| I-172 | 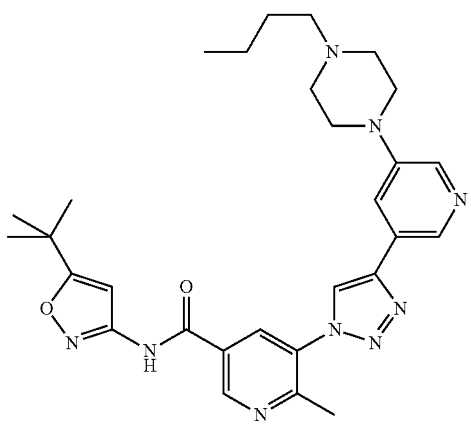 [SMILES: CCCCN1CCN(c2cncc(-c3cn(-c4cc(C(=O)Nc5cc(C(C)(C)C)on5)cnc4C)nn3)c2)CC1] | 1.96 | 544 |

TABLE 1-continued

Example compounds I-1 to I-207

| # | Structure | t_{Ret.} (HPLC) [min] | MS (M + H)+ |
|---|---|---|---|
| I-173 | 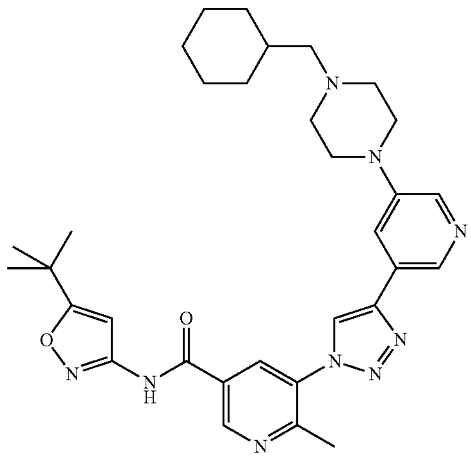 [SMILES: Cc1ncc(C(=O)Nc2cc(C(C)(C)C)on2)cc1-n1cc(-c2cncc(N3CCN(CC4CCCCC4)CC3)c2)nn1] | 2.24 | 584 |
| I-174 | 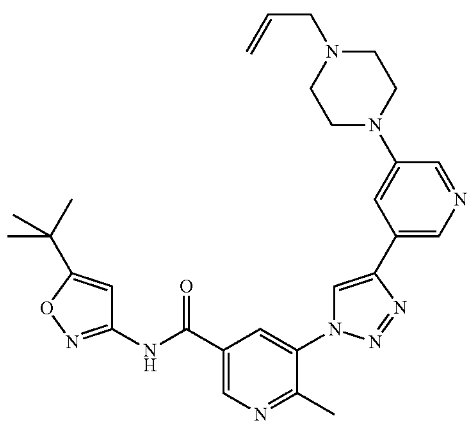 [SMILES: C=CCN1CCN(c2cncc(-c3cn(-c4cc(C(=O)Nc5cc(C(C)(C)C)on5)cnc4C)nn3)c2)CC1] | 1.74 | 528 |
| I-175 | 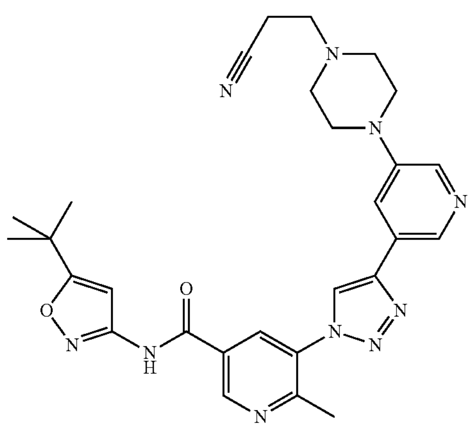 [SMILES: Cc1ncc(C(=O)Nc2cc(C(C)(C)C)on2)cc1-n1cc(-c2cncc(N3CCN(CCC#N)CC3)c2)nn1] | 1.58 | 541 |

TABLE 1-continued

Example compounds I-1 to I-207

| # | Structure | t<sub>Ret.</sub> (HPLC) [min] | MS (M + H)<sup>+</sup> |
|---|---|---|---|
| I-176 | 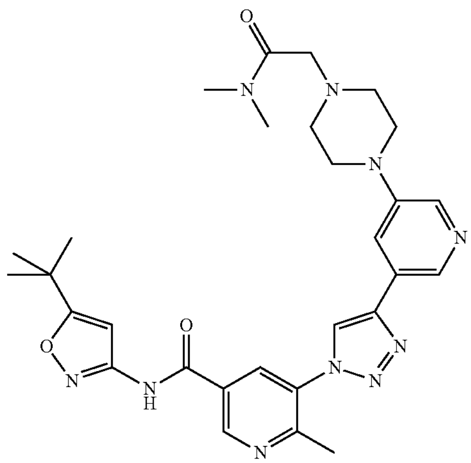 [SMILES: Cc1ncc(C(=O)Nc2cc(C(C)(C)C)on2)cc1-n1cc(-c2cncc(N3CCN(CC(=O)N(C)C)CC3)c2)nn1] | 1.54 | 573 |
| I-177 | 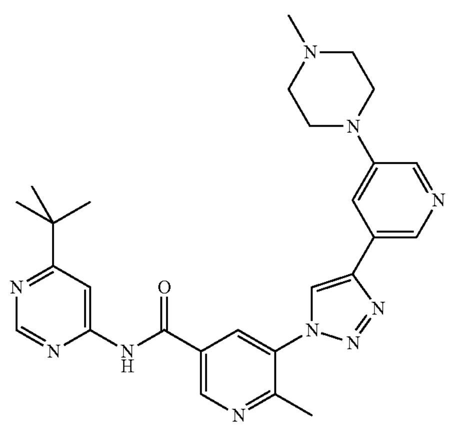 [SMILES: Cc1ncc(C(=O)Nc2cc(C(C)(C)C)ncn2)cc1-n1cc(-c2cncc(N3CCN(C)CC3)c2)nn1] | 1.66 | 513 |
| I-178 | 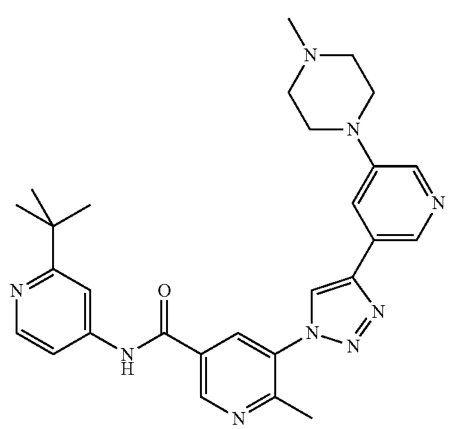 | 1.66 | 512 |

TABLE 1-continued
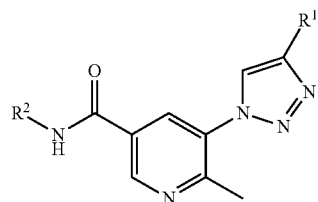
Example compounds I-1 to I-207
| # | Structure | $t_{Ret.}$ (HPLC) [min] | MS (M + H)+ |
|---|---|---|---|
| I-179 | 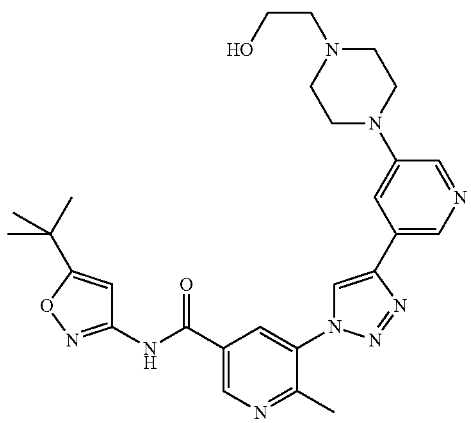 [SMILES: Cc1ncc(C(=O)Nc2cc(C(C)(C)C)on2)cc1-n1cc(-c2cncc(N3CCN(CCO)CC3)c2)nn1] | 1.43 | 532 |
| I-180 | 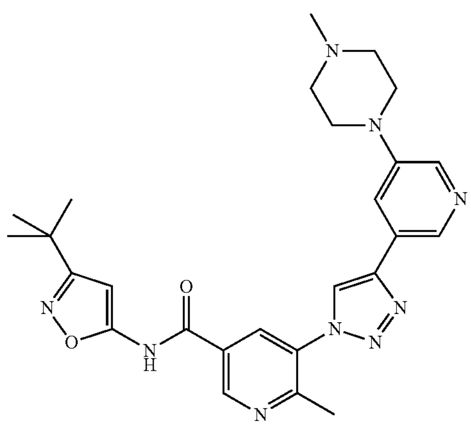 [SMILES: Cc1ncc(C(=O)Nc2cc(C(C)(C)C)no2)cc1-n1cc(-c2cncc(N3CCN(C)CC3)c2)nn1] | 1.09 | 502 |
| I-181 | 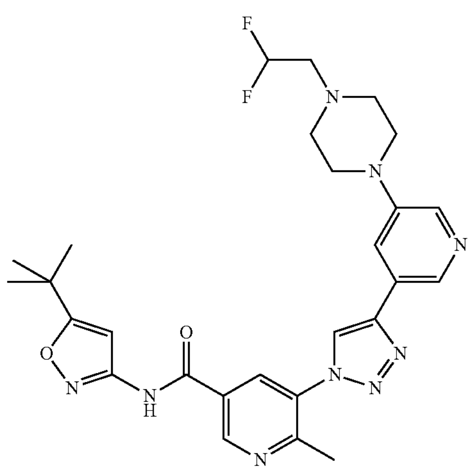 [SMILES: Cc1ncc(C(=O)Nc2cc(C(C)(C)C)on2)cc1-n1cc(-c2cncc(N3CCN(CC(F)F)CC3)c2)nn1] | 1.86 | 552 |

TABLE 1-continued

Example compounds I-1 to I-207

| # | Structure | t_Ret. (HPLC) [min] | MS (M + H)+ |
|---|---|---|---|
| I-182 | 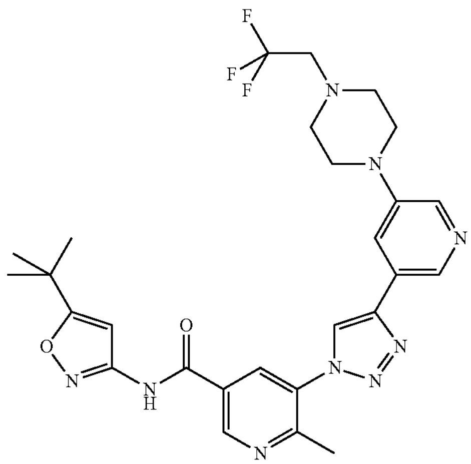 [SMILES: Cc1ncc(C(=O)Nc2cc(C(C)(C)C)on2)cc1-n1cc(-c2cncc(N3CCN(CC(F)(F)F)CC3)c2)nn1] | 1.89 | 570 |
| I-183 | 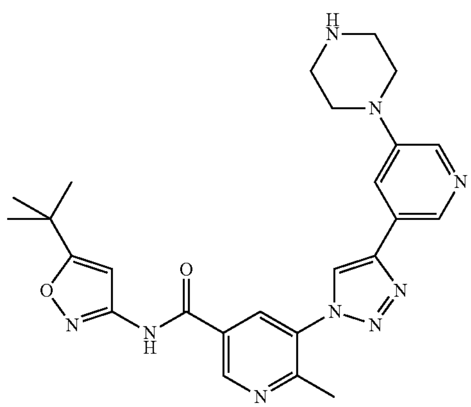 [SMILES: Cc1ncc(C(=O)Nc2cc(C(C)(C)C)on2)cc1-n1cc(-c2cncc(N3CCNCC3)c2)nn1] | 1.42 | 488 |
| I-184 | 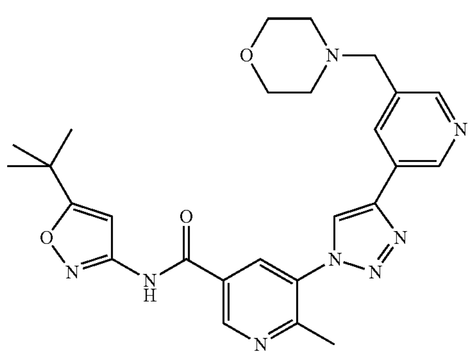 [SMILES: Cc1ncc(C(=O)Nc2cc(C(C)(C)C)on2)cc1-n1cc(-c2cncc(CN3CCOCC3)c2)nn1] | 1.53 | 503 |

TABLE 1-continued
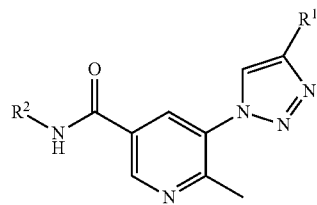
Example compounds I-1 to I-207
| # | Structure | t_Ret. (HPLC) [min] | MS (M + H)+ |
|---|---|---|---|
| I-185 | 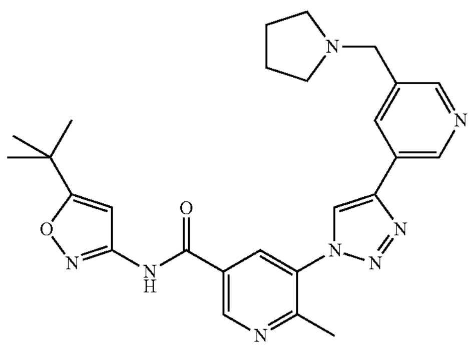 [SMILES: Cc1ncc(C(=O)Nc2cc(C(C)(C)C)on2)cc1-n1cc(-c2cncc(CN3CCCC3)c2)nn1] | 1.69 | 487 |
| I-186 | 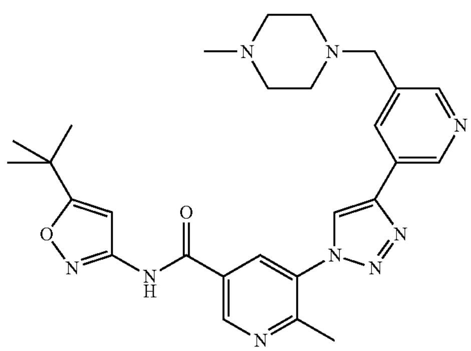 [SMILES: Cc1ncc(C(=O)Nc2cc(C(C)(C)C)on2)cc1-n1cc(-c2cncc(CN3CCN(C)CC3)c2)nn1] | 1.50 | 516 |
| I-187 | 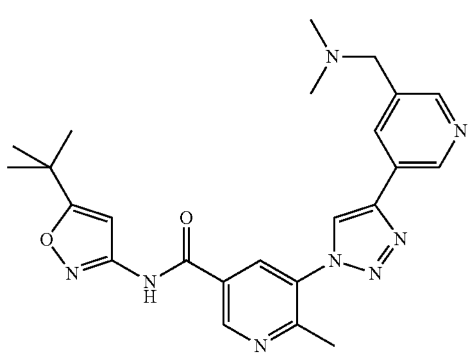 [SMILES: Cc1ncc(C(=O)Nc2cc(C(C)(C)C)on2)cc1-n1cc(-c2cncc(CN(C)C)c2)nn1] | 1.57 | 461 |

TABLE 1-continued
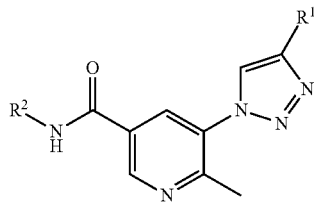
Example compounds I-1 to I-207
| # | Structure | t_Ret. (HPLC) [min] | MS (M + H)+ |
|---|---|---|---|
| I-188 | 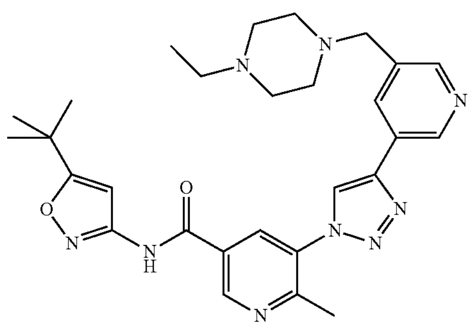 [SMILES: CCN1CCN(Cc2cncc(-c3cn(-c4cc(C(=O)Nc5cc(C(C)(C)C)on5)cnc4C)nn3)c2)CC1] | 1.59 | 530 |
| I-189 | 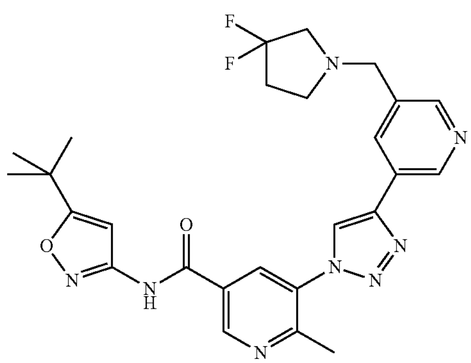 [SMILES: Cc1ncc(C(=O)Nc2cc(C(C)(C)C)on2)cc1-n1cc(-c2cncc(CN3CCC(F)(F)C3)c2)nn1] | 1.75 | 523 |
| I-190 | 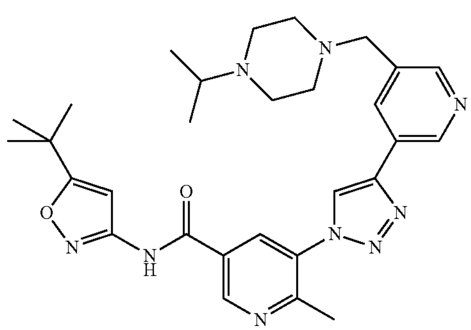 [SMILES: Cc1ncc(C(=O)Nc2cc(C(C)(C)C)on2)cc1-n1cc(-c2cncc(CN3CCN(C(C)C)CC3)c2)nn1] | 1.68 | 544 |

TABLE 1-continued
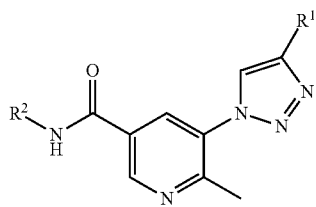
Example compounds I-1 to I-207
| # | Structure | t$_{Ret.}$ (HPLC) [min] | MS (M + H)$^+$ |
|---|---|---|---|
| I-191 | 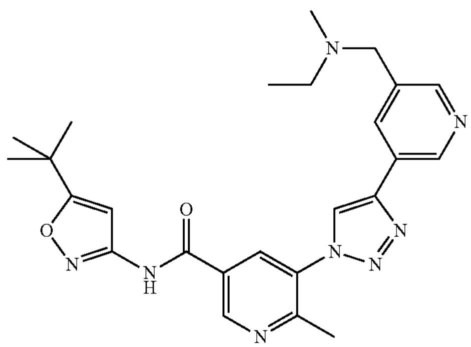 [SMILES: CCN(C)Cc1cncc(-c2cn(-c3cc(C(=O)Nc4cc(C(C)(C)C)on4)cnc3C)nn2)c1] | 1.77 | 475 |
| I-192 | 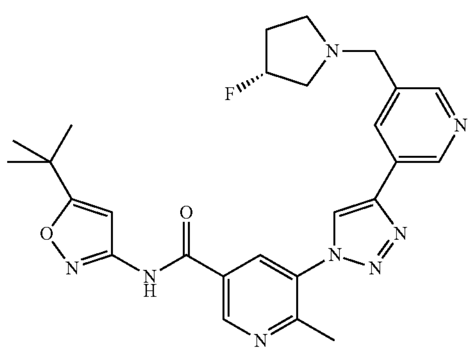 [SMILES: Cc1ncc(C(=O)Nc2cc(C(C)(C)C)on2)cc1-n1cc(-c2cncc(CN3CC[C@@H](F)C3)c2)nn1] | 1.65 | 505 |
| I-193 | 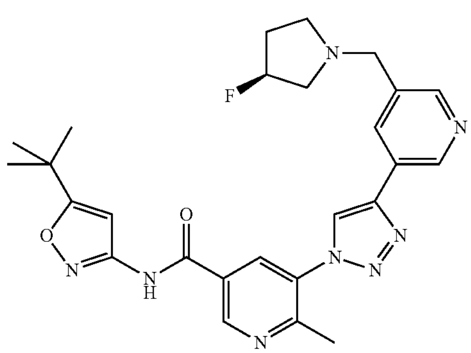 [SMILES: Cc1ncc(C(=O)Nc2cc(C(C)(C)C)on2)cc1-n1cc(-c2cncc(CN3CC[C@H](F)C3)c2)nn1] | 1.65 | 505 |

TABLE 1-continued
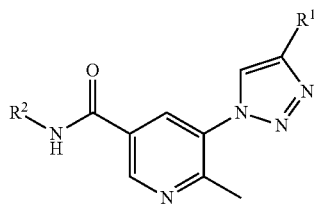
Example compounds I-1 to I-207
| # | Structure | $t_{Ret.}$ (HPLC) [min] | MS (M + H)+ |
|---|---|---|---|
| I-194 | 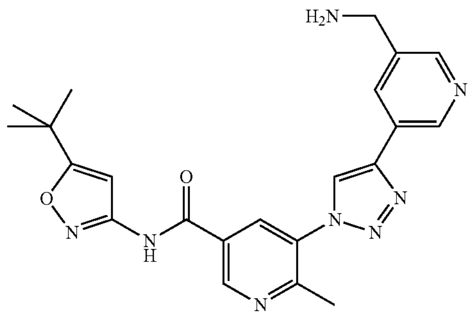 [SMILES: Cc1ncc(C(=O)Nc2cc(C(C)(C)C)on2)cc1-n1cc(-c2cncc(CN)c2)nn1] | 1.37 | 433 |
| I-195 | 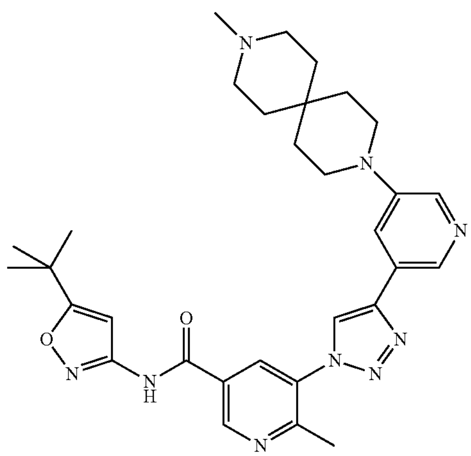 [SMILES: Cc1ncc(C(=O)Nc2cc(C(C)(C)C)on2)cc1-n1cc(-c2cncc(N3CCC4(CCN(C)CC4)CC3)c2)nn1] | 1.80 | 570 |
| I-196 | 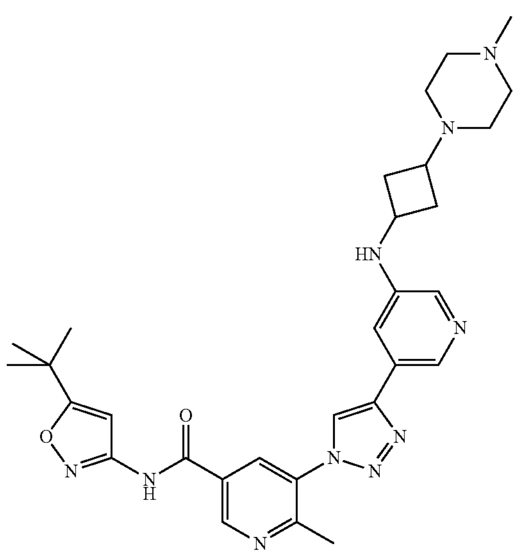 [SMILES: Cc1ncc(C(=O)Nc2cc(C(C)(C)C)on2)cc1-n1cc(-c2cncc(NC3CC(N4CCN(C)CC4)C3)c2)nn1] | 1.49 | 571 |

TABLE 1-continued
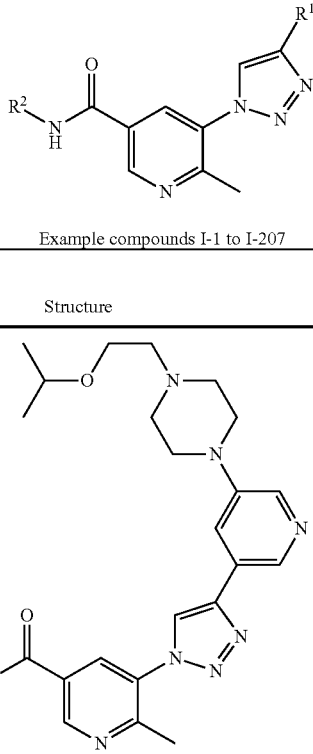
Example compounds I-1 to I-207
| # | Structure | $t_{Ret.}$ (HPLC) [min] | MS (M + H)+ |
|---|---|---|---|
| I-197 | 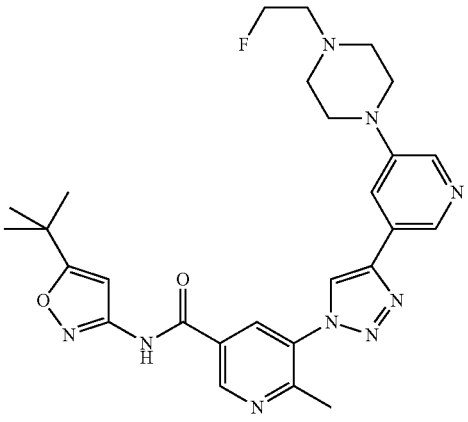 | 1.80 | 574 |
| I-198 | 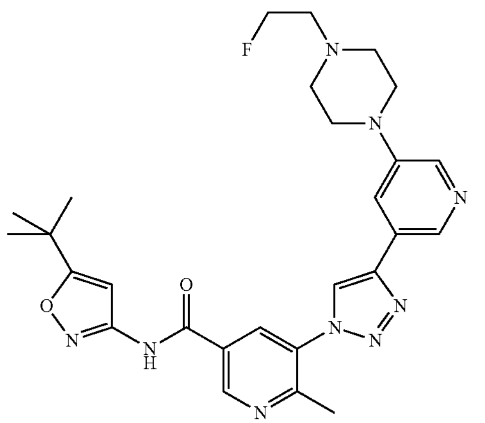 | 1.61 | 534 |
| I-199 | 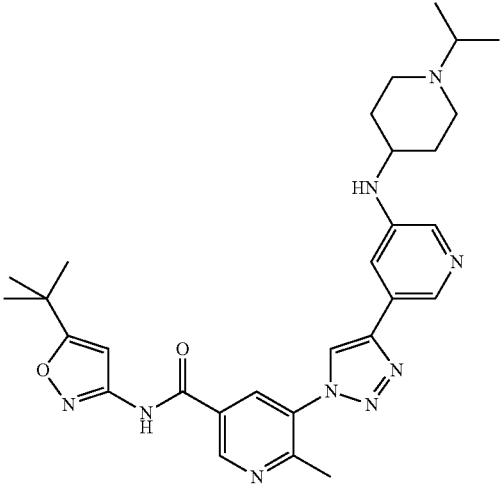 [SMILES: Cc1ncc(C(=O)Nc2cc(C(C)(C)C)on2)cc1-n1cc(-c2cncc(NC3CCN(C(C)C)CC3)c2)nn1] | 1.76 | 554 |

US 8,778,929 B2
TABLE 1-continued
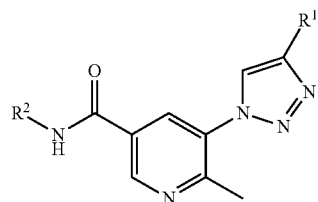
Example compounds I-1 to I-207
| # | Structure | t_{Ret.} (HPLC) [min] | MS (M + H)+ |
|---|-----------|------------------------|-------------|
| I-200 | 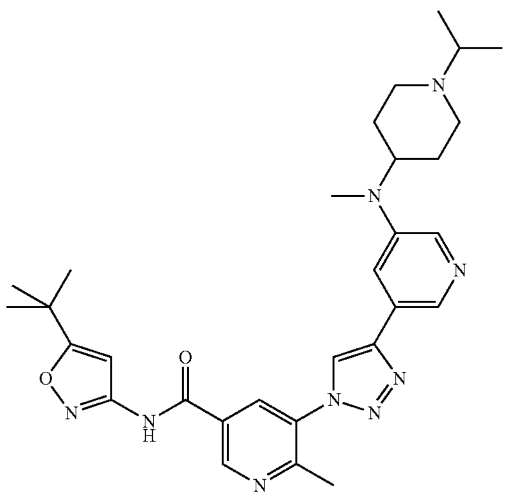 [SMILES: Cc1ncc(C(=O)Nc2cc(C(C)(C)C)on2)cc1-n1cc(-c2cncc(N(C)C3CCN(C(C)C)CC3)c2)nn1] | 1.86 | 558 |
| I-201 | 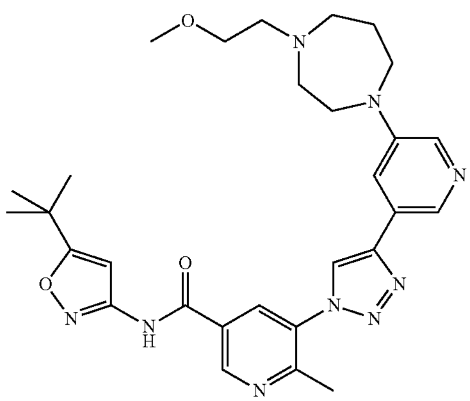 [SMILES: COCCN1CCCN(c2cncc(-c3cn(-c4cc(C(=O)Nc5cc(C(C)(C)C)on5)cnc4C)nn3)c2)CC1] | 1.64 | 560 |
| I-202 | 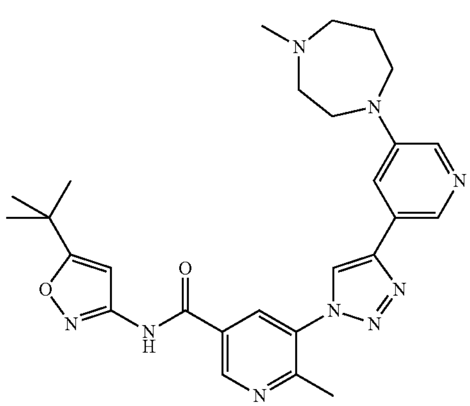 [SMILES: Cc1ncc(C(=O)Nc2cc(C(C)(C)C)on2)cc1-n1cc(-c2cncc(N3CCCN(C)CC3)c2)nn1] | 1.61 | 516 |

TABLE 1-continued
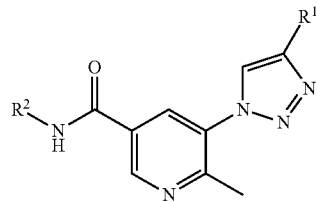
Example compounds I-1 to I-207
| # | Structure | t$_{Ret.}$ (HPLC) [min] | MS (M + H)$^+$ |
|---|---|---|---|
| I-203 | 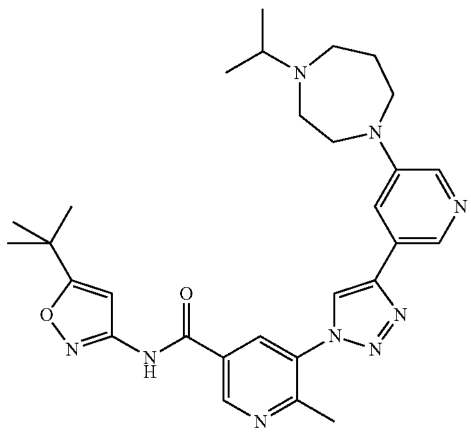 [SMILES: Cc1ncc(C(=O)Nc2cc(C(C)(C)C)on2)cc1-n1cc(-c2cncc(N3CCCN(C(C)C)CC3)c2)nn1] | | |
| I-204 | 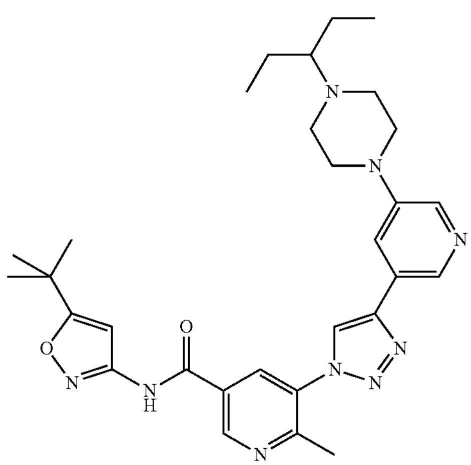 [SMILES: CCC(CC)N1CCN(c2cncc(-c3cn(-c4cc(C(=O)Nc5cc(C(C)(C)C)on5)cnc4C)nn3)c2)CC1] | 2.15 | 558 |

TABLE 1-continued
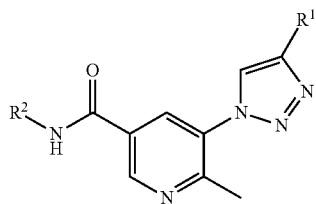
Example compounds I-1 to I-207
| # | Structure | $t_{Ret.}$ (HPLC) [min] | MS (M + H)+ |
|---|---|---|---|
| I-205 | 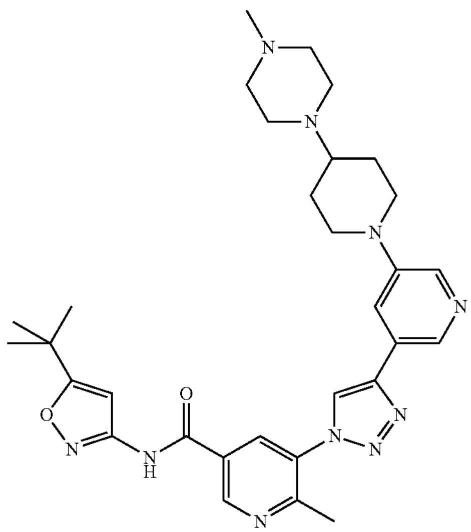 [SMILES: Cc1ncc(C(=O)Nc2cc(C(C)(C)C)on2)cc1-n1cc(-c2cncc(N3CCC(N4CCN(C)CC4)CC3)c2)nn1] | 1.60 | 585 |
| I-206 | 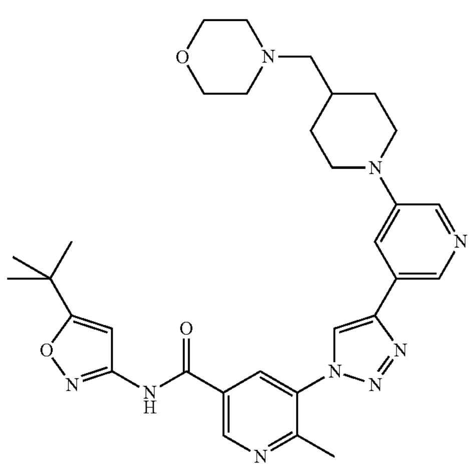 [SMILES: Cc1ncc(C(=O)Nc2cc(C(C)(C)C)on2)cc1-n1cc(-c2cncc(N3CCC(CN4CCOCC4)CC3)c2)nn1] | 1.72 | 586 |

TABLE 1-continued

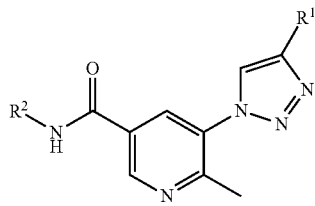

Example compounds I-1 to I-207

| # | Structure | t$_{Ret.}$ (HPLC) [min] | MS (M + H)$^+$ |
|---|---|---|---|
| I-207 | 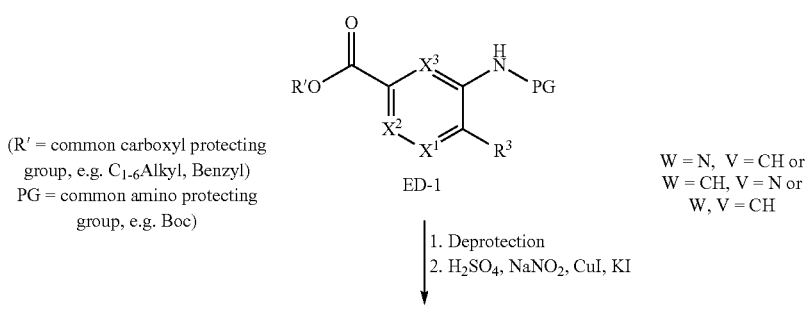 | | |

Reaction scheme B

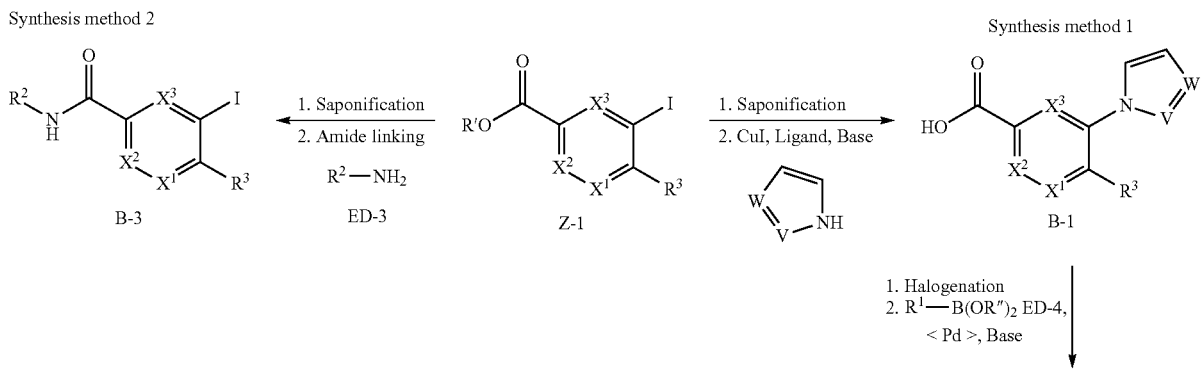

(R' = common carboxyl protecting group, e.g. C$_{1-6}$Alkyl, Benzyl)
PG = common amino protecting group, e.g. Boc)

W = N, V = CH or
W = CH, V = N or
W, V = CH

1. Deprotection
2. H$_2$SO$_4$, NaNO$_2$, CuI, KI

Synthesis method 2

1. Saponification
2. Amide linking

R$^2$—NH$_2$

Synthesis method 1

1. Saponification
2. CuI, Ligand, Base

1. Halogenation
2. R$^1$—B(OR″)$_2$ ED-4,
   < Pd >, Base

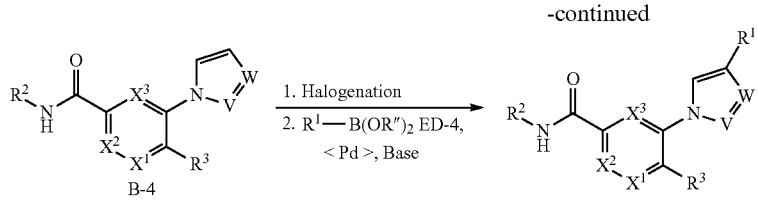 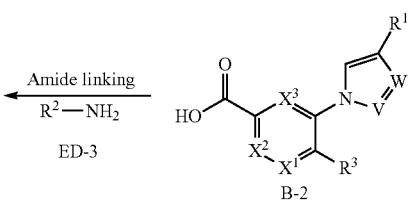

Example Compounds of Type II:

Compounds with an N-linked pyrrole, pyrazole or imidazole ring (type II) may for example be prepared by one of the synthesis routes (synthesis method 1 and 2) shown in Reaction scheme B.

The educts used are again heteroaromatic, protected amino acid esters ED-1. These are converted into the iodides Z-1 (SANDMEYER reaction) after the amino protecting group has been cleaved in sulphuric sodium nitrite solution in the presence of copper iodide and potassium iodide.

SUZUKI reaction, as these three transformations may also be carried out with the ester. Finally compounds of type II are obtained by amide coupling with components ED-3.

Alternatively (synthesis method 2) the order of the reaction is changed and first of all the amide coupling with amino components ED-3 to form iodides B-3 is carried out directly after the saponification of Z-1. After an ULLMANN-like substitution has been carried out to obtain B-4 analogously to synthesis method 1 and after selective halogenation and SUZUKI reaction, compounds of type II are also obtained.

Reaction scheme C

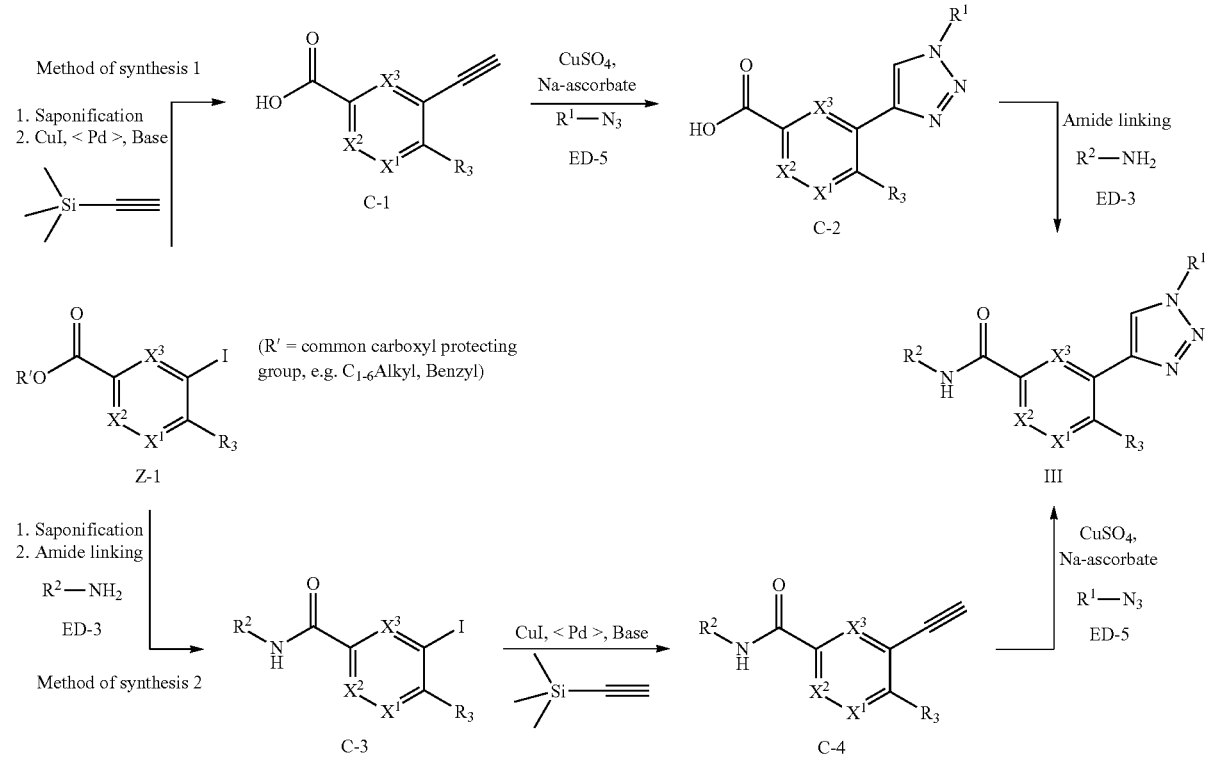

The iodides Z-1 may then first of all (synthesis method 1) be saponified and then substituted by pyrrole, imidazole or pyrazole in the manner of an ULLMANN reaction with copper catalysis, to obtain the acids B-1. Selective halogenation with for example bromine, iodine, N-bromosuccinimide, N-iodosuccinimide or other halogenating reagents known from the literature and subsequent palladium-catalysed SUZUKI cross-coupling reaction with a heteroarylboric acid $R^1B(OH)_2$ or a heteroarylboric acid derivative $R^1B(OR'')_2$ (ED-4) leads to the free acids B-2. If desired the saponification of the carboxylate —C(O)OR' may also only take place after the sequence of the ULLMANN-like substitution, halogenation and Example Compounds of Type III:

Compounds with a C-linked triazole ring (type III) may for example be prepared by one of the synthesis routes (synthesis method 1 and 2) shown in Reaction scheme C.

Starting from iodides Z-1 (cf. Reaction scheme B) first of all the ester function is cleaved (synthesis method 1) and then a palladium-catalysed SONOGASHIRA cross-coupling reaction with trimethylsilylacetylene and CuI is carried out, to obtain the alkyne C-1. This is followed by a copper-catalysed 1,3-dipolar cycloaddition between C-1 and heteroarylazides ED-5, thus forming the C-linked triazole ring. By comparison with the formation of the N-linked triazole ring according to reaction scheme A the reactivities "1,3-dipol" and "dipolarophil" regarding the groups thus introduced are precisely reversed. The final amide coupling with amines ED-3 leads to compounds III. If desired the saponification according to synthesis method 1 may also be carried out before this amide coupling, as all the transformations are comparable with the ester function as well. According to synthesis method 2, example compounds III may alternatively be prepared by a different order of the reaction sequence from that in synthesis method 1.

Starting from iodides Z-1 after saponification a palladium-catalysed cross-coupling reaction is carried out with the boric acid derivatives Z-3 (synthesis method 1), to obtain the intermediates D-1. After a final amidation the end compounds IV are obtained. If desired, the saponification described may also take place just before this final amidation. The components Z-3 needed for this sequence are prepared beforehand starting from pyrrole, imidazole or pyrazole in a copper-catalysed cross-coupling reaction with the corresponding heteroarylhalide ED-6, subsequent halogenation at the heteroaryl with for example bromine, iodine, N-bromosuccinimide, N-iodosuc- Reaction scheme D

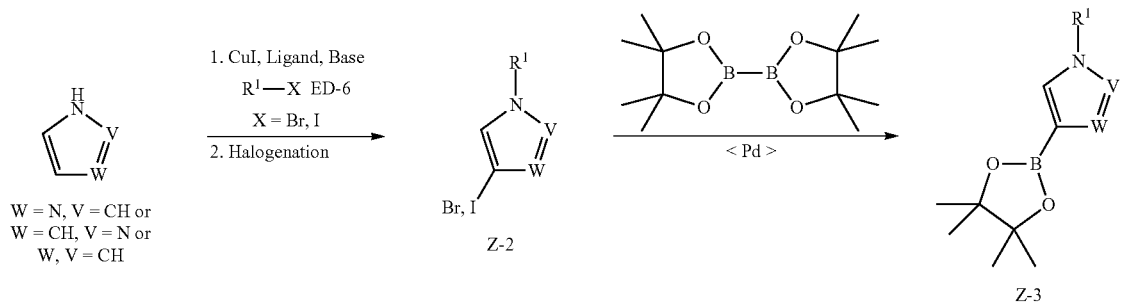

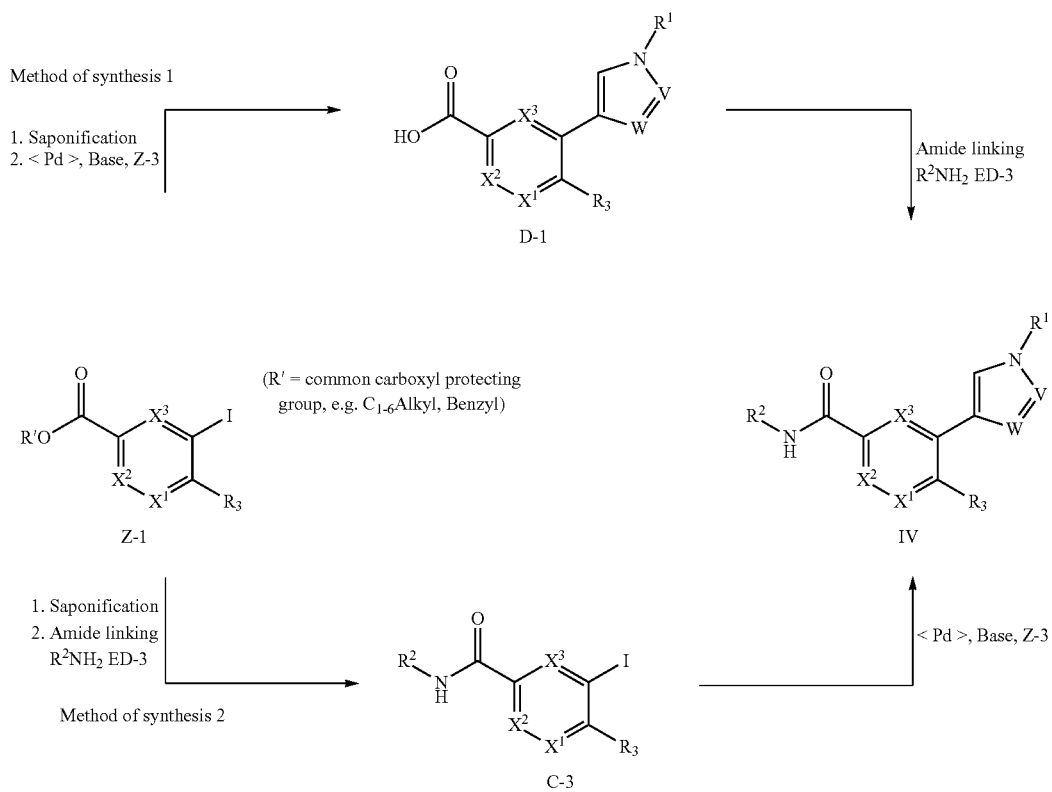

Example Compounds of Type IV:

Compounds with a C-linked pyrrole, pyrazole or imidazole ring (type IV) may for example be prepared by one of the synthesis routes (synthesis method 1 and 2) shown in Reaction scheme D.

cinimide or other halogenating reagents known from the literature and a final, palladium-catalysed cross-coupling reaction with bis-pinacolborane.

According to synthesis method 2 the reaction steps of synthesis method 1 are rearranged in their order and the compounds IV are obtained via the intermediates C-3 (cf. Reaction scheme C).

Reaction scheme E
Part 1
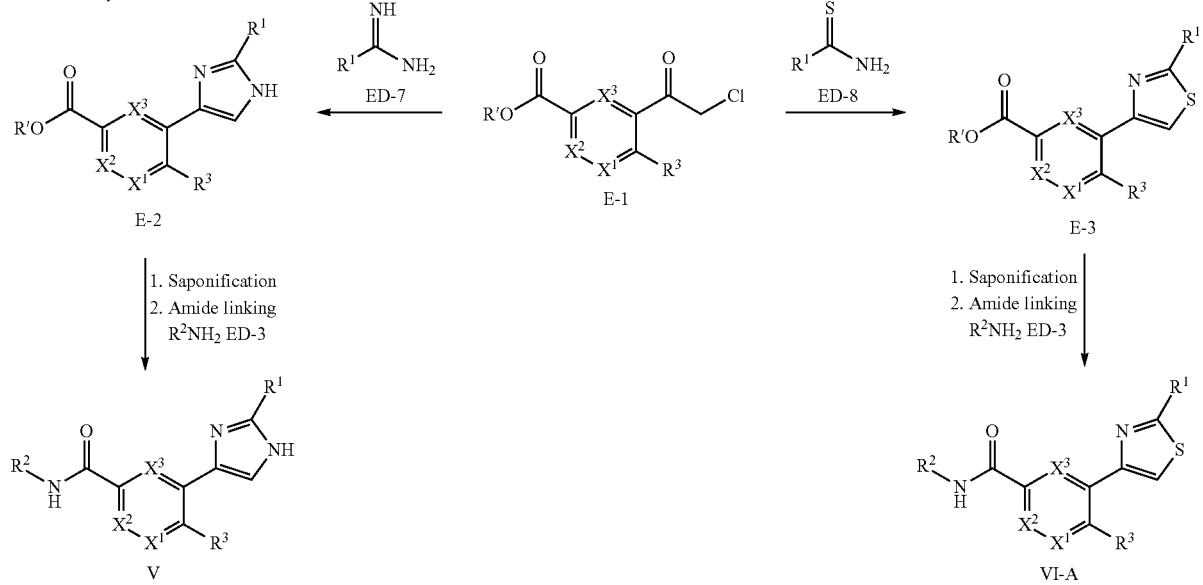
Part 2
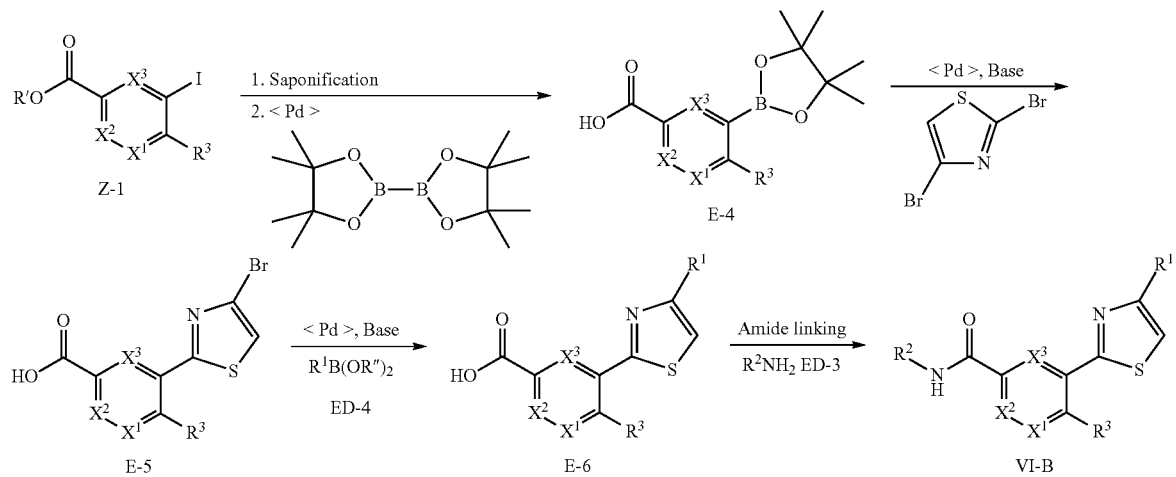
Example Compounds of Type V, VI-A and VI-B:
Compounds with an imidazole ring C-linked via the 4-position in each case (type V) or with a thiazole ring C-linked via the 4- or 2-position (type VI-A and type VI-B) may be obtained by cyclisation from iodides Z-1 (Reaction Scheme E). In order to synthesise the Example compounds of type V and VI-A (part 1) the iodides Z-1 are metallised in the first reaction step by iPrMgCl in the presence of CuCN and then reacted with chloroacetyl chloride to obtain α-chloroketones E-1.

The reaction of E-1 with heteroarylamidines ED-7 leads to imidazole intermediates E-2 (synthesis method 1), while reaction with heteroarylthioamides ED-8 yields thiazole intermediates E-3 (synthesis method 2). Both E-2 and E-3 may then be amidated after saponification to form the end compounds.

To synthesise the example compounds of type VI-B (part 2) the iodides Z-1 are saponified in the first reaction step and then, with palladium catalysis, converted into the boric acid derivatives E-4, e.g. by reaction with bis-pinacolborane. By two successive palladium-catalysed SUZUKI reactions first of all the thiazole ring is introduced with 2,4-dibromothiazole (intermediates E-5) and then the group $R^1$ is introduced via the boric acids or boric acid derivatives ED-4 (intermediates E-6). By final amide linking with amines ED-3 the end compounds of type VI-B are obtained. If desired the saponification described may also be carried out just before this final amidation.

Reaction scheme F

Part 1

($R'$ = common carboxyl protecting group, e.g. $C_{1-6}$Alkyl, Benzyl)

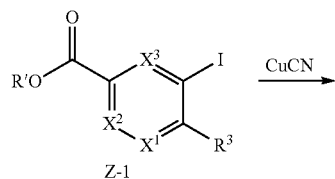

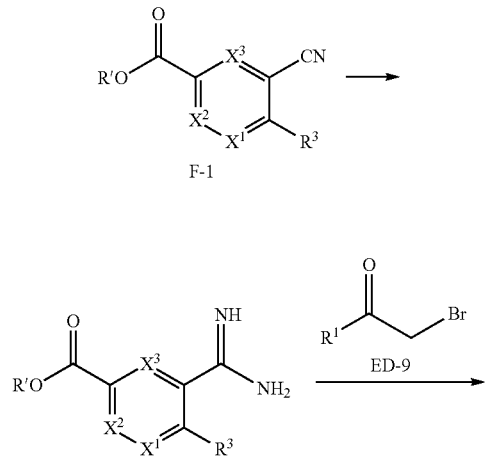

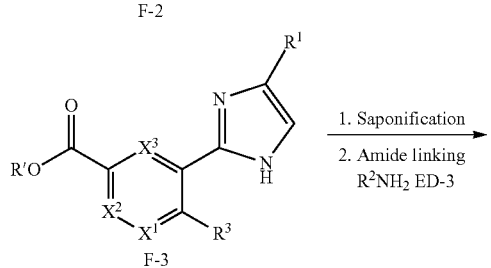

-continued

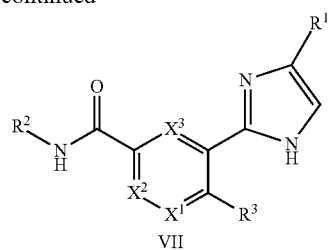

Part 2

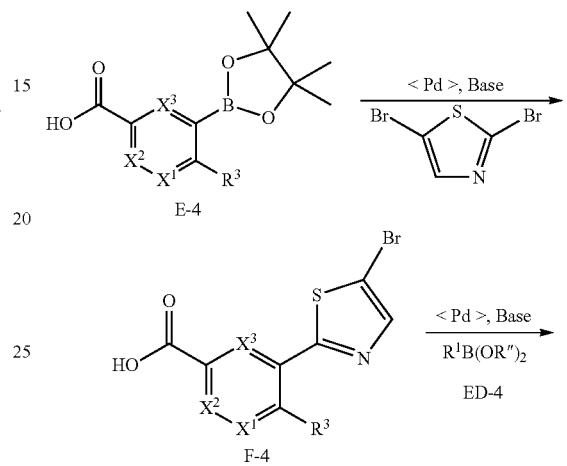

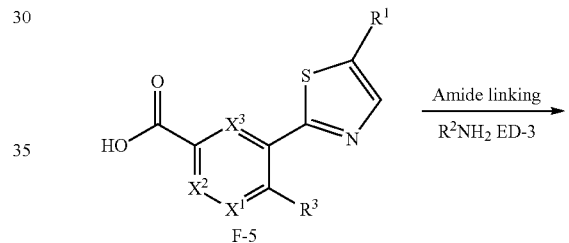

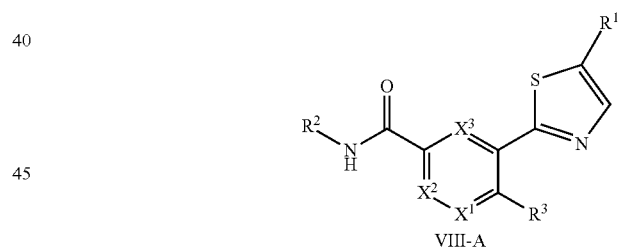

Part 3

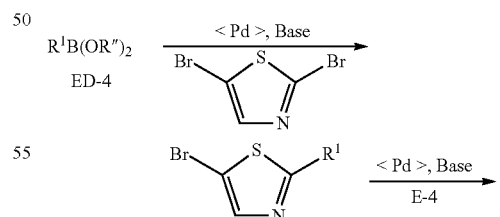

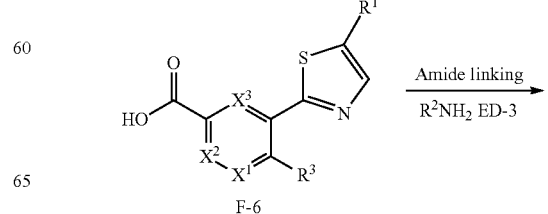

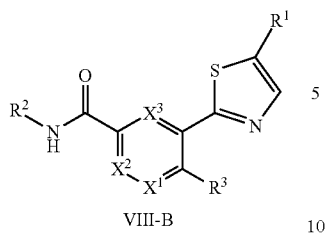

VIII-B

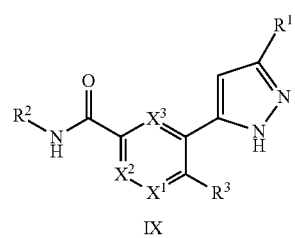

IX

Example Compounds of Type VII (Reaction Scheme F, Part 1):

Compounds with an imidazole ring C-linked via the 2-position (type VII) may be obtained by cyclisation from iodides Z-1. The latter are substituted in the first reaction step by CuCN to form the nitriles F-1 and converted by aminolysis into the amidines F-2. The imidazole ring is formed by the reaction with heteroaryl-α-bromomethylketones ED-9 and lastly the intermediates F-3 are saponified and amidated. By comparison with the synthesis of the imidazole ring C-linked in the 4 position according to Reaction scheme E (type V) the reactivities "α-haloketone" and "amidine" are exactly reversed with regard to the groups thus introduced.

Example Compounds of Type VIII-A (Reaction Scheme F, Part 2):

Compounds with a thiazole ring C-linked via the 2-position may be obtained starting from the boric acid derivatives E-4 (cf. Reaction scheme E). First of all the thiazole ring is introduced with 2,5-dibromothiazols (intermediate F-4) and then the group $R^1$ is introduced via the boric acids or boric acid derivatives ED-4 (intermediate F-5) by two successive palladium-catalysed Suzuki reactions. By final amide linking with amines ED-3 the end compounds of type VIII-A are obtained. If desired the saponification described for the synthesis of E-4 (cf. Reaction scheme E) may also be carried out just before this final amidation.

Example Compounds of Type VIII-B (Reaction Scheme F, Part 3):

Compounds with a thiazole ring C-linked via the 5-position (type VIII-B) may be obtained starting from the boric acids or boric acid derivatives E-4.

First of all, in a first palladium-catalysed Suzuki cross-coupling reaction the boric acids or boric acid derivatives ED-4 are reacted with 2,5-dibromothiazole in order to introduce $R^1$. In another Suzuki reaction with the boric acid derivatives E-4 the carboxylic acids F-6 are obtained, which are then converted in a subsequent amide coupling with the amines ED-3 into the end compounds of type VIII-B.

Reaction scheme G

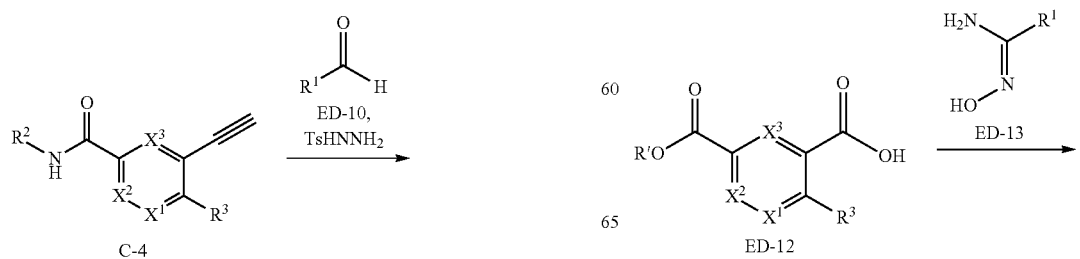

C-4

Example Compounds of Type IX:

Compounds with a pyrazole ring C-linked via the 5-position (type IX) may be obtained by cyclisation from alkynes C-4 (cf. Reaction scheme C), which undergo cycloaddition with tosylhydrazones. The tosylhydrazones are generated in situ from the corresponding heteroarylaldehydes ED-10 and tosylhydrazine.

Alternatively the cycloaddition described may also be carried out on alkynes C-1. In this case subsequent amidation with amines ED-3 has to take place.

Reaction scheme H

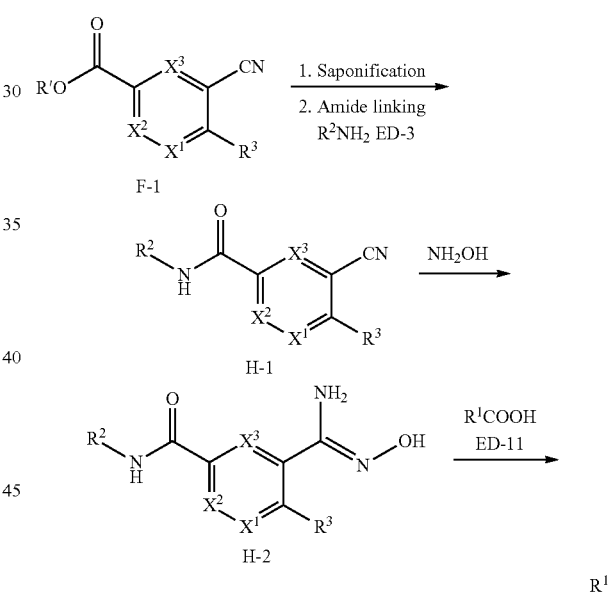

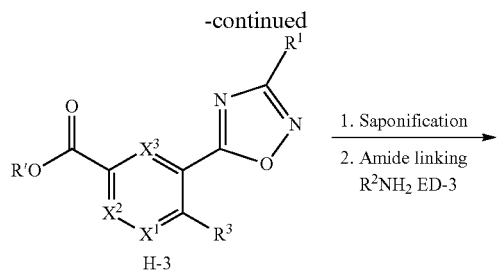

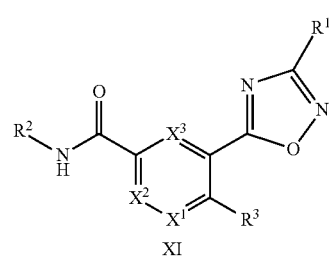

Example Compounds of Type X:

Compounds with a 2,4-oxadiazole ring C-linked via the 3-position (type X) may be obtained by cyclisation from nitriles F-1 (cf. Reaction scheme F). In a first step F-1 is saponified and the free acid is amidated with an amine ED-3 (H-1). After the subsequent addition of hydroxylamine to form the intermediate H-2, this is cyclised with heteroaryl-carboxylic acids ED-11 to obtain compounds X.

Example Compounds of Type XI:

Compounds with a 2,4-oxadiazole ring C-linked via the 5-position (type XI) may be obtained by cyclisation from carboxylic acids ED-12, by condensing them with heteroaryl-hydroxyamidines ED-13. The intermediate H-3 thus obtained is saponified and amidated to form compounds XI.

Reaction scheme I

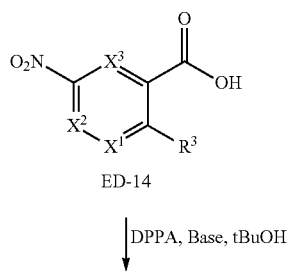

Method of synthesis 2

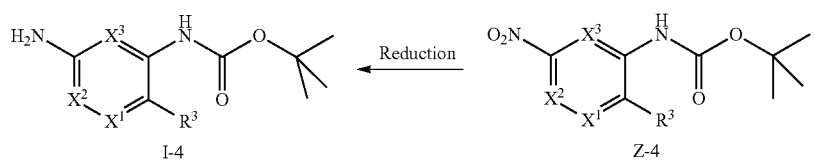

Method of synthesis 1

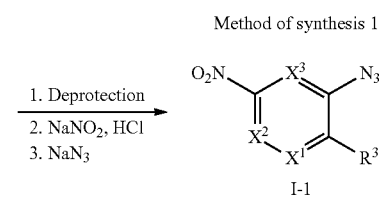

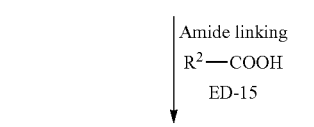

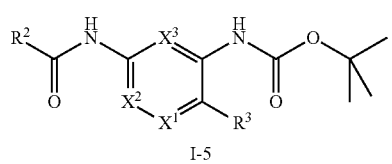

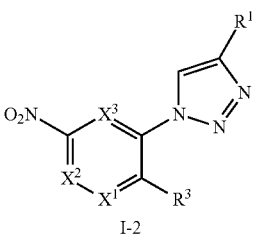

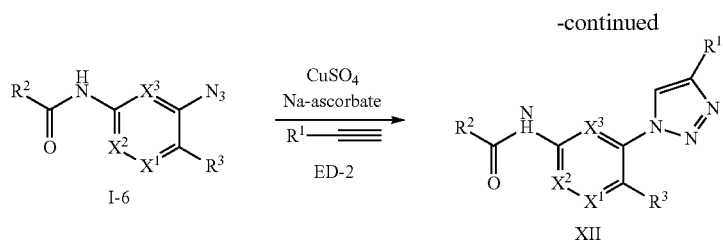 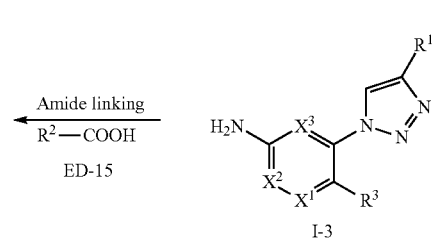

Example Compounds of Type XII:

Compounds according to the invention with an N-linked triazole ring (type XII) may be prepared for example by one of the synthesis routes (synthesis method 1 and 2) illustrated in Reaction scheme I. Compounds of Type XII have an inverted amide bond, compared with those of Type I.

Starting from the nitrocarboxylic acids ED-14 first of all the transformation to form the Boc-protected anilines Z-4 is carried out in a Curtius reaction using DPPA and tert-butanol as well as a base, for example N-methylmorpholine.

After the cleaving of the Boc protective group, e.g. with TFA or HCl, diazotisation with sodium nitrite in hydrochloric acid solution and reaction of the diazonium salt with sodium azide, the azides I-1 are obtained (synthesis method 1). By a copper-catalysed 1,3-dipolar cycloaddition reaction with alkynes ED-2 the triazole ring is synthesised and the intermediate I-2 obtained is then reduced to the aniline I-3. The nitro group may be reduced using methods known from the literature, such as for example the use of hydrogen in the presence of palladium on activated charcoal or iron in the presence of ammonium chloride. Finally the anilines I-3 are amidated with carboxylic acids ED-15.

According to synthesis method 2 the reaction steps known from synthesis method 1 are carried out in an altered sequence.

Synthesis of Examples XII-1-XII-78 a) Method of Synthesising I-1a

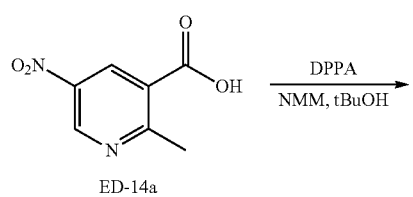

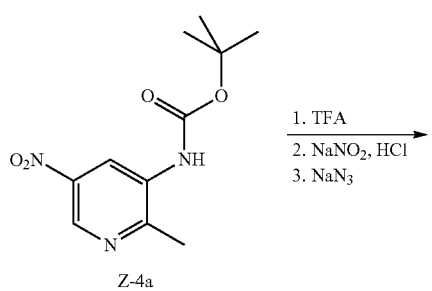

ED-14a (1.01 g, 5.52 mmol) is placed in tBuOH (50 mL), combined with DPPA (1.8 mL, 8.35 mmol) and NMM (724 μL, 6.59 mmol) and refluxed for 15 h. After cooling, saturated sodium chloride solution is added and the mixture is extracted several times with EE. The combined organic phases are washed with saturated sodium chloride solution, dried on $MgSO_4$, filtered and evaporated down using the rotary evaporator. The residue is taken up in some water and freeze-dried. The Z-4a thus obtained (HPLC-MS: $t_{Ret.}$=1.73 min; MS $(M+H)^+$=254) is used without further purification.

Z-4a (1.25 g, 4.94 mmol) is placed in DCM (15 mL), combined with TFA (7 mL) and the mixture is stirred for 2 h at RT. The mixture is diluted with DCM (20 mL) and extracted with $H_2O$ (2×40 mL) and 2 N hydrochloric acid (3×40 mL). The combined aqueous phases are made basic with sodium hydroxide solution and extracted with EE (3×75 mL). The combined organic phases are washed with saturated $NaHCO_3$ solution, dried on $MgSO_4$, filtered and evaporated down. The residue (730 mg, 4.77 mmol) is placed in 2 N hydrochloric acid (25 mL), cooled to 0° C. and mixed dropwise with a $NaNO_2$ solution (395 mg, 5.72 mmol in 2 mL $H_2O$). After 30 min, $NaN_3$ (341 mg, 5.25 mmol dissolved in 2 mL $H_2O$) is added at 0° C. and the mixture is stirred for a further 30 min. The reaction mixture is diluted with $H_2O$ and extracted 3× with EE. The combined organic phases are dried on $MgSO_4$, filtered and evaporated down. The azide I-1a obtained (HPLC-MS: $t_{Ret.}$=1.30 min) is used without further purification.

Analogously to the method of synthesising I-1a, further azides I-1 are obtained from the corresponding educts ED-13.

b) Method of Synthesising I-2a

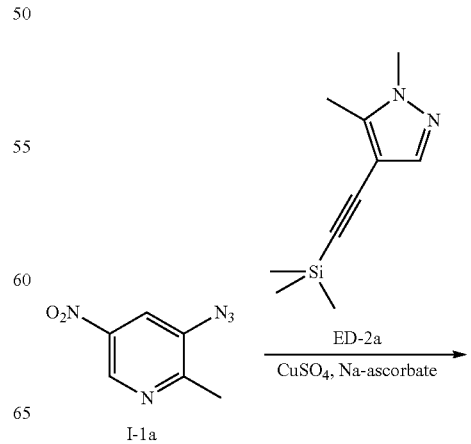

-continued

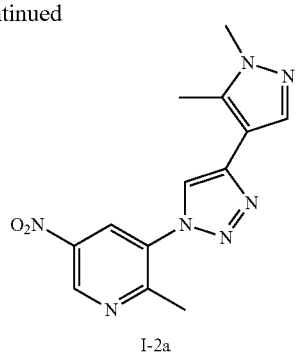

I-2a

In order to cleave the trimethylsilyl group, 1,5-dimethyl-4-trimethylsilanylethynyl-1H-pyrazole ED-2a (1.65 g, 8.61 mmol) is placed in MeOH (20 mL) and stirred together with $K_2CO_3$ (1.22 g, 8.85 mmol) for 1.5 h at RT. Then I-1a (854 mg, 4.77 mmol), sodium ascorbate (594 mg, 3.00 mmol in 2 mL $H_2O$) and 2.2 mL of a 0.8 M aqueous $CuSO_4$ solution are added and the mixture is stirred overnight at RT. The reaction mixture is evaporated down using the rotary evaporator, taken up in $H_2O$ and extracted 3× with EE. The combined organic phases are dried on $MgSO_4$, filtered and evaporated down. The residue is taken up in a little DMF and water, during which time a portion of I-2a is precipitated and filtered off. The mother liquor is purified by normal phase chromatography. The product-containing fractions of I-2a (HPLC-MS: $t_{Ret.}$=1.35 min; MS $(M+H)^+$=300) are evaporated down.

Analogously to the method of synthesising I-2a further intermediates I-2 are obtained from the corresponding components I-1 and ED-2.

c) Method of Synthesising I-3a

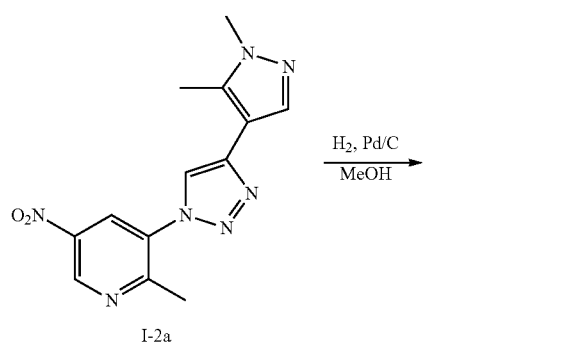

I-2a (485 mg, 1.62 mmol) is taken up in MeOH (10 mL), combined with Pd/C (10%, 186 mg, 1.75 mmol) and hydrogenated for 3 h at 50 PSI in the hydrogenating autoclave. The catalyst is filtered off, the mother liquor is evaporated down, it is taken up in a little 2 N hydrochloric acid and freeze-dried. The I-3a thus obtained (HPLC-MS: $t_{Ret.}$=0.99 min; MS $(M+H)^+$=270) is further used without any further purification steps.

Analogously to this method further anilines I-3 may also be obtained reductively from the corresponding nitro compounds I-2.

d) Method of Synthesising Example Compound XII-1

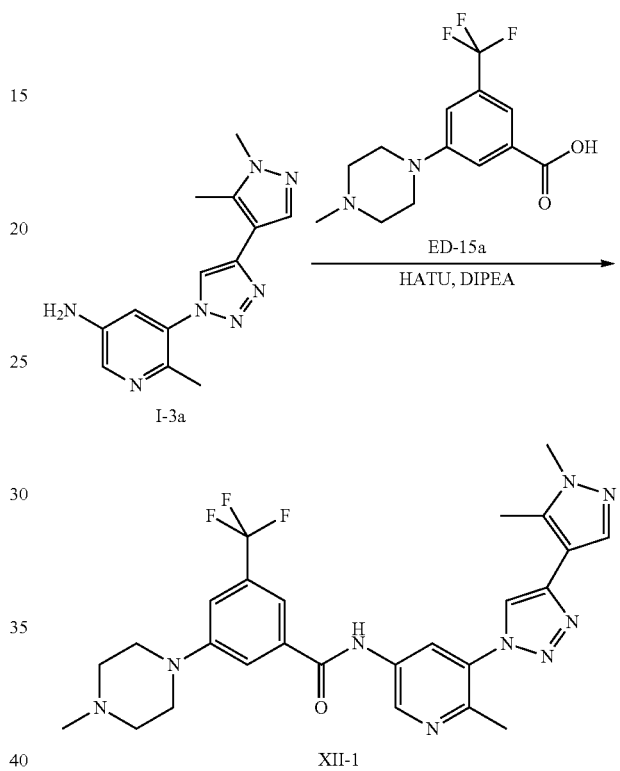

Benzoic acid ED-15a (56.6 mg, 0.20 mmol) is placed in THF, combined with HATU (73.7 mg, 0.23 mmol) and DIPEA (88 µL, 0.52 mmol) and stirred for 30 min at RT. Then I-3a (50.0 mg, 0.16 mmol) is added and the mixture is stirred for 3 d at 50° C. The reaction mixture is evaporated down using the rotary evaporator, the residue is taken up in a little DMF and $H_2O$ and purified by preparative HPLC. The product-containing fractions of XII-1 (HPLC-MS: $t_{Ret.}$=1.79 min; MS $(M+H)^+$=540) are combined and freeze-dried.

e) Method of Synthesising I-5a

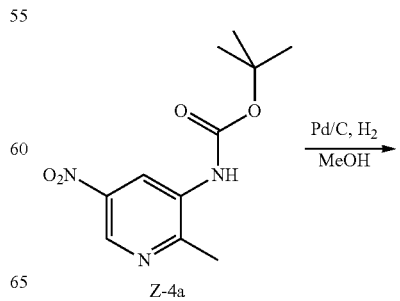

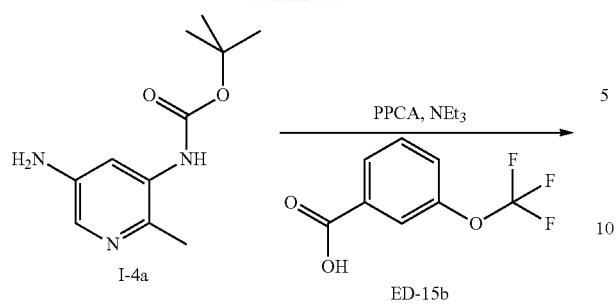

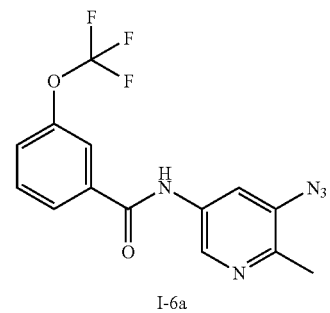

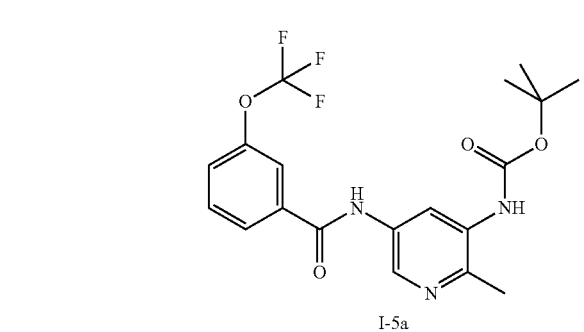

Z-4a (1.79 g, 7.07 mmol) is placed in MeOH (80 mL), combined with Pd/C (188 mg, 10%) and hydrogenated for 2 h under 4 bar hydrogen pressure at RT. The catalyst is filtered off and the filtrate is evaporated down using the rotary evaporator. The residue is taken up in a little MeCN and H$_2$O and freeze-dried. I-4a is obtained (HPLC-MS: t$_{Ret.}$=1.20 min; MS (M+H)$^+$=224), which is used further without any further purification. I-4a (1.51 g, 6.76 mmol) and ED-15b (1.52 g, 7.31 mmol) are placed in THF (20 mL) and combined with NEt$_3$ (3.0 mL). Then propanephosphonic acid cycloanhydride (5.9 mL, 50% in EtOAc) is added dropwise and the mixture is stirred for 2 h at RT. Then it is evaporated down using the rotary evaporator, the residue is taken up in H$_2$O and extracted three times with DCM. The combined organic phases are dried on MgSO$_4$, filtered and evaporated down using the rotary evaporator. The I-5a (HPLC-MS: t$_{Ret.}$=1.93 min; MS (M+H)$^+$=412) thus obtained is used further without any further purification steps.

Analogously to this method other amides I-5 may also be obtained by amidation with other carboxylic acids ED-15 from the corresponding aminopyridines I-4.

f) Method of Synthesising I-6a

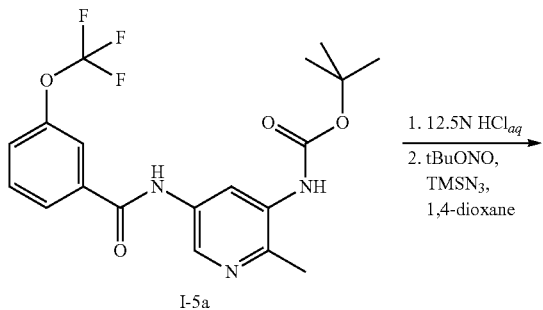

I-5a (3.36 g, 6.78 mmol) is stirred overnight in 12.5 N hydrochloric acid (10 mL) at 50° C. After cooling the reaction mixture is combined with H$_2$O (10 mL), neutralised with sodium hydroxide solution (8 N) and extracted three times with DCM. The combined organic phases are dried on MgSO$_4$, filtered and evaporated down using the rotary evaporator. The residue (HPLC-MS: t$_{Ret.}$=1.43 min; MS (M+H)$^+$= 312) is taken up in a little H$_2$O and MeCN and freeze-dried.

The free amine thus obtained (1.60 g, 5.15 mmol) is placed in 1,4-dioxane (20 mL), mixed successively with TMS-N$_3$ (0.7 mL, 8.60 mmol) and tert.-butylnitrite (3.0 mL, 25.3 mmol) and stirred overnight at RT. Then the mixture is diluted with DCM and washed three times with saturated NaHCO$_3$ solution. The organic phase is dried on MgSO$_4$, filtered and evaporated down using the rotary evaporator. The I-6a thus obtained is used further without any further purification steps.

Analogously to this method further azides I-6 are also obtained from the protected aminopyridines I-5.

g) Method of Synthesising ED-2f

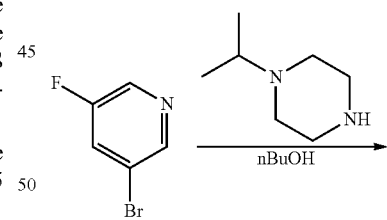

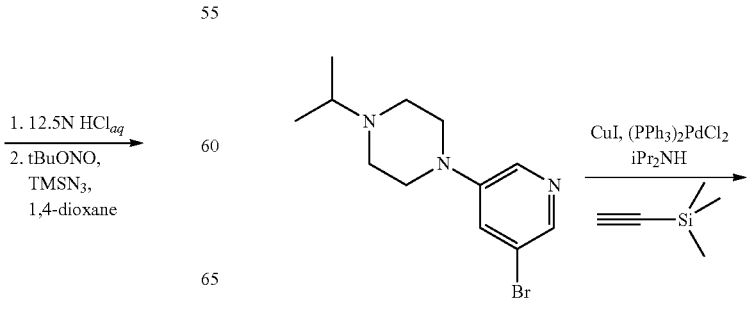

229

-continued

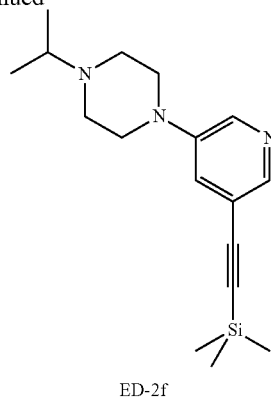

ED-2f

3-Bromo-5-fluoro-pyridine (4.26 g, 23.5 mmol) and isopropylpiperazine (7.58 g, 59.1 mmol) are placed in n-BuOH (16 mL) and stirred for 6 d at 100° C. After cooling the reaction mixture is acidified with 0.1 N hydrochloric acid and extracted three times with EtOAc. The aqueous phase is adjusted to pH 10 with sodium hydroxide solution and extracted three times with DCM. The combined organic phases are dried on MgSO$_4$, filtered and evaporated down using the rotary evaporator. The residue is taken up in a little DCM and added to 4 g of polymer-bound isocyanate pre-swollen in DCM (made by Argonaut, Art. No. 800260) and the mixture is stirred for 2 h at RT. Then the polymer resin is filtered off, the mixture is washed with DCM and evaporated down using the rotary evaporator. The substituted 3-bromopyridine thus obtained (HPLC-MS: $t_{Ret.}$=1.59 min; MS (M+H)$^+$=284) is used further without any further purification steps.

The substituted 3-bromo-pyridine obtained (3.88 g, 8.18 mmol), CuI (124 mg, 0.65 mmol) and (PPh$_3$)$_2$PdCl$_2$ (95.0 mg, 0.14 mmol) are placed under protective gas in diisopropylamine (5 mL), combined with TMS-acetylene (1.5 mL, 10.6 mmol) and stirred for 30 min at 100° C. in the microwave. After cooling the reaction mixture is diluted with 1 N hydrochloric acid and extracted three times with DCM. The acidic aqueous phase is adjusted to pH 9 and extracted three times with DCM. The combined organic phases are dried on MgSO$_4$, filtered and evaporated down using the rotary evaporator. The residue is purified by normal phase chromatography. The product-containing fractions of ED-2f (HPLC-MS: $t_{Ret.}$=2.13 min; MS (M+H)$^+$=203) are evaporated down and dried under a high vacuum.

Analogously to this method further TMS-protected acetylenes ED-2 are obtained from 3-bromo-5-fluoro-pyridine.

230 h) Method of Synthesising Example Compound XII-42

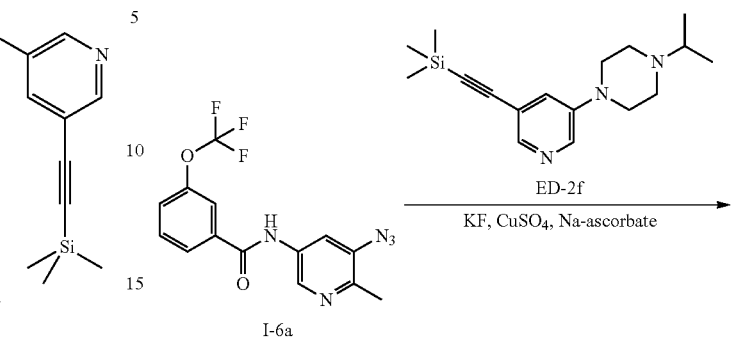

ED-2f (140 mg, 0.46 mmol) is placed in MeOH (10 mL), combined with KF (60 mg, 1.03 mmol) and stirred overnight at RT. Then I-6a (132 mg, 0.31 mmol) is added, the mixture is stirred for 5 min, aqueous sodium ascorbate solution (180 μL, 1 M) and aqueous CuSO$_4$ solution (150 μL, 1 M) are added successively and the mixture is stirred at 45° C. for 48 h. Then it is made basic with 1 N sodium hydroxide solution and extracted three times with EtOAc. The combined organic phases are dried on MgSO$_4$, filtered and evaporated down using the rotary evaporator. The residue is taken up in a little DMF and H$_2$O and purified by preparative HPLC. The product-containing fractions of XII-42 (HPLC-MS: $t_{Ret.}$=1.92 min; MS (M+H)$^+$=567) are combined and freeze-dried.

Analogously to the above described reaction methods a) to d) (synthesis method 1) for synthesising the example compound XII-1 or e) to h) (synthesis method 2) for synthesising the example compound XII-42 the following Examples XII-2 to XII-41, as well as XII-43 to XII-78 (Table 2) or comparable further Examples may be obtained from the corresponding precursors, which are either commercially obtainable or may be prepared using methods known from the literature.

TABLE 2
Example compounds XII-1 bis XII-78
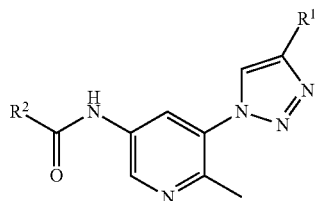
| # | Structure | $t_{Ret.}$ (HPLC) [min] | MS (M + H)+ |
|---|---|---|---|
| XII-1 | 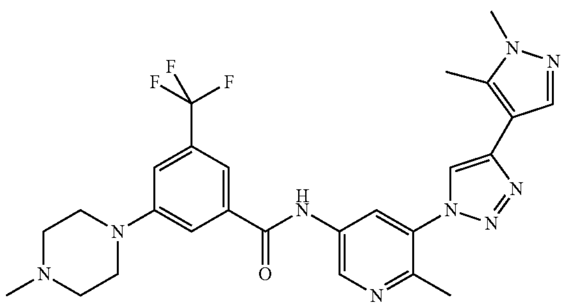 [SMILES: Cc1ncc(NC(=O)c2cc(N3CCN(C)CC3)cc(C(F)(F)F)c2)cc1-n1cc(-c2cnn(C)c2C)nn1] | 1.79 | 540 |
| XII-2 | 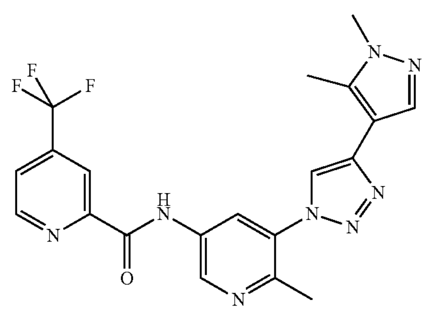 [SMILES: Cc1ncc(NC(=O)c2cc(C(F)(F)F)ccn2)cc1-n1cc(-c2cnn(C)c2C)nn1] | 1.73 | 443 |
| XII-3 | 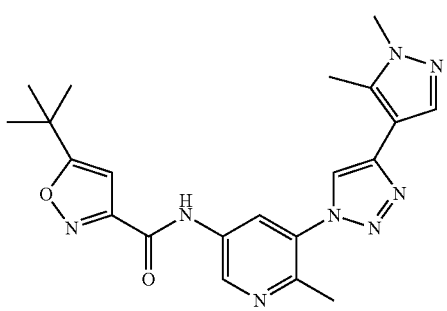 [SMILES: Cc1ncc(NC(=O)c2cc(C(C)(C)C)on2)cc1-n1cc(-c2cnn(C)c2C)nn1] | 1.74 | 421 |
| XII-4 | 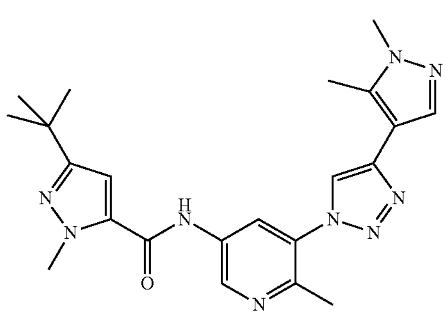 [SMILES: Cc1ncc(NC(=O)c2cc(C(C)(C)C)nn2C)cc1-n1cc(-c2cnn(C)c2C)nn1] | | |

TABLE 2-continued
Example compounds XII-1 bis XII-78
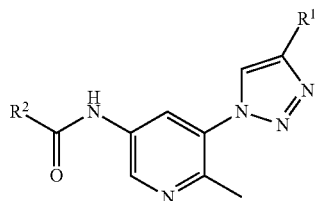
| # | Structure | t_Ret. (HPLC) [min] | MS (M + H)+ |
|---|---|---|---|
| XII-5 | 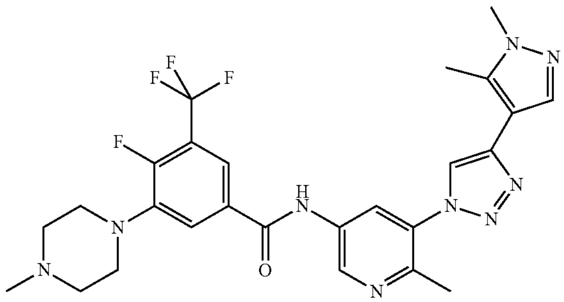 [SMILES: Cc1ncc(NC(=O)c2cc(N3CCN(C)CC3)c(F)c(C(F)(F)F)c2)cc1-n1cc(-c2cnn(C)c2C)nn1] | 1.87 | 558 |
| XII-6 | 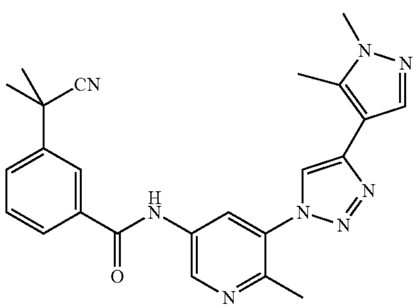 [SMILES: Cc1ncc(NC(=O)c2cccc(C(C)(C)C#N)c2)cc1-n1cc(-c2cnn(C)c2C)nn1] | 1.63 | (M − H)− = 439 |
| XII-7 | 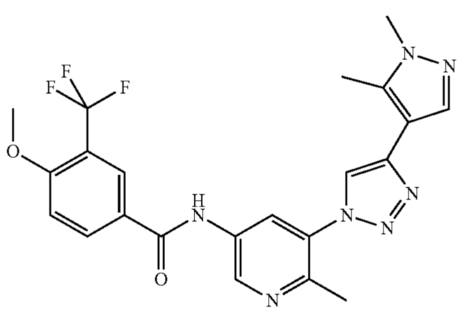 [SMILES: COc1ccc(C(=O)Nc2cnc(C)c(-n3cc(-c4cnn(C)c4C)nn3)c2)cc1C(F)(F)F] | 1.77 | 472 |
| XII-8 | 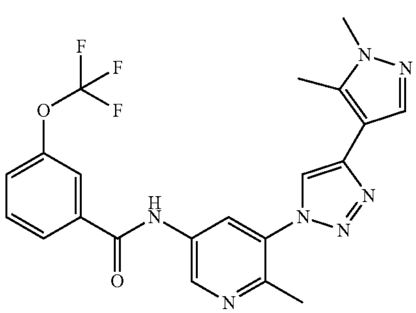 [SMILES: Cc1ncc(NC(=O)c2cccc(OC(F)(F)F)c2)cc1-n1cc(-c2cnn(C)c2C)nn1] | 1.79 | 458 |

TABLE 2-continued

Example compounds XII-1 bis XII-78

| # | Structure | t_Ret. (HPLC) [min] | MS (M + H)+ |
|---|-----------|---------------------|-------------|
| XII-9 | 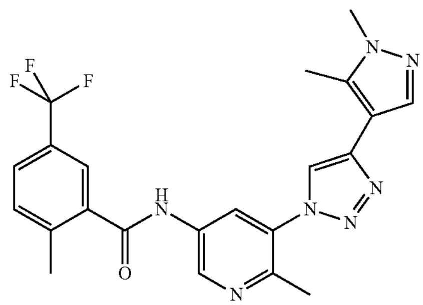 [SMILES: Cc1ccc(C(F)(F)F)cc1C(=O)Nc1cnc(C)c(-n2cc(-c3cnn(C)c3C)nn2)c1] | 1.78 | 456 |
| XII-10 | 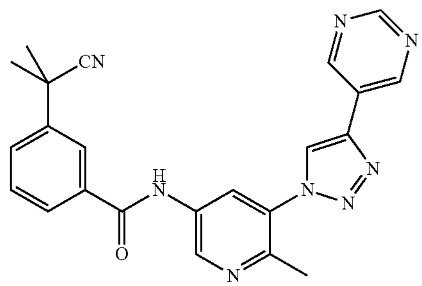 | 1.53 | (M − H)− = 423 |
| XII-11 | 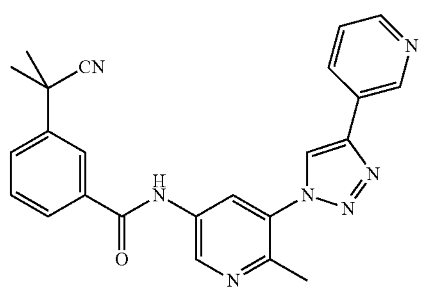 [SMILES: Cc1ncc(NC(=O)c2cccc(C(C)(C)C#N)c2)cc1-n1cc(-c2cncnc2)nn1] | 1.68 | 424 |
| XII-12 | 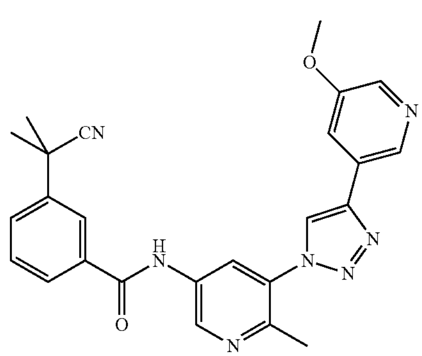 [SMILES: COc1cncc(-c2cn(-c3cc(NC(=O)c4cccc(C(C)(C)C#N)c4)cnc3C)nn2)c1] | 1.66 | 454 |

TABLE 2-continued

Example compounds XII-1 bis XII-78

| # | Structure | t_Ret. (HPLC) [min] | MS (M + H)+ |
|---|---|---|---|
| XII-13 | 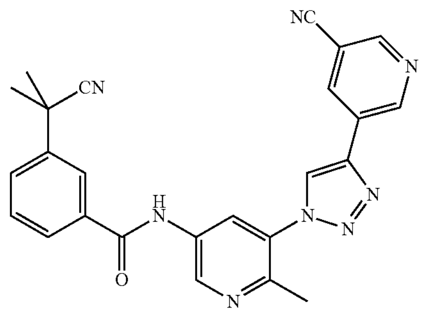 [SMILES: Cc1ncc(NC(=O)c2cccc(C(C)(C)C#N)c2)cc1-n1cc(-c2cncc(C#N)c2)nn1] | 1.70 | (M − H)− = 447 |
| XII-14 | 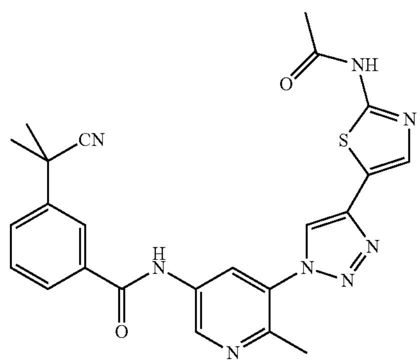 [SMILES: CC(=O)Nc1ncc(-c2cn(-c3cc(NC(=O)c4cccc(C(C)(C)C#N)c4)cnc3C)nn2)s1] | 1.46 | (M − H)− = 485 |
| XII-15 | 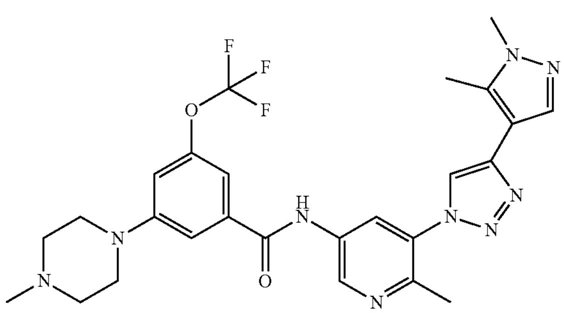 [SMILES: Cc1ncc(NC(=O)c2cc(OC(F)(F)F)cc(N3CCN(C)CC3)c2)cc1-n1cc(-c2cnn(C)c2C)nn1] | 1.79 | 556 |
| XII-16 | 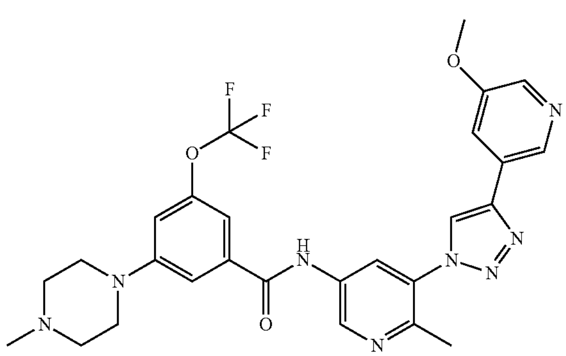 [SMILES: COc1cncc(-c2cn(-c3cc(NC(=O)c4cc(OC(F)(F)F)cc(N5CCN(C)CC5)c4)cnc3C)nn2)c1] | 1.87 | 569 |

TABLE 2-continued

Example compounds XII-1 bis XII-78

| # | Structure | $t_{Ret.}$ (HPLC) [min] | MS (M + H)⁺ |
|---|---|---|---|
| XII-17 | 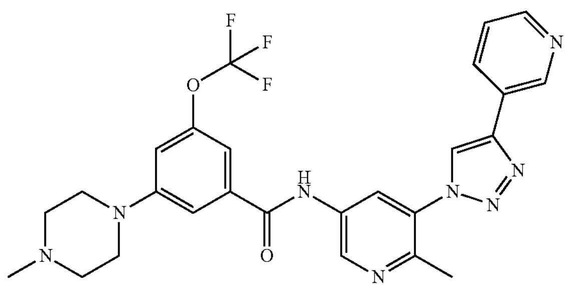 | 1.82 | 539 |
| XII-18 | 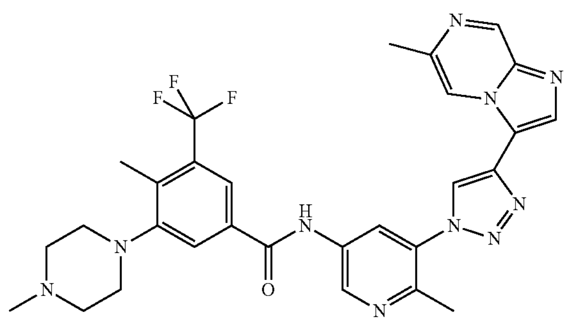 [SMILES: Cc1cn2c(-c3cn(-c4cc(NC(=O)c5cc(N6CCN(C)CC6)c(C)c(C(F)(F)F)c5)cnc4C)nn3)cnc2cn1] | 1.92 | 591 |
| XII-19 | 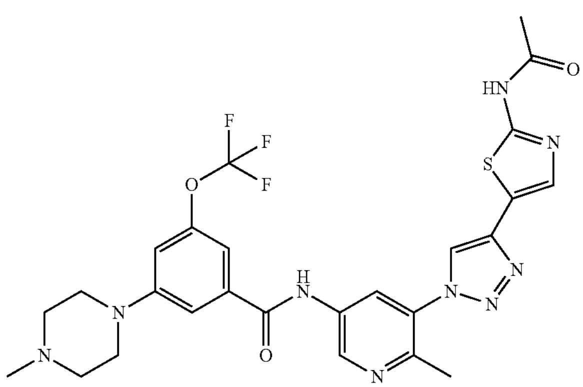 [SMILES: CC(=O)Nc1ncc(-c2cn(-c3cc(NC(=O)c4cc(OC(F)(F)F)cc(N5CCN(C)CC5)c4)cnc3C)nn2)s1] | 1.66 | 602 |
| XII-20 | 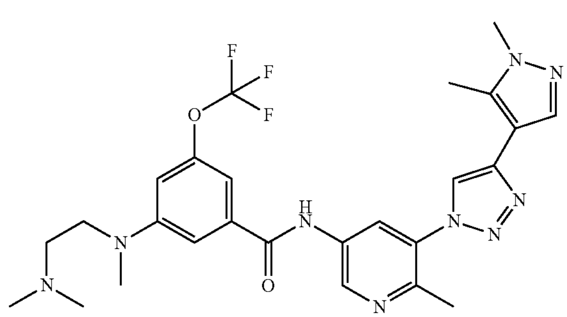 [SMILES: Cc1ncc(NC(=O)c2cc(OC(F)(F)F)cc(N(C)CCN(C)C)c2)cc1-n1cc(-c2cnn(C)c2C)nn1] | 1.86 | 558 |

US 8,778,929 B2

TABLE 2-continued

Example compounds XII-1 bis XII-78

| # | Structure | $t_{Ret.}$ (HPLC) [min] | MS (M + H)⁺ |
|---|---|---|---|
| XII-21 | 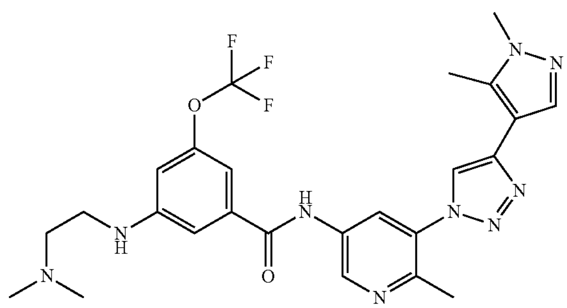 [SMILES: Cc1ncc(NC(=O)c2cc(NCCN(C)C)cc(OC(F)(F)F)c2)cc1-n1cc(-c2cnn(C)c2C)nn1] | 1.78 | 544 |
| XII-22 | 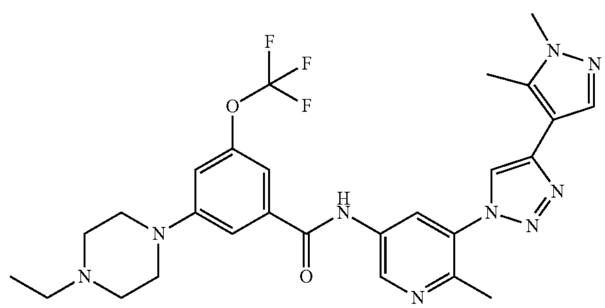 [SMILES: CCN1CCN(c2cc(OC(F)(F)F)cc(C(=O)Nc3cnc(C)c(-n4cc(-c5cnn(C)c5C)nn4)c3)c2)CC1] | 1.86 | 570 |
| XII-23 | 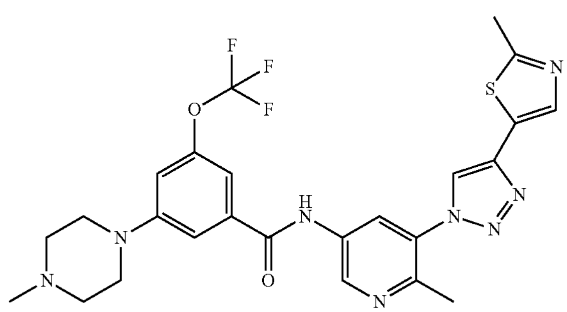 [SMILES: Cc1ncc(-c2cn(-c3cc(NC(=O)c4cc(OC(F)(F)F)cc(N5CCN(C)CC5)c4)cnc3C)nn2)s1] | 1.85 | 559 |
| XII-24 | 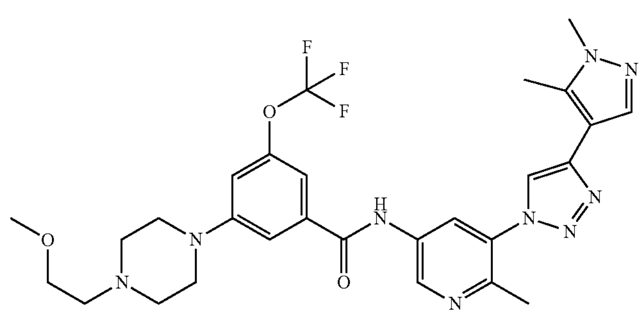 [SMILES: COCCN1CCN(c2cc(OC(F)(F)F)cc(C(=O)Nc3cnc(C)c(-n4cc(-c5cnn(C)c5C)nn4)c3)c2)CC1] | 1.81 | 600 |

TABLE 2-continued

Example compounds XII-1 bis XII-78

| # | Structure | t_Ret. (HPLC) [min] | MS (M + H)+ |
|---|---|---|---|
| XII-25 | 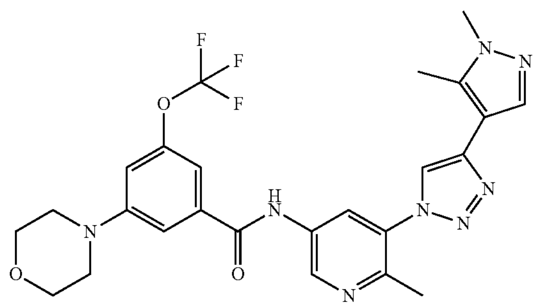 [SMILES: Cc1ncc(NC(=O)c2cc(OC(F)(F)F)cc(N3CCOCC3)c2)cc1-n1cc(-c2cnn(C)c2C)nn1] | 1.77 | 543 |
| XII-26 | 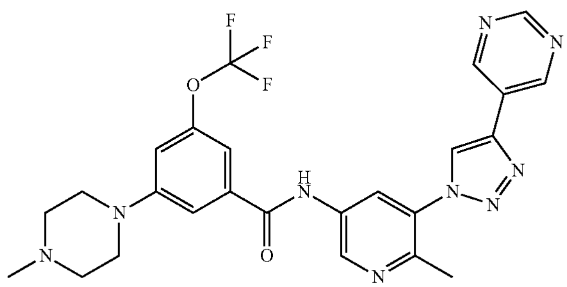 [SMILES: Cc1ncc(NC(=O)c2cc(OC(F)(F)F)cc(N3CCN(C)CC3)c2)cc1-n1cc(-c2cncnc2)nn1] | 1.73 | 540 |
| XII-27 | 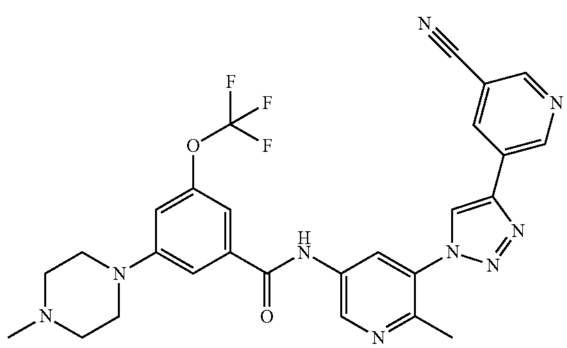 [SMILES: Cc1ncc(NC(=O)c2cc(OC(F)(F)F)cc(N3CCN(C)CC3)c2)cc1-n1cc(-c2cncc(C#N)c2)nn1] | 1.86 | 564 |
| XII-28 | 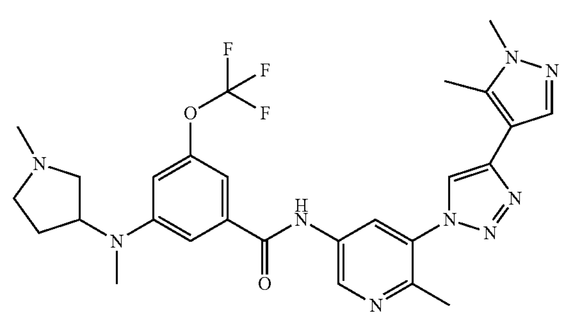 [SMILES: Cc1ncc(NC(=O)c2cc(OC(F)(F)F)cc(N(C)C3CCN(C)C3)c2)cc1-n1cc(-c2cnn(C)c2C)nn1] | 1.86 | 570 |

TABLE 2-continued

Example compounds XII-1 bis XII-78

| # | Structure | $t_{Ret.}$ (HPLC) [min] | MS (M + H)⁺ |
|---|---|---|---|
| XII-29 | | 1.87 | 570 |
| XII-30 | | 1.70 | 539 |
| XII-31 | | 1.79 | 582 |

TABLE 2-continued
Example compounds XII-1 bis XII-78
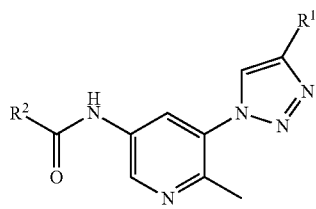
| # | Structure | t_Ret. (HPLC) [min] | MS (M + H)+ |
|---|---|---|---|
| XII-32 | | 1.97 | 566 |
| XII-33 | | 1.83 | 582 |
| XII-34 | | 1.64 | 522 |

US 8,778,929 B2
TABLE 2-continued
Example compounds XII-1 bis XII-78
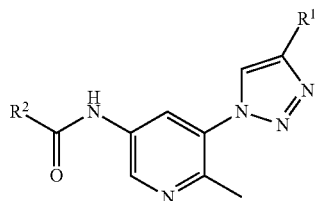
| # | Structure | $t_{Ret.}$ (HPLC) [min] | MS (M + H)⁺ |
|---|---|---|---|
| XII-35 | 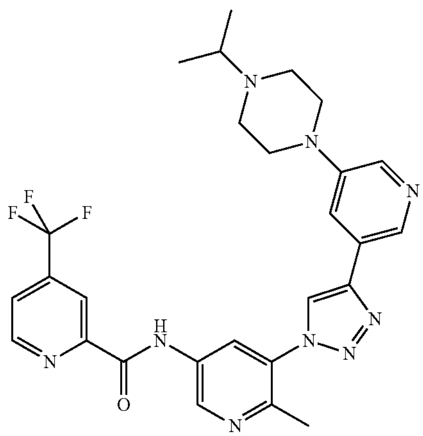 [SMILES: Cc1ncc(NC(=O)c2cc(C(F)(F)F)ccn2)cc1-n1cc(-c2cncc(N3CCN(C(C)C)CC3)c2)nn1] | 1.89 | 552 |
| XII-36 | 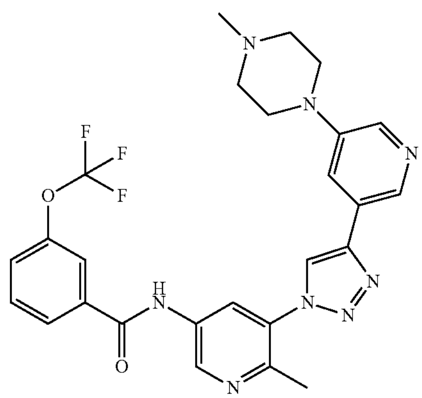 [SMILES: Cc1ncc(NC(=O)c2cccc(OC(F)(F)F)c2)cc1-n1cc(-c2cncc(N3CCN(C)CC3)c2)nn1] | 1.77 | 539 |
| XII-37 | 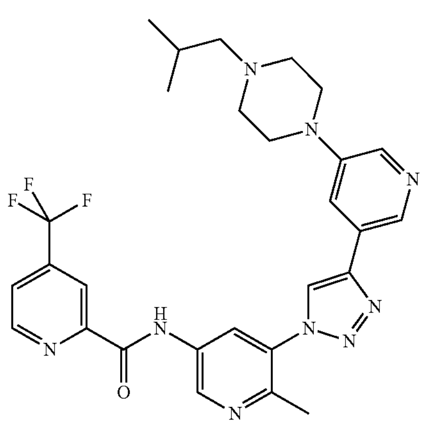 [SMILES: Cc1ncc(NC(=O)c2cc(C(F)(F)F)ccn2)cc1-n1cc(-c2cncc(N3CCN(CC(C)C)CC3)c2)nn1] | 2.11 | 566 |

TABLE 2-continued

Example compounds XII-1 bis XII-78

| # | Structure | t_{Ret.} (HPLC) [min] | MS (M + H)+ |
|---|---|---|---|
| XII-38 | 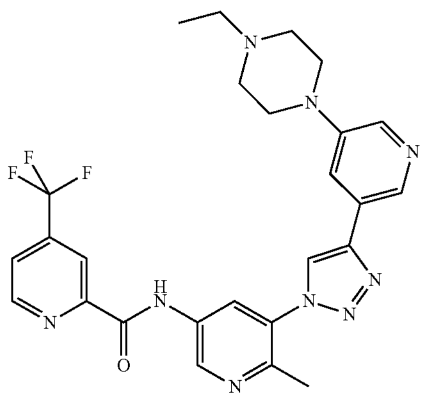 [SMILES: CCN1CCN(c2cncc(-c3cn(-c4cc(NC(=O)c5cc(C(F)(F)F)ccn5)cnc4C)nn3)c2)CC1] | 1.76 | 538 |
| XII-39 | 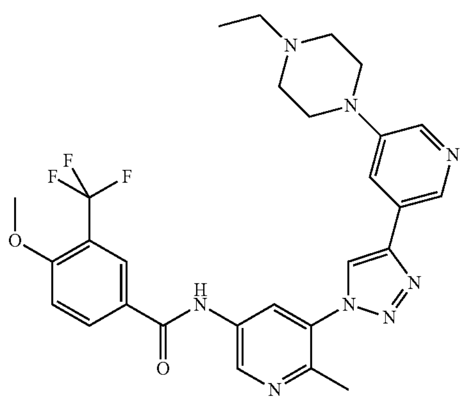 [SMILES: CCN1CCN(c2cncc(-c3cn(-c4cc(NC(=O)c5ccc(OC)c(C(F)(F)F)c5)cnc4C)nn3)c2)CC1] | 1.80 | 567 |
| XII-40 | 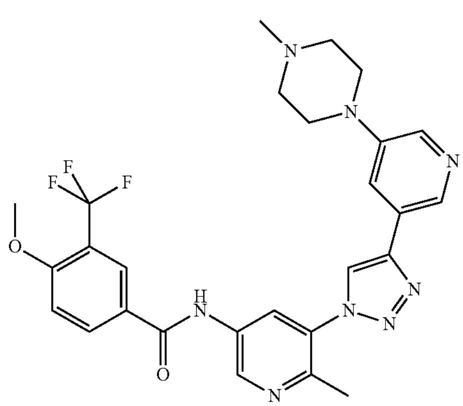 [SMILES: COc1ccc(C(=O)Nc2cnc(C)c(-n3cc(-c4cncc(N5CCN(C)CC5)c4)nn3)c2)cc1C(F)(F)F] | 1.71 | 553 |

US 8,778,929 B2
TABLE 2-continued
Example compounds XII-1 bis XII-78
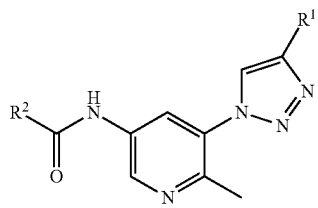
| # | Structure | t$_{Ret.}$ (HPLC) [min] | MS (M + H)$^+$ |
|---|---|---|---|
| XII-41 | 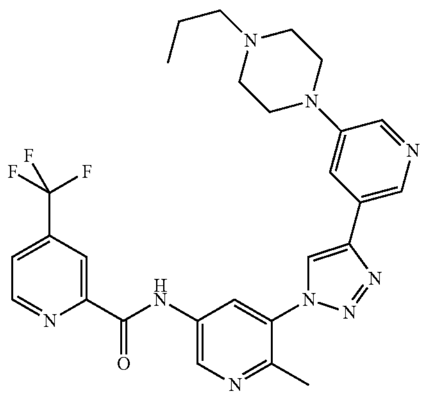 [SMILES: CCCN1CCN(c2cncc(-c3cn(-c4cc(NC(=O)c5cc(C(F)(F)F)ccn5)cnc4C)nn3)c2)CC1] | 1.88 | 552 |
| XII-42 | 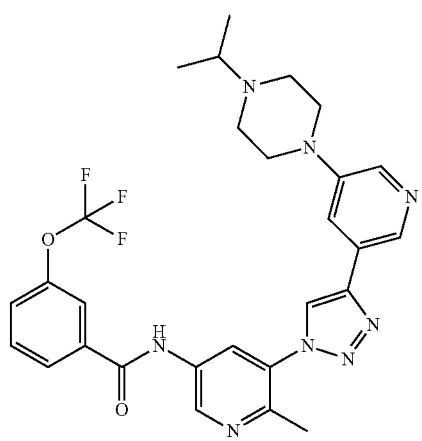 [SMILES: Cc1ncc(NC(=O)c2cccc(OC(F)(F)F)c2)cc1-n1cc(-c2cncc(N3CCN(C(C)C)CC3)c2)nn1] | 1.92 | 567 |
| XII-43 | 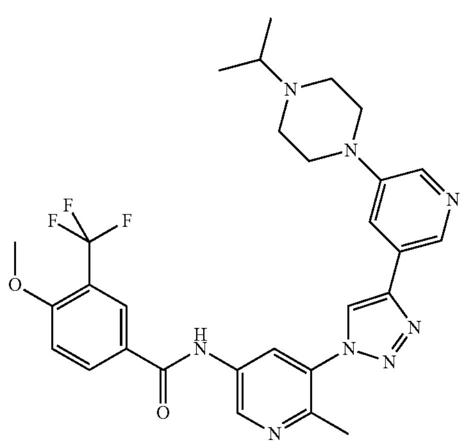 [SMILES: COc1ccc(C(=O)Nc2cnc(C)c(-n3cc(-c4cncc(N5CCN(C(C)C)CC5)c4)nn3)c2)cc1C(F)(F)F] | 1.88 | 581 |

TABLE 2-continued

Example compounds XII-1 bis XII-78

| # | Structure | $t_{Ret.}$ (HPLC) [min] | MS (M + H)+ |
|---|---|---|---|
| XII-44 | 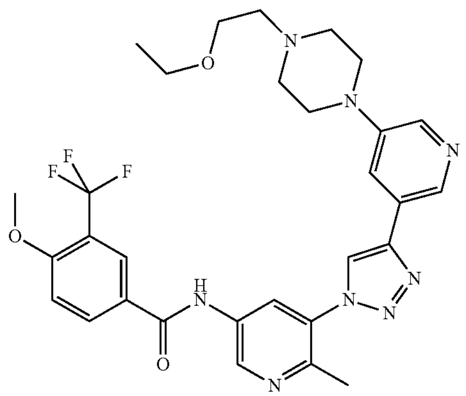 [SMILES: CCOCCN1CCN(c2cncc(-c3cn(-c4cc(NC(=O)c5ccc(OC)c(C(F)(F)F)c5)cnc4C)nn3)c2)CC1] | 1.86 | 611 |
| XII-45 | 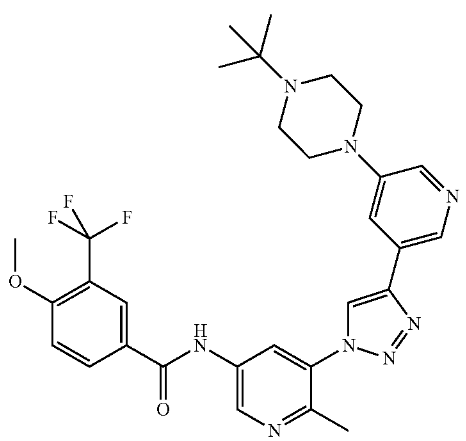 [SMILES: COc1ccc(C(=O)Nc2cnc(C)c(-n3cc(-c4cncc(N5CCN(C(C)(C)C)CC5)c4)nn3)c2)cc1C(F)(F)F] | 2.12 | 595 |
| XII-46 | 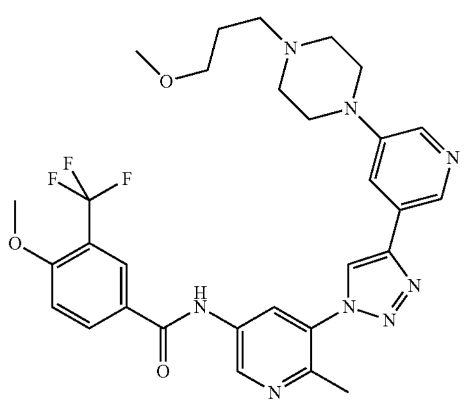 [SMILES: COCCCN1CCN(c2cncc(-c3cn(-c4cc(NC(=O)c5ccc(OC)c(C(F)(F)F)c5)cnc4C)nn3)c2)CC1] | 1.79 | 611 |

TABLE 2-continued

Example compounds XII-1 bis XII-78

| # | Structure | t_Ret. (HPLC) [min] | MS (M + H)+ |
|---|---|---|---|
| XII-47 | | 2.01 | 581 |
| XII-48 | | 1.82 | 597 |
| XII-49 | | 1.82 | 562 |

TABLE 2-continued
Example compounds XII-1 bis XII-78
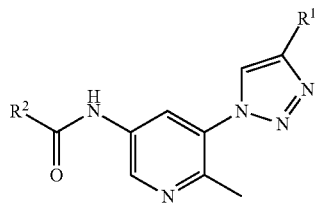
| # | Structure | $t_{Ret.}$ (HPLC) [min] | MS (M + H)+ |
|---|---|---|---|
| XII-50 | | 1.80 | 550 |
| XII-51 | | 1.71 | 536 |
| XII-52 | | 1.64 | 510 |

TABLE 2-continued

Example compounds XII-1 bis XII-78

| # | Structure | t$_{Ret.}$ (HPLC) [min] | MS (M + H)$^+$ |
|---|---|---|---|
| XII-53 | 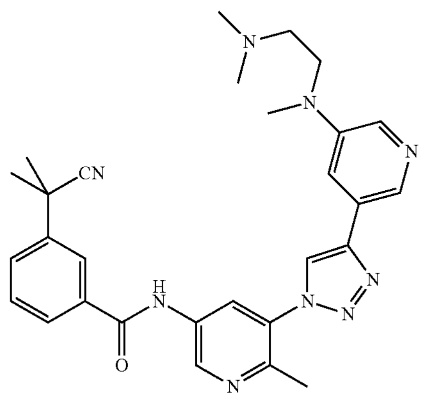 [SMILES: Cc1ncc(NC(=O)c2cccc(C(C)(C)C#N)c2)cc1-n1cc(-c2cncc(N(C)CCN(C)C)c2)nn1] | 1.70 | 524 |
| XII-54 | 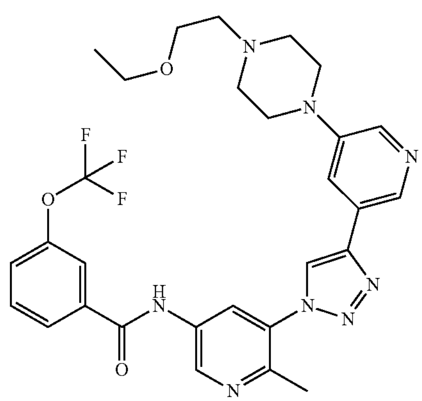 [SMILES: CCOCCN1CCN(c2cncc(-c3cn(-c4cc(NC(=O)c5cccc(OC(F)(F)F)c5)cnc4C)nn3)c2)CC1] | 1.97 | 597 |
| XII-55 | 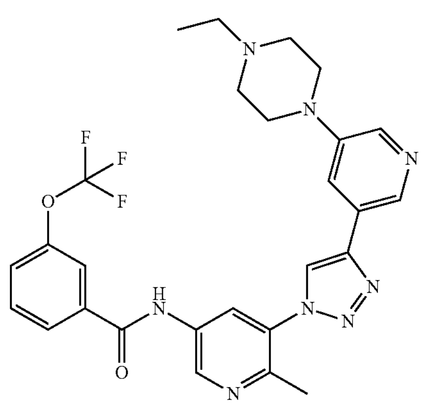 [SMILES: CCN1CCN(c2cncc(-c3cn(-c4cc(NC(=O)c5cccc(OC(F)(F)F)c5)cnc4C)nn3)c2)CC1] | 1.83 | 553 |

TABLE 2-continued
Example compounds XII-1 bis XII-78
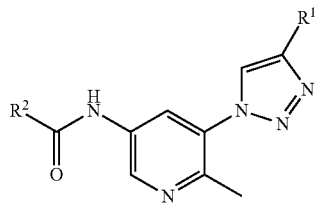
| # | Structure | t_Ret. (HPLC) [min] | MS (M + H)+ |
|---|---|---|---|
| XII-56 | | | |
| XII-57 | | 1.66 | 524 |
| XII-58 | | | |

TABLE 2-continued
Example compounds XII-1 bis XII-78
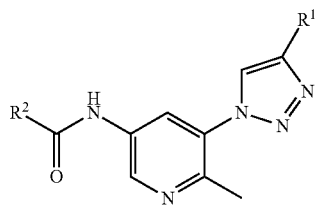
| # | Structure | t$_{Ret.}$ (HPLC) [min] | MS (M + H)$^+$ |
|---|---|---|---|
| XII-59 | | | |
| XII-60 | | | |
| XII-61 | | | |

TABLE 2-continued
Example compounds XII-1 bis XII-78
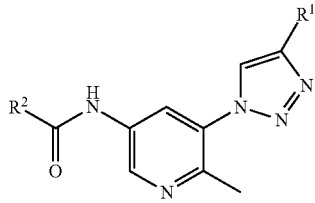
| # | Structure | t_Ret. (HPLC) [min] | MS (M + H)+ |
|---|---|---|---|
| XII-62 | 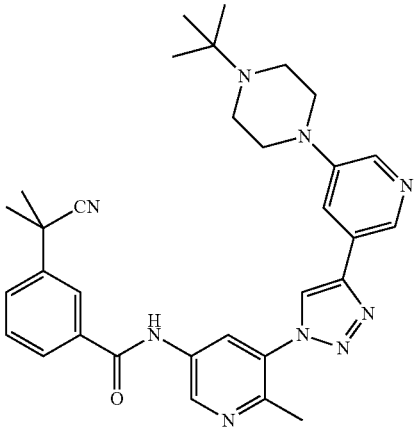 [SMILES: Cc1ncc(NC(=O)c2cccc(C(C)(C)C#N)c2)cc1-n1cc(-c2cncc(N3CCN(C(C)(C)C)CC3)c2)nn1] | | |
| XII-63 | 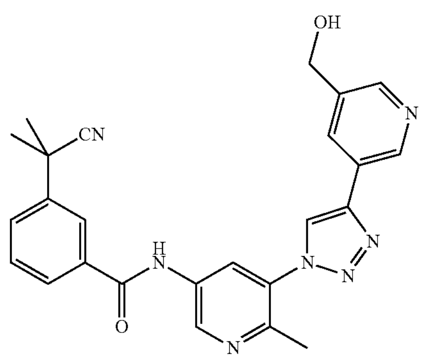 [SMILES: Cc1ncc(NC(=O)c2cccc(C(C)(C)C#N)c2)cc1-n1cc(-c2cncc(CO)c2)nn1] | 1.48 | 454 |
| XII-64 | 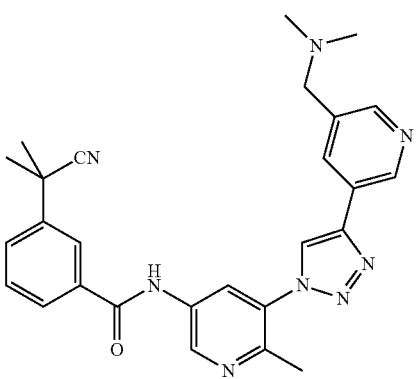 [SMILES: Cc1ncc(NC(=O)c2cccc(C(C)(C)C#N)c2)cc1-n1cc(-c2cncc(CN(C)C)c2)nn1] | 1.73 | 481 |

TABLE 2-continued
Example compounds XII-1 bis XII-78
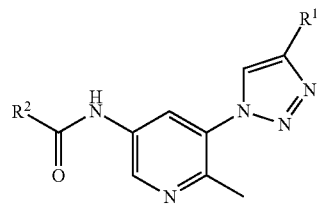
| # | Structure | t_Ret. (HPLC) [min] | MS (M + H)+ |
|---|---|---|---|
| XII-65 | 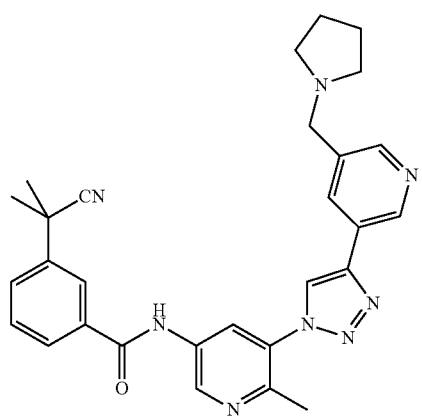 [SMILES: Cc1ncc(NC(=O)c2cccc(C(C)(C)C#N)c2)cc1-n1cc(-c2cncc(CN3CCCC3)c2)nn1] | 1.76 | 507 |
| XII-66 | 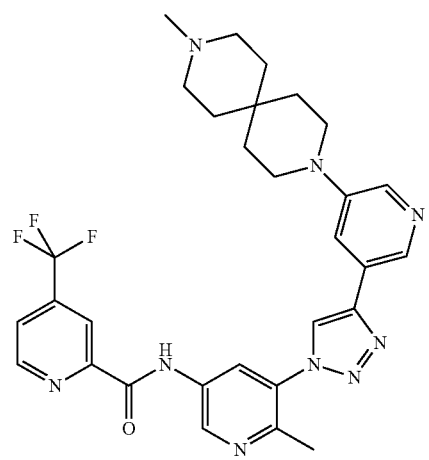 [SMILES: Cc1ncc(NC(=O)c2cc(C(F)(F)F)ccn2)cc1-n1cc(-c2cncc(N3CCC4(CCN(C)CC4)CC3)c2)nn1] | | |

TABLE 2-continued
Example compounds XII-1 bis XII-78
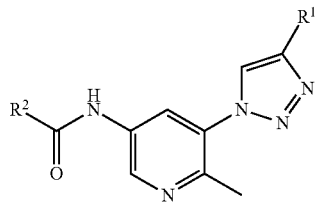
| # | Structure | $t_{Ret.}$ (HPLC) [min] | MS (M + H)$^+$ |
|---|---|---|---|
| XII-67 | 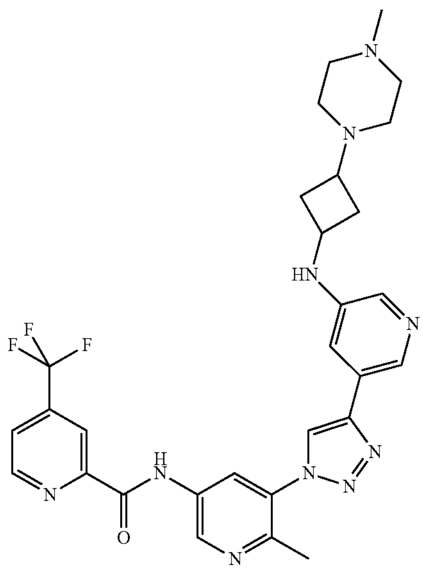 [SMILES: Cc1ncc(NC(=O)c2cc(C(F)(F)F)ccn2)cc1-n1cc(-c2cncc(NC3CC(N4CCN(C)CC4)C3)c2)nn1] | | |
| XII-68 | 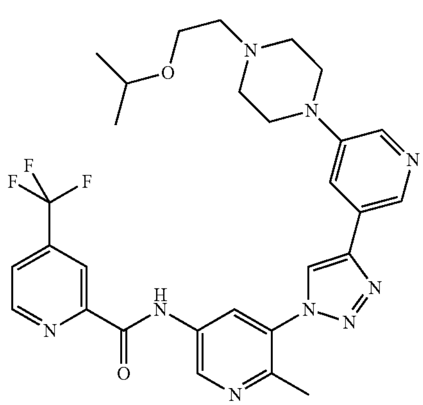 [SMILES: Cc1ncc(NC(=O)c2cc(C(F)(F)F)ccn2)cc1-n1cc(-c2cncc(N3CCN(CCOC(C)C)CC3)c2)nn1] | | |

TABLE 2-continued
Example compounds XII-1 bis XII-78
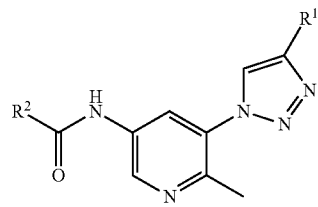
| # | Structure | $t_{Ret.}$ (HPLC) [min] | MS (M + H)+ |
|---|---|---|---|
XII-69
XII-70
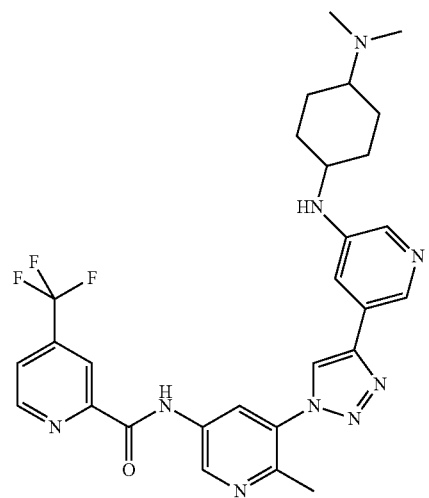 [SMILES: Cc1ncc(NC(=O)c2cc(C(F)(F)F)ccn2)cc1-n1cc(-c2cncc(NC3CCC(N(C)C)CC3)c2)nn1]

TABLE 2-continued
Example compounds XII-1 bis XII-78
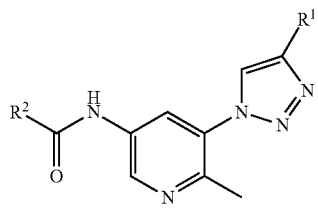
| # | Structure | $t_{Ret.}$ (HPLC) [min] | MS (M + H)$^+$ |
|---|---|---|---|
| XII-71 | 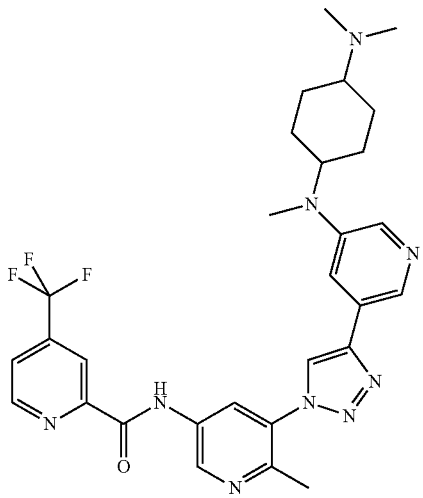 [SMILES: Cc1ncc(NC(=O)c2cc(C(F)(F)F)ccn2)cc1-n1cc(-c2cncc(N(C)C3CCC(N(C)C)CC3)c2)nn1] | | |
| XII-72 | 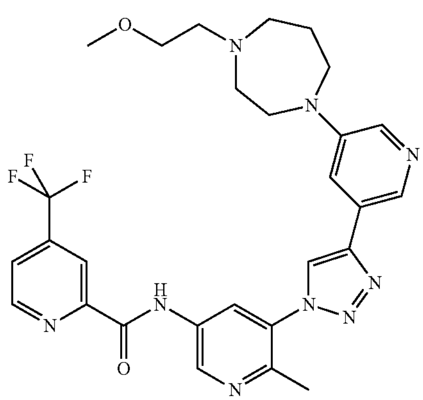 [SMILES: COCCN1CCCN(c2cncc(-c3cn(-c4cc(NC(=O)c5cc(C(F)(F)F)ccn5)cnc4C)nn3)c2)CC1] | | |
| XII-73 | 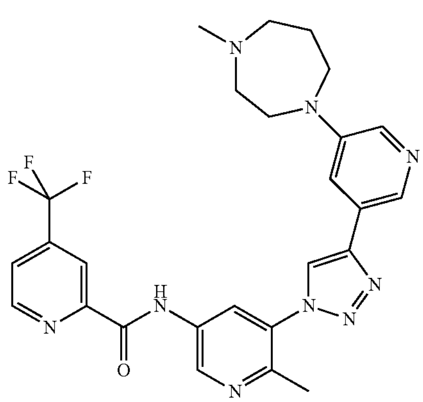 [SMILES: Cc1ncc(NC(=O)c2cc(C(F)(F)F)ccn2)cc1-n1cc(-c2cncc(N3CCCN(C)CC3)c2)nn1] | | |

TABLE 2-continued
Example compounds XII-1 bis XII-78
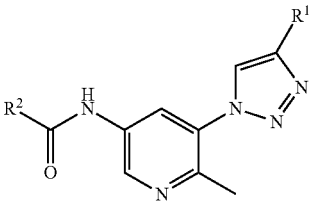
| # | Structure | $t_{Ret.}$ (HPLC) [min] | MS (M + H)+ |
|---|---|---|---|
| XII-74 | 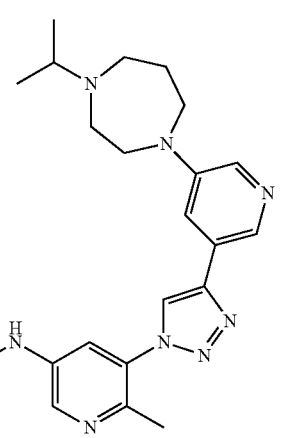 | | |
| XII-75 | 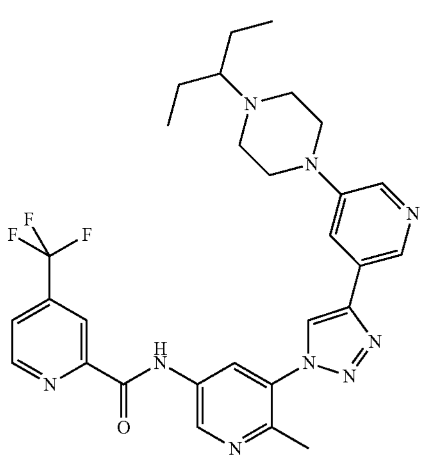 [SMILES: CCC(CC)N1CCN(c2cncc(-c3cn(-c4cc(NC(=O)c5cc(C(F)(F)F)ccn5)cnc4C)nn3)c2)CC1] | | |

TABLE 2-continued

Example compounds XII-1 bis XII-78

| # | Structure | $t_{Ret.}$ (HPLC) [min] | MS (M + H)$^+$ |
|---|---|---|---|
| XII-76 | 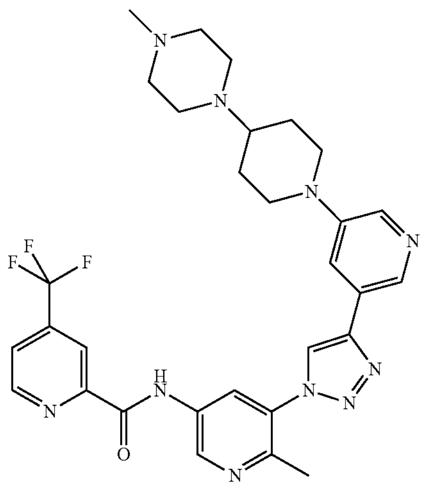 [SMILES: Cc1ncc(NC(=O)c2cc(C(F)(F)F)ccn2)cc1-n1cc(-c2cncc(N3CCC(N4CCN(C)CC4)CC3)c2)nn1] | | |
| XII-77 | 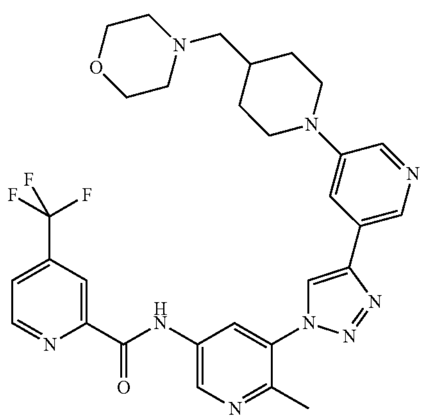 [SMILES: Cc1ncc(NC(=O)c2cc(C(F)(F)F)ccn2)cc1-n1cc(-c2cncc(N3CCC(CN4CCOCC4)CC3)c2)nn1] | | |
| XII-78 | 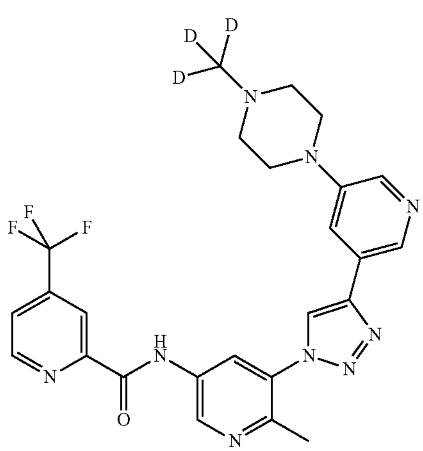 [SMILES: [2H]C([2H])([2H])N1CCN(c2cncc(-c3cn(-c4cc(NC(=O)c5cc(C(F)(F)F)ccn5)cnc4C)nn3)c2)CC1] | | |

Reaction scheme J

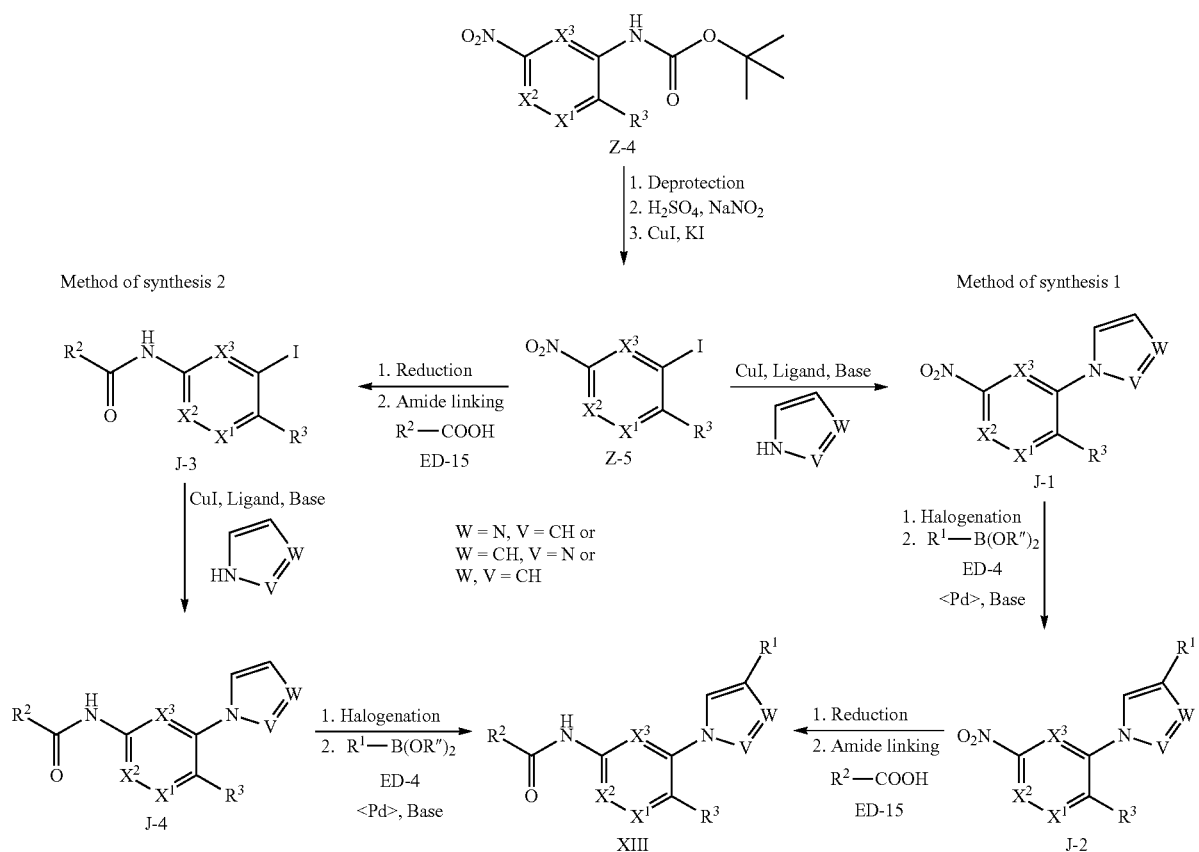

Example Compounds of Type XIII:

Compounds with an N-linked pyrrole, pyrazole or imidazole ring (type XIII) may for example be prepared using one of the synthesis routes (synthesis method 1 and 2) shown in Reaction scheme J. Compounds of Type XIII have an inverted amide bond compared with those of Type II.

Starting from the Boc-protected nitroanilines Z-4 (cf. Reaction scheme I) first of all the transformation into the iodides Z-5 is carried out by cleaving the protective group, diazotisation and SANDMEYER reaction.

The iodides Z-5 may then undergo an ULLMANN-like substitution by pyrrole, imidazole or pyrazole (synthesis method 1) with copper catalysis, to obtain the nitro compounds J-1. A selective halogenation with for example bromine, iodine, N-bromosuccinimide, N-iodosuccinimide or other halogenating reagents known from the literature and subsequent palladium-catalysed SUZUKI cross-coupling reaction with a heteroarylboric acid or derivative thereof ED-4 results in intermediates J-2, which are finally reduced and amidated with acids ED-15 to form the end compounds XIII.

According to synthesis method 2 the reaction steps known from synthesis method 1 are carried out in a different order.

Reaction scheme K

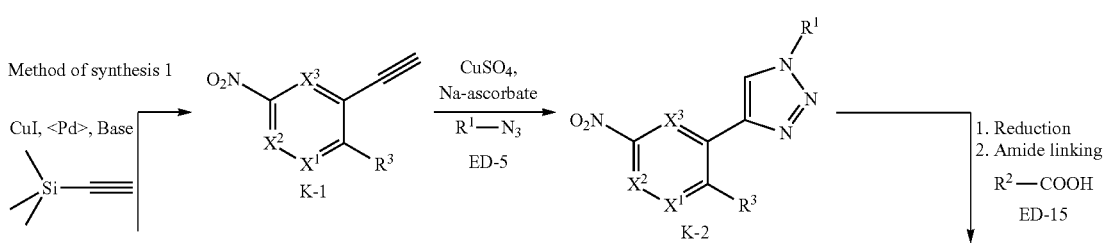

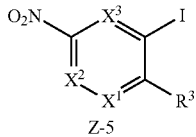
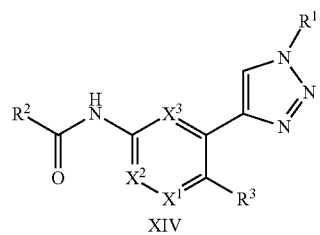

Example Compounds of Type XIV:

Compounds with a C-linked triazole ring (type XIV) may for example be prepared by one of the synthesis routes (synthesis method 1 and 2) shown in Reaction scheme K. Compounds of Type XIV have an inverted amide bond compared with those of Type III. Starting from iodides Z-5 (cf. Reaction scheme J) first of all (synthesis method 1) a palladium-catalysed SONOGASHIRA cross-coupling reaction is carried out with trimethylsilylacetylene and CuI, to obtain the alkyne K-1. This is followed by a copper-catalysed 1,3-dipolar cycloaddition between K-1 and heteroarylazides ED-5, thus synthesising the C-linked triazole ring. Compared with the synthesis of the N-linked triazole ring according to Reaction scheme A or I the reactivities "1,3-dipole" and "dipolarophil" relating to the groups thus introduced are reversed completely. The final amide coupling after reduction with acids ED-14 leads to compounds XIV.

According to synthesis method 2 Example compounds XIV may alternatively be prepared by a change in the order of the reaction sequence, compared with synthesis method 1.

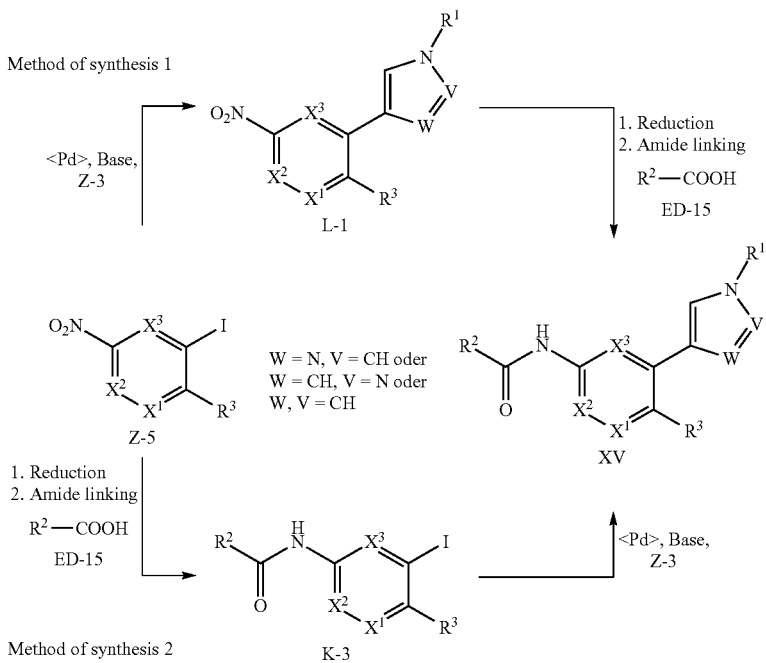

Example Compounds of Type XV:

Compounds with a C-linked pyrrole, pyrazole or imidazole ring (type XV) may for example be prepared using one of the synthesis routes (synthesis method 1 and 2) illustrated in Reaction scheme L. Compounds of Type XV have an inverted amide bond compared with those of Type IV.

Starting from iodides Z-5 (cf. Reaction scheme J) first of all (synthesis method 1) a palladium-catalysed SUZUKI cross-coupling reaction is carried out with boric acid derivatives Z-3 (cf. Reaction scheme D), to obtain the nitro compounds L-1.

These are converted into the Example compounds of type XV by reduction of the nitro group and subsequent amide coupling with the acids ED-15.

According to synthesis method 2 Example compounds XV may alternatively be prepared by a change in the order of the reaction sequence, compared with synthesis method 1.

Example Compounds of Type XVI and XVII-A (Reaction Scheme M, Part 1):

Compounds having in each case an imidazole ring C-linked via the 4-position (type XVI) or a C-linked thiazole ring (type XVII-A) may be obtained from the iodides Z-5.

Reaction scheme M

Part 1

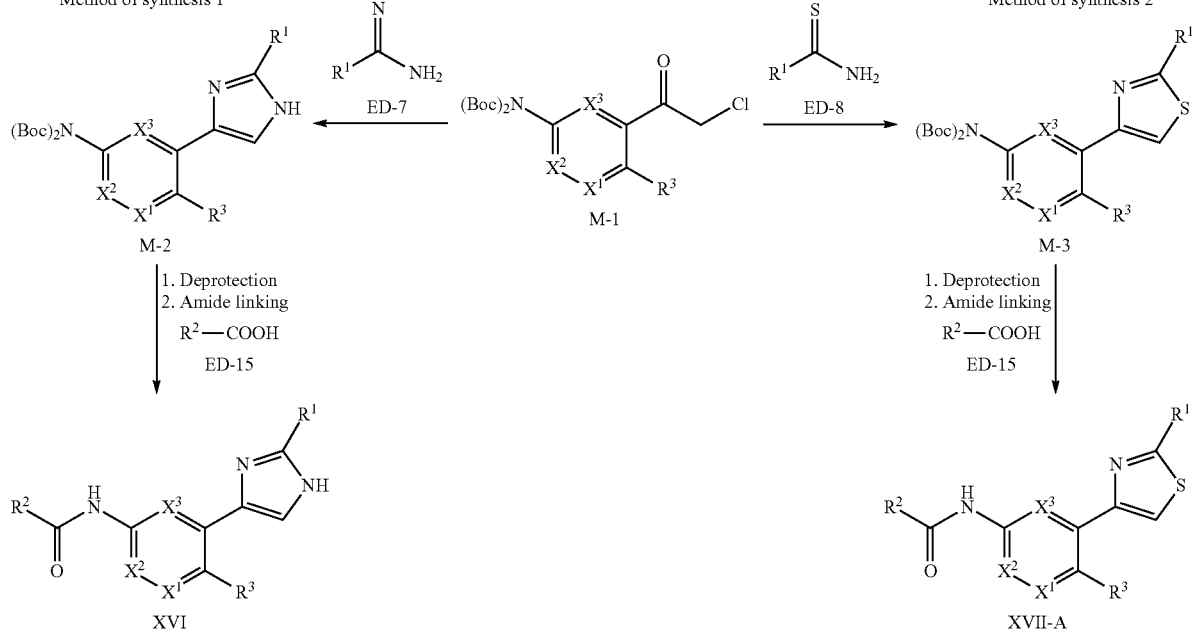

Part 2

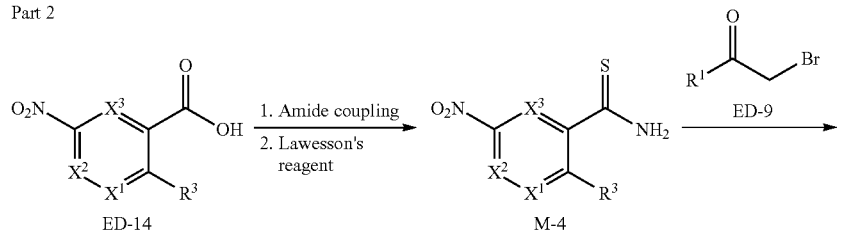

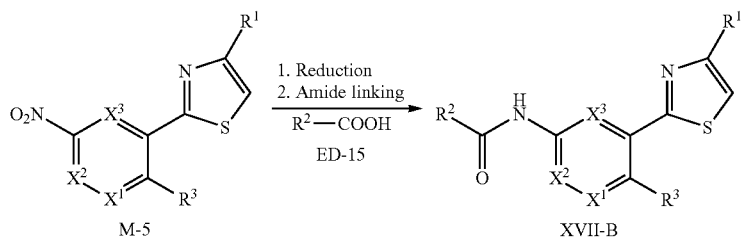

Compounds of Type XVI and XVII-A have an inverted amide bond compared with those of Type V, VI-A and VI-B (cf. Reaction scheme E).

First, iodide Z-5 is reduced and the amino group obtained is protected by two Boc-protective groups. The iodides thus obtained Z-6 are metallised by iPrMgCl in the presence of CuCN and then reacted with chloroacetyl chloride to form α-chloroketones M-1.

The reaction of M-1 with heteroarylamidines ED-7 leads to imidazole intermediates M-2 (synthesis method 1), while reaction with heteroarylthioamides ED-8 leads to thiazole intermediates M-3 (synthesis method 2). Both M-2 and M-3 may then be amidated after saponification to form the end compounds.

Example Compounds of Type XVII-B (Reaction Scheme M, Part 2):

Compounds with a thiazole ring C-linked via the 2-position (type XVII-B) may be obtained from the carboxylic acids ED-14. Compounds of Type XVII-B have an inverted amide bond compared with those of Type VI-B.

First of all the carboxylic acid ED-14 is converted into the thioamide M-4 by amide coupling and reaction with LAWESSON's reagent. Cyclisation with α-bromoketones ED-9 and subsequent reduction of the nitro group with final amide coupling with carboxylic acids ED-15 yields the end compounds of type XVII-B

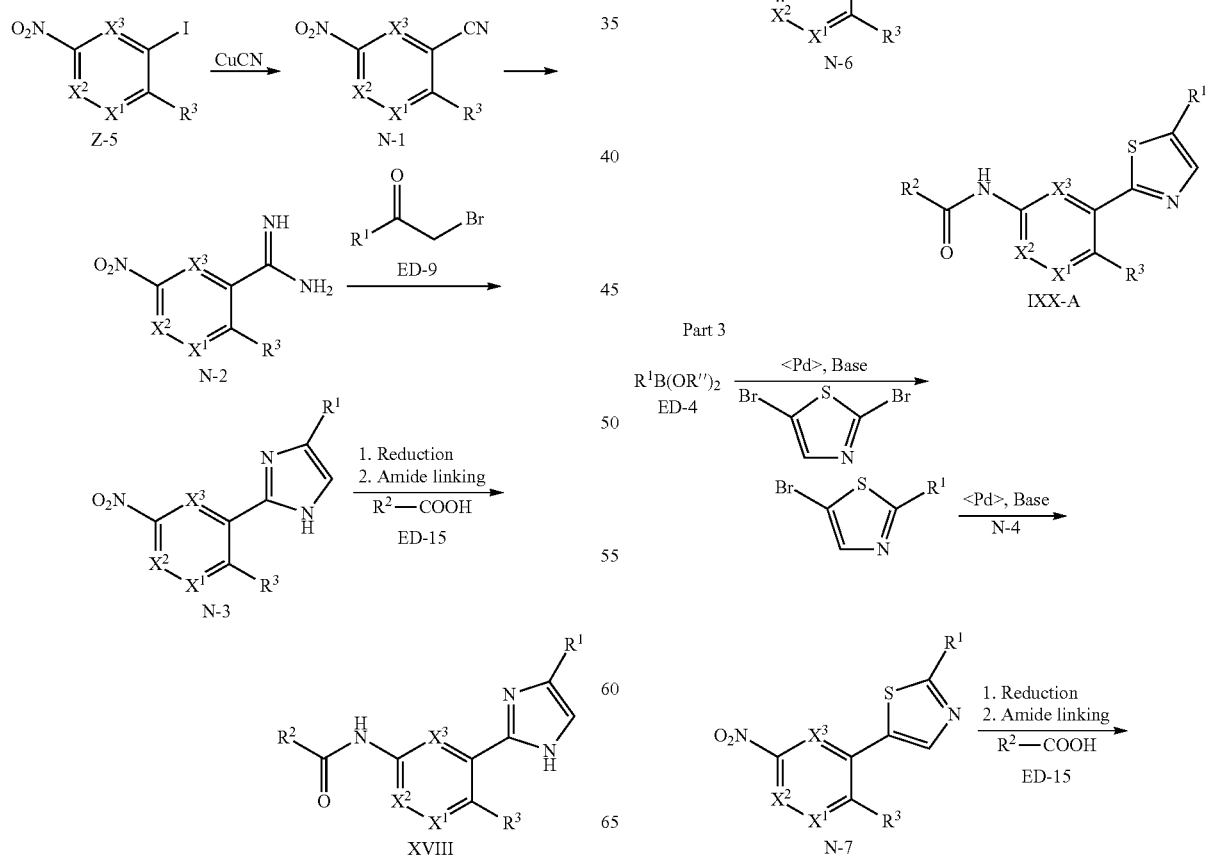

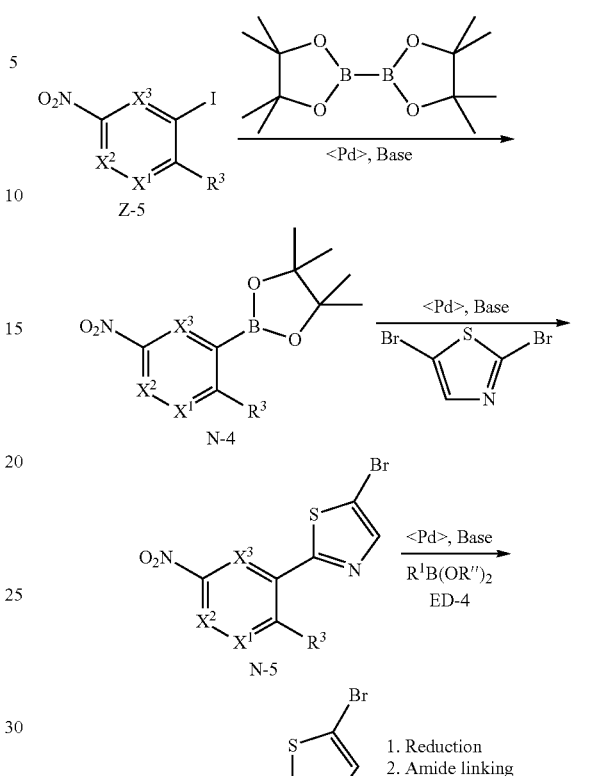

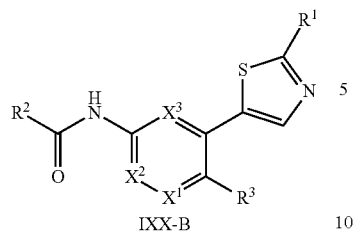

IXX-B

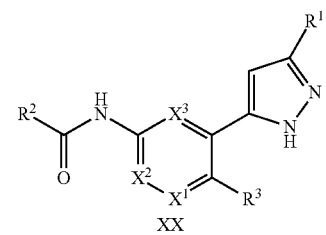

XX

Compounds of Type XVIII, IXX-A and IXX-B have an inverted amide bond compared with those of Type VII, VIII-A and VIII-B (cf. Reaction scheme F).

Example Compounds of Type XVIII (Reaction Scheme N, Part 1):

Compounds with an imidazole ring C-linked via the 2-position (type XVIII) may be obtained by cyclisation from iodides Z-5. Compounds of Type XVIII have an inverted amide bond compared with those of Type VII.

The iodides Z-5 are substituted by CuCN in the first reaction step to form the nitriles N-1 and converted by aminolysis into the amidines N-2. The imidazole ring is formed by the reaction with heteroaryl-α-bromomethylketones ED-9 and finally the intermediates N-3 are reduced and amidated.

Example Compounds of Type IXX-A (Reaction Scheme N, Part 2):

Compounds with a thiazole ring C-linked via the 2-position (type IXX-A) may also be obtained starting from iodides Z-5. The synthesis is carried out by first of all preparing the boric acid derivatives N-4 from Z-5, e.g. by reacting with bis-pinacolborane with palladium catalysis, and then reacting them in a palladium-catalysed SUZUKI cross-coupling reaction with 2,4-dibromothiazole or 2,5-dibromothiazole to obtain the intermediates N-5. By further SUZUKI reaction with the boric acids or boric acid derivatives ED-4 the group $R^1$ is then introduced (intermediate N-6), before finally obtaining the end compounds after reduction and amidation with ED-15.

Example Compounds of Type IXX-B (reaction scheme N, Part 3):

Compounds with a thiazole ring C-linked via the 5-position (type IXX-B) may be obtained starting from the boric acids or boric acid derivatives N-4. First of all, in a first palladium-catalysed SUZUKI cross-coupling reaction the boric acids or boric acid derivatives ED-4 are reacted with 2,5-dibromothiazole to introduce $R^1$. In another SUZUKI reaction with the boric acid derivatives N-4 the nitro compounds N-7 are obtained, which are then converted into the end compounds of type IXX-B by reduction and finally amide coupling with the carboxylic acids ED-15.

Reaction Scheme O

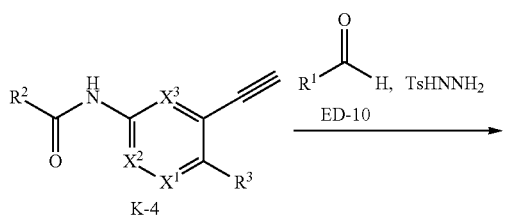

K-4

Example Compounds of Type XX:

Compounds with a pyrazole ring C-linked via the 5-position (type XX) may be obtained by cyclisation from the alkynes K-4 (cf. Reaction scheme K), which undergo cycloaddition with tosylhydrazones. The tosylhydrazones are generated in situ from the corresponding heteroarylaldehydes ED-10 and tosylhydrazine. Compounds of Type XX have an inverted amide bond compared with those of Type IX.

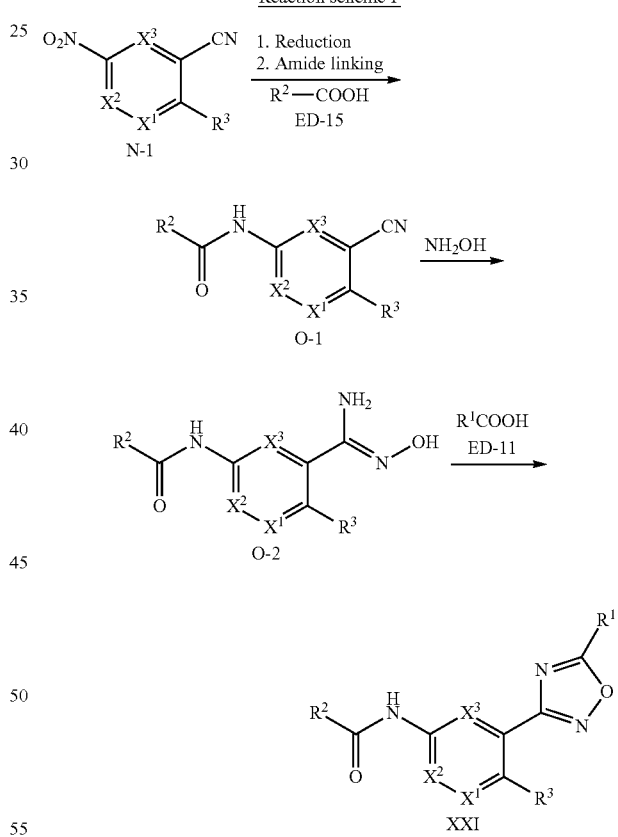

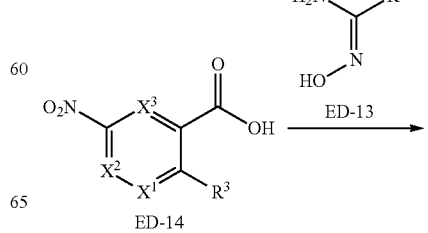

ED-14

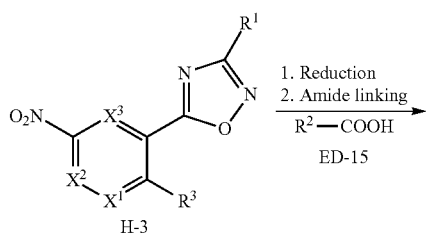
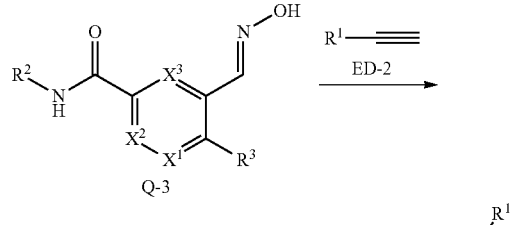
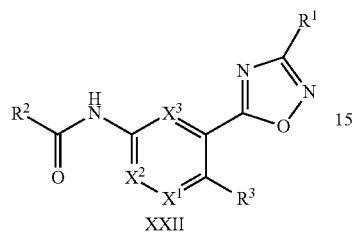
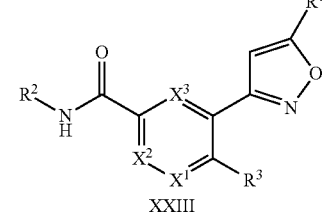

Example Compounds of Type XXI:

Compounds with a 2,4-oxadiazole ring C-linked via the 3-position (type XXI) may be obtained by cyclisation from nitriles N-1 (cf. Reaction scheme N). In a first step the nitro group in N-1 is reduced and the free amino group is amidated with a carboxylic acid ED-15 (O-1). After the subsequent addition of hydroxylamine to the intermediate O-2, this is cyclised with heteroarylcarboxylic acids ED-11 to form compounds XXI. Compounds of Type XXI have an inverted amide bond compared with those of Type X.

Example Compounds of Type XXII:

Compounds with a 2,4-oxadiazole ring C-linked via the 5-position (type XXII) may be obtained by cyclisation from carboxylic acids ED-14, by reacting them with heteroarylhydroxyamidines ED-13. The intermediate O-3 thus obtained is reduced and amidated with carboxylic acids ED-15 to form compounds XXII. Compounds of Type XXII have an inverted amide bond compared with those of Type XI.

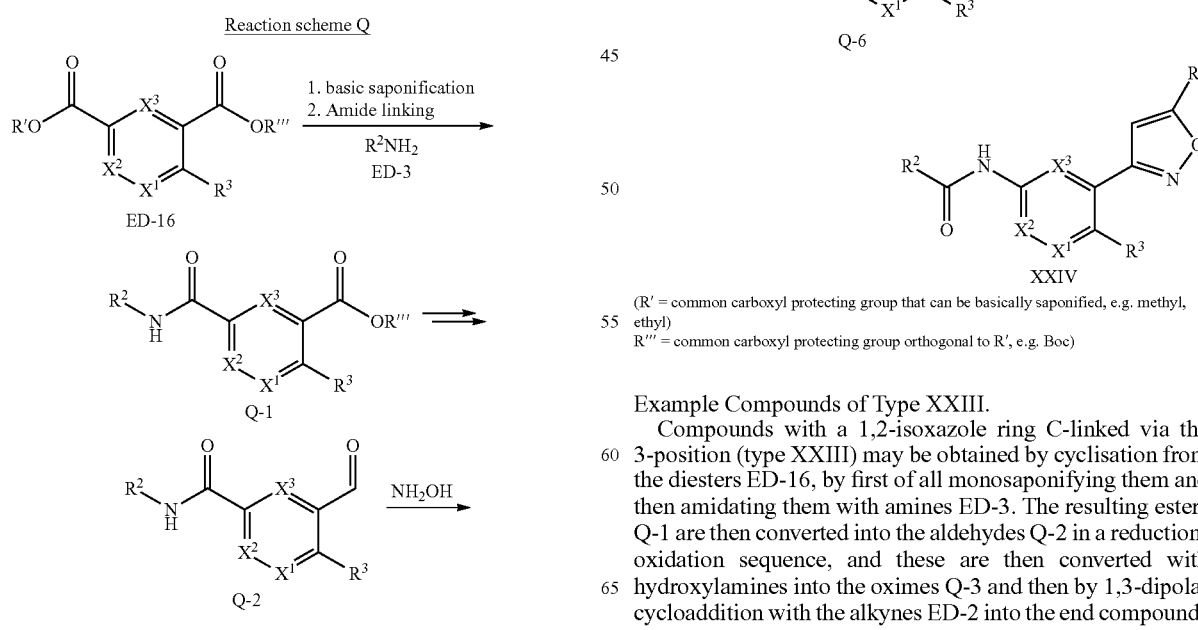

(R' = common carboxyl protecting group that can be basically saponified, e.g. methyl, ethyl)
R''' = common carboxyl protecting group orthogonal to R', e.g. Boc)

Example Compounds of Type XXIII.

Compounds with a 1,2-isoxazole ring C-linked via the 3-position (type XXIII) may be obtained by cyclisation from the diesters ED-16, by first of all monosaponifying them and then amidating them with amines ED-3. The resulting esters Q-1 are then converted into the aldehydes Q-2 in a reduction-oxidation sequence, and these are then converted with hydroxylamines into the oximes Q-3 and then by 1,3-dipolar cycloaddition with the alkynes ED-2 into the end compounds XXIII. To ensure that in the diester ED-16 only the carboxylate group —COOR' is selectively saponified, the groups R' and R'" must have orthogonal reactivities in relation to the saponification conditions (e.g. —COOR' basically saponifiable, —COOR'" acidically saponifiable)

Example Compounds of Type XXIV:

Compounds with a 1,2-isoxazole ring C-linked via the 3-position and an inverted amide bond (type XXIV) may be obtained by cyclisation from the carboxylic acids ED-14, by first of all esterifying the acid function, reducing the nitro function and then amidating with the carboxylic acids ED-15. The esters Q-4 thus obtained are then transformed in a reduction-oxidation sequence into the aldehydes Q-5, which are then converted with hydroxylamines into the oximes Q-6 and then by 1,3-dipolar cycloaddition with the alkynes ED-2 into the end compounds XXIV.

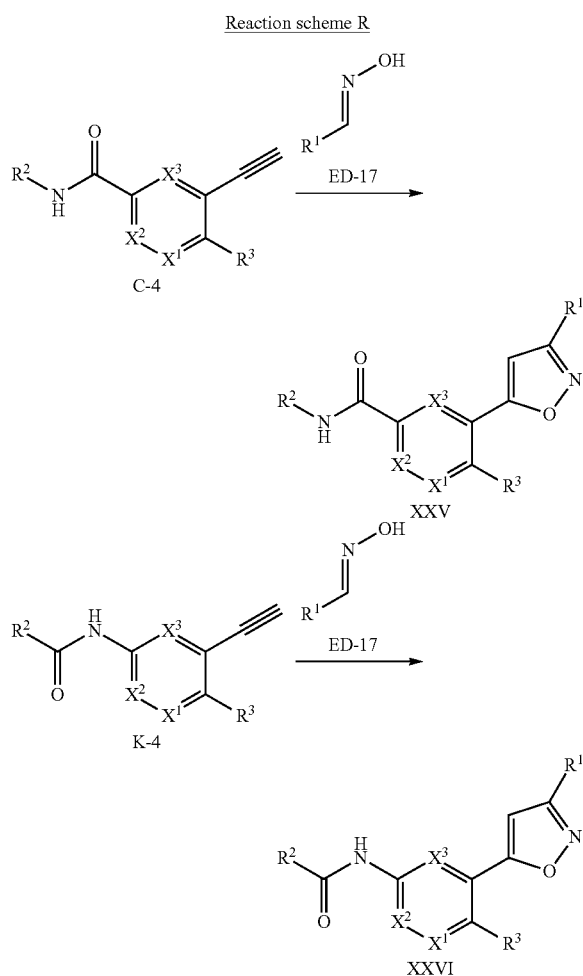

Example Compounds of Type XXV and XXVI:

Compounds with a 1,2-isoxazole ring C-linked via the 5-position (type XXV) may be obtained by 1,3-dipolar cycloaddition from the alkynes C-4 and the oximes ED-17. The corresponding compounds with an inverted amide bond (type XXVI) may be obtained in the same way from the alkynes K-4.

Further References to Reaction Schemes A to R and all the Types of Example Compounds (I to XXVI):

For amide coupling reactions, methods for activating the carboxylic acids are used which are known from the literature. Thus, for example, the acids may be converted for example with SOCl$_2$, oxalyl chloride/DMF or the GHOSEZ reagent (1-chloro-N,N,2-trimethylpropenylamine) into the acid chlorides, which are reacted with the corresponding amines with the addition of an auxiliary base such as e.g. TEA, DIPEA, pyridine or other common organic bases to form the amides. Alternatively the carboxylic acids may be activated with special coupling reagents such as e.g. HATU, TBTU, DCC, EDC, PyBOP, CDI and other reagents known from the literature and reacted as described above with amines and auxiliary bases to form the amides.

Both the group $R^1$ and the group $R^2$ of compounds I to XXVI according to the invention may be modified in other reaction steps not shown in the Schemes, to obtain further compounds I to XXVI according to the invention. These reaction steps may be reactions of substitution, alkylation, acylation or addition. Examples of such a modification are the compounds I-35 to I-41 according to the invention (Table 1), which are prepared by BUCHWALD-HARTWIG reaction from the compound I-34 according to the invention.

A representative number of the educt components ED-1 to ED-17 needed for synthesising compounds according to the invention are commercially obtainable or may be prepared routinely using generally known methods. In addition, they may be prepared according to or analogously to the literature cited below.

Heteroarylalkynes ED-2 may be prepare from the corresponding halides using methods known from the literature by a palladium-catalysed SONOGASHIRA cross-coupling reaction with trimethylsilylacetylene in the presence of copper(I) iodide. The trimethylsilyl-protected alkyns thus formed are reacted in situ by cleaving the trimethysilyl group with $K_2CO_3$ or KF to form the terminal alkynes. Alternatively alkynes ED-2 may also be prepared by BESTMANN-OHIRA reaction from the corresponding heteroarylaldehydes $R^1$CHO (ED-10). The aldehydes ED-10 required for this may be synthesised according to methods known from the literature, e.g. by VILSMAIER-HAACK formylation of the corresponding heteroaromatic groups.

The heteroarylboric acids or -boric acid derivatives ED-4 to be used in SUZUKI reactions are prepared from the corresponding heteroarylhalides ED-6, which are obtained by halogenation from the heteroaromatic groups.

Heteroarylazides ED-5 are obtained from heteroarylamines $R^1$—$NH_2$ by hydrochloric acid diazotisation and substitution with sodium azide.

Heteroarylamidines ED-7 may be obtained by PINNER reaction from heteroarylnitriles CN, and heteroarylthioamides ED-8 may be obtained from heteroarylcarboxylic acids by amidation and reaction with LAWESSON'S reagent.

Heteroarylbromomethylketones ED-9 are obtained from heteroarylhalides ED-6 by metallisation with magnesium and acylation with bromoacetyl chloride or bromide or alternatively from heteroarylcarboxylic acids ED-11 by WEINREB amidation with N,O-dimethylhydroxylamine, subsequent reaction with methyllithium or a methyl-GRIGNARD compound and finally selective α-bromination.

Heteroarylhydroxyamidines ED-13 are prepared by the addition of hydroxylamines to heteroarylnitriles $R^1$—CN.

Heteroaryloximes ED-17 are obtained from aldehydes ED-10 and hydroxylamines.

Moreover, on the synthesis of other educt components or methods of cyclisation, reference may be made to the following publications:

WO 2004/050642, WO 2005/056535, WO 2005/090333, WO 2005/115991, US 2006/100204, WO 2008/003770, WO

2009/003999, WO 2009/003998, WO 2008/089034, WO 2007/056016, WO 2007/075896, WO 2008/021388, WO 2005/023761

Six-membered cyclic heteroaryl component ED-16 (diester) can be transformed by monosaponification and subsequent CURTIUS degradation into the components ED-12 or ED-1:

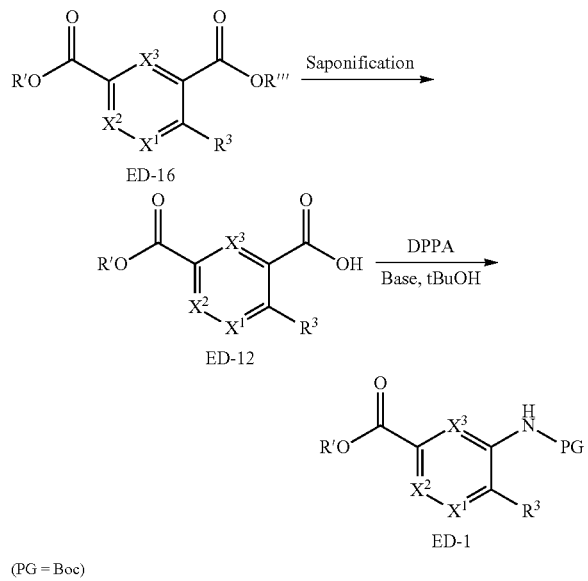

(PG = Boc)

The following Examples describe the biological activity of the compounds according to the invention, without restricting the invention to these Examples.

Compounds of general formula (1) are characterised by their many possible applications in the therapeutic field. Particular mention should be made of those applications in which the inhibition of specific signal enzymes, particularly the inhibiting effect on the proliferation of cultivated human tumour cells but also on the proliferation of other cells such as endothelial cells, for example, are involved.

Kinase test B-Raf (V600E)

In a dilution series 10 μL of test substance solution are placed in a multiwell plate. The dilution series is selected so that generally a range of concentrations of 2 μM to 0.119 nM or 0.017 nM is covered. If necessary the initial concentration of 2 μM is changed to 50 μM, 10 μM or 0.4 μM or 0.2857 μM and further dilution is carried out accordingly. The final concentration of DMSO is 5%. 10 μL of the B-Raf (V600E)-kinase solution are pipetted in (containing 0.5 ng B-Raf (V600E)-kinase in 20 mM Tris-HCl pH 7.5, 0.1 mM EDTA, 0.1 mM EGTA, 0.286 mM sodium orthovanadate, 10% glycerol, 1 mg/mL bovine serum albumin, 1 mM dithiothreitol) and the mixture is incubated for 1 h at RT under with shaking The kinase reaction is started by the addition of 20 μL ATP solution [final concentration: 250 μM ATP, 30 mM Tris-HCl pH 7.5, 0.02% Brij, 0.2 mM sodium orthovanadate, 10 mM magnesium acetate, 0.1 mM EGTA, phosphatase cocktail (Sigma, # P2850, dilution recommended by the manufacturer), 0.1 mM EGTA] and 10 μL MEK1 solution [containing 50 ng biotinylated MEK1 (prepared from purified MEK1 according to standard procedure, e.g. with EZ-Link Sulpho-NHS-LC-Biotin reagent, Pierce, # 21335) and carried out for 60 min at RT with constant shaking. The reaction is stopped by the addition of 12 μL of a 100 mM EDTA solution and incubation is continued for a further 5 min. 55 μL of the reaction solution are transferred into a streptavidin-coated plate (e.g. Streptawell HighBond, Roche, #11989685001) and shaken gently for 1 h at RT, in order to bind biotinylated MEK1 to the plate. After elimination of the liquid the plate is washed five times with 200 μL of 1×PBS and 100 μL solution of primary antibody plus europium-labelled secondary antibody [Anti Phospho-MEK (Ser217/221), Cell Signaling, # 9121 and Eu-N1 labeled goat-anti-rabbit antibody, Perkin Elmer, #AD0105], the primary antibody is diluted 1:2000 and the secondary antibody is diluted to 0.4-0.5 μg/mL in Delfia Assay Buffer (Perkin Elmer, #1244-111). After 1 h shaking at RT the solution is poured away and washed five times with 200 μL Delfia Wash Buffer (Perkin Elmer, #4010-0010/ #1244-114). After the addition of 200 μL Enhancement Solution (Perkin Elmer, #4001-0010/#1244-105) the mixture is shaken for 10 min at RT and then measured in a Wallac Victor using the program "Delfia Time Resolved Fluorescence (Europium)". $IC_{50}$ values are obtained from these dosage-activity curves using a software program (GraphPadPrizm).

Most of the example compounds of Type I to XXVI exhibit good to very good inhibitory effects in this B-Raf (V600E) inhibition test, i.e. an $IC_{50}$ value of less than 5 μM, generally less than 1 μM.

In order to demonstrate that compounds according to the invention have an inhibitory activity via different structural elements, Table 3 shows the % CTL values of the compound examples at a concentration of 2 μM (exceptions are marked accordingly). A value of 100% indicates no inhibition while a value of 0% indicates total inhibition. The % CTL values denote the residual activity of the enzyme after the addition of the inhibitory compound in the solvent DMSO in relation to the enzyme activity in the solvent DMSO without the addition of a compound (control). The values were determined using the B-Raf(V600E)-kinase test described above.

TABLE 3

| # | % CTL |
|---|---|
| I-1 | 7.6 |
| I-2 | 8.0 |
| I-3 | 8.7 |
| I-4 | 1.7 |
| I-6 | 2.1 |
| I-7 | 2.0 |
| I-8 | 1.6 |
| I-9 | 1.4 |
| I-10 | 1.1 |
| I-12 | 1.8 |
| I-13 | 2.3 |
| I-14 | 1.4 |
| I-15 | 1.4 |
| I-16 | 2.0* |
| I-18 | 2.4 |
| I-20 | 1.9 |
| I-21 | 2.2 |
| I-23 | 5.9 |
| I-24 | 1.0 |
| I-25 | 2.2 |
| I-26 | 1.4 |
| I-27 | 3.3 |
| I-29 | 2.5 |
| I-30 | 6.9 |
| I-32 | 1.5 |
| I-33 | 1.4 |
| I-34 | 1.5 |
| I-35 | 1.7 |
| I-36 | 1.8 |
| I-37 | 2.5 |
| I-38 | 2.4 |
| I-39 | 1.5 |
| I-40 | 1.4 |

TABLE 3-continued

| # | % CTL |
|---|---|
| I-41 | 1.1 |
| I-42 | 1.6 |
| I-43 | 1.1 |
| I-44 | 3.3 |
| I-45 | 3.2 |
| I-46 | 6.1 |
| I-47 | 2.0 |
| I-48 | 1.7 |
| I-49 | 6.2 |
| I-50 | 2.2 |
| I-51 | 4.0 |
| I-52 | 1.6 |
| I-53 | 1.4 |
| I-54 | 1.2 |
| I-55 | 1.2 |
| I-56 | 1.4 |
| I-57 | 2.3 |
| I-58 | 5.5 |
| I-59 | 13.4 |
| I-60 | 7.2 |
| I-61 | 8.1 |
| I-62 | 2.8 |
| I-63 | 4.6 |
| I-64 | 6.6 |
| I-65 | 7.1 |
| I-66 | 6.4 |
| I-67 | 2.9 |
| I-68 | 4.7 |
| I-69 | 2.8 |
| I-70 | 10.4 |
| I-71 | 5.5 |
| I-72 | 5.1 |
| I-73 | 1.7 |
| I-74 | 9.0 |
| I-75 | 7.3 |
| I-76 | 2.0*** |
| I-77 | 1.9 |
| I-78 | 2.8 |
| I-79 | 3.6 |
| I-80 | 1.9 |
| I-81 | 1.2 |
| I-82 | 1.6 |
| I-83 | 1.1 |
| I-84 | 2.4 |
| I-85 | 1.1 |
| I-86 | 1.4 |
| I-87 | 1.7 |
| I-88 | 1.3 |
| I-89 | 1.5 |
| I-90 | 2.1 |
| I-91 | 2.5 |
| I-92 | 2.5 |
| I-93 | 3.5 |
| I-94 | 3.5 |
| I-95 | 3.1 |
| I-96 | 3.4 |
| I-97 | 3.3 |
| I-98 | 3.0 |
| I-99 | 1.9 |
| I-100 | 3.0 |
| I-101 | 1.3*** |
| I-102 | 4.6 |
| I-103 | 3.8 |
| I-104 | 2.1 |
| I-105 | 2.0*** |
| I-106 | 1.3 |
| I-107 | 1.6 |
| I-108 | 1.7 |
| I-109 | 1.8 |
| I-110 | 1.3 |
| I-111 | 1.8 |
| I-112 | 2.0 |
| I-113 | 2.9 |
| I-114 | 15.6** |
| I-115 | 1.9 |
| I-116 | 3.1 |
| I-117 | 3.1 |
| I-118 | 2.6 |
| I-119 | 1.8 |
| I-120 | 1.7 |
| I-121 | 2.3*** |
| I-122 | 1.8 |
| I-123 | 5.8 |
| I-124 | 1.9 |
| I-125 | 1.2 |
| I-126 | 5.7 |
| I-127 | 6.1 |
| I-128 | 5.3 |
| I-130 | 2.2 |
| I-131 | 2.2 |
| I-132 | 1.0 |
| I-134 | 2.6 |
| I-135 | 2.6 |
| I-136 | 2.5 |
| I-137 | 2.5 |
| I-138 | 2.5 |
| I-139 | 2.5 |
| I-140 | 2.2 |
| I-141 | 2.1 |
| I-142 | 1.5 |
| I-143 | 2.2 |
| I-144 | 1.9 |
| I-145 | 2.2 |
| I-146 | 2.0 |
| I-147 | 3.1 |
| I-148 | 4.0 |
| I-149 | 2.1 |
| I-150 | 4.1 |
| I-151 | 4.5 |
| I-152 | 2.4 |
| I-153 | 1.8 |
| I-154 | 2.9 |
| I-155 | 2.6 |
| I-164 | 9.9 |
| I-165 | 8.9 |
| I-166 | 7.9 |
| I-167 | 7.9 |
| I-168 | 9.8 |
| I-169 | 8.4 |
| I-170 | 7.5 |
| I-171 | 7.7 |
| I-172 | 8.0 |
| I-173 | 2.4 |
| I-174 | 8.1 |
| I-175 | 8.1 |
| I-176 | 6.7 |
| I-177 | 1.9 |
| I-178 | 2.3 |
| I-179 | 2.6 |
| I-180 | 2.9 |
| I-181 | 2.3 |
| I-182 | 2.1 |
| I-183 | 1.8 |
| I-184 | 2.5 |
| I-185 | 1.7 |
| I-186 | 1.5 |
| I-187 | 4.1 |
| I-188 | 1.5 |
| I-189 | 3.8 |
| I-190 | 4.1 |
| I-191 | 3.0 |
| I-192 | 1.9 |
| I-193 | 3.6 |
| I-194 | 2.1 |
| I-195 | 0.8 |
| I-196 | 1.0 |
| I-197 | 1.0 |
| I-198 | 1.7 |
| I-199 | 1.6 |
| I-200 | 1.0 |
| I-201 | 1.6 |
| I-202 | 1.6 |
| I-204 | 1.0 |
| I-205 | 0.8 |
| I-206 | 0.9 |
| XII-1 | 4.4 |

TABLE 3-continued

| # | % CTL |
|---|---|
| XII-2 | 4.6 |
| XII-3 | 4.7 |
| XII-5 | 1.8 |
| XII-6 | 4.7 |
| XII-7 | 4.7 |
| XII-8 | 6.4 |
| XII-9 | 6.6 |
| XII-10 | 2.5 |
| XII-11 | 1.5*** |
| XII-12 | 5.2 |
| XII-13 | 0.9 |
| XII-14 | 0.9* |
| XII-15 | 0.8 |
| XII-16 | 0.7 |
| XII-17 | 0.9 |
| XII-18 | 2.1 |
| XII-19 | 6.5 |
| XII-20 | 1.6 |
| XII-21 | 1.5 |
| XII-22 | 3.4 |
| XII-23 | 7.2 |
| XII-24 | 3.8 |
| XII-25 | 3.9 |
| XII-26 | 2.2 |
| XII-27 | 2.4 |
| XII-28 | 2.0 |
| XII-29 | 1.6 |
| XII-30 | 1.8 |
| XII-31 | 1.9 |
| XII-32 | 2.9 |
| XII-33 | 1.7 |
| XII-34 | 0.8 |
| XII-35 | 1.7 |
| XII-36 | 1.3 |
| XII-37 | 2.3 |
| XII-38 | 2.1 |
| XII-39 | 2.5 |
| XII-40 | 3.0* |
| XII-41 | 3.1 |
| XII-42 | 4.3 |
| XII-43 | 2.1 |
| XII-44 | 1.9 |
| XII-45 | 2.9 |
| XII-46 | 1.8 |
| XII-47 | 4.0 |
| XII-48 | 2.4 |
| XII-49 | 2.3 |
| XII-50 | 6.8 |
| XII-51 | 2.3 |
| XII-52 | 7.0 |
| XII-53 | 7.0 |
| XII-54 | 10.8 |
| XII-55 | 1.8 |
| XII-57 | 0.9 |
| XII-63 | 3.8 |
| XII-64 | 0.9 |
| XII-65 | 0.9 |

*Measurement at 0.29 µM
**Measurement at 1.02 µM
***Measurement at 1.43 µM

Measurement of the Inhibition of the Proliferation of Cultivated Human Melanoma Cells (SK-MEL-28, B-RAF$^{V600E}$ Mutated)

For measuring the proliferation of cultivated human tumour cells, cells of the melanoma cell line SK-MEL-28 [American Type Culture Collection (ATCC)] are cultivated in MEM medium, supplemented with 10% foetal calf serum, 2% sodium bicarbonate, 1 mM sodium pyruvate, 1% non-essential amino acids (e.g. from Cambrex, # BE13-114E) and 2 mM glutamine. SK-MEL28 cells are placed in 96-well flat bottomed dishes in a density of 2500 cells per well in supplemented MEM medium (see above) and incubated overnight in an incubator (at 37° C. and 5% $CO_2$). The active substances are added to the cells in different concentrations, so that a concentration range of 50 µM to 3.2 nM is covered. If necessary the initial concentration of 50 µM is changed to 10 µM or 2 µM and further dilution is carried out accordingly (to 0.6 nM or 0.12 nM). After an incubation period of a further 72 h 20 µL AlamarBlue reagent (Serotec Ltd., # BUF012B) are added to each well and the cells are incubated for a further 3-6 h. The colour change of the AlamarBlue reagent is determined in a fluorescence spectrophotometer (e.g. Gemini, Molecular Devices). $EC_{50}$ values are calculated using a software program (GraphPadPrizm).

Most of the example compounds of type I to XXVI exhibit a good to very good activity in the cellular SK-MEL-28 assay, i.e. example compounds of type I and XII (Table 3) have an $EC_{50}$ value of less than 10 µM, generally less than 3 µM.

Measurement of the Inhibition of the Proliferation of Cultivated Human Melanoma Cells (A375, B-RAF$^{V600E}$ Mutated)

For measuring the proliferation of cultivated human tumour cells, cells of the melanoma cell line A375 [American Type Culture Collection (ATCC)] are cultivated in DMEM medium, supplemented with 10% foetal calf serum and 2% sodium bicarbonate. Test substances are tested on A375 cells according to the procedure described for SK-MEL28 cells (see above), but seeding them at 5000 cells per well.

Most of the example compounds of types I to XXVI show good to very good activity in the cellular A375 assay, i.e. example compounds of type I and XII (Table 3) have an $EC_{50}$ value of less than 10 µM, generally less than 3 µM.

The active substances are characterised in that they have a significantly lower antiproliferative effect on cell lines that do not have a B-RAF mutation, i.e. the $EC_{50}$ value is generally higher, by a factor of 10, than the $EC_{50}$ value of B-RAF mutated cell lines.

The cellular selectivity of the active substances is demonstrated by the fact that the $EC_{50}$ value of the phospho-ERK reduction correlates with the $EC_{50}$ value of the antiproliferative activity in B-RAF mutated cell lines.

Measurement of the Reduction in the Phospho-ERK Signal in Cultivated Human Melanoma Cells (SK-MEL-28, B-RAF$^{V600E}$ Mutated)

In order to measure the reduction in the phospho-ERK signal of cultivated human tumour cells, cells of the melanoma cell line SK-MEL-28 [American Type Culture Collection (ATCC)] are cultivated in MEM medium, supplemented with 10% foetal calf serum, 2% sodium bicarbonate, 1 mM sodium pyruvate, 1% non-essential amino acids (e.g. from Cambrex, # BE13-114E) and 2 mM glutamine. SK-MEL28 cells are placed in 96-well flat bottomed dishes at a density of 7500 cells per well in supplemented MEM medium (see above) and incubated overnight in an incubator (at 37° C. and 5% $CO_2$). The active substances are added to the cells in different concentrations, so that a concentration range of 10 µM to 2.4 nM is covered. If necessary the initial concentration of 10 µM is changed to 50 µM or 2.5 µM and further dilution is carried out accordingly (to 12.2 nM or 0.6 nM). After an incubation period of a further 2 h the cells are fixed with 4% formaldehyde and rendered permeable with 0.1% Triton X-100 in PBS. Non-specific antibody binding is reduced by incubation with 5% skimmed milk powder dissolved in TBS-T.

Phosphorylated ERK is detected with a mouse monoclonal anti-diphosphorylated ERK1/2 antibody (from Sigma, #M8159). After washing steps with 0.1% Tween 20 in PBS the bound first antibody is detected by the second antibody (peroxidase coupled polyclonal rabbit anti mouse IgG from DAKO #P0161). After further washing steps, the substrate (TMB Peroxidase Substrate Solution from Bender MedSystems #BMS406) is added. The colour reaction is stopped after a few minutes with 1 M phosphoric acid. The colour is measured with a Spectra max Plus reader from Molecular Devices at 450 nm. $EC_{50}$ values are calculated using a software program (GraphPadPrizm).

The substances of the present invention are B-RAF-kinase inhibitors. As can be demonstrated by DNA staining followed by FACS or Cellomics Array Scan analysis, the inhibition of proliferation achieved by means of the compounds according to the invention is brought about above all by preventing entry into the DNA synthesis phase. The treated cells arrest in the G1 phase of the cell cycle.

Accordingly, the compounds according to the invention are also tested on other tumour cells. For example these compounds are effective on the colon carcinoma line, e.g. Colo205, and may be used in this and other indications. This demonstrates the usefulness of the compounds according to the invention for the treatment of different types of tumours.

On the basis of their biological properties the compounds of general formula (1) according to the invention, their tautomers, racemates, enantiomers, diastereomers, mixtures thereof and the salts of all the above-mentioned forms are suitable for treating diseases characterised by excessive or abnormal cell proliferation.

Such diseases include for example: viral infections (e.g. HIV and Kaposi's sarcoma); inflammatory and autoimmune diseases (e.g. colitis, arthritis, Alzheimer's disease, glomerulonephritis and wound healing); bacterial, fungal and/or parasitic infections; leukaemias, lymphomas and solid tumours (e.g. carcinomas and sarcomas), skin diseases (e.g. psoriasis); diseases based on hyperplasia which are characterised by an increase in the number of cells (e.g. fibroblasts, hepatocytes, bones and bone marrow cells, cartilage or smooth muscle cells or epithelial cells (e.g. endometrial hyperplasia)); bone diseases and cardiovascular diseases (e.g. restenosis and hypertrophy). They are also suitable for protecting proliferating cells (e.g. hair, intestinal, blood and progenitor cells) from DNA damage caused by radiation, UV treatment and/or cytostatic treatment.

For example, the following cancers may be treated with compounds according to the invention, without being restricted thereto: brain tumours such as for example acoustic neurinoma, astrocytomas such as pilocytic astrocytomas, fibrillary astrocytoma, protoplasmic astrocytoma, gemistocytary astrocytoma, anaplastic astrocytoma and glioblastoma, brain lymphomas, brain metastases, hypophyseal tumour such as prolactinoma, HGH (human growth hormone) producing tumour and ACTH producing tumour (adrenocorticotropic hormone), craniopharyngiomas, medulloblastomas, meningeomas and oligodendrogliomas; nerve tumours (neoplasms) such as for example tumours of the vegetative nervous system such as neuroblastoma sympathicum, ganglioneuroma, paraganglioma (pheochromocytoma, chromaffinoma) and glomus-caroticum tumour, tumours on the peripheral nervous system such as amputation neuroma, neurofibroma, neurinoma (neurilemmoma, Schwannoma) and malignant Schwannoma, as well as tumours of the central nervous system such as brain and bone marrow tumours; intestinal cancer such as for example carcinoma of the rectum, colon, anus, small intestine and duodenum; eyelid tumours such as basalioma or basal cell carcinoma; pancreatic cancer or carcinoma of the pancreas; bladder cancer or carcinoma of the bladder; lung cancer (bronchial carcinoma) such as for example small-cell bronchial carcinomas (oat cell carcinomas) and non-small cell bronchial carcinomas such as plate epithelial carcinomas, adenocarcinomas and large-cell bronchial carcinomas; breast cancer such as for example mammary carcinoma such as infiltrating ductal carcinoma, colloid carcinoma, lobular invasive carcinoma, tubular carcinoma, adenocystic carcinoma and papillary carcinoma; non-Hodgkin's lymphomas (NHL) such as for example Burkitt's lymphoma, low-malignancy non-Hodgkin's lymphomas (NHL) and mucosis fungoides; uterine cancer or endometrial carcinoma or corpus carcinoma; CUP syndrome (Cancer of Unknown Primary); ovarian cancer or ovarian carcinoma such as mucinous, endometrial or serous cancer; gall bladder cancer; bile duct cancer such as for example Klatskin tumour; testicular cancer such as for example seminomas and non-seminomas; lymphoma (lymphosarcoma) such as for example malignant lymphoma, Hodgkin's disease, non-Hodgkin's lymphomas (NHL) such as chronic lymphatic leukaemia, leukaemic reticuloendotheliosis, immunocytoma, plasmocytoma (multiple myeloma), immunoblastoma, Burkitt's lymphoma, T-zone mycosis fungoides, large-cell anaplastic lymphoblastoma and lymphoblastoma; laryngeal cancer such as for example tumours of the vocal cords, supraglottal, glottal and subglottal laryngeal tumours; bone cancer such as for example osteochondroma, chondroma, chondroblastoma, chondromyxoid fibroma, osteoma, osteoid osteoma, osteoblastoma, eosinophilic granuloma, giant cell tumour, chondrosarcoma, osteosarcoma, Ewing's sarcoma, reticulo-sarcoma, plasmocytoma, fibrous dysplasia, juvenile bone cysts and aneurysmatic bone cysts; head and neck tumours such as for example tumours of the lips, tongue, floor of the mouth, oral cavity, gums, palate, salivary glands, throat, nasal cavity, paranasal sinuses, larynx and middle ear; liver cancer such as for example liver cell carcinoma or hepatocellular carcinoma (HCC); leukaemias, such as for example acute leukaemias such as acute lymphatic/lymphoblastic leukaemia (ALL), acute myeloid leukaemia (AML); chronic leukaemias such as chronic lymphatic leukaemia (CLL), chronic myeloid leukaemia (CML); stomach cancer or gastric carcinoma such as for example papillary, tubular and mucinous adenocarcinoma, signet ring cell carcinoma, adenosquamous carcinoma, small-cell carcinoma and undifferentiated carcinoma; melanomas such as for example superficially spreading, nodular, lentigo-maligna and acral-lentiginous melanoma; renal cancer such as for example kidney cell carcinoma or hypernephroma or Grawitz's tumour; oesophageal cancer or carcinoma of the esophagus; penile cancer; prostate cancer; throat cancer or carcinomas of the pharynx such as for example nasopharynx carcinomas, oropharynx carcinomas and hypopharynx carcinomas; retinoblastoma such as for example vaginal cancer or vaginal carcinoma; plate epithelial carcinomas, adenocarcinomas, in situ carcinomas, malignant melanomas and sarcomas; thyroid carcinomas such as for example papillary, follicular and medullary thyroid carcinoma, as well as anaplastic carcinomas; spinalioma, epidormoid carcinoma and plate epithelial carcinoma of the skin; thymomas, cancer of the urethra and cancer of the vulva.

The new compounds may be used for the prevention, short-term or long-term treatment of the above-mentioned diseases, optionally also in combination with radiotherapy or other "state-of-the-art" compounds, such as e.g. cytostatic or cytotoxic substances, cell proliferation inhibitors, anti-angiogenic substances, steroids or antibodies.

The compounds of general formula (1) may be used on their own or in combination with other active substances according to the invention, optionally also in combination with other pharmacologically active substances.

Chemotherapeutic agents which may be administered in combination with the compounds according to the invention, include, without being restricted thereto, hormones, hormone analogues and antihormones (e.g. tamoxifen, toremifene, raloxifene, fulvestrant, megestrol acetate, flutamide, nilutamide, bicalutamide, aminoglutethimide, cyproterone acetate, finasteride, buserelin acetate, fludrocortisone, fluoxymesterone, medroxyprogesterone, octreotide), aromatase inhibitors (e.g. anastrozole, letrozole, liarozole, vorozole, exemestane, atamestane), LHRH agonists and antagonists (e.g. goserelin acetate, luprolide), inhibitors of growth factors (growth factors such as for example "platelet derived growth factor" and "hepatocyte growth factor", inhibitors are for example "growth factor" antibodies, "growth factor receptor" antibodies and tyrosinekinase inhibitors, such as for example cetuximab, gefitinib, imatinib, lapatinib and trastuzumab); antimetabolites (e.g. antifolates such as methotrexate, raltitrexed, pyrimidine analogues such as 5-fluorouracil, capecitabin and gemcitabin, purine and adenosine analogues such as mercaptopurine, thioguanine, cladribine and pentostatin, cytarabine, fludarabine); antitumour antibiotics (e.g. anthracyclins such as doxorubicin, daunorubicin, epirubicin and idarubicin, mitomycin-C, bleomycin, dactinomycin, plicamycin, streptozocin); platinum derivatives (e.g. Cisplatin, oxaliplatin, carboplatin); alkylation agents (e.g. Estramustin, meclorethamine, melphalan, chlorambucil, busulphan, dacarbazin, cyclophosphamide, ifosfamide, temozolomide, nitrosoureas such as for example carmustin and lomustin, thiotepa); antimitotic agents (e.g. Vinca alkaloids such as for example vinblastine, vindesin, vinorelbin and vincristine; and taxanes such as paclitaxel, docetaxel); topoisomerase inhibitors (e.g. epipodophyllotoxins such as for example etoposide and etopophos, teniposide, amsacrin, topotecan, irinotecan, mitoxantron) and various chemotherapeutic agents such as amifostin, anagrelid, clodronat, filgrastin, interferon alpha, leucovorin, rituximab, procarbazine, levamisole, mesna, mitotane, pamidronate and porfimer.

Suitable preparations include for example tablets, capsules, suppositories, solutions—particularly solutions for injection (s.c., i.v., i.m.) and infusion—elixirs, emulsions or dispersible powders. The content of the pharmaceutically active compound(s) should be in the range from 0.1 to 90 wt.-%, preferably 0.5 to 50 wt.-% of the composition as a whole, i.e. in amounts which are sufficient to achieve the dosage range specified below. The doses specified may, if necessary, be given several times a day.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. with the addition of isotonic agents, preservatives such as p-hydroxybenzoates, or stabilisers such as alkali metal salts of ethylenediamine tetraacetic acid, optionally using emulsifiers and/or dispersants, whilst if water is used as the diluent, for example, organic solvents may optionally be used as solvating agents or dissolving aids, and transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose) emulsifiers (e.g. lignin, spent sulphite liquors, methylcellulose, starch and polyvinylpyrrolidone) and lubricants (e.g. magnesium stearate, talc, stearic acid and sodium lauryl sulphate).

The preparations are administered by the usual methods, preferably by oral or transdermal route, most preferably by oral route. For oral administration the tablets may, of course contain, apart from the abovementioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

For parenteral use, solutions of the active substances with suitable liquid carriers may be used.

The dosage for intravenous use is from 1-1000 mg per hour, preferably between 5 and 500 mg per hour.

However, it may sometimes be necessary to depart from the amounts specified, depending on the body weight, the route of administration, the individual response to the drug, the nature of its formulation and the time or interval over which the drug is administered. Thus, in some cases it may be sufficient to use less than the minimum dose given above, whereas in other cases the upper limit may have to be exceeded. When administering large amounts it may be advisable to divide them up into a number of smaller doses spread over the day.

The formulation examples which follow illustrate the present invention without restricting its scope:
Examples of Pharmaceutical Formulations
A)

| Tablets | per tablet |
|---|---|
| active substance according to formula (1) | 100 mg |
| lactose | 140 mg |
| corn starch | 240 mg |

305
-continued

| Tablets | per tablet |
|---|---|
| polyvinylpyrrolidone | 15 mg |
| magnesium stearate | 5 mg |
| | 500 mg |

The finely ground active substance, lactose and some of the corn starch are mixed together.

The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

B)

| Tablets | per tablet |
|---|---|
| active substance according to formula (1) | 80 mg |
| lactose | 55 mg |
| corn starch | 190 mg |
| microcrystalline cellulose | 35 mg |
| polyvinylpyrrolidone | 15 mg |
| sodium-carboxymethyl starch | 23 mg |
| magnesium stearate | 2 mg |
| | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodiumcarboxymethyl starch and the magnesium stearate are added and mixed in and the mixture is compressed to form tablets of a suitable size.

C)

| Ampoule solution | |
|---|---|
| active substance according to formula (1) | 50 mg |
| sodium chloride | 50 mg |
| water for inj. | 5 mL |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

306

The invention claimed is:

1. A compound of formula (1)

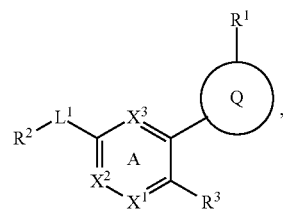

wherein
R$^1$ denotes a 5- or 6-membered monocyclic or 9 or 10-membered bicyclic heteroaryl optionally substituted by one or more identical or different R$^b$ and/or R$^c$, with the partial structure (i)

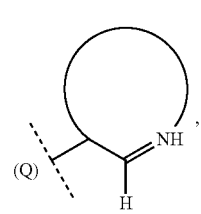

wherein the ring that binds directly to Q is heteroaromatic;

R$^2$ is a group optionally substituted by one or more identical or different R$^b$ and/or R$^c$, selected from among C$_{6-10}$aryl and 5-12 membered heteroaryl;

R$^3$ is selected from among hydrogen, —CN, —NO$_2$, —NH$_2$, —NH(C$_{1-4}$alkyl), —N(C$_{1-4}$alkyl)$_2$, C$_{1-4}$alkyl, C$_{1-4}$haloalkyl, C$_{1-4}$alkoxy, C$_{1-4}$haloalkoxy, C$_{3-5}$cycloalkyl and halogen;

X$^1$ is N;
X$^2$ is CR$^4$;
X$^3$ is CR$^4$;
wherein each R$^4$ is selected independently of one another from among hydrogen, —CN, —NO$_2$, —NH$_2$, —NH(C$_{1-4}$alkyl), —N(C$_{1-4}$alkyl)$_2$, C$_{1-4}$alkyl, C$_{1-4}$haloalkyl, C$_{1-4}$alkoxy, C$_{1-4}$haloalkoxy, C$_{3-5}$cycloalkyl and halogen;

Q is selected from among

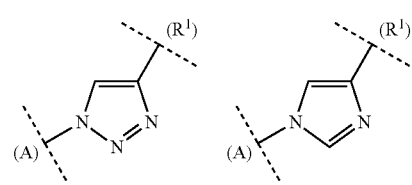

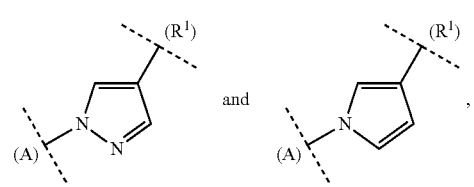

while in the five-membered ring heteroaryls described above one to three cyclic hydrogen atoms may each be substituted independently of one another by $C_{1-6}$alkyl;

$L^1$ is selected from among —C(O)NH— and —NHC(O)—;

each $R^b$ is a suitable substituent and is selected independently of one another from among —$OR^c$, —$SR^c$, —$NR^cR^c$, —$ONR^cR^c$, —$N(OR^c)R^c$, —$NR^gNR^cR^c$, halogen, —CN, —$NO_2$, —$N_3$, —$C(O)R^c$, —$C(O)OR^c$, —$C(O)NR^cR^c$, —$C(O)NR^gNR^cR^c$, —$C(O)NR^gOR^c$, —$C(NR^g)R^c$, —$N=CR^cR^c$, —$C(NR^g)OR^c$, —$C(NR^g)NR^cR^c$, —$C(NR^g)NR^gNR^cR^c$, —$C(NOR^g)R^c$, —$C(NOR^g)NR^cR^c$, —$C(NNR^gR^g)R^c$, —$OS(O)R^c$, —$OS(O)OR^c$, —$OS(O)NR^cR^c$, —$OS(O)_2R^c$, —$OS(O)_2$ $OR^c$, —$OS(O)_2NR^cR^c$, —$OC(O)R^c$, —$OC(O)OR^c$, —$OC(O)NR^cR^c$, —$OC(NR^g)R^c$, —$OC(NR^g)NR^cR^c$, —$ONR^gC(O)R^c$, —$S(O)R^c$, —$S(O)OR^c$, —$S(O)NR^c R^c$, —$S(O)_2R^c$, —$S(O)_2OR^c$, —$S(O)_2NR^cR^c$, —$NR^gC(O)R^c$, —$NR^gC(O)OR^c$, —$NR^gC(O)NR^cR^c$, —$NR^gC(O)NR^gNR^cR^c$, —$NR^gC(NR^g)R^c$, —$N=CR^cNR^cR^c$, —$NR^gC(NR^g)OR^c$, —$NR^gC(NR^g)NR^cR^c$, —$NR^gC(NOR^g)R^c$, —$NR^gS(O)R^c$, —$NR^gS(O)OR^c$, —$NR^gS(O)_2R^c$, —$NR^gS(O)_2OR^c$, —$NR^gS(O)_2NR^cR^c$, —$NR^gNR^gC(O)R^c$, —$NR^gNR^gC(O)NR^cR^c$, —$NR^gNR^gC(NR^g)R^c$ and —$N(OR^g)C(O)R^c$ and the bivalent substituents =O, =S, =$NR^g$, =$NOR^g$, =$NNR^gR^g$ and =$NNR^gC(O)NR^gR^g$, while these bivalent substituents may only be substituents in non-aromatic ring systems;

each $R^c$ independently of one another denotes hydrogen or a group optionally substituted by one or more identical or different $R^d$ and/or $R^e$, selected from among $C_{1-6}$alkyl, 2-6 membered heteroalkyl, $C_{1-6}$haloalkyl, $C_{3-10}$cycloalkyl, $C_{6-10}$aryl, 5-12 membered heteroaryl and 3-14 membered heterocycloalkyl;

each $R^d$ is a suitable substituent and is selected independently of one another from among —$OR^e$, —$SR^e$, —$NR^eR^e$, —$ONR^eR^e$, —$N(OR^e)R^e$, —$N(R^g)NR^eR^e$, halogen, —CN, —$NO_2$, —$N_3$, —$C(O)R^e$, —$C(O)OR^e$, —$C(O)NR^eR^e$, —$C(O)NR^gNR^eR^e$, —$C(O)NR^gOR^e$, —$C(NR^g)R^e$, —$N=CR^eR^e$, —$C(NR^g)OR^e$, —$C(NR^g)NR^eR^e$, —$C(NR^g)NR^gNR^eR^e$, —$C(NOR^g)R^e$, —$C(NOR^g)NR^eR^e$, —$C(NNR^gR^g)R^e$, —$OS(O)R^e$, —$OS(O)OR^e$, —$OS(O)NR^eR^e$, —$OS(O)_2R^e$, —$OS(O)_2$ $OR^e$, —$OS(O)_2NR^eR^e$, —$OC(O)R^e$, —$OC(O)OR^e$, —$OC(O)NR^eR^e$, —$OC(NR^g)R^e$, —$OC(NR^g)NR^eR^e$, —$ONR^gC(O)R^e$, —$S(O)R^e$, —$S(O)OR^e$, —$S(O)NR^e R^e$, —$S(O)_2R^e$, —$S(O)_2OR^e$, —$S(O)_2NR^eR^e$, —$NR^gC(O)R^e$, —$NR^gC(O)OR^e$, —$NR^gC(O)NR^eR^e$, —$NR^gC(O)NR^gNR^eR^e$, —$NR^gC(NR^g)R^e$, —$N=CR^eNR^eR^e$, —$NR^gC(NR^g)OR^e$, —$NR^gC(NR^g)NR^eR^e$, —$NR^gC(NR^g)SR^e$, —$NR^gC(NOR^g)R^e$, —$NR^gS(O)R^e$, —$NR^gS(O)OR^e$, —$NR^gS(O)_2R^e$, —$NR^gS(O)_2OR^e$, —$NR^gS(O)_2NR^eR^e$, —$NR^gNR^gC(O)R^e$, —$NR^gNR^gC(O)NR^eR^e$, —$NR^gNR^gC(NR^g)R^e$ and —$N(OR^g)C(O)R^e$ and the bivalent substituents =O, =S, =$NR^g$, =$NOR^g$, =$NNR^gR^g$ and =$NNR^gC(O)NR^gR^g$, while these bivalent substituents may only be substituents in non-aromatic ring systems;

each $R^e$ independently of one another denotes hydrogen or a group optionally substituted by one or more identical or different $R^f$ and/or $R^g$, selected from among $C_{1-6}$alkyl, 2-6 membered heteroalkyl, $C_{1-6}$haloalkyl, $C_{3-10}$cycloalkyl, $C_{6-10}$aryl, 5-12 membered heteroaryl and 3-14 membered heterocycloalkyl;

each $R^f$ is a suitable substituent and is selected independently of one another from among —$OR^g$, —$SR^g$, —$NR^gR^g$, —$ONR^gR^g$, —$N(OR^g)R^g$, —$N(R^h)NR^gR^g$, halogen, —CN, —$NO_2$, —$N_3$, —$C(O)R^g$, —$C(O)OR^g$, —$C(O)NR^gR^g$, —$C(O)NR^hNR^gR^g$, —$C(O)NR^hOR^g$, —$C(NR^h)R^g$, —$N=CR^gR^g$, —$C(NR^h)OR^g$, —$C(NR^h)NR^gR^g$, —$C(NR^h)NR^hNR^gR^g$, —$C(NOR^h)R^g$, —$C(NOR^h)NR^gR^g$, —$C(NNR^hR^h)R^g$, —$OS(O)R^g$, —$OS(O)OR^g$, —$OS(O)NR^gR^g$, —$OS(O)_2R^g$, —$OS(O)_2$ $OR^g$, —$OS(O)_2NR^gR^g$, —$OC(O)R^g$, —$OC(O)OR^g$, —$OC(O)NR^gR^g$, —$OC(NR^h)R^g$, —$OC(NR^h)NR^gR^g$, —$ONR^hC(O)R^g$, —$S(O)R^g$, —$S(O)OR^g$, —$S(O)NR^g R^g$, —$S(O)_2R^g$, —$S(O)_2OR^g$, —$S(O)_2NR^g R^g$, —$NR^hC(O)R^g$, —$NR^hC(O)OR^g$, —$NR^hC(O)NR^g R^g$, —$NR^hC(O)NR^hNR^gR^g$, —$NR^hC(NR^h)R^g$, —$N=CR^gNR^gR^g$, —$NR^hC(NR^h)OR^g$, —$NR^hC(NR^h)NR^gR^g$, —$NR^hC(NOR^h)R^g$, —$NR^hS(O)R^g$, —$NR^hS(O)OR^g$, —$NR^hS(O)_2R^g$, —$NR^hS(O)_2OR^g$, —$NR^hS(O)_2NR^gR^g$, —$NR^hNR^hC(O)R^g$, —$NR^hNR^hC(O)NR^gR^g$, —$NR^hNR^hC(NR^h)R^g$ and —$N(OR^h)C(O)R^g$ and the bivalent substituents =O, =S, =$NR^h$, =$NOR^h$, =$NNR^hR^h$ and =$NNR^hC(O)NR^hR^h$, while these bivalent substituents may only be substituents in non-aromatic ring systems;

each $R^g$ independently of one another denotes hydrogen or a group optionally substituted by one or more identical or different $R^h$, selected from among $C_{1-6}$alkyl, 2-6 membered heteroalkyl, $C_{1-6}$haloalkyl, $C_{3-10}$cycloalkyl, $C_{6-10}$aryl, 5-12 membered heteroaryl and 3-14 membered heterocycloalkyl;

each $R^h$ is selected independently of one another from among hydrogen, $C_{1-6}$alkyl, 2-6 membered heteroalkyl, $C_{1-6}$haloalkyl, $C_{3-10}$cycloalkyl, $C_{6-10}$aryl, 5-12 membered heteroaryl and 3-14 membered heterocycloalkyl;

while the compounds (1) may optionally also be present in the form of their tautomers, racemates, enantiomers, diastereomers and mixtures thereof, or also as pharmacologically acceptable salts of all the above-mentioned forms.

2. A compound of formula (1)

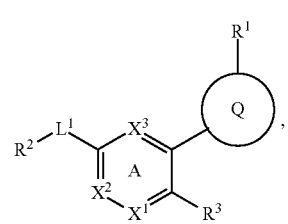

(1)

wherein
$R^1$ is a 5-10 membered heteroaryl optionally substituted by one or more identical or different $R^b$ and/or $R^c$;
$R^2$ is a group optionally substituted by one or more identical or different $R^b$ and/or $R^c$, selected from among $C_{6-10}$aryl and 5-12 membered heteroaryl;
$R^3$ is selected from among hydrogen, —CN, —$NO_2$, —$NH_2$, —$NH(C_{1-4}$alkyl), —$N(C_{1-4}$alkyl$)_2$, $C_{1-4}$alkyl, $C_{1-4}$haloalkyl, $C_{1-4}$alkoxy, $C_{1-4}$haloalkoxy, $C_{3-5}$cycloalkyl and halogen;
$X^1$ is N;
$X^2$ is $CR^4$;
$X^3$ is $CR^4$;
wherein each $R^4$ is selected independently of one another from among hydrogen, —CN, —$NO_2$, —NH$_2$, —NH(C$_{1-4}$alkyl), —N(C$_{1-4}$alkyl)$_2$, C$_{1-4}$alkyl, C$_{1-4}$haloalkyl, C$_{1-4}$alkoxy, C$_{1-4}$haloalkoxy, C$_{3-5}$cycloalkyl and halogen;

Q is a five-membered heteroaromatic group with one to three heteroatoms, selected independently of one another from among nitrogen, oxygen and sulphur, optionally substituted by a C$_{1-6}$alkyl
while the ring A and R$^1$ are arranged in a 1,3 position with one another in terms of their link to Q and the rings A and Q are linked by a carbon-carbon bond;

L$^1$ is selected from among —C(O)NH— and —NHC(O)—;

each R$^b$ is a suitable substituent and is selected independently of one another from among —OR$^c$, —SR$^c$, —NR$^c$R$^c$, —ONR$^c$R$^c$, —N(OR$^c$)R$^c$, —NR$^g$NR$^c$R$^c$, halogen, —CN, —NO$_2$, —N$_3$, —C(O)R$^c$, —C(O)OR$^c$, —C(O)NR$^c$R$^c$, —C(O)NR$^g$NR$^c$R$^c$, —C(O)NR$^g$OR$^c$, —C(NR$^g$)R$^c$, —N=CR$^c$R$^c$, —C(NR$^g$)OR$^c$, —C(NR$^g$)NR$^c$R$^c$, —C(NR$^g$)NR$^g$NR$^c$R$^c$, —C(NOR$^g$)R$^c$, —C(NOR$^g$)NR$^c$R$^c$, —C(NNR$^g$R$^g$)R$^c$, —OS(O)R$^c$, —OS(O)OR$^c$, —OS(O)NR$^c$R$^c$, —OS(O)$_2$R$^c$, —OS(O)$_2$ OR$^c$, —OS(O)$_2$NR$^c$R$^c$, —OC(O)R$^c$, —OC(O)OR$^c$, —OC(O)NR$^c$R$^c$, —OC(NR$^g$)R$^c$, —OC(NR$^g$)NR$^c$R$^c$, —ONR$^g$C(O)R$^c$, —S(O)R$^c$, —S(O)OR$^c$, —S(O)NR$^c$ R$^c$, —S(O)$_2$R$^c$, —S(O)$_2$OR$^c$, —S(O)$_2$NR$^c$R$^c$, —NR$^g$C(O)R$^c$, —NR$^g$C(O)OR$^c$, —NR$^g$C(O)NR$^c$R$^c$, —NR$^g$C(O)NR$^g$NR$^c$R$^c$, —NR$^g$C(NR$^g$)R$^c$, —N=CR$^c$NR$^c$R$^c$, —NR$^g$C(NR$^g$)OR$^c$, —NR$^g$C(NR$^g$)NR$^c$R$^c$, —NR$^g$C(NOR$^g$)R$^c$, —NR$^g$S(O)R$^c$, —NR$^g$S(O)OR$^c$, —NR$^g$S(O)$_2$R$^c$, —NR$^g$S(O)$_2$OR$^c$, —NR$^g$S(O)$_2$NR$^c$R$^c$, —NR$^g$NR$^g$C(O)R$^c$, —NR$^g$NR$^g$C(O)NR$^c$R$^c$, —NR$^g$NR$^g$C(NR$^g$)R$^c$ and —N(OR$^g$)C(O)R$^c$ and the bivalent substituents =O, =S, =NR$^g$, =NOR$^g$, =NNR$^g$R$^g$ and =NNR$^g$C(O)NR$^g$R$^g$, while these bivalent substituents may only be substituents in non-aromatic ring systems;

each R$^c$ independently of one another denotes hydrogen or a group optionally substituted by one or more identical or different R$^d$ and/or R$^e$, selected from among C$_{1-6}$alkyl, 2-6 membered heteroalkyl, C$_{1-6}$haloalkyl, C$_{3-10}$cycloalkyl, C$_{6-10}$aryl, 5-12 membered heteroaryl and 3-14 membered heterocycloalkyl;

each R$^d$ is a suitable substituent and is selected independently of one another from among —OR$^e$, —SR$^e$, —NR$^e$R$^e$, —ONR$^e$R$^e$, —N(OR$^e$)R$^e$, —N(R$^g$)NR$^e$R$^e$, halogen, —CN, —NO$_2$, —N$_3$, —C(O)R$^e$, —C(O)OR$^e$, —C(O)NR$^e$R$^e$, —C(O)NR$^g$NR$^e$R$^e$, —C(O)NR$^g$OR$^e$, —C(NR$^g$)R$^e$, —N=CR$^e$R$^e$, —C(NR$^g$)OR$^e$, —C(NR$^g$)NR$^e$R$^e$, —C(NR$^g$)NR$^g$NR$^e$R$^e$, —C(NOR$^g$)R$^e$, —C(NOR$^g$)NR$^e$R$^e$, —C(NNR$^g$R$^g$)R$^e$, —OS(O)R$^e$, —OS(O)OR$^e$, —OS(O)NR$^e$R$^e$, —OS(O)$_2$R$^e$, —OS(O)$_2$ OR$^e$, —OS(O)$_2$NR$^e$R$^e$, —OC(O)R$^e$, —OC(O)OR$^e$, —OC(O)NR$^e$R$^e$, —OC(NR$^g$)R$^e$, —OC(NR$^g$)NR$^e$R$^e$, —ONR$^g$C(O)R$^e$, —S(O)R$^e$, —S(O)OR$^e$, —S(O)NR$^e$ R$^e$, —S(O)$_2$R$^e$, —S(O)$_2$OR$^e$, —S(O)$_2$NR$^e$R$^e$, —NR$^g$C(O)R$^e$, —NR$^g$C(O)OR$^e$, —NR$^g$C(O)NR$^e$R$^e$, —NR$^g$C(O)NR$^g$NR$^e$R$^e$, —NR$^g$C(NR$^g$)R$^e$, —N=CR$^e$NR$^e$R$^e$, —NR$^g$C(NR$^g$)OR$^e$, —NR$^g$C(NR$^g$)NR$^e$R$^e$, —NR$^g$C(NR$^g$)SR$^e$, —NR$^g$C(NOR$^g$)R$^e$, —NR$^g$S(O)R$^e$, —NR$^g$S(O)OR$^e$, —NR$^g$S(O)$_2$R$^e$, —NR$^g$S(O)$_2$OR$^e$, —NR$^g$S(O)$_2$NR$^e$R$^e$, —NR$^g$NR$^g$C(O)R$^e$, —NR$^g$NR$^g$C(O)NR$^e$R$^e$, —NR$^g$NR$^g$C(NR$^g$)R$^e$ and —N(OR$^g$)C(O)R$^e$ and the bivalent substituents =O, =S, =NR$^g$, =NOR$^g$, =NNR$^g$R$^g$ and =NNR$^g$C(O)NR$^g$R$^g$, while these bivalent substituents may only be substituents in non-aromatic ring systems;

each R$^e$ independently of one another denotes hydrogen or a group optionally substituted by one or more identical or different R$^f$ and/or R$^g$, selected from among C$_{1-6}$alkyl, 2-6 membered heteroalkyl, C$_{1-6}$haloalkyl, C$_{3-10}$cycloalkyl, C$_{6-10}$aryl, 5-12 membered heteroaryl and 3-14 membered heterocycloalkyl;

each R$^f$ is a suitable substituent and is selected independently of one another from among —OR$^g$, —SR$^g$, —NR$^g$R$^g$, —ONR$^g$R$^g$, —N(OR$^g$)R$^g$, —N(R$^h$)NR$^g$R$^g$, halogen, —CN, —NO$_2$, —N$_3$, —C(O)R$^g$, —C(O)OR$^g$, —C(O)NR$^g$R$^g$, —C(O)NR$^h$NR$^g$R$^g$, —C(O)NR$^h$OR$^g$, —C(NR$^h$)R$^g$, —N=CR$^g$R$^g$, —C(NR$^h$)OR$^g$, —C(NR$^h$)NR$^g$R$^g$, —C(NR$^h$)NR$^h$NR$^g$R$^g$, —C(NOR$^h$)R$^g$, —C(NOR$^h$)NR$^g$R$^g$, —C(NNR$^h$R$^h$)R$^g$, —OS(O)R$^g$, —OS(O)OR$^g$, —OS(O)NR$^g$R$^g$, —OS(O)$_2$R$^g$, —OS(O)$_2$ OR$^g$, —OS(O)$_2$NR$^g$R$^g$, —OC(O)R$^g$, —OC(O)OR$^g$, —OC(O)NR$^g$R$^g$, —OC(NR$^h$)R$^g$, —OC(NR$^h$)NR$^g$R$^g$, —ONR$^h$C(O)R$^g$, —S(O)R$^g$, —S(O)OR$^g$, —S(O)NR$^g$ R$^g$, —S(O)$_2$R$^g$, —S(O)$_2$OR$^g$, —S(O)$_2$NR$^g$ R$^g$, —NR$^h$C(O)R$^g$, —NR$^h$C(O)OR$^g$, —NR$^h$C(O)NR$^g$ R$^g$, —NR$^h$C(O)NR$^h$NR$^g$R$^g$, —NR$^h$C(NR$^h$)R$^g$, —N=CR$^h$NR$^g$R$^g$, —NR$^h$C(NR$^h$)OR$^g$, —NR$^h$C(NR$^h$)NR$^g$R$^g$, —NR$^h$C(NOR$^h$)R$^g$, —NR$^h$S(O)R$^g$, —NR$^h$S(O)OR$^g$, —NR$^h$S(O)$_2$R$^g$, —NR$^h$S(O)$_2$OR$^g$, —NR$^h$S(O)$_2$NR$^g$R$^g$, —NR$^h$NR$^h$C(O)R$^g$, —NR$^h$NR$^h$C(O)NR$^g$R$^g$, —NR$^h$NR$^h$C(NR$^h$)R$^g$ and —N(OR$^h$)C(O)R$^g$ and the bivalent substituents =O, =S, =NR$^h$, =NOR$^h$, =NNR$^h$R$^h$ and =NNR$^h$C(O)NR$^h$R$^h$, while these bivalent substituents may only be substituents in non-aromatic ring systems;

each R$^g$ independently of one another denotes hydrogen or a group optionally substituted by one or more identical or different R$^h$, selected from among C$_{1-6}$alkyl, 2-6 membered heteroalkyl, C$_{1-6}$haloalkyl, C$_{3-10}$cycloalkyl, C$_{6-10}$aryl, 5-12 membered heteroaryl and 3-14 membered heterocycloalkyl;

each R$^h$ is selected independently of one another from among hydrogen, C$_{1-6}$alkyl, 2-6 membered heteroalkyl, C$_{1-6}$haloalkyl, C$_{3-10}$cycloalkyl, C$_{6-10}$aryl, 5-12 membered heteroaryl and 3-14 membered heterocycloalkyl;

while the compounds (1) may optionally also be present in the form of their tautomers, racemates, enantiomers, diastereomers and mixtures thereof, or also as pharmacologically acceptable salts of all the above-mentioned forms.

3. The compound according to claim 2, wherein
Q is selected from among

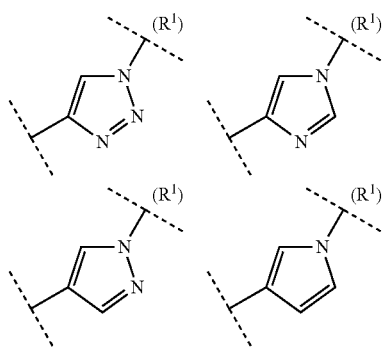

-continued

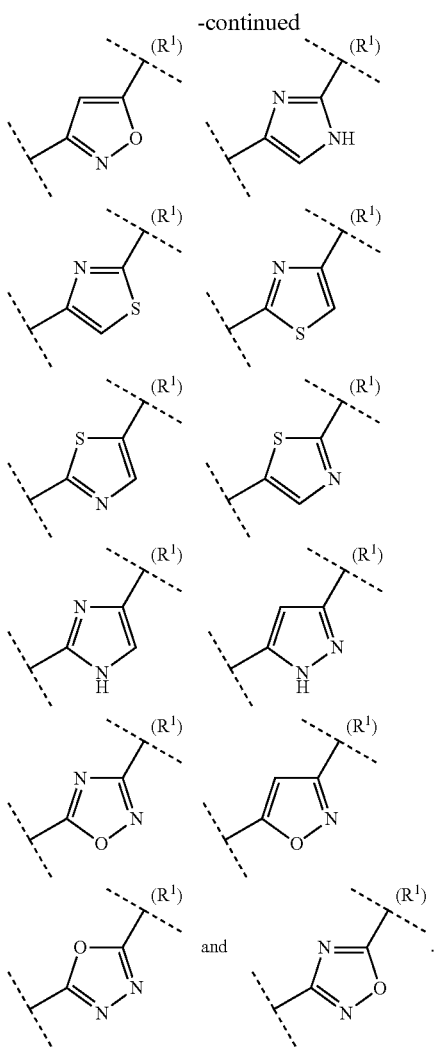

4. The compound according to claim 3, wherein
$R^1$ is a 5- or 6-membered monocyclic or 9 or 10-membered bicyclic heteroaryl optionally substituted by one or more identical or different $R^b$ and/or $R^c$ wherein
each $R^b$ is selected independently of one another from among —$OR^c$, —$SR^c$, —$NR^cR^c$, —$ONR^cR^c$, —$N(OR^c)R^c$, —$NR^gNR^cR^c$, halogen, —CN, —$NO_2$, —$N_3$, —$C(O)R^c$, —$C(O)OR^c$, —$C(O)NR^cR^c$, —$C(O)NR^gNR^cR^c$, —$C(O)NR^gOR^c$, —$C(NR^g)R^c$, —N=$CR^cR^c$, —$C(NR^g)OR^c$, —$C(NR^g)NR^cR^c$, —$C(NR^g)NR^gNR^cR^c$, —$C(NOR^c)R^c$, —$C(NOR^g)NR^cR^c$, —$C(NNR^gR^g)R^c$, —$OS(O)R^c$, —$OS(O)OR^c$, —$OS(O)NR^cR^c$, —$OS(O)_2R^c$, —$OS(O)_2OR^c$, —$OS(O)_2NR^cR^c$, —$OC(O)R^c$, —$OC(O)OR^c$, —$OC(O)NR^cR^c$, —$OC(NR^g)R^c$, —$OC(NR^g)NR^cR^c$, —$ONR^gC(O)R^c$, —$S(O)R^c$, —$S(O)OR^c$, —$S(O)NR^cR^c$, —$S(O)_2R^c$, —$S(O)_2OR^c$, —$S(O)_2NR^cR^c$, —$NR^gC(O)R^c$, —$NR^gC(O)OR^c$, —$NR^gC(O)NR^cR^c$, —$NR^gC(O)NR^gNR^cR^c$, —$NR^gC(NR^g)R^c$, —N=$CR^cNR^cR^c$, —$NR^gC(NR^g)OR^c$, —$NR^gC(NR^g)NR^cR^c$, —$NR^gC(NOR^g)R^c$, —$NR^gS(O)R^c$, —$NR^gS(O)OR^c$, —$NR^gS(O)_2R^c$, —$NR^gS(O)_2OR^c$, —$NR^gS(O)_2NR^cR^c$, —$NR^gNR^gC(O)R^c$, —$NR^gC(O)NR^cR^c$, —$NR^gNR^gC(NR^g)R^c$ and —$N(OR^c)C(O)R^c$ and the bivalent substituents =O, =S, =$NR^g$, =$NOR^g$, =$NNR^gR^g$ and =$NNR^gC(O)NR^gR^g$, while these bivalent substituents may only be substituents in non-aromatic ring systems; and
each $R^c$ independently of one another denotes hydrogen or a group optionally substituted by one or more identical or different $R^d$ and/or $R^e$, selected from among $C_{1-6}$alkyl, 2-6 membered heteroalkyl, $C_{1-6}$haloalkyl, $C_{3-10}$cycloalkyl, $C_{6-10}$aryl, 5-12 membered heteroaryl and 3-14 membered heterocycloalkyl.

5. The compound according to claim 1,
wherein $R^1$ is a heteroaryl which is substituted by one or more identical or different $R^{b2}$ and/or $R^{c2}$;
each $R^{b2}$ is a suitable substituent and is selected independently of one another from among halogen, —$OR^{c2}$, —$NR^{c2}R^{c2}$, —$SR^{c2}$, —$C(O)R^{c2}$, —$S(O)_2R^{c2}$, —$S(O)R^{c2}$, —$C(O)OR^{c2}$, —$NHC(O)R^{c2}$, —$C(O)NR^{c2}R^{c2}$, —$NHC(O)OR^{c2}$, —CN, —$NO_2$ and the bivalent substituent =O, while this bivalent substituent may only be a substituent in non-aromatic ring systems;
each $R^{c2}$ independently of one another denotes hydrogen or a group optionally substituted by one or more identical or different $R^{d2}$ and/or $R^{e2}$, selected from among $C_{1-6}$alkyl, $C_{1-6}$haloalkyl, $C_{3-10}$cycloalkyl, $C_{6-10}$aryl, 5-12 membered heteroaryl and 3-14 membered heterocycloalkyl;
each $R^{d2}$ is a suitable substituent and is selected independently of one another from among —$OR^{e2}$, —$NR^{e2}R^{e2}$, halogen and —$C(O)OR^{e2}$;
each $R^{e2}$ independently of one another denotes hydrogen or a group optionally substituted by one or more identical or different $R^{f2}$ and/or $R^{g2}$, selected from among $C_{1-6}$alkyl, $C_{1-6}$haloalkyl, $C_{3-10}$cycloalkyl, $C_{6-10}$aryl and 3-14 membered heterocycloalkyl;
each $R^{f2}$ is a suitable substituent and is selected independently of one another from among —$OR^{g2}$, —CN, —$C(O)NR^{g2}R^{g2}$ and halogen;
each $R^{g2}$ are each selected independently of one another from among hydrogen, $C_{1-6}$alkyl, —$C_{1-6}$haloalkyl, $C_{3-10}$cycloalkyl and $C_{6-10}$aryl.

6. The compound according to claim 5, wherein
$R^1$ denotes

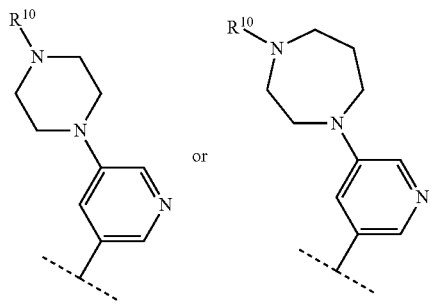

and $R^{10}$ is selected from among hydrogen, $C_{1-6}$alkyl, $C_{1-6}$haloalkyl and $C_{3-6}$cycloalkyl,
while the above-mentioned groups, wherever possible, may optionally be substituted by one or more identical or different substituents, selected from among —OH, —$OC_{1-6}$alkyl, —$C_{1-6}$haloalkyl, —$OC_{3-6}$cyloalkyl, $C_{3-6}$cyloalkyl, —CN, —$C(O)NH_2$, —$C(O)NH(C_{1-6}$alkyl) and —$C(O)N(C_{1-6}$alkyl)$_2$.

7. The compound according to claim 5, wherein R¹ denotes

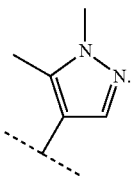

8. The compound according to claim 1, wherein
X¹ denotes N, X² denotes CR$^{4-1}$ and X³ denotes CR$^{4-2}$ and R$^{4-1}$ and R$^{4-2}$ are each selected independently of one another from among hydrogen, fluorine, chlorine and methyl and at least one of the groups R$^{4-1}$ and R$^{4-2}$ denotes hydrogen.

9. The compound according to claim 1, wherein
R² is a group optionally substituted by one or more identical or different R$^b$ and/or R$^c$, selected from among phenyl and 5-6 membered heteroaryl,
and R$^b$ and R$^c$ are defined as in claim 1.

10. The compound according to claim 9,
wherein R² is a heteroaryl which is selected from among furyl, thienyl, pyrrolyl, oxazolyl, thiazolyl, triazolyl, isoxazolyl, isothiazolyl, pyrazolyl, imidazolyl, oxadiazolyl, thiadiazolyl, pyridyl and pyrimidyl, and is optionally substituted by one or two substituents, each independently selected from among C$_{3-7}$cycloalkyl, phenyl, 4-7 membered heterocycloalkyl, methyl, ethyl, n-propyl, isopropyl, n-butyl, 1-methylpropyl, isobutyl, sec.-butyl, tert.-butyl, n-pentyl, 1-methylbutyl, 1-ethylpropyl, isopentyl, neopentyl, trifluoromethyl, difluoromethyl, fluoromethyl, ten.-butoxy, trifluoromethoxy,

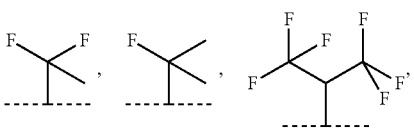

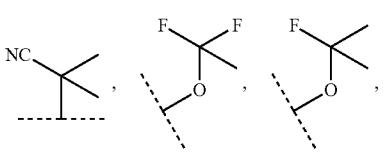

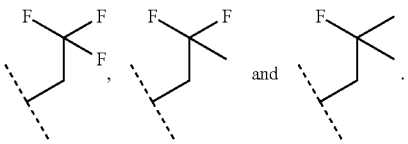

11. The compound according to claim 9, wherein R² denotes a phenyl

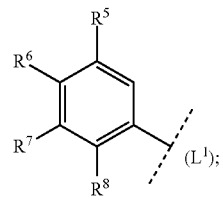

R⁵ is selected from among hydrogen, C$_{1-6}$alkyl, —OC$_{1-6}$ alkyl, C$_{1-6}$haloalkyl, —OC$_{1-6}$haloalkyl, C$_{3-7}$cycloalkyl and 3-7 membered heterocycloalkyl, all the above-mentioned groups optionally being substituted by C$_{1-6}$alkyl, —CN or —OH;

R⁶ is selected from among hydrogen, C$_{1-6}$alkyl, —OC$_{1-6}$ alkyl, C$_{1-6}$haloalkyl, —OC$_{1-6}$haloalkyl, —CN, —OH, halogen, —NHC$_{1-6}$alkyl and —N(C$_{1-6}$alkyl)$_2$, the latter two optionally being substituted in the alkyl moiety by a substituents —N(C$_{1-6}$alkyl)$_2$;

R⁷ is selected from among hydrogen, —OC$_{1-6}$alkyl, halogen, —NHS(O)$_2$C$_{1-6}$alkyl, —S(O)$_2$NH$_2$, —S(O)$_2$ NHC$_{1-6}$alkyl, —S(O)$_2$N(C$_{1-6}$alkyl)$_2$,

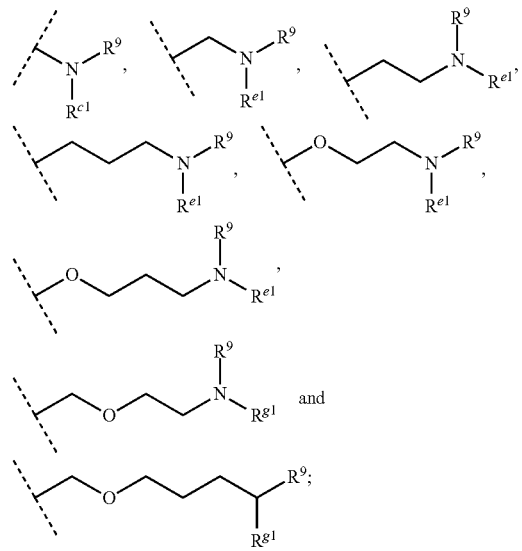

R⁹ is selected from among hydrogen and C$_{1-6}$alkyl;
R$^{c1}$ denotes hydrogen or a group optionally substituted by one or more identical or different R$^{d1}$ and/or R$^{e1}$, selected from among C$_{1-6}$alkyl and 3-14 membered heterocycloalkyl;
each R$^{d1}$ is a suitable substituent and is selected independently of one another from among —OR$^{e1}$, —NR$^{e1}$R$^{e1}$ and halogen;
each R$^{e1}$ independently of one another denotes hydrogen or a group optionally substituted by one or more identical or different R$^{f1}$ and/or R$^{g1}$, selected from among C$_{1-6}$alkyl, C$_{1-6}$haloalkyl, C$_{3-10}$cycloalkyl, C$_{6-10}$aryl, 5-12 membered heteroaryl and 3-14 membered heterocycloalkyl;
each R$^{f1}$ is a suitable substituent and is selected independently of one another from among —OR$^{g1}$, —NR$^{g1}$R$^{g1}$ and halogen and the bivalent substituent ═O, which may only be a substituent in non-aromatic ring systems;

each R$^{g1}$ independently of one another denotes hydrogen or a group optionally substituted by one or more identical or different R$^{h1}$, selected from among C$_{1-6}$alkyl, C$_{3-10}$cycloalkyl, 5-12 membered heteroaryl and 3-14 membered heterocycloalkyl;

each R$^{h1}$ is C$_{1-6}$alkyl;

or the group —NR$^9$R$^{c1}$ denotes a nitrogen-containing, 3-14 membered heterocycloalkyl or 5-12 membered heteroaryl, optionally substituted by one or more identical or different group(s) selected from among R$^{d1}$ and R$^{e1}$;

the group —NR$^9$R$^{e1}$ denotes a nitrogen-containing, 3-14 membered heterocycloalkyl or 5-12 membered heteroaryl, optionally substituted by one or more identical or different group(s) selected from among R$^{f1}$ and R$^{g1}$;

the group —NR$^9$R$^{g1}$ denotes a nitrogen-containing, 3-14 membered heterocycloalkyl or 5-12 membered heteroaryl, optionally substituted by one or more identical or different group(s) R$^{h1}$;

R$^8$ is selected from among hydrogen, C$_{1-6}$alkyl, —OC$_{1-6}$ alkyl, —CN, halogen, 5-12 membered heteroaryl and 3-14 membered heterocycloalkyl.

12. The compound according to claim 11, wherein R$^5$ is selected from among

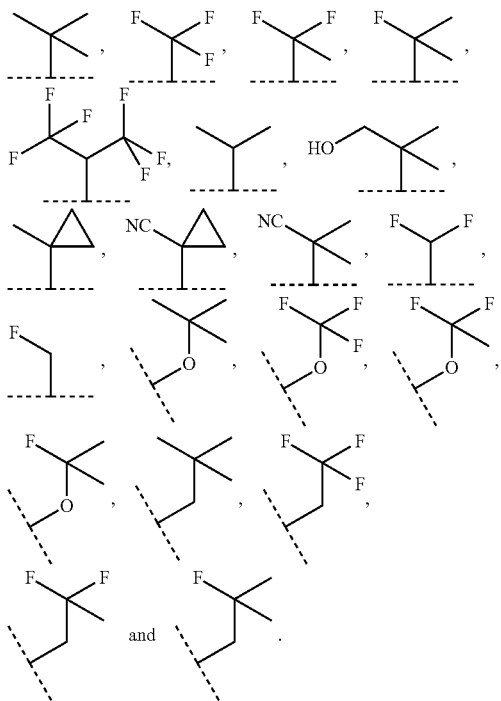

13. The compound according to claim 1 selected from among

I-1 N-(5-tert-butyl-isoxazol-3-yl)-5-[4-(1,5-dimethyl-1H-pyrazol-4-yl)-1,2,3-triazol-1-y]-6-methyl-nicotinamide;

I-2 5-[4-(1,5-dimethyl-1H-pyrazol-4-yl)-1,2,3-triazol-1-yl]-6-methyl-N-(4-trifluoromethyl-pyridin-2-yl)-nicotinamide;

I-3 5-[4-(1,5-dimethyl-1H-pyrazol-4-yl)-1,2,3-triazol-1-yl]-6-methyl-N-[3-(4-methyl-piperazin-1-yl)-5-trifluoromethyl-phenyl]-nicotinamide;

I-4 N-(5-tert-butyl-2-methyl-2H-pyrazol-3-yl)-5-[4-(1,5-dimethyl-1H-pyrazol-4-yl)-1,2,3-triazol-1-yl]-6-methyl-nicotinamide;

I-5 N-(5-tert-butyl-2H-pyrazol-3-yl)-5-[4-(1,5-dimethyl-1H-pyrazol-4-yl)-1,2,3-triazol-1-yl]-6-methyl-nicotinamide;

I-6 5-[4-(1,5-dimethyl-1H-pyrazol-4-yl)-1,2,3-triazol-1-yl]-6-methyl-N-[4-methyl-3-(4-methyl-piperazin-1-yl)-5-trifluoromethyl-phenyl]-nicotinamide;

I-7 5-[4-(1,5-dimethyl-1H-pyrazol-4-yl)-1,2,3-triazol-1-yl]-N-(4-methoxy-3-trifluoromethyl-phenyl)-6-methyl-nicotinamide;

I-8 5-[4-(1,5-dimethyl-1H-pyrazol-4-yl)-1,2,3-triazol-1-yl]-6-methyl-N-(2-methyl-5-trifluoromethyl-phenyl)-nicotinamide;

I-9 N-(5-tert-butyl-3-methanesulphonylamino-2-methoxy-phenyl)-5-[4-(1,5-dimethyl-1H-pyrazol-4-yl)-1,2,3-triazol-1-yl]-6-methyl-nicotinamide;

I-10 5-[4-(1,5-dimethyl-1H-pyrazol-4-yl)-1,2,3-triazol-1-yl]-N-[4-fluoro-3-(4-methyl-piperazin-1-yl)-5-trifluoromethyl-phenyl]-6-methyl-nicotinamide;

I-11 5-[4-(1,5-dimethyl-1H-pyrazol-4-yl)-1,2,3-triazol-1-yl]-N-(3-fluoro-5-trifluoromethyl-phenyl)-6-methyl-nicotinamide;

I-12 5-[4-(1,5-dimethyl-1H-pyrazol-4-yl)-1,2,3-triazol-1-yl]-6-methyl-N-(3-pyrrolidin-1-ylmethyl-5-trifluoromethyl-phenyl)-nicotinamide;

I-13 5-[4-(1,5-dimethyl-1H-pyrazol-4-yl)-1,2,3-triazol-1-yl]-N-[3-(isopropylamino-methyl)-2-methoxy-5-trifluoromethyl-phenyl]-6-methyl-nicotinamide;

I-14 5-[4-(2-acetylamino-thiazol-5-yl)-1,2,3-triazol-1-yl]-6-methyl-N-(4-trifluoromethyl-pyridin-2-yl)-nicotinamide;

I-15 5-[4-(2-acetylamino-thiazol-5-yl)-1,2,3-triazol-1-yl]-6-methyl-N-(3-pyrrolidin-1-ylmethyl-5-trifluoromethyl-phenyl)-nicotinamide;

I-16 5-[4-(2-acetylamino-thiazol-5-yl)-1,2,3-triazol-1-yl]-6-methyl-N-[3-(4-methyl-piperazin-1-yl)-5-trifluoromethyl-phenyl]-nicotinamide;

I-17 5-[4-(2-acetylamino-thiazol-5-yl)-1,2,3-triazol-1-yl]-N-(5-tert-butyl-isoxazol-3-yl)-6-methyl-nicotinamide;

I-18 6-methyl-N-[3-(4-methyl-piperazin-1-yl)-5-trifluoromethyl-phenyl]-5-(4-pyrimidin-5-yl-1,2,3-triazol-1-yl)-nicotinamide;

I-19 N-[4-fluoro-3-(4-methyl-piperazin-1-yl)-5-trifluoromethyl-phenyl]-6-methyl-5-(4-pyrimidin-5-yl-1,2,3-triazol-1-yl)-nicotinamide;

I-20 N-[3-(4-ethyl-piperazin-1-yl)-4-methyl-5-trifluoromethyl-phenyl]-6-methyl-5-(4-pyrimidin-5-yl-1,2,3-triazol-1-yl)-nicotinamide;

I-21 N-(5-tert-butyl-isoxazol-3-yl)-6-methyl-5-(4-pyrimidin-5-yl-1,2,3-triazol-1-yl)-nicotinamide;

I-22 N-(5-tert-butyl-2-methyl-2H-pyrazol-3-yl)-6-methyl-5-(4-pyrimidin-5-yl-1,2,3-triazol-1-yl)-nicotinamide;

I-23 6-methyl-5-(4-pyrimidin-5-yl-1,2,3-triazol-1-yl)-N-(4-trifluoromethyl-pyridin-2-yl)-nicotinamide;

I-24 5-[4-(5-methoxy-pyridin-3-yl)-1,2,3-triazol-1-yl]-6-methyl-N-[3-(4-methyl-piperazin-1-yl)-5-trifluoromethyl-phenyl]-nicotinamide;

I-25 N-[4-fluoro-3-(4-methyl-piperazin-1-yl)-5-trifluoromethyl-phenyl]-5-[4-(5-methoxy-pyridin-3-yl)-1,2,3-triazol-1-yl]-6-methyl-nicotinamide;

I-26 N-[3-(4-ethyl-piperazin-1-yl)-4-methyl-5-trifluoromethyl-phenyl]-5-[4-(5-methoxy-pyridin-3-yl)-1,2,3-triazol-1-yl]-6-methyl-nicotinamide;

I-27 N-(5-tert-butyl-isoxazol-3-yl)-5-[4-(5-methoxy-pyridin-3-yl)-1,2,3-triazol-1-yl]-6-methyl-nicotinamide;

I-28 N-(5-tert-butyl-2-methyl-2H-pyrazol-3-yl)-5-[4-(5-methoxy-pyridin-3-yl)-1,2,3-triazol-1-yl]-6-methyl-nicotinamide;

I-29 5-[4-(5-methoxy-pyridin-3-yl)-1,2,3-triazol-1-yl]-6-methyl-N-(4-trifluoromethyl-pyridin-2-yl)-nicotinamide;

I-30 N-(5-tert-butyl-2-methyl-2H-pyrazol-3-yl)-6-methyl-5-[4-(6-methyl-imidazo[1,2-a]pyrazin-3-yl)-1,2,3-triazol-1-yl]-nicotinamide;

I-31 N-(5-tert-butyl-isoxazol-3-yl)-6-methyl-5-[4-(6-methyl-imidazo[1,2-a]pyrazin-3-yl)-1,2,3-triazol-1-yl]-nicotinamide;

I-32 6-methyl-5-[4-(6-methyl-imidazo[1,2-a]pyrazin-3-yl)-1,2,3-triazol-1-yl]-N-(4-trifluoromethyl-pyridin-2-yl)-nicotinamide;

I-33 N-(4-methoxy-3-trifluoromethyl-phenyl)-6-methyl-5-[4-(6-methyl-imidazo [1,2-a]pyrazin-3-yl)-1,2,3-triazol-1-yl]-nicotinamide;

I-34 5-[4-(5-bromo-pyridin-3-yl)-1,2,3-triazol-1-yl]-N-(5-tert-butyl-isoxazol-3-yl)-6-methyl-nicotinamide;

I-35 N-(5-tert-butyl-isoxazol-3-yl)-6-methyl-5-[4-(5-morpholin-4-yl-pyridin-3-yl)-1,2,3-triazol-1-yl]-nicotinamide;

I-36 N-(5-tert-butyl-isoxazol-3-yl)-6-methyl-5-[4-(5-perhydro-1,4-oxazepin-4-yl-pyridin-3-yl)-1,2,3-triazol-1-yl]-nicotinamide;

I-37 N-(5-tert-butyl-isoxazol-3-yl)-6-methyl-5-{4-[5-(tetrahydro-furan-3-ylamino)-pyridin-3-yl]-1,2,3-triazol-1-yl}-nicotinamide;

I-38 N-(5-tert-butyl-isoxazol-3-yl)-6-methyl-5-(4-{5-[methyl-(tetrahydro-furan-3-yl)-amino]-pyridin-3-yl}-1,2,3-triazol-1-yl)-nicotinamide;

I-39 N-(5-tert-butyl-isoxazol-3-yl)-6-methyl-5-{4-[5-(4-methyl-piperazin-1-yl)-pyridin-3-yl]-1,2,3-triazol-1-yl}-nicotinamide;

I-40 N-(5-tert-butyl-isoxazol-3-yl)-6-methyl-5-{4-[5-(tetrahydro-pyran-4-ylamino)-pyridin-3-yl]-1,2,3-triazol-1-yl}-nicotinamide;

I-41 N-(5-tert-butyl-isoxazol-3-yl)-5-{4-[5-(2-methoxy-ethylamino)-pyridin-3-yl]-1,2,3-triazol-1-yl}-6-methyl-nicotinamide;

I-42 N-(3-tert-butyl-isoxazol-5-yl)-5-[4-(1,5-dimethyl-1H-pyrazol-4-yl)-1,2,3-triazol-1-yl]-6-methyl-nicotinamide;

I-43 N-[3-(4-ethyl-piperazin-1-yl)-4-methyl-5-trifluoromethyl-phenyl]-6-methyl-5-(4-thiazol-5-yl-1,2,3-triazol-1-yl)-nicotinamide;

I-44 6-methyl-5-[4-(6-methyl-imidazo[1,2-a]pyrazin-3-yl)-1,2,3-triazol-1-yl]-N-[4-methyl-3-(4-methyl-piperazin-1-yl)-5-trifluoromethyl-phenyl]-nicotinamide;

I-45 6-methyl-5-[4-(6-methyl-imidazo[1,2-a]pyrazin-3-yl)-1,2,3-triazol-1-yl]-N-[3-(4-methyl-piperazin-1-yl)-5-trifluoromethyl-phenyl]-nicotinamide;

I-46 N-[3-(4-ethyl-piperazin-1-yl)-4-methyl-5-trifluoromethyl-phenyl]-6-methyl-5-(4-pyridin-3-yl-1,2,3-triazol-1-yl)-nicotinamide;

I-47 5-[4-(6-acetylamino-pyridin-3-yl)-1,2,3-triazol-1-yl]-N-[3-(4-ethyl-piperazin-1-yl)-4-methyl-5-trifluoromethyl-phenyl]-6-methyl-nicotinamide;

I-48 5-[4-(2-acetylamino-thiazol-5-yl)-1,2,3-triazol-1-yl]-N-[3-(4-ethyl-piperazin-1-yl)-4-methyl-5-trifluoromethyl-phenyl]-6-methyl-nicotinamide;

I-49 5-[4-(5-cyano-pyridin-3-yl)-1,2,3-triazol-1-yl]-N-[3-(4-ethyl-piperazin-1-yl)-4-methyl-5-trifluoromethyl-phenyl]-6-methyl-nicotinamide;

I-50 N-[3-(isopropylamino-methyl)-4-methoxy-5-trifluoromethyl-phenyl]-6-methyl-5-[4-(6-methyl-imidazo[1,2-a]pyrazin-3-yl)-1,2,3-triazol-1-yl]-nicotinamide;

I-51 6-methyl-N-[3-(4-methyl-piperazin-1-yl)-5-trifluoromethoxy-phenyl]-5-(4-thiazol-5-yl-1,2,3-triazol-1-yl)-nicotinamide;

I-52 N-(4-chloro-3-dimethylaminomethyl-5-trifluoromethyl-phenyl)-5-[4-(1,5-dimethyl-1H-pyrazol-4-yl)-1,2,3-triazol-1-yl]-6-methyl-nicotinamide;

I-53 N-(4-chloro-3-pyrrolidin-1-ylmethyl-5-trifluoromethyl-phenyl)-5-[4-(1,5-dimethyl-1H-pyrazol-4-yl)-1,2,3-triazol-1-yl]-6-methyl-nicotinamide;

I-54 N-[4-chloro-3-(isopropylamino-methyl)-5-trifluoromethyl-phenyl]-5-[4-(1,5-dimethyl-1H-pyrazol-4-yl)-1,2,3-triazol-1-yl]-6-methyl-nicotinamide;

I-55 N-[4-chloro-3-(isobutylamino-methyl)-5-trifluoromethyl-phenyl]-5-[4-(1,5-dimethyl-1H-pyrazol-4-yl)-1,2,3-triazol-1-yl]-6-methyl-nicotinamide;

I-56 N-(3-bromo-4-methyl-5-trifluoromethyl-phenyl)-5-[4-(1,5-dimethyl-1H-pyrazol-4-yl)-1,2,3-triazol-1-yl]-6-methyl-nicotinamide;

I-57 5-[4-(1,5-dimethyl-1H-pyrazol-4-yl)-1,2,3-triazol-1-yl]-N-[3-(4-ethyl-piperazin-1-yl)-4-methyl-5-trifluoromethyl-phenyl]-6-methyl-nicotinamide;

I-58 5-[4-(1,5-dimethyl-1H-pyrazol-4-yl)-1,2,3-triazol-1-yl]-N-[3-(4-isopropyl-piperazin-1-yl)-5-trifluoromethyl-phenyl]-6-methyl-nicotinamide;

I-59 5-[4-(1,5-dimethyl-1H-pyrazol-4-yl)-1,2,3-triazol-1-yl]-N-[3-(4-ethyl-piperazin-1-yl)-5-trifluoromethyl-phenyl]-6-methyl-nicotinamide;

I-60 N-{3-[(2-dimethylamino-ethyl)-methyl-amino]-5-trifluoromethyl-phenyl}-5-[4-(1,5-dimethyl-1H-pyrazol-4-yl)-1,2,3-triazol-1-yl]-6-methyl-nicotinamide;

I-61 5-[4-(1,5-dimethyl-1H-pyrazol-4-yl)-1,2,3-triazol-1-yl]-6-methyl-N-(4-methyl-3-morpholin-4-yl-5-trifluoromethyl-phenyl)-nicotinamide;

I-62 N-(3-bromo-5-trifluoromethyl-phenyl)-5-[4-(1,5-dimethyl-1H-pyrazol-4-yl)-1,2,3-triazol-1-yl]-6-methyl-nicotinamide;

I-63 N-[3-((S)-3-dimethylamino-pyrrolidin-1-yl)-4-methyl-5-trifluoromethyl-phenyl]-5-[4-(1,5-dimethyl-1H-pyrazol-4-yl)-1,2,3-triazol-1-yl]-6-methyl-nicotinamide;

I-64 N-(4-methoxy-3-trifluoromethyl-phenyl)-6-methyl-5-(4-pyrimidin-5-yl-1,2,3-triazol-1-yl)-nicotinamide;

I-65 N-[3-((R)-3-dimethylamino-pyrrolidin-1-yl)-4-methyl-5-trifluoromethyl-phenyl]-5-[4-(1,5-dimethyl-1H-pyrazol-4-yl)-1,2,3-triazol-1-yl]-6-methyl-nicotinamide;

I-66 5-[4-(1,5-dimethyl-1H-pyrazol-4-yl)-1,2,3-triazol-1-yl]-6-methyl-N-(4-methyl-3-piperidin-1-yl-5-trifluoromethyl-phenyl)-nicotinamide;

I-67 6-methyl-N-[4-methyl-3-(4-methyl-piperazin-1-yl)-5-trifluoromethyl-phenyl]-5-(4-pyrimidin-5-yl-1,2,3-triazol-1-yl)-nicotinamide;

I-68 5-[4-(1,5-dimethyl-1H-pyrazol-4-yl)-1,2,3-triazol-1-yl]-N-(3-ethylamino-4-methyl-5-trifluoromethyl-phenyl)-6-methyl-nicotinamide;

I-69 5-[4-(1,5-dimethyl-1H-pyrazol-4-yl)-1,2,3-triazol-1-yl]-6-methyl-N-(3-morpholin-4-yl-5-trifluoromethyl-phenyl)-nicotinamide;

I-70 N-[3-(2-dimethylamino-ethylamino)-4-methyl-5-trifluoromethyl-phenyl]-5-[4-(1,5-dimethyl-1H-pyrazol-4-yl)-1,2,3-triazol-1-yl]-6-methyl-nicotinamide;

I-71 N-{3-[(2-dimethylamino-ethyl)-methyl-amino]-4-methyl-5-trifluoromethyl-phenyl}-5-[4-(1,5-dimethyl-1H-pyrazol-4-yl)-1,2,3-triazol-1-yl]-6-methyl-nicotinamide;

I-72 6-methyl-5-(4-pyrimidin-5-yl-1,2,3-triazol-1-yl)-N-(3-pyrrolidin-1-ylmethyl-5-trifluoromethyl-phenyl)-nicotinamide;

I-73 N-(3-diethylamino-5-trifluoromethyl-phenyl)-5-[4-(1,5-dimethyl-1H-pyrazol-4-yl)-1,2,3-triazol-1-yl]-6-methyl-nicotinamide;

I-74 5-[4-(1,5-dimethyl-1H-pyrazol-4-yl)-1,2,3-triazol-1-yl]-6-methyl-N-(3-piperidin-1-yl-5-trifluoromethyl-phenyl)-nicotinamide;

I-75 5-[4-(1,5-dimethyl-1H-pyrazol-4-yl)-1,2,3-triazol-1-yl]-N-(3-ethylamino-5-trifluoromethyl-phenyl)-6-methyl-nicotinamide;

I-76 N-[3-((R)-3-dimethylamino-pyrrolidin-1-yl)-5-trifluoromethyl-phenyl]-5-[4-(1,5-dimethyl-1H-pyrazol-4-yl)-1,2,3-triazol-1-yl]-6-methyl-nicotinamide;

I-77 N-[3-((S)-3-dimethylamino-pyrrolidin-1-yl)-5-trifluoromethyl-phenyl]-5-[4-(1,5-dimethyl-1H-pyrazol-4-yl)-1,2,3-triazol-1-yl]-6-methyl-nicotinamide;

I-78 N-[3-(2-dimethylamino-ethylamino)-5-trifluoromethyl-phenyl]-5-[4-(1,5-dimethyl-1H-pyrazol-4-yl)-1,2,3-triazol-1-yl]-6-methyl-nicotinamide;

I-79 6-methyl-N-[3-(4-methyl-imidazol-1-yl)-5-trifluoromethyl-phenyl]-5-(4-pyrimidin-5-yl-1,2,3-triazol-1-yl)-nicotinamide;

I-80 N-(5-tert-butyl-isoxazol-3-yl)-6-methyl-5-(4-pyridin-3-yl-1,2,3-triazol-1-yl)-nicotinamide;

I-81 6-methyl-5-(4-thiazol-5-yl-1,2,3-triazol-1-yl)-N-(4-trifluoromethyl-pyridin-2-yl)-nicotinamide;

I-82 N-(5-tert-butyl-isoxazol-3-yl)-6-methyl-5-(4-thiazol-5-yl-1,2,3-triazol-1-yl)-nicotinamide;

I-83 N-(5-tert-butyl-2H-pyrazol-3-yl)-6-methyl-5-(4-thiazol-5-yl-1,2,3-triazol-1-yl)-nicotinamide;

I-84 N-(5-tert-butyl-2H-pyrazol-3-yl)-5-[4-(5-methoxy-pyridin-3-yl)-1,2,3-triazol-1-yl]-6-methyl-nicotinamide;

I-85 5-[4-(5-methoxy-pyridin-3-yl)-1,2,3-triazol-1-yl]-6-methyl-N-[3-(4-methyl-piperazin-1-yl)-5-trifluoromethoxy-phenyl]-nicotinamide;

I-86 5-[4-(1,5-dimethyl-1H-pyrazol-4-yl)-1,2,3-triazol-1-yl]-6-methyl-N-[3-(1-methyl-piperidin-4-yl)-5-trifluoromethyl-phenyl]-nicotinamide;

I-87 5-[4-(1,5-dimethyl-1H-pyrazol-4-yl)-1,2,3-triazol-1-yl]-6-methyl-N-[3-(1-methyl-1,2,3,6-tetrahydro-pyridin-4-yl)-5-trifluoromethyl-phenyl]-nicotinamide;

I-88 5-[4-(1,5-dimethyl-1H-pyrazol-4-yl)-1,2,3-triazol-1-yl]-6-methyl-N-[3-(-1,2,3,6-tetrahydro-pyridin-4-yl)-5-trifluoromethyl-phenyl]-nicotinamide;

I-89 N-(4-methoxy-3-trifluoromethyl-phenyl)-6-methyl-5-(4-thiazol-5-yl-1,2,3-triazol-1-yl)-nicotinamide;

I-90 N-(4-chloro-3-pyrrolidin-1-ylmethyl-5-trifluoromethyl-phenyl)-5-[-4-(5-methoxy-pyridin-3-yl)-1,2,3-triazol-1-yl]-6-methyl-nicotinamide;

I-91 5-[4-(5-methoxy-pyridin-3-yl)-1,2,3-triazol-1-yl]-6-methyl-N-(3-pyrrolidin-1-ylmethyl-5-trifluoromethyl-phenyl)-nicotinamide;

I-92 5-[4-(5-methoxy-pyridin-3-yl)-1,2,3-triazol-1-yl]-N-(4-methoxy-3-trifluoromethyl-phenyl)-6-methyl-nicotinamide;

I-93 N-(3-dimethylaminomethyl-4-methyl-5-trifluoromethyl-phenyl)-5-[4-(1,5-dimethyl-1H-pyrazol-4-yl)-1,2,3-triazol-1-yl]-6-methyl-nicotinamide;

I-94 5-[4-(1,5-dimethyl-1H-pyrazol-4-yl)-1,2,3-triazol-1-yl]-N-(3-{[(2-methoxy-ethyl)-methyl-amino]-methyl}-4-methyl-5-trifluoromethyl-phenyl)-6-methyl-nicotinamide;

I-95 5-[4-(1,5-dimethyl-1H-pyrazol-4-yl)-1,2,3-triazol-1-yl]-N-[3-(isobutylamino-methyl)-4-methoxy-5-trifluoromethyl-phenyl]-6-methyl-nicotinamide;

I-96 5-[4-(1,5-dimethyl-1H-pyrazol-4-yl)-1,2,3-triazol-1-yl]-N-(4-methoxy-3-{[(2-methoxy-ethyl)-methyl-amino]-methyl}-5-trifluoromethyl-phenyl)-6-methyl-nicotinamide;

I-97 5-[4-(1,5-dimethyl-1H-pyrazol-4-yl)-1,2,3-triazol-1-yl]-N-[3-(1-ethyl--1,2,3,6-tetrahydro-pyridin-4-yl)-4-methyl-5-trifluoromethyl-phenyl]-6-methyl-nicotinamide;

I-98 N-[3-(1-cyclopropylmethyl--1,2,3,6-tetrahydro-pyridin-4-yl)-4-methyl-5-trifluoromethyl-phenyl]-5-[4-(1,5-dimethyl-1H-pyrazol-4-yl)-1,2,3-triazol-1-yl]-6-methyl-nicotinamide;

I-99 N-[3-(1-sec-butyl--1,2,3,6-tetrahydro-pyridin-4-yl)-4-methyl-5-trifluoromethyl-phenyl]-5-[4-(1,5-dimethyl-1H-pyrazol-4-yl)-1,2,3-triazol-1-yl]-6-methyl-nicotinamide;

I-100 N-(3-bromo-2-methyl-5-trifluoromethyl-phenyl)-5-[4-(1,5-dimethyl-1H-pyrazol-4-yl)-1,2,3-triazol-1-yl]-6-methyl-nicotinamide;

I-101 5-[4-(1,5-dimethyl-1H-pyrazol-4-yl)-1,2,3-triazol-1-yl]-6-methyl-N-[2-methyl-3-(4-methyl-piperazin-1-yl)-5-trifluoromethyl-phenyl]-nicotinamide;

I-102 N-(3-dimethylaminomethyl-2-methoxy-5-trifluoromethyl-phenyl)-5-[4-(1,5-dimethyl-1H-pyrazol-4-yl)-1,2,3-triazol-1-yl]-6-methyl-nicotinamide;

I-103 5-[4-(1,5-dimethyl-1H-pyrazol-4-yl)-1,2,3-triazol-1-yl]-N-[3-(isopropylamino-methyl)-4-methoxy-5-trifluoromethyl-phenyl]-6-methyl-nicotinamide;

I-104 5-[4-(1,5-dimethyl-1H-pyrazol-4-yl)-1,2,3-triazol-1-yl]-N-(2-methoxy-3-pyrrolidin-1-ylmethyl-5-trifluoromethyl-phenyl)-6-methyl-nicotinamide;

I-105 5-[4-(1,5-dimethyl-1H-pyrazol-4-yl)-1,2,3-triazol-1-yl]-N-[3-(isobutylamino-methyl)-2-methoxy-5-trifluoromethyl-phenyl]-6-methyl-nicotinamide;

I-106 N-(3-dimethylaminomethyl-5-trifluoromethyl-phenyl)-5-[4-(1,5-dimethyl-1H-pyrazol-4-yl)-1,2,3-triazol-1-yl]-6-methyl-nicotinamide;

I-107 5-[4-(1,5-dimethyl-1H-pyrazol-4-yl)-1,2,3-triazol-1-yl]-N-[3-(isopropylamino-methyl)-5-trifluoromethyl-phenyl]-6-methyl-nicotinamide;

I-108 5-[4-(1,5-dimethyl-1H-pyrazol-4-yl)-1,2,3-triazol-1-yl]-N-[3-(isobutylamino-methyl)-5-trifluoromethyl-phenyl]-6-methyl-nicotinamide;

I-109 5-[4-(1,5-dimethyl-1H-pyrazol-4-yl)-1,2,3-triazol-1-yl]-N-(3-{[(2-methoxy-ethyl)-methyl-amino]-methyl}-5-trifluoromethyl-phenyl)-6-methyl-nicotinamide;

I-110 5-[4-(1,5-dimethyl-1H-pyrazol-4-yl)-1,2,3-triazol-1-yl]-6-methyl-N-(3-methylaminomethyl-5-trifluoromethyl-phenyl)-nicotinamide;

I-111 N-(3-cyclopropylaminomethyl-5-trifluoromethyl-phenyl)-5-[4-(1,5-dimethyl-1H-pyrazol-4-yl)-1,2,3-triazol-1-yl]-6-methyl-nicotinamide;

I-112 5-[4-(1,5-dimethyl-1H-pyrazol-4-yl)-1,2,3-triazol-1-yl]-N-(2-methoxy-3-{[(2-methoxy-ethyl)-methyl-amino]-methyl}-5-trifluoromethyl-phenyl)-6-methyl-nicotinamide;

I-113 5-[4-(1,5-dimethyl-1H-pyrazol-4-yl)-1,2,3-triazol-1-yl]-N-(3-hydroxymethyl-4-methoxy-5-trifluoromethyl-phenyl)-6-methyl-nicotinamide;

I-114 5-[4-(1,5-dimethyl-1H-pyrazol-4-yl)-1,2,3-triazol-1-yl]-6-methyl-N-(2-methyl-3-piperidin-1-yl-5-trifluoromethyl-phenyl)-nicotinamide;

I-115 N-(4-chloro-3-hydroxymethyl-5-trifluoromethyl-phenyl)-5-[4-(1,5-dimethyl-1H-pyrazol-4-yl)-1,2,3-triazol-1-yl]-6-methyl-nicotinamide;

I-116 5-[4-(1,5-dimethyl-1H-pyrazol-4-yl)-1,2,3-triazol-1-yl]-N-(4-methoxy-3-pyrrolidin-1-ylmethyl-5-trifluoromethyl-phenyl)-6-methyl-nicotinamide;

I-117 N-(3-dimethylaminomethyl-4-methoxy-5-trifluoromethyl-phenyl)-5-[4-(1,5-dimethyl-1H-pyrazol-4-yl)-1,2,3-triazol-1-yl]-6-methyl-nicotinamide;

I-118 5-[4-(1,5-dimethyl-1H-pyrazol-4-yl)-1,2,3-triazol-1-yl]-6-methyl-N-(2-methyl-3-perhydro-1,4-oxazepin-4-yl-5-trifluoromethyl-phenyl)-nicotinamide;

I-119 N-{3-[(2-dimethylamino-ethyl)-methyl-amino]-2-methyl-5-trifluoromethyl-phenyl}-5-[4-(1,5-dimethyl-1H-pyrazol-4-yl)-1,2,3-triazol-1-yl]-6-methyl-nicotinamide;

I-120 5-[4-(1,5-dimethyl-1H-pyrazol-4-yl)-1,2,3-triazol-1-yl]-N-[3-(4-ethyl-piperazin-1-yl)-2-methyl-5-trifluoromethyl-phenyl]-6-methyl-nicotinamide;

I-121 5-[4-(1,5-dimethyl-1H-pyrazol-4-yl)-1,2,3-triazol-1-yl]-6-methyl-N-(2-methyl-3-pyrrolidin-1-yl-5-trifluoromethyl-phenyl)-nicotinamide;

I-122 5-[4-(1,5-dimethyl-1H-pyrazol-4-yl)-1,2,3-triazol-1-yl]-6-methyl-N-(2-methyl-3-morpholin-4-yl-5-trifluoromethyl-phenyl)-nicotinamide;

I-123 6-methyl-N-(3-pyrrolidin-1-ylmethyl-5-trifluoromethyl-phenyl)-5-(4-thiazol-5-yl-1,2,3-triazol-1-yl)-nicotinamide;

I-124 6-methyl-N-[3-(4-methyl-piperazin-1-yl)-5-trifluoromethoxy-phenyl]-5-(4-pyrimidin-5-yl-1,2,3-triazol-1-yl)-nicotinamide;

I-125 5-[4-(1,5-dimethyl-1H-pyrazol-4-yl)-1,2,3-triazol-1-yl]-6-methyl-N-[4-methyl-3-(1-methyl-1,2,3,6-tetrahydro-pyridin-4-yl)-5-trifluoromethyl-phenyl]-nicotinamide;

I-126 5-[4-(1,5-dimethyl-1H-pyrazol-4-yl)-1,2,3-triazol-1-yl]-6-methyl-N-[4-methyl-3-(1,2,3,6-tetrahydro-pyridin-4-yl)-5-trifluoromethyl-phenyl]-nicotinamide;

I-127 N-(4-chloro-3-pyrrolidin-1-ylmethyl-5-trifluoromethyl-phenyl)-6-methyl-5-(4-thiazol-5-yl-1,2,3-triazol-1-yl)-nicotinamide;

I-128 N-[4-Fluoro-3-(4-methyl-piperazin-1-yl)-5-trifluoromethyl-phenyl]-6-methyl-5-(4-thiazol-5-yl-1,2,3-triazol-1-yl)-nicotinamide;

I-129 N-(4-methoxy-3-pyrrolidin-1-ylmethyl-5-trifluoromethyl-phenyl)-6-methyl-5-[4-(6-methyl-imidazo[1,2-a]pyrazin-3-yl)-1,2,3-triazol-1-yl]-nicotinamide;

I-130 5-[4-(1,5-dimethyl-1H-pyrazol-4-yl)-1,2,3-triazol-1-yl]-6-methyl-N-(4-methyl-3-pyrrolidin-1-ylmethyl-5-trifluoromethyl-phenyl)-nicotinamide;

I-131 5-[4-(1,5-dimethyl-1H-pyrazol-4-yl)-1,2,3-triazol-1-yl]-N-[3-(isobutylamino-methyl)-4-methyl-5-trifluoromethyl-phenyl]-6-methyl-nicotinamide;

I-132 5-[4-(1,5-dimethyl-1H-pyrazol-4-yl)-1,2,3-triazol-1-yl]-N-[3-(isopropylamino-methyl)-4-methyl-5-trifluoromethyl-phenyl]-6-methyl-nicotinamide;

I-133 N-(5-tert-butyl-isoxazol-3-yl)-5-[4-(5-fluoro-pyridin-3-yl)-1,2,3-triazol-1-yl]-6-methyl-nicotinamide;

I-134 N-(5-tert-butyl-isoxazol-3-yl)-5-{4-[5-(4-ethyl-piperazin-1-yl)-pyridin-3-yl]-1,2,3-triazol-1-yl}-6-methyl-nicotinamide;

I-135 N-(5-tert-butyl-isoxazol-3-yl)-5-(4-{5-[4-(2-methoxy-ethyl)-piperazin-1-yl]-pyridin-3-yl}-1,2,3-triazol-1-yl)-6-methyl-nicotinamide;

I-136 N-(5-tert-butyl-isoxazol-3-yl)-6-methyl-5-[4-(4-morpholin-4-yl-3,4,5,6-tetrahydro-2H-[1,3]'-bipyridinyl-5'-yl)-[1,2,3]-triazol-1-yl]-nicotinamide;

I-137 N-(5-tert-butyl-isoxazol-3-yl)-5-{4-[5-(4-cyclopropylmethyl-piperazin-1-yl)-pyridin-3-yl]-1,2,3-triazol-1-yl}-6-methyl-nicotinamide;

I-138 N-(5-tert-butyl-isoxazol-3-yl)-5-{4-[5-(2-dimethylamino-ethylamino)-pyridin-3-yl]-1,2,3-triazol-1-yl}-6-methyl-nicotinamide;

I-139 N-(5-tert-butyl-isoxazol-3-yl)-6-methyl-5-[4-(3,4,5,6,3',4',5',6'-octahydro-2H,2'H-[1,4';1',3'']-terpyridin-5''-yl)-[1,2,3]-triazol-1-yl]-nicotinamide;

I-140 N-(5-tert-butyl-isoxazol-3-yl)-5-{4-[5-(4-isopropyl-piperazin-1-yl)-pyridin-3-yl]-1,2,3-triazol-1-yl}-6-methyl-nicotinamide;

I-141 N-(5-tert-butyl-isoxazol-3-yl)-5-(4-{5-[(2-dimethylamino-ethyl)-methyl-amino]-pyridin-3-yl}-1,2,3-triazol-1-yl)-6-methyl-nicotinamide;

I-142 N-(4-chloro-3-trifluoromethyl-phenyl)-6-methyl-5-{4-[5-(4-methyl-piperazin-1-yl)-pyridin-3-yl]-1,2,3-triazol-1-yl}-nicotinamide;

I-143 N-(5-tert-butyl-isoxazol-3-yl)-5-{4-[5-((R)-3-dimethylamino-pyrrolidin-1-yl)-pyridin-3-yl]-1,2,3-triazol-1-yl}-6-methyl-nicotinamide;

I-144 6-methyl-5-{4-[5-(4-methyl-piperazin-1-yl)-pyridin-3-yl]-1,2,3-triazol-1-yl}-N-(4-trifluoromethyl-pyridin-2-yl)-nicotinamide;

I-145 N-(5-tert-butyl-isoxazol-3-yl)-5-{4-[5-((S)-3-dimethylamino-pyrrolidin-1-yl)-pyridin-3-yl]-1,2,3-triazol-1-yl}-6-methyl-nicotinamide;

I-146 N-(4-methoxy-3-trifluoromethyl-phenyl)-6-methyl-5-{4-[5-(4-methyl-piperazin-1-yl)-pyridin-3-yl]-1,2,3-triazol-1-yl}-nicotinamide;

I-147 N-(3-tert-butyl-4-chloro-phenyl)-6-methyl-5-{4-[5-(4-methyl-piperazin-1-yl)-pyridin-3-yl]-1,2,3-triazol-1-yl}-nicotinamide;

I-148 N-(4-tert-butyl-thiazol-2-yl)-5-{4-[5-(4-isopropyl-piperazin-1-yl)-pyridin-3-yl]-1,2,3-triazol-1-yl}-6-methyl-nicotinamide;

I-149 5-{4-[5-(4-isopropyl-piperazin-1-yl)-pyridin-3-yl]-1,2,3-triazol-1-yl}-N-(1-isopropyl-1H-1,2,3-triazol-4-yl)-6-methyl-nicotinamide;

I-150 5-{4-[5-(4-isopropyl-piperazin-1-yl)-pyridin-3-yl]-1,2,3-triazol-1-yl}-N-(1-isopropyl-1H-pyrazol-4-yl)-6-methyl-nicotinamide;

I-151 N-(1-isopropyl-5-methyl-1H-pyrazol-4-yl)-5-{4-[5-(4-isopropyl-piperazin-1-yl)-pyridin-3-yl]-1,2,3-triazol-1-yl}-6-methyl-nicotinamide;

I-152 5-{4-[5-(4-isopropyl-piperazin-1-yl)-pyridin-3-yl]-1,2,3-triazol-1-yl}-6-methyl-N-(4-trifluoromethyl-pyridin-2-yl)-nicotinamide;

I-153 N-(5-tert-butyl-1,3,4-thiadiazol-2-yl)-5-{4-[5-(4-isopropyl-piperazin-1-yl)-pyridin-3-yl]-1,2,3-triazol-1-yl}-6-methyl-nicotinamide;

I-154 N-(3-isopropyl-isoxazol-5-yl)-5-{4-[5-(4-isopropyl-piperazin-1-yl)-pyridin-3-yl]-1,2,3-triazol-1-yl}-6-methyl-nicotinamide;

I-155 N-(6-tert-butyl-pyrimidin-4-yl)-5-{4-[5-(4-isopropyl-piperazin-1-yl)-pyridin-3-yl]-1,2,3-triazol-1-yl}-6-methyl-nicotinamide;

I-156 5-{4-[5-(4-isopropyl-piperazin-1-yl)-pyridin-3-yl]-1,2,3-triazol-1-yl}-6-methyl-N-(3-trifluoromethyl-isoxazol-5-yl)-nicotinamide;

I-157 N-[3-(1-Fluoro-1-methyl-ethyl)-isoxazol-5-yl]-5-{4-[5-(4-isopropyl-piperazin-1-yl)-pyridin-3-yl]-1,2,3-triazol-1-yl}-6-methyl-nicotinamide;

I-158 N-[3-(1,1-dimethyl-propyl)-isoxazol-5-yl]-5-{4-[5-(4-isopropyl-piperazin-1-yl)-pyridin-3-yl]-1,2,3-triazol-1-yl}-6-methyl-nicotinamide;

I-159 N-(3-tert-butyl-isoxazol-5-yl)-5-{4-[5-(4-isopropyl-piperazin-1-yl)-pyridin-3-yl]-1,2,3-triazol-1-yl}-6-methyl-nicotinamide;

I-160 N-[3-(2,2-dimethyl-propyl)-isoxazol-5-yl]-5-{4-[5-(4-isopropyl-piperazin-1-yl)-pyridin-3-yl]-1,2,3-triazol-1-yl}-6-methyl-nicotinamide;

I-161 N-(2-tert-butyl-pyridin-4-yl)-5-{4-[5-(4-isopropyl-piperazin-1-yl)-pyridin-3-yl]-1,2,3-triazol-1-yl}-6-methyl-nicotinamide;

I-162 N-(3-tert-butyl-1,2,4-thiadiazol-5-yl)-5-{4-[5-(4-isopropyl-piperazin-1-yl)-pyridin-3-yl]-1,2,3-triazol-1-yl}-6-methyl-nicotinamide;

I-163 N-(5-tert-butyl-4-methyl-4H-1,2,4-triazol-3-yl)-5-{4-[5-(4-isopropyl-piperazin-1-yl)-pyridin-3-yl]-1,2,3-triazol-1-yl}-6-methyl-nicotinamide;

I-164 N-(5-tert-butyl-isoxazol-3-yl)-6-methyl-5-{4-[5-(4-propyl-piperazin-1-yl)-pyridin-3-yl]-1,2,3-triazol-1-yl}-nicotinamide;

I-165 N-(5-tert-butyl-isoxazol-3-yl)-5-{4-[5-(4-cyclopropyl-piperazin-1-yl)-pyridin-3-yl]-1,2,3-triazol-1-yl}-6-methyl-nicotinamide;

I-166 N-(5-tert-butyl-isoxazol-3-yl)-5-{4-[5-(4-cyclopentyl-piperazin-1-yl)-pyridin-3-yl]-1,2,3-triazol-1-yl}-6-methyl-nicotinamide;

I-167 N-(5-tert-butyl-isoxazol-3-yl)-5-{4-[5-(4-tert-butyl-piperazin-1-yl)-pyridin-3-yl]-1,2,3-triazol-1-yl}-6-methyl-nicotinamide;

I-168 N-(5-tert-butyl-isoxazol-3-yl)-5-(4-{5-[(4-(3-hydroxy-propyl)-piperazin-1-yl]-pyridin-3-yl}-1,2,3-triazol-1-yl)-6-methyl-nicotinamide;

I-169 N-(5-tert-butyl-isoxazol-3-yl)-5-(4-{5-[(4-(3-methoxy-propyl)-piperazin-1-yl]-pyridin-3-yl}-1,2,3-triazol-1-yl)-6-methyl-nicotinamide;

I-170 N-(5-tert-butyl-isoxazol-3-yl)-5-(4-{5-[4-(2-ethoxy-ethyl)-piperazin-1-yl]-pyridin-3-yl}-1,2,3-triazol-1-yl)-6-methyl-nicotinamide;

I-171 N-(5-tert-butyl-isoxazol-3-yl)-5-{4-[5-(4-isobutyl-piperazin-1-yl)-pyridin-3-yl]-1,2,3-triazol-1-yl}-6-methyl-nicotinamide;

I-172 N-(5-tert-butyl-isoxazol-3-yl)-5-{4-[5-(4-butyl-piperazin-1-yl)-pyridin-3-yl]-1,2,3-triazol-1-yl}-6-methyl-nicotinamide;

I-173 N-(5-tert-butyl-isoxazol-3-yl)-5-{4-[5-(4-cyclohexylmethyl-piperazin-1-yl)-pyridin-3-yl]-1,2,3-triazol-1-yl}-6-methyl-nicotinamide;

I-174 5-{4-[5-(4-allyl-piperazin-1-yl)-pyridin-3-yl]-1,2,3-triazol-1-yl}-N-(5-tert-butyl-isoxazol-3-yl)-6-methyl-nicotinamide;

I-175 N-(5-tert-butyl-isoxazol-3-yl)-5-(4-{5-[4-(2-cyano-ethyl)-piperazin-1-yl]-pyridin-3-yl}-1,2,3-triazol-1-yl)-6-methyl-nicotinamide;

I-176 N-(5-tert-butyl-isoxazol-3-yl)-5-{4-[5-(4-dimethylcarbamoylmethyl-piperazin-1-yl)-pyridin-3-yl]-1,2,3-triazol-1-yl}-6-methyl-nicotinamide;

I-177 N-(6-tert-butyl-pyrimidin-4-yl)-6-methyl-5-{4-[5-(4-methyl-piperazin-1-yl)-pyridin-3-yl]-1,2,3-triazol-1-yl}-nicotinamide;

I-178 N-(2-tert-butyl-pyridin-4-yl)-6-methyl-5-{4-[5-(4-methyl-piperazin-1-yl)-pyridin-3-yl]-1,2,3-triazol-1-yl}-nicotinamide;

I-179 N-(5-tert-butyl-isoxazol-3-yl)-5-(4-{5-[4-(2-hydroxy-ethyl)-piperazin-1-yl]-pyridin-3-yl}-1,2,3-triazol-1-yl)-6-methyl-nicotinamide;

I-180 N-(3-tert-butyl-isoxazol-5-yl)-6-methyl-5-{4-[5-(4-methyl-piperazin-1-yl)-pyridin-3-yl]-1,2,3-triazol-1-yl}-nicotinamide;

I-181 N-(5-tert-butyl-isoxazol-3-yl)-5-(4-{5-[4-(2,2-difluoro-ethyl)-piperazin-1-yl]-pyridin-3-yl}-1,2,3-triazol-1-yl)-6-methyl-nicotinamide;

I-182 N-(5-tert-butyl-isoxazol-3-yl)-6-methyl-5-(4-{5-[4-(2,2,2-trifluoro-ethyl)-piperazin-1-yl]-pyridin-3-yl}-1,2,3-triazol-1-yl)-nicotinamide;

I-183 N-(5-tert-butyl-isoxazol-3-yl)-6-methyl-5-[4-(5-piperazin-1-yl-pyridin-3-yl)-1,2,3-triazol-1-yl]-nicotinamide;

I-184 N-(5-tert-butyl-isoxazol-3-yl)-6-methyl-5-[4-(5-morpholin-4-ylmethyl-pyridin-3-yl)-1,2,3-triazol-1-yl]-nicotinamide;

I-185 N-(5-tert-butyl-isoxazol-3-yl)-6-methyl-5-[4-(5-pyrrolidin-1-ylmethyl-pyridin-3-yl)-1,2,3-triazol-1-yl]-nicotinamide;

I-186 N-(5-tert-butyl-isoxazol-3-yl)-6-methyl-5-{4-[5-(4-methyl-piperazin-1-ylmethyl)-pyridin-3-yl]-1,2,3-triazol-1-yl}-nicotinamide;

I-187 N-(5-tert-butyl-isoxazol-3-yl)-5-[4-(5-dimethylaminomethyl-pyridin-3-yl)-1,2,3-triazol-1-yl]-6-methyl-nicotinamide;

I-188 N-(5-tert-butyl-isoxazol-3-yl)-5-{4-[5-(4-ethyl-piperazin-1-ylmethyl)-pyridin-3-yl]-1,2,3-triazol-1-yl}-6-methyl-nicotinamide;

I-189 N-(5-tert-butyl-isoxazol-3-yl)-5-{4-[5-(3,3-difluoro-pyrrolidin-1-ylmethyl)-pyridin-3-yl]-1,2,3-triazol-1-yl}-6-methyl-nicotinamide;

I-190 N-(5-tert-butyl-isoxazol-3-yl)-5-{4-[5-(4-isopropyl-piperazin-1-ylmethyl)-pyridin-3-yl]-1,2,3-triazol-1-yl}-6-methyl-nicotinamide;

I-191 N-(5-tert-butyl-isoxazol-3-yl)-5-(4-{5-[(ethyl-methyl-amino)-methyl]-pyridin-3-yl}-1,2,3-triazol-1-yl)-6-methyl-nicotinamide;

I-192 N-(5-tert-butyl-isoxazol-3-yl)-5-{4-[5-((R)-3-fluoro-pyrrolidin-1-ylmethyl)-pyridin-3-yl]-1,2,3-triazol-1-yl}-6-methyl-nicotinamide;

I-193 N-(5-tert-butyl-isoxazol-3-yl)-5-{4-[5-((S)-3-fluoro-pyrrolidin-1-ylmethyl)-pyridin-3-yl]-1,2,3-triazol-1-yl}-6-methyl-nicotinamide;

I-194 5-[4-(5-aminomethyl-pyridin-3-yl)-1,2,3-triazol-1-yl]-N-(5-tert-butyl-isoxazol-3-yl)-6-methyl-nicotinamide;

XII-1 N-{5-[4-(1,5-dimethyl-1H-pyrazol-4-yl)-1,2,3-triazol-1-yl]-6-methyl-pyridin-3-yl}-3-(4-methyl-piperazin-1-yl)-5-trifluoromethyl-benzamide;

XII-2 4-trifluoromethyl-pyridine-2-carboxylic acid {5-[4-(1,5-dimethyl-1H-pyrazol-4-yl)-1,2,3-triazol-1-yl]-6-methyl-pyridin-3-yl}-amide;

XII-3 5-tert-butyl-isoxazole-3-carboxylic acid {5-[4-(1,5-dimethyl-1H-pyrazol-4-yl)-1,2,3-triazol-1-yl]-6-methyl-pyridin-3-yl}-amide;

XII-4 5-tert-butyl-2-methyl-2H-pyrazole-3-carboxylic acid {5-[4-(1,5-dimethyl-1H-pyrazol-4-yl)-1,2,3-triazol-1-yl]-6-methyl-pyridin-3-yl}-amide;

XII-5 N-{5-[4-(1,5-dimethyl-1H-pyrazol-4-yl)-1,2,3-triazol-1-yl]-6-methyl-pyridin-3-yl}-4-fluoro-3-(4-methyl-piperazin-1-yl)-5-trifluoromethyl-benzamide;

XII-6 3-(cyano-dimethyl-methyl)-N-{5-[4-(1,5-dimethyl-1H-pyrazol-4-yl)-1,2,3-triazol-1-yl]-6-methyl-pyridin-3-yl}-benzamide;

XII-7 N-{5-[4-(1,5-dimethyl-1H-pyrazol-4-yl)-1,2,3-triazol-1-yl]-6-methyl-pyridin-3-yl}-4-methoxy-3-trifluoromethyl-benzamide;

XII-8 N-{5-[4-(1,5-dimethyl-1H-pyrazol-4-yl)-1,2,3-triazol-1-yl]-6-methyl-pyridin-3-yl}-3-trifluoromethoxy-benzamide;

XII-9 N-{5-[4-(1,5-dimethyl-1H-pyrazol-4-yl)-1,2,3-triazol-1-yl]-6-methyl-pyridin-3-yl}-2-methyl-5-trifluoromethyl-benzamide;

XII-10 3-(cyano-dimethyl-methyl)-N-[6-methyl-5-(4-pyrimidin-5-yl-1,2,3-triazol-1-yl)-pyridin-3-yl]-benzamide;

XII-11 3-(cyano-dimethyl-methyl)-N-[6-methyl-5-(4-pyridin-3-yl-1,2,3-triazol-1-yl)-pyridin-3-yl]-benzamide;

XII-12 3-(cyano-dimethyl-methyl)-N-{5-[4-(5-methoxy-pyridin-3-yl)-1,2,3-triazol-1-yl]-6-methyl-pyridin-3-yl}-benzamide;

XII-13 3-(cyano-dimethyl-methyl)-N-{5-[4-(5-cyano-pyridin-3-yl)-1,2,3-triazol-1-yl]-6-methyl-pyridin-3-yl}-benzamide;

XII-14 N-{5-[4-(2-acetylamino-thiazol-5-yl)-1,2,3-triazol-1-yl]-6-methyl-pyridin-3-yl}-3-(cyano-dimethyl-methyl)-benzamide;

XII-15 N-{5-[4-(1,5-dimethyl-1H-pyrazol-4-yl)-1,2,3-triazol-1-yl]-6-methyl-pyridin-3-yl}-3-(4-methyl-piperazin-1-yl)-5-trifluoromethoxy-benzamide;

XII-16 N-{5-[4-(1,5-methoxy-pyridin-3-yl)-1,2,3-triazol-1-yl]-6-methyl-pyridin-3-yl}-3-(4-methyl-piperazin-1-yl)-5-trifluoromethoxy-benzamide;

XII-17 3-(4-methyl-piperazin-1-yl)-N-[6-methyl-5-(4-pyridin-3-yl-1,2,3-triazol-1-yl)-pyridin-3-yl]-5-trifluoromethoxy-benzamide;

XII-18 4-methyl-N-{6-methyl-5-[4-(6-methyl-imidazo[1,2-a]pyrazin-3-yl)-1,2,3-triazol-1-yl]-pyridin-3-yl}-3-(4-methyl-piperazin-1-yl)-5-trifluoromethyl-benzamide;

XII-19 N-{5-[4-(2-acetylamino-thiazol-5-yl)-1,2,3-triazol-1-yl]-6-methyl-pyridin-3-yl}-3-(4-methyl-piperazin-1-yl)-5-trifluoromethoxy-benzamide;

XII-20 3-[(2-dimethylamino-ethyl)-methyl-amino]-N-{5-[4-(1,5-dimethyl-1H-pyrazol-4-yl)-1,2,3-triazol-1-yl]-6-methyl-pyridin-3-yl}-5-trifluoromethoxy-benzamide;

XII-21 3-(2-dimethylamino-ethylamino)-N-{5-[4-(1,5-dimethyl-1H-pyrazol-4-yl)-1,2,3-triazol-1-yl]-6-methyl-pyridin-3-yl}-5-trifluoromethoxy-benzamide;

XII-22 N-{5-[4-(1,5-dimethyl-1H-pyrazol-4-yl)-1,2,3-triazol-1-yl]-6-methyl-pyridin-3-yl}-3-(4-ethyl-piperazin-1-yl)-5-trifluoromethoxy-benzamide;

XII-23 N-{6-methyl-5-[4-(2-methyl-thiazol-5-yl)-1,2,3-triazol-1-yl]-pyridin-3-yl}-3-(4-methyl-piperazin-1-yl)-5-trifluoromethoxy-benzamide;

XII-24 N-{5-[4-(1,5-dimethyl-1H-pyrazol-4-yl)-1,2,3-triazol-1-yl]-6-methyl-pyridin-3-yl}-3-[4-(2-methoxy-ethyl)-piperazin-1-yl]-5-trifluoromethoxy-benzamide;

XII-25 N-{5-[4-(1,5-dimethyl-1H-pyrazol-4-yl)-1,2,3-triazol-1-yl]-6-methyl-pyridin-3-yl}-3-morpholin-4-yl-5-trifluoromethoxy-benzamide;

XII-26 3-(4-methyl-piperazin-1-yl)-N-[6-methyl-5-(4-pyrimidin-5-yl-1,2,3-triazol-1-yl)-pyridin-3-yl]-5-trifluoromethoxy-benzamide;

XII-27 N-{5-[4-(5-cyano-pyridin-3-yl)-1,2,3-triazol-1-yl]-6-methyl-pyridin-3-yl}-3-(4-methyl-piperazin-1-yl)-5-trifluoromethoxy-benzamide;

XII-28 N-{5-[4-(1,5-dimethyl-1H-pyrazol-4-yl)-1,2,3-triazol-1-yl]-6-methyl-pyridin-3-yl}-3-[methyl-(1-methyl-pyrrolidin-3-yl)-amino]-5-trifluoromethoxy-benzamide;

XII-29 3-(3-dimethylamino-pyrrolidin-1-yl)-N-{5-[4-(1,5-dimethyl-1H-pyrazol-4-yl)-1,2,3-triazol-1-yl]-6-methyl-pyridin-3-yl}-5-trifluoromethoxy-benzamide;

XII-30 N-{5-[4-(1,5-dimethyl-1H-pyrazol-4-yl)-1,2,3-triazol-1-yl]-6-methyl-pyridin-3-yl}-3-(1,2,3,6-tetrahydro-pyridin-4-yl)-5-trifluoromethoxy-benzamide;

XII-31 4-trifluoromethyl-pyridine-2-carboxylic acid [5-(4-{5-[4-(3-methoxy-propyl)-piperazin-1-yl]-pyridin-3-yl}-1,2,3-triazol-1-yl)-6-methyl-pyridin-3-yl]-amide;

XII-32 4-trifluoromethyl-pyridine-2-carboxylic acid (5-{4-[5-(4-tert-butyl-piperazin-1-yl)-pyridin-3-yl]-1,2,3-triazol-1-yl}-6-methyl-pyridin-3-yl)-amide;

XII-33 4-trifluoromethyl-pyridine-2-carboxylic acid [5-(4-{5-[4-(2-ethoxy-ethyl)-piperazin-1-yl]-pyridin-3-yl}-1,2,3-triazol-1-yl)-6-methyl-pyridin-3-yl]-amide;

XII-34 3-(cyano-dimethyl-methyl)-N-(6-methyl-5-{4-[5-(4-methyl-piperazin-1-yl)-pyridin-3-yl]-1,2,3-triazol-1-yl}-pyridin-3-yl)-benzamide;

XII-35 4-trifluoromethyl-pyridine-2-carboxylic acid (5-{4-[5-(4-isopropyl-piperazin-1-yl)-pyridin-3-yl]-1,2,3-triazol-1-yl}-6-methyl-pyridin-3-yl)-amide;

XII-36 N-(6-methyl-5-{4-[5-(4-methyl-piperazin-1-yl)-pyridin-3-yl]-1,2,3-triazol-1-yl}-pyridin-3-yl)-3-trifluoromethoxy-benzamide;

XII-37 4-trifluoromethyl-pyridine-2-carboxylic acid (5-{4-[5-(4-isobutyl-piperazin-1-yl)-pyridin-3-yl]-1,2,3-triazol-1-yl}-6-methyl-pyridin-3-yl)-amide;

XII-38 4-trifluoromethyl-pyridine-2-carboxylic acid (5-{4-[5-(4-ethyl-piperazin-1-yl)-pyridin-3-yl]-1,2,3-triazol-1-yl}-6-methyl-pyridin-3-yl)-amide;

XII-39 N-(5-{4-[5-(4-ethyl-piperazin-1-yl)-pyridin-3-yl]-1,2,3-triazol-1-yl}-6-methyl-pyridin-3-yl)-4-methoxy-3-trifluoromethyl-benzamide;

XII-40 4-methoxy-N-(6-methyl-5-{4-[5-(4-methyl-piperazin-1-yl)-pyridin-3-yl]-1,2,3-triazol-1-yl}-pyridin-3-yl)-3-trifluoromethyl-benzamide;

XII-41 4-trifluoromethyl-pyridine-2-carboxylic acid (6-methyl-5-{4-[5-(4-propyl-piperazin-1-yl)-pyridin-3-yl]-1,2,3-triazol-1-yl}-pyridin-3-yl)-amide;

XII-42 N-(5-{4-[5-(4-isopropyl-piperazin-1-yl)-pyridin-3-yl]-1,2,3-triazol-1-yl}-6-methyl-pyridin-3-yl)-3-trifluoromethoxy-benzamide;

XII-43 N-(5-{4-[5-(4-isopropyl-piperazin-1-yl)-pyridin-3-yl]-1,2,3-triazol-1-yl}-6-methyl-pyridin-3-yl)-4-methoxy-3-trifluoromethyl-benzamide;

XII-44 N-[5-(4-{5-[4-(2-ethoxy-ethyl)-piperazin-1-yl]-pyridin-3-yl}-1,2,3-triazol-1-yl)-6-methyl-pyridin-3-yl]-4-methoxy-3-trifluoromethyl-benzamide;

XII-45 N-(5-{4-[5-(4-tert-butyl-piperazin-1-yl)-pyridin-3-yl]-1,2,3-triazol-1-yl}-6-methyl-pyridin-3-yl)-4-methoxy-3-trifluoromethyl-benzamide;

XII-46 4-methoxy-N-[5-(4-{5-[4-(3-methoxy-propyl)-piperazin-1-yl]-pyridin-3-yl}-1,2,3-triazol-1-yl)-6-methyl-pyridin-3-yl]-3-trifluoromethyl-benzamide;

XII-47 N-(5-{4-[5-(4-tert-butyl-piperazin-1-yl)-pyridin-3-yl]-1,2,3-triazol-1-yl}-6-methyl-pyridin-3-yl)-3-trifluoromethoxy-benzamide;

XII-48 N-[5-(4-{5-[4-(3-methoxy-propyl)-piperazin-1-yl]-pyridin-3-yl}-1,2,3-triazol-1-yl)-6-methyl-pyridin-3-yl]-3-trifluoromethoxy-benzamide;

XII-49 3-(cyano-dimethyl-methyl)-N-(5-{4-[5-(4-cyclopropylmethyl-piperazin-1-yl)-pyridin-3-yl]-1,2,3-triazol-1-yl}-6-methyl-pyridin-3-yl)-benzamide;

XII-50 3-(cyano-dimethyl-methyl)-N-(5-{4-[5-(4-isopropyl-piperazin-1-yl)-pyridin-3-yl]-1,2,3-triazol-1-yl}-6-methyl-pyridin-3-yl)-benzamide;

XII-51 3-(cyano-dimethyl-methyl)-N-(5-{4-[5-(4-ethyl-piperazin-1-yl)-pyridin-3-yl]-1,2,3-triazol-1-yl}-6-methyl-pyridin-3-yl)-benzamide;

XII-52 3-(cyano-dimethyl-methyl)-N-(5-{4-[5-(2-dimethylamino-ethylamino)-pyridin-3-yl]-1,2,3-triazol-1-yl}-6-methyl-pyridin-3-yl)-benzamide;

XII-53 3-(cyano-dimethyl-methyl)-N-[5-(4-{5-[(2-dimethylamino-ethyl)-methyl-amino]-pyridin-3-yl}-1,2,3-triazol-1-yl)-6-methyl-pyridin-3-yl]-benzamide;

XII-54 N-[5-(4-{5-[4-(2-ethoxy-ethyl)-piperazin-1-yl]-pyridin-3-yl}-1,2,3-triazol-1-yl)-6-methyl-pyridin-3-yl]-3-trifluoromethoxy-benzamide;

XII-55 N-(5-{4-[5-(4-ethyl-piperazin-1-yl)-pyridin-3-yl]-1,2,3-triazol-1-yl}-6-methyl-pyridin-3-yl)-3-trifluoromethoxy-benzamide;

XII-56 N-(5-{4-[5-(4-cyclopropylmethyl-piperazin-1-yl)-pyridin-3-yl]-1,2,3-triazol-1-yl}-6-methyl-pyridin-3-yl)-3-trifluoromethoxy-benzamide;

XII-57 4-trifluoromethyl-pyridine-2-carboxylic acid (6-methyl-5-{4-[5-(4-methyl-piperazin-1-yl)-pyridin-3-yl]-1,2,3-triazol-1-yl}-pyridin-3-yl)-amide;

XII-58 3-(cyano-dimethyl-methyl)-N-[5-(4-{5-[4-(3-methoxy-propyl)-piperazin-1-yl]-pyridin-3-yl}-1,2,3-triazol-1-yl)-6-methyl-pyridin-3-yl]-benzamide;

XII-59 4-methoxy-N-(6-methyl-5-{4-[5-(4-propyl-piperazin-1-yl)-pyridin-3-yl]-1,2,3-triazol-1-yl}-pyridin-3-yl)-3-trifluoromethyl-benzamide;

XII-60 N-(5-{4-[5-(4-cyclopropylmethyl-piperazin-1-yl)-pyridin-3-yl]-1,2,3-triazol-1-yl}-6-methyl-pyridin-3-yl)-4-methoxy-3-trifluoromethyl-benzamide;

XII-61 3-(cyano-dimethyl-methyl)-N-[5-(4-{5-[4-(2-ethoxy-ethyl)-piperazin-1-yl]-pyridin-3-yl}-1,2,3-triazol-1-yl)-6-methyl-pyridin-3-yl]-benzamide;

XII-62 N-(5-{4-[5-(4-tert-butyl-piperazin-1-yl)-pyridin-3-yl]-1,2,3-triazol-1-yl}-6-methyl-pyridin-3-yl)-3-(cyano-dimethyl-methyl)-benzamide;

XII-63 3-(cyano-dimethyl-methyl)-N-{5-[4-(5-hydroxymethyl-pyridin-3-yl)-1,2,3-triazol-1-yl]-6-methyl-pyridin-3-yl}-benzamide;

XII-64 3-(cyano-dimethyl-methyl)-N-{5-[4-(5-dimethylaminomethyl-pyridin-3-yl)-1,2,3-triazol-1-yl]-6-methyl-pyridin-3-yl}-benzamide;

XII-65 3-(cyano-dimethyl-methyl)-N-{6-methyl-5-[4-(5-pyrrolidin-1-ylmethyl-pyridin-3-yl)-1,2,3-triazol-1-yl]-pyridin-3-yl}-benzamide;

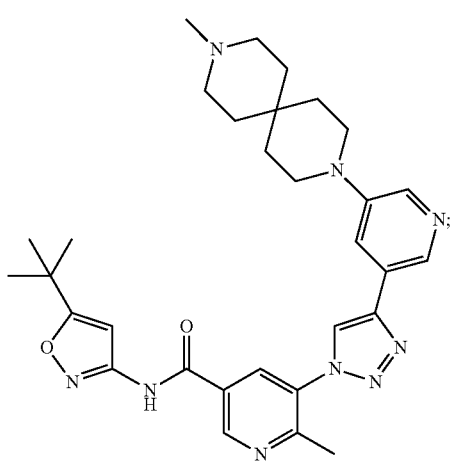

I-195

-continued

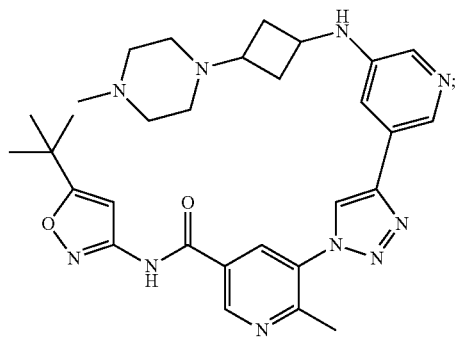

I-196

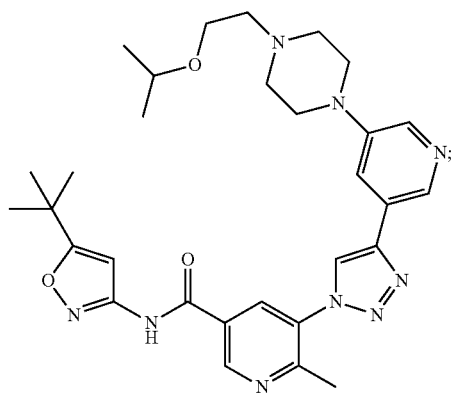

I-197

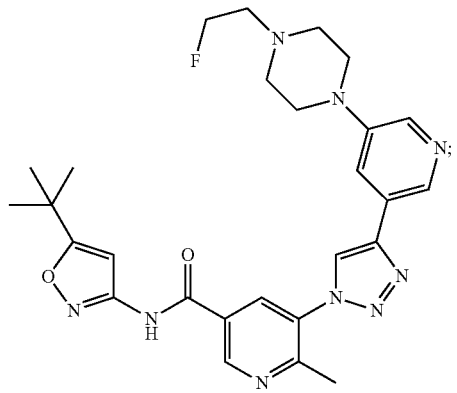

I-198

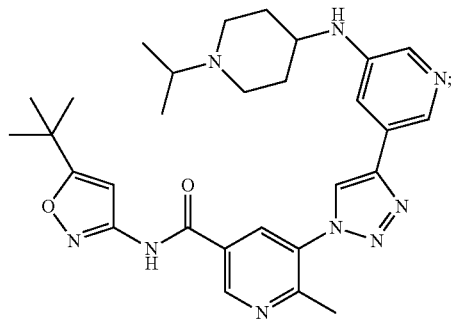

I-199

I-200
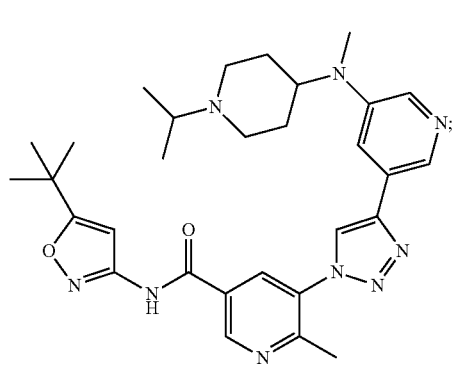
I-201
I-202
I-203
I-204
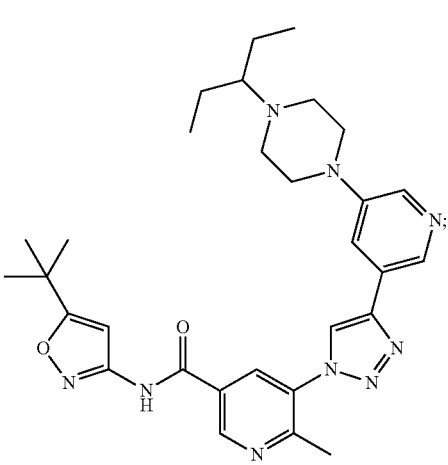
I-205
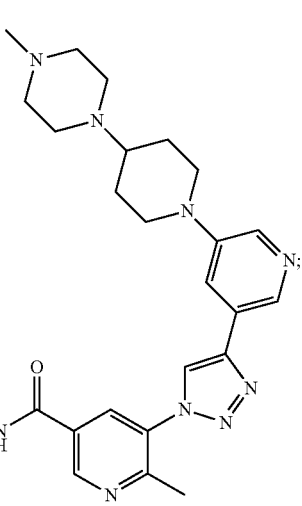
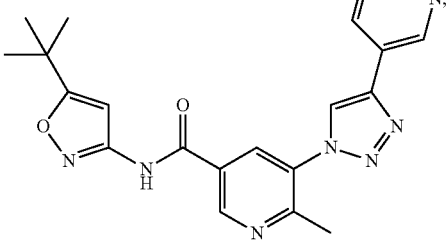
I-206
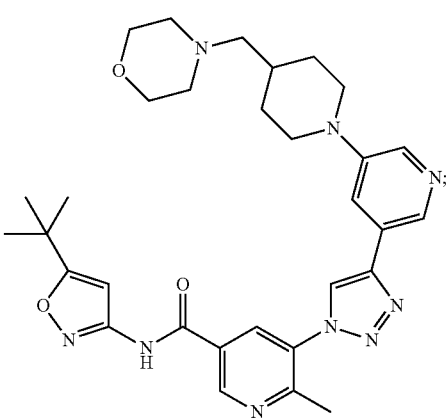

XII-66
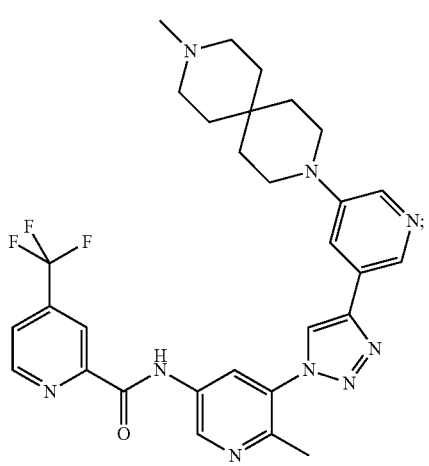
XII-67
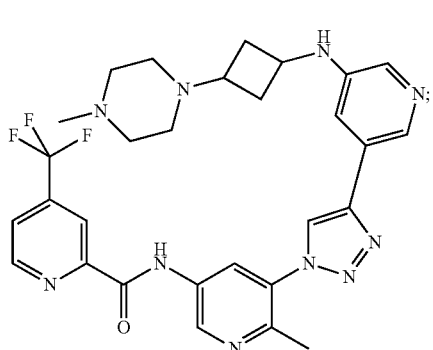
XII-68
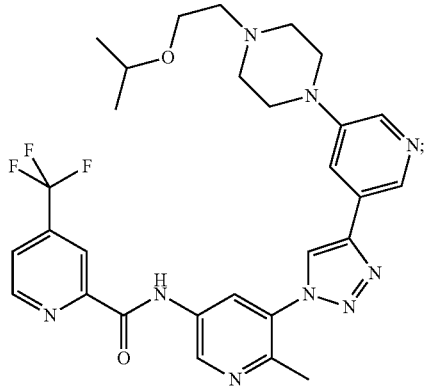
XII-69
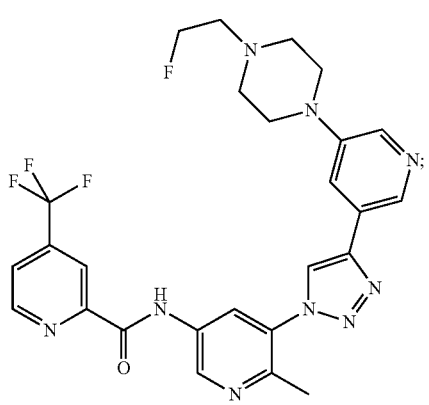
XII-70
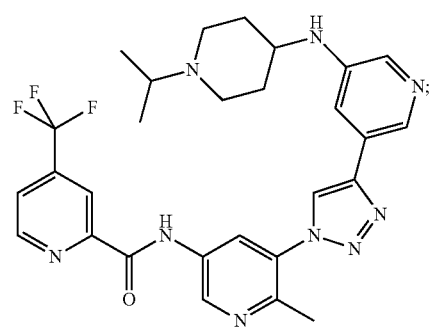
XII-71
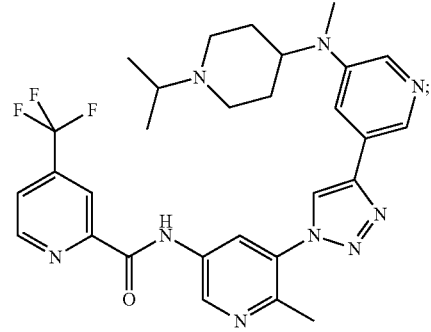
XII-72
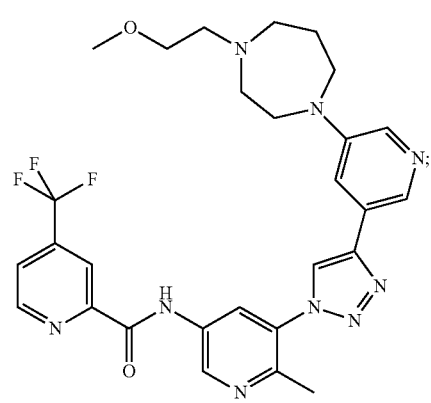
XII-73
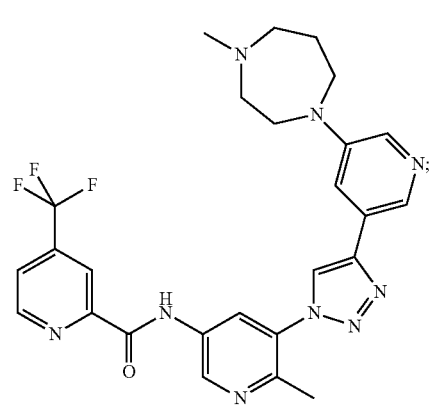

XII-74
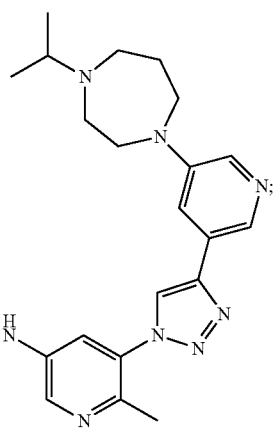
XII-75
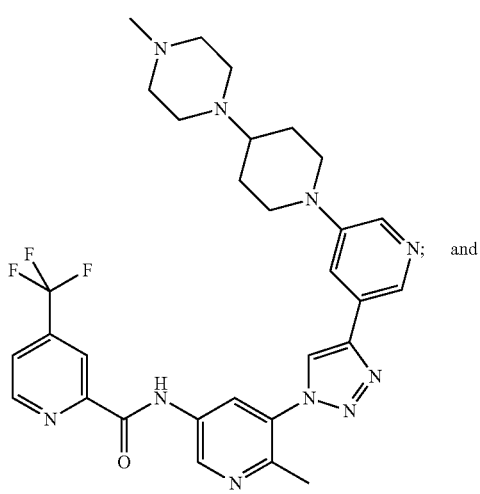
XII-76
XII-77
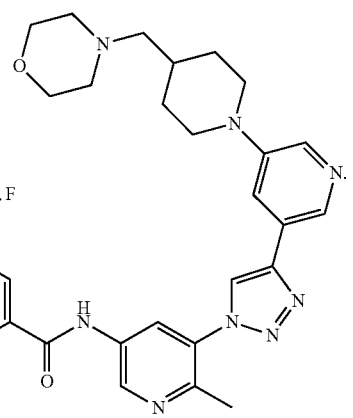
14. A pharmaceutical preparation, containing as active substance one or more compounds of formula (1) according to claim 1 or the pharmacologically acceptable salts thereof, optionally in combination with conventional excipients and/or carriers.
* * * * *